United States Patent
Speerschneider et al.

(10) Patent No.: US 11,225,487 B2
(45) Date of Patent: Jan. 18, 2022

(54) 7-MEMBERED AZA-HETEROCYCLIC CONTAINING δ-OPIOID RECEPTOR MODULATING COMPOUNDS, METHODS OF USING AND MAKING THE SAME

(71) Applicant: Trevena, Inc., Chesterbrook, PA (US)

(72) Inventors: Aimee Crombie Speerschneider, Chesterbrook, PA (US); Dennis Shinji Yamashita, Chesterbrook, PA (US); Philip Michael Pitis, Chesterbrook, PA (US); Michael John Hawkins, Chesterbrook, PA (US); Guodong Liu, Chesterbrook, PA (US); Tamara Ann Miskowski Daubert, Chesterbrook, PA (US); Catherine C. K. Yuan, Chesterbrook, PA (US); Robert Borbo Kargbo, Chesterbrook, PA (US); Robert Jason Herr, Chesterbrook, PA (US); Donna Romero, Chesterbrook, PA (US)

(73) Assignee: Trevena, Inc., Chesterbrook, PA (US)

(*) Notice: Subject to any disclaimer, the term of this patent is extended or adjusted under 35 U.S.C. 154(b) by 112 days.

(21) Appl. No.: 16/486,539

(22) PCT Filed: Feb. 15, 2018

(86) PCT No.: PCT/US2018/018303
§ 371 (c)(1),
(2) Date: Aug. 16, 2019

(87) PCT Pub. No.: WO2018/152286
PCT Pub. Date: Aug. 23, 2018

(65) Prior Publication Data
US 2021/0061812 A1 Mar. 4, 2021

Related U.S. Application Data

(60) Provisional application No. 62/460,386, filed on Feb. 17, 2017.

(51) Int. Cl.
| | | |
|---|---|---|
| *C07D 487/08* | (2006.01) |
| *A61P 25/22* | (2006.01) |
| *A61P 23/00* | (2006.01) |
| *A61P 25/24* | (2006.01) |
| *C07D 223/04* | (2006.01) |
| *C07D 403/12* | (2006.01) |
| *C07D 403/14* | (2006.01) |
| *C07D 405/14* | (2006.01) |
| *C07D 417/14* | (2006.01) |

(52) U.S. Cl.
CPC .......... *C07D 487/08* (2013.01); *A61P 23/00* (2018.01); *A61P 25/22* (2018.01); *A61P 25/24* (2018.01); *C07D 223/04* (2013.01); *C07D 403/12* (2013.01); *C07D 403/14* (2013.01); *C07D 405/14* (2013.01); *C07D 417/14* (2013.01)

(58) Field of Classification Search
CPC .. C07D 487/08; C07D 417/14; C07D 223/04; C07D 405/14; C07D 403/12; C07D 403/14; A61P 25/24; A61P 25/22; A61P 23/00
See application file for complete search history.

(56) References Cited

U.S. PATENT DOCUMENTS

| | | | |
|---|---|---|---|
| 3,863,633 A | 2/1975 | Ryde et al. | |
| 3,867,519 A | 2/1975 | Michaels | |
| 3,868,445 A | 2/1975 | Ryde et al. | |
| 3,960,150 A | 6/1976 | Hussain et al. | |
| 3,963,025 A | 6/1976 | Whitaker et al. | |
| 4,115,538 A | 9/1978 | Satoh et al. | |
| 4,186,184 A | 1/1980 | Zaffaroni | |
| 4,209,514 A * | 6/1980 | Gruenfeld ............ C07D 223/10 514/212.08 |
| 4,303,637 A | 12/1981 | Shell et al. | |
| 5,086,063 A | 2/1992 | Ciganek et al. | |
| 5,436,128 A | 7/1995 | Harpold et al. | |
| 5,443,505 A | 8/1995 | Wong et al. | |
| 5,869,079 A | 2/1999 | Wong et al. | |
| 6,465,453 B1 * | 10/2002 | Hauser ..................... A61P 43/00 514/217.03 |
| 7,098,203 B2 | 8/2006 | Wu et al. | |
| 7,488,745 B2 | 2/2009 | Yu et al. | |

(Continued)

FOREIGN PATENT DOCUMENTS

| | | | |
|---|---|---|---|
| JP | 2010527974 A | 8/2010 |
| JP | 2014506583 A | 3/2014 |

(Continued)

OTHER PUBLICATIONS

Lee; J. Am. Chem. Soc. 2006, 128, 7, 2178-2179. DOI: 10.1021/ja057592b (Year: 2006).*

(Continued)

*Primary Examiner* — Daniel R Carcanague
(74) *Attorney, Agent, or Firm* — Troutman Pepper Sanders Hamilton LLP

(57) ABSTRACT

The present embodiments are directed, in part, to compounds, or pharmaceutically acceptable salts thereof, or pharmaceutical compositions thereof for modulating the activity of delta opioid receptor, biased and/or unbiased, and/or methods for treating pain, migraines, headaches, depression, Parkinsons Disease, anxiety, and/or overactive bladder, and other disorders and conditions described herein or any combination thereof.

17 Claims, 74 Drawing Sheets

(56) References Cited

U.S. PATENT DOCUMENTS

| | | | |
|---|---|---|---|
| 7,504,424 | B2 | 3/2009 | Yu et al. |
| 8,173,678 | B2 | 5/2012 | Carroll et al. |
| 8,664,214 | B2 | 3/2014 | Braje et al. |
| 10,246,436 | B2* | 4/2019 | Speerschneider .... C07D 401/12 |
| 2002/0028821 | A1 | 3/2002 | Howard |
| 2007/0043015 | A1 | 2/2007 | DeVita et al. |
| 2007/0129419 | A1 | 6/2007 | Grundschober et al. |
| 2009/0042896 | A1 | 2/2009 | Jablonski et al. |
| 2011/0245232 | A1 | 10/2011 | Braje et al. |
| 2012/0010212 | A1 | 1/2012 | Nettekoven et al. |
| 2012/0245181 | A1* | 9/2012 | Yamashita ........... C07D 405/12 514/252.03 |
| 2014/0335190 | A1 | 11/2014 | Pettersson |
| 2015/0225424 | A1* | 8/2015 | Guillemont .......... C07D 498/04 514/211.06 |
| 2016/0052882 | A1 | 2/2016 | Vardanyan et al. |
| 2017/0210725 | A1* | 7/2017 | Speerschneider .... A61K 31/445 |
| 2019/0202803 | A1* | 7/2019 | Speerschneider ....... A61P 13/10 |
| 2020/0231564 | A9* | 7/2020 | Speerschneider ....... A61P 25/16 |
| 2021/0061790 | A1* | 3/2021 | Speerschneider ....... A61P 29/00 |

FOREIGN PATENT DOCUMENTS

| | | |
|---|---|---|
| WO | 199800401 A1 | 1/1998 |
| WO | 200198267 A1 | 12/2001 |
| WO | 200200651 A2 | 1/2002 |
| WO | 2003084948 A1 | 10/2003 |
| WO | 2006019768 A1 | 2/2006 |
| WO | 2007050980 A2 | 5/2007 |
| WO | 2007106469 A2 | 9/2007 |
| WO | 2009062319 A1 | 5/2009 |
| WO | 2012129562 A2 | 9/2012 |
| WO | 2013182612 A1 | 12/2013 |
| WO | 2016210403 A1 | 12/2016 |
| WO | 2017040545 A1 | 3/2017 |

OTHER PUBLICATIONS

National Center for Biotechnology Information. PubChem Compound Summary for CID 23146852. https://pubchem.ncbi.nlm.nih.gov/compound/23146852. Create Date Dec. 5, 2007. (Year: 2007).*

National Center for Biotechnology Information. PubChem Compound Summary for CID 123379529. https://pubchem.ncbi.nlm.nih.gov/compound/123379529. Create Date Jan. 24, 2017. (Year: 2017).*

Mayo Clinic Publication; "Parkinson's Disease", Downloaded Feb. 22, 2021 from https://www.mayoclinic.org/diseases-conditions/parkinsons-disease/symptoms-causes/syc-20376055. (Year: 2021).*

Tuthill; Bioorganic & Medicinal Chemistry Letters 14 (2004) 5693-5697. (Year: 2004).*

Sakya; Tetrahedron Letters 53 (2012) 723-725. (Year: 2012).*

Peppin; Journal of Clinical Pharmacy and Therapeutics, 2015, 40, 155-166. DOI: 10.1111/jcpt.12244 (Year: 2015).*

During et al., "Controlled Release of Dopamine from a Polymeric Brain Implant: In Vivo Characterization", Ann. Neurol. (1989)25:351-356.

Elitzin VI, "Development of a new synthesis for the large-scale preparation of triple reuptake inhibitor (−)-GSK1360707" Organic Process Research and Development, 2010, 14(4), 912-917.

Felley-Bosco, et al., "Constitutive Expression of Inducible Nitric Oxide Synthase in Human Bronchial Epithelial Cells Induces c-fos and Stimulates the cGMP Pathway", American Journal of Respiratory Cell and Molecular Biology (1994) vol. 11 pp. 160-164.

Fujimori et al., "Design, synthesis and biological evaluation of a novel series of peripheral-selective noradrenaline reuptake inhibitor," Bioorg. Med. Chem. (2015) 23: 5000-5014.

Groarke et al., Visualization of Agonist-induced Association and Trafficking of Green Fluorescent Protein-tagged Forms of Both b-Arrestin-1 and the Thyrotropin-releasing Hormone Receptor-1*, J. of Biological Chemistry (1999)vol. 274, No. 33, pp. 23263-23269.

Homan et al., "Structural and Functional Analysis of G Protein-Coupled Receptor Kinase Inhibition by Paroxetine and a Rationally Designed Analog," Molecular Pharmacology (2014); 85(2): 237-248.

Howard et al., "Intracerebral drug delivery in rats with lesion-induced memory deficits", J Neurosurg (1989) 71:105-112.

Hudzik et al., "Preclinical Pharmacology of AZD2327: A Highly Selective Agonist of the—Opioid Receptor", JPET 338:195-204,(2011).

Journigan et al. Designing bifunclional NOP receptor-mu opioid receptor ligands from NOP-receptor selective scaffolds. Part 11, Bioorg Med Chem, 2014, 2508-2516, 22(8).

Kroeger et al., "Constitutive and Agonist-dependent Homo-oligomerization of the Thyrotropin-releasing Hormone Receptor", Journal of Biological Chemistry (2001) vol. 276, No. 16, Issue of Apr. 20, pp. 12736-12743.

LaBuda CJ, "Pharmacological evaluation of the selective spinal nerve ligation model of neuropalhic pain in the rat", Journal of Neuroscience Methods, 2005, 144, 175-18.

Langer "New Methods of Drug Delivery", Science, (1990)vol. 249; pp. 1527-1533.

Langer et al., "Chemical and Physical Structure of Polymers as Carriers for Controlled Release of Bioactive Agents: A Review", JMS-Rev. Macromol. Chem. Phys., C23(1), 61-126 (1983).

Levy et al., "Inhibition of Calcification of Bioprosthetic Heart Valves by Local Controlled-Release Diphosphonate", Science, New Series, vol. 228, No. 4696 pp. 190-192 (1985).

Mabrouk et al., "Stimulation of delta opioid receptors located in substantia nigra reticulata but not globus pallidus or striatum restores motor activitiy in 6-hydroxydopamine lesioned rats: new insights into the role of delta receptors in parkinsonism", J. Neurochem. (2008) 107, 1647-1659.

Marti et al., "Blockade of nociceptin/orphanin FQ transmission in rat substantia nigra reverses haloperidol-induced akinesia and normalizes nigral glutamate release", J Neurochem. (2004) 91, 1501-1504.

Misteli et al., "Applications of the green fluorescent protein incell biology and biotechnology". Nature Biotechnology (1997) Vo. 15 pp. 961-964.

Nonfinal Office Action dated Apr. 18, 2018 in U.S. Appl. No. 15/252,112.

Notice of Allowance dated Nov. 15, 2018 in U.S. Appl. No. 15/252,112.

Offermanns et al., "Ga15 and Ga16 Couple a Wide Variety of Receptors to Phospholipase C*", Journal Bilogical Chemistry (1995) vol. 270, No. 25, Issue of Jun. 23, pp. 15175-15180.

Pradhan et al., "The delta opioid receptor: an evolving target for the treatment of brain disorders", Trends Pharmacol Sci. (2011) 32(10): 581-590.

Pubchem Compound Summary for CID 67131456, U.S. National Library of Medicine 2012 pp. 1-13.

PubChem Compound Summary for CID 76849249 U.S. National Library of of Medicine (2014).

Pubchem—CID 10359344 Create Dale Oct. 25, 2006, p. 3.

Rajewski, et al. "Pharmaceutical Applications of Cyclodextrins. 2. In Vivo Drug Delivery", Journal of Pharmaceutical Sciences (1996) vol. 85, No. 11, pp. 1142-1169.

Sanberg et al., "The Catalepsy Test: Its Ups and Downs", Behavioral Neuroscience (1988) vol. 102, No. 5, 748-759.

Saudek et al., "A Preliminary trial of the programmable implantable medication system for insulin delivery", New Englande Journal of Medicine, (1989) vol. 321, No. 9, pp. 574-579.

Vilpoux et al., "Differential effects of chronic antidepressant treatments on m- and d-opioid receptors in rat brain," European Journal of Pharmacology (2002) 443:85-93.

Dunam et al., "Possible Involvement of Opioidergic and Serotonergic Mechanisms in Antinocipeptive Effect of Paroxetine in Acute Pain", J Pharmacol Sci 94, 16-165 (2004).

Tuthil et al., "Azepinone as a conformational constraint in the design of k-opioid receptor agonists", Boorganic & Medicinal Chemistry Letters 14: pp. 5693-5697 (2004).

(56) References Cited

OTHER PUBLICATIONS

NonFinal Office Action dated Feb. 2, 2021 in U.S. Appl. No. 16/286,700.

* cited by examiner

Figure 1

| Structure | Compound | Name | calc. MW | LCMS |
|---|---|---|---|---|
| | C0001 | 3-{[(trans)-5-(4-methoxyphenyl)azepan-4-yl]methoxy}benzonitrile | 336.43 | 337 |
| | C0002 | 6-{[(trans)-5-(4-methoxyphenyl)azepan-4-yl]methoxy}-2,3-dihydro-1H-isoindol-1-one | 366.45 | 367.1 |
| | C0003 | 3-{[(trans)-5-(4-methoxyphenyl)-1-propylazepan-4-yl]methoxy}benzonitrile | 378.51 | 379.1 |
| | C0004 | 6-{[(trans)-5-(4-methoxyphenyl)-1-propylazepan-4-yl]methoxy}-2,3-dihydro-1H-isoindol-1-one | 408.53 | 409.1 |
| | C0005 | 4-{[(trans)-5-(4-methoxyphenyl)azepan-4-yl]methoxy}benzonitrile | 336.43 | 337 |
| | C0006 | 2-{[(trans)-5-(4-methoxyphenyl)azepan-4-yl]methoxy}benzonitrile | 336.43 | 337.1 |
| | C0007 | 3-{[(trans)-5-(4-methoxyphenyl)azepan-4-yl]methoxy}benzamide | 354.44 | 355.1 |
| | C0008 | 3-{[(trans)-4-(4-methoxyphenyl)azepan-3-yl]methoxy}benzonitrile | 336.43 | 337.1 |

Figure 1

| Structure | ID | Name | | |
|---|---|---|---|---|
| 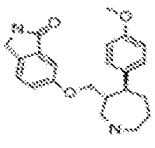 | C0009 | 6-{[(trans)-4-(4-methoxyphenyl)azepan-3-yl]methoxy}-2,3-dihydro-1H-isoindol-1-one | 366.45 | 367.1 |
| 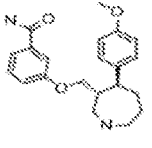 | C0010 | 3-{[(trans)-4-(4-methoxyphenyl)azepan-3-yl]methoxy}benzamide | 354.44 | 355.1 |
| 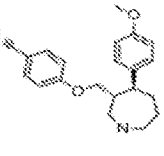 | C0011 | 4-{[(trans)-4-(4-methoxyphenyl)azepan-3-yl]methoxy}benzonitrile | 336.43 | 337 |
| 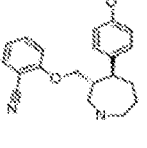 | C0012 | 2-{[(trans)-4-(4-methoxyphenyl)azepan-3-yl]methoxy}benzonitrile | 336.43 | 337.1 |
| 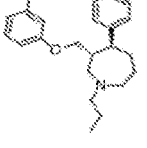 | C0013 | 3-{[(trans)-4-(4-methoxyphenyl)-1-propylazepan-3-yl]methoxy}benzonitrile | 378.51 | 379.1 |
| 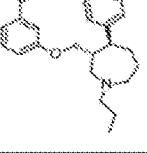 | C0014 | 3-{[(trans)-4-(4-methoxyphenyl)-1-propylazepan-3-yl]methoxy}benzamide | 396.52 | 397.1 |
| 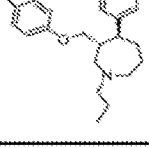 | C0015 | 6-{[(trans)-4-(4-methoxyphenyl)-1-propylazepan-3-yl]methoxy}-2,3-dihydro-1H-isoindol-1-one | 408.53 | 409.1 |
| 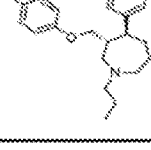 | C0016 | 4-{[(trans)-4-(4-methoxyphenyl)-1-propylazepan-3-yl]methoxy}benzonitrile | 378.51 | 379.1 |

Figure 1

| Structure | ID | Name | MW | MS |
|---|---|---|---|---|
| 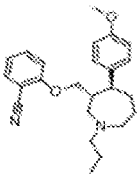 | C0017 | 2-{[(trans)-4-(4-methoxyphenyl)-1-propylazepan-3-yl]methoxy}benzonitrile | 378.51 | 379.1 |
| 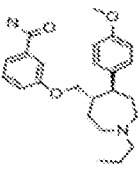 | C0018 | 3-{[(trans)-5-(4-methoxyphenyl)-1-propylazepan-4-yl]methoxy}benzamide | 396.52 | 397.1 |
| 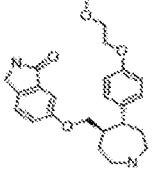 | C0019 | 6-{[(trans)-5-[4-(2-methoxyethoxy)phenyl]azepan-4-yl]methoxy}-2,3-dihydro-1H-isoindol-1-one | 410.51 | 411.1 |
| 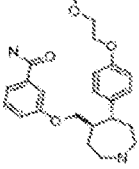 | C0020 | 3-{[(trans)-5-[4-(2-methoxyethoxy)phenyl]azepan-4-yl]methoxy}benzamide | 398.5 | 399.1 |
| 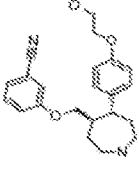 | C0021 | 3-{[(trans)-5-[4-(2-methoxyethoxy)phenyl]azepan-4-yl]methoxy}benzonitrile | 380.48 | 381.1 |
| 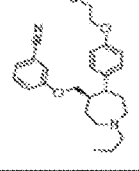 | C0022 | 3-{[(trans)-5-[4-(2-methoxyethoxy)phenyl]-1-propylazepan-4-yl]methoxy}benzonitrile | 422.56 | 423.1 |
| 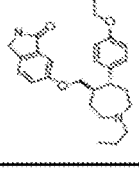 | C0023 | 6-{[(trans)-5-[4-(2-methoxyethoxy)phenyl]-1-propylazepan-4-yl]methoxy}-2,3-dihydro-1H-isoindol-1-one | 452.59 | 453.1 |
| 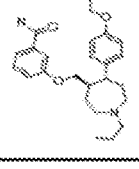 | C0024 | 3-{[(trans)-5-[4-(2-methoxyethoxy)phenyl]-1-propylazepan-4-yl]methoxy}benzamide | 440.58 | 441.2 |

Figure 1

| | | | | |
|---|---|---|---|---|
| 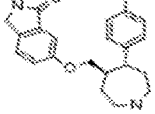 | C0025 | 6-{[(trans)-5-(4-fluorophenyl)azepan-4-yl]methoxy}-2,3-dihydro-1H-isoindol-1-one | 354.42 | 355 |
| 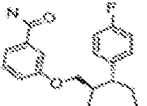 | C0026 | 3-{[(trans)-5-(4-fluorophenyl)azepan-4-yl]methoxy}benzamide | 342.41 | 343 |
| 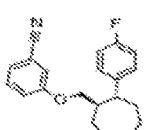 | C0027 | 3-{[(trans)-5-(4-fluorophenyl)azepan-4-yl]methoxy}benzonitrile | 324.39 | 325.1 |
| 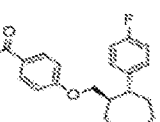 | C0028 | 4-{[(trans)-5-(4-fluorophenyl)azepan-4-yl]methoxy}benzamide | 342.41 | 343.1 |
| 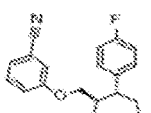 | C0029 | 3-{[(trans)-5-(4-fluorophenyl)-1-propylazepan-4-yl]methoxy}benzonitrile | 366.47 | 367.1 |
| 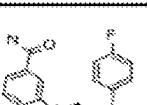 | C0030 | 3-{[(trans)-5-(4-fluorophenyl)-1-propylazepan-4-yl]methoxy}benzamide | 384.49 | 385.1 |
|  | C0031 | 4-{[(trans)-5-(4-fluorophenyl)-1-propylazepan-4-yl]methoxy}benzamide | 384.49 | 385.1 |
| 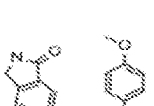 | C0032 | 6-{[5-(4-methoxyphenyl)-2,3,6,7-tetrahydro-1H-azepin-4-yl]methoxy}-2,3-dihydro-1H-isoindol-1-one | 364.44 | 365 |

Figure 1

| Structure | ID | Name | MW | MS |
|---|---|---|---|---|
| 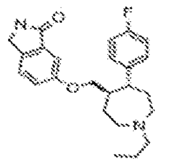 | C0033 | 6-{[(trans)-5-(4-fluorophenyl)-1-propylazepan-4-yl]methoxy}-2,3-dihydro-1H-isoindol-1-one | 396.5 | 397 |
| 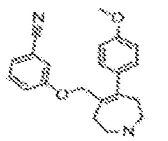 | C0034 | 3-{[5-(4-methoxyphenyl)-2,3,6,7-tetrahydro-1H-azepin-4-yl]methoxy}benzonitrile | 334.41 | 334.9 |
| 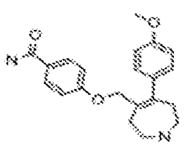 | C0035 | 4-{[5-(4-methoxyphenyl)-2,3,6,7-tetrahydro-1H-azepin-4-yl]methoxy}benzamide | 352.43 | 353 |
| 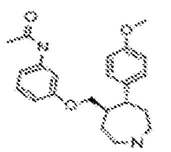 | C0036 | N-(3-{[(trans)-5-(4-methoxyphenyl)azepan-4-yl]methoxy}phenyl)acetamide | 368.47 | 369.1 |
| 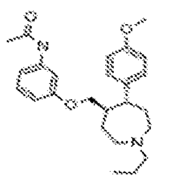 | C0037 | N-(3-{[(trans)-5-(4-methoxyphenyl)-1-propylazepan-4-yl]methoxy}phenyl)acetamide | 410.55 | 411.1 |
| 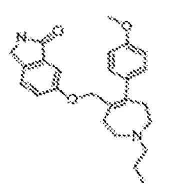 | C0038 | 6-{[5-(4-methoxyphenyl)-1-propyl-2,3,6,7-tetrahydro-1H-azepin-4-yl]methoxy}-2,3-dihydro-1H-isoindol-1-one | 406.52 | 407.1 |
| 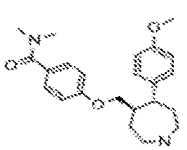 | C0039 | 3-{[(trans)-5-(4-methoxyphenyl)azepan-4-yl]methoxy}-N,N-dimethylbenzamide | 382.5 | 383.1 |
| 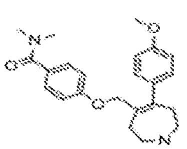 | C0040 | 4-{[5-(4-methoxyphenyl)-2,3,6,7-tetrahydro-1H-azepin-4-yl]methoxy}-N,N-dimethylbenzamide | 380.48 | 381 |

Figure 1

| | | | | |
|---|---|---|---|---|
| 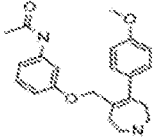 | C0041 | N-(3-{[5-(4-methoxyphenyl)-2,3,6,7-tetrahydro-1H-azepin-4-yl]methoxy}phenyl)acetamide | 366.45 | 367 |
| 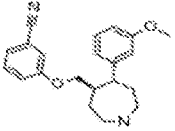 | C0042 | 3-{[(trans)-5-(3-methoxyphenyl)azepan-4-yl]methoxy}benzonitrile | 336.43 | 337.1 |
| 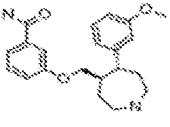 | C0043 | 3-{[(trans)-5-(3-methoxyphenyl)azepan-4-yl]methoxy}benzamide | 354.44 | 355.1 |
| 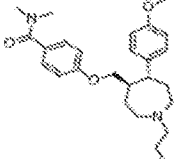 | C0044 | 3-{[(trans)-5-(4-methoxyphenyl)-1-propylazepan-4-yl]methoxy}benzamide | 424.58 | 425.1 |
| 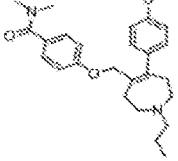 | C0045 | 4-{[5-(4-methoxyphenyl)-1-propyl-2,3,6,7-tetrahydro-1H-azepin-4-yl]methoxy}-N,N-dimethylbenzamide | 422.56 | 423.1 |
| 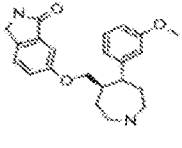 | C0046 | 6-{[(trans)-5-(3-methoxyphenyl)azepan-4-yl]methoxy}-2,3-dihydro-1H-isoindol-1-one | 366.45 | 367 |
| 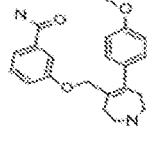 | C0047 | 3-{[5-(4-methoxyphenyl)-2,3,6,7-tetrahydro-1H-azepin-4-yl]methoxy}benzamide | 352.43 | 353 |
| 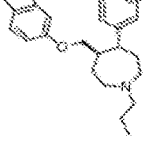 | C0048 | 6-{[(trans)-5-(3-methoxyphenyl)-1-propylazepan-4-yl]methoxy}-2,3-dihydro-1H-isoindol-1-one | 408.53 | 409.1 |

Figure 1

| | | | | |
|---|---|---|---|---|
| 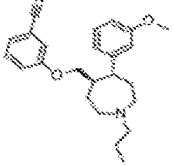 | C0049 | 3-{[(trans)-5-(3-methoxyphenyl)-1-propylazepan-4-yl]methoxy}benzonitrile | 378.51 | 379.1 |
| 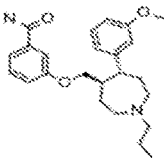 | C0050 | 3-{[(trans)-5-(3-methoxyphenyl)-1-propylazepan-4-yl]methoxy}benzamide | 396.52 | 397.1 |
| 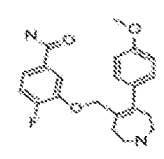 | C0051 | 4-fluoro-3-{[5-(4-methoxyphenyl)-2,3,6,7-tetrahydro-1H-azepin-4-yl]methoxy}benzamide | 370.42 | 371 |
| 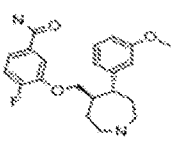 | C0052 | 4-fluoro-3-{[(trans)-5-(3-methoxyphenyl)azepan-4-yl]methoxy}benzamide | 372.43 | 373 |
| 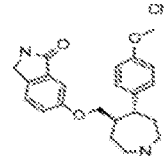 | C0053 | (−)-6-{2-[(trans)-5-(4-methoxyphenyl)azepan-4-yl]ethyl}-2,3-dihydro-1H-isoindol-1-one | 366.45 | 367.1 |
| 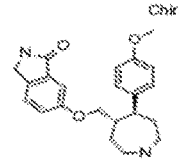 | C0054 | (+)-6-{[(trans)-5-(4-methoxyphenyl)azepan-4-yl]methoxy}-2,3-dihydro-1H-isoindol-1-one | 366.45 | 367 |
| 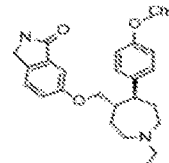 | C0055 | (+)-6-{[(trans)-1-ethyl-5-(4-methoxyphenyl)azepan-4-yl]methoxy}-2,3-dihydro-1H-isoindol-1-one | 408.53 | 409.1 |
| 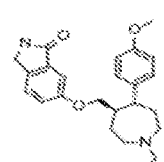 | C0056 | (−)-6-{2-[(trans)-5-(4-methoxyphenyl)-1-propylazepan-4-yl]ethyl}-2,3-dihydro-1H-isoindol-1-one | 408.53 | 409.3 |

Figure 1

| Structure | ID | Name | MW | M+1 |
|---|---|---|---|---|
| 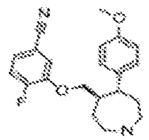 | C0057 | 4-fluoro-3-{[(trans)-5-(4-methoxyphenyl)azepan-4-yl]methoxy}benzonitrile | 354.42 | 355 |
| 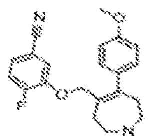 | C0058 | 4-fluoro-3-{[5-(4-methoxyphenyl)-2,3,6,7-tetrahydro-1H-azepin-4-yl]methoxy}benzonitrile | 352.4 | 353.1 |
| 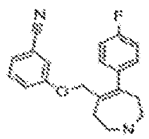 | C0059 | 3-{[5-(4-fluorophenyl)-2,3,6,7-tetrahydro-1H-azepin-4-yl]methoxy}benzonitrile | 322.38 | 323 |
| 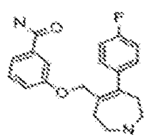 | C0060 | 3-{[5-(4-fluorophenyl)-2,3,6,7-tetrahydro-1H-azepin-4-yl]methoxy}benzamide | 340.39 | 341 |
| 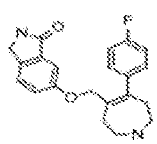 | C0061 | 6-{[5-(4-fluorophenyl)-2,3,6,7-tetrahydro-1H-azepin-4-yl]methoxy}-2,3-dihydro-1H-isoindol-1-one | 352.4 | 353 |
| 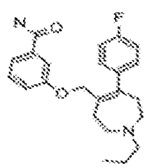 | C0062 | 3-{[5-(4-fluorophenyl)-1-propyl-2,3,6,7-tetrahydro-1H-azepin-4-yl]methoxy}benzamide | 382.47 | 383 |
| 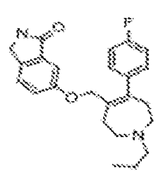 | C0063 | 6-{[5-(4-fluorophenyl)-1-propyl-2,3,6,7-tetrahydro-1H-azepin-4-yl]methoxy}-2,3-dihydro-1H-isoindol-1-one | 394.48 | 395 |
| 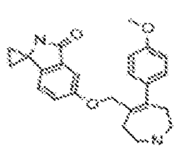 | C0064 | 5'-{[5-(4-methoxyphenyl)-2,3,6,7-tetrahydro-1H-azepin-4-yl]methoxy}-2',3'-dihydrospiro[cyclopropane-1,1'-isoindole]-3'-one | 390.47 | 391 |

Figure 1

| | | | | |
|---|---|---|---|---|
| 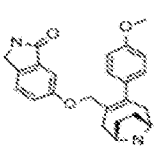 | C0065 | (±)-6-{[4-(4-methoxyphenyl)-9-azabicyclo[4.2.1]non-3-en-3-yl]methoxy}-2,3-dihydro-1H-isoindol-1-one | 390.47 | 391.2 |
| 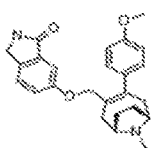 | C0066 | (±)-6-{[4-(4-methoxyphenyl)-9-propyl-9-azabicyclo[4.2.1]non-3-en-3-yl]methoxy}-2,3-dihydro-1H-isoindol-1-one | 432.55 | 433.2 |
| 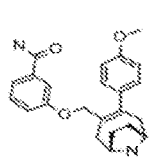 | C0067 | (±)-3-{[4-(4-methoxyphenyl)-9-azabicyclo[4.2.1]non-3-en-3-yl]methoxy}benzamide | 378.46 | 379.2 |
| 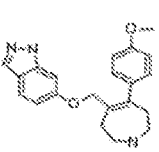 | C0068 | 6-{[5-(4-methoxyphenyl)-2,3,6,7-tetrahydro-1H-azepin-4-yl]methoxy}-1H-indazole | 349.43 | 350.2 |
| 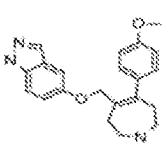 | C0069 | 5-{[5-(4-methoxyphenyl)-2,3,6,7-tetrahydro-1H-azepin-4-yl]methoxy}-1H-indazole | 349.43 | 350.2 |
| 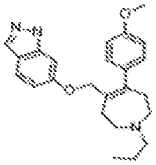 | C0070 | 6-{[5-(4-methoxyphenyl)-1-propyl-2,3,6,7-tetrahydro-1H-azepin-4-yl]methoxy}-1H-indazole | 391.51 | 392.2 |
| 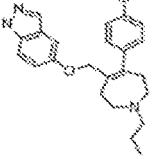 | C0071 | 5-{[5-(4-methoxyphenyl)-1-propyl-2,3,6,7-tetrahydro-1H-azepin-4-yl]methoxy}-1H-indazole | 391.51 | 392.2 |
| 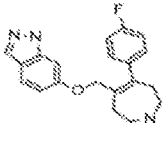 | C0072 | 6-{[5-(4-fluorophenyl)-2,3,6,7-tetrahydro-1H-azepin-4-yl]methoxy}-1H-indazole | 337.39 | 338.2 |

Figure 1

| Structure | ID | Name | MW | MS |
|---|---|---|---|---|
| 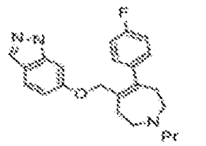 | C0073 | 6-{[5-(4-fluorophenyl)-1-propyl-2,3,6,7-tetrahydro-1H-azepin-4-yl]methoxy}-1H-indazole | 379.47 | 380.2 |
| 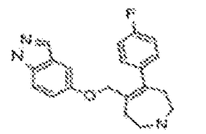 | C0074 | 5-{[5-(4-fluorophenyl)-2,3,6,7-tetrahydro-1H-azepin-4-yl]methoxy}-1H-indazole | 337.39 | 338 |
| 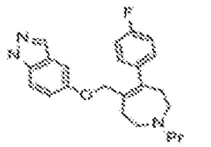 | C0075 | 5-{[5-(4-fluorophenyl)-1-propyl-2,3,6,7-tetrahydro-1H-azepin-4-yl]methoxy}-1H-indazole | 379.47 | 380.1 |
| 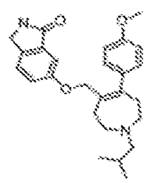 | C0076 | 6-{[5-(4-methoxyphenyl)-1-(2-methylpropyl)-2,3,6,7-tetrahydro-1H-azepin-4-yl]methoxy}-2,3-dihydro-1H-isoindol-1-one | 420.54 | 421.2 |
| 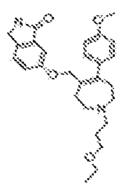 | C0077 | 6-{[1-(3-ethoxyethyl)-5-(4-methoxyphenyl)-2,3,6,7-tetrahydro-1H-azepin-4-yl]methoxy}-2,3-dihydro-1H-isoindol-1-one | 450.57 | 451.3 |
| 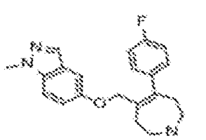 | C0078 | 5-{[5-(4-fluorophenyl)-2,3,6,7-tetrahydro-1H-azepin-4-yl]methoxy}-1-methyl-1H-indazole | 351.42 | 352.1 |
| 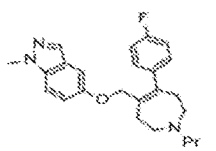 | C0079 | 5-{[5-(4-fluorophenyl)-1-propyl-2,3,6,7-tetrahydro-1H-azepin-4-yl]methoxy}-1-methyl-1H-indazole | 393.5 | 394.3 |
| 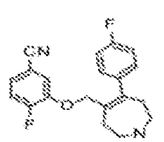 | C0080 | 4-fluoro-3-{[5-(4-fluorophenyl)-2,3,6,7-tetrahydro-1H-azepin-4-yl]methoxy}benzonitrile | 340.37 | 341.1 |

Figure 1

| | | | | |
|---|---|---|---|---|
| 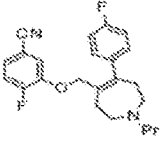 | C0081 | 4-fluoro-3-{[5-(4-fluorophenyl)-1-propyl-2,3,6,7-tetrahydro-1H-azepin-4-yl]methoxy}benzonitrile | 382.45 | 383.1 |
| 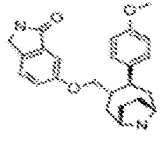 | C0082 | 6-{2-[(cis, trans)-4-(4-methoxyphenyl)-9-azabicyclo[4.2.1]nonan-3-yl]ethyl}-2,3-dihydro-1H-isoindol-1-one | 392.49 | 393.2 |
| 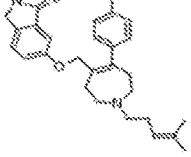 | C0083 | 6-{[5-(4-methoxyphenyl)-1-(4-methylpent-3-en-1-yl)-2,3,6,7-tetrahydro-1H-azepin-4-yl]methoxy}-2,3-dihydro-1H-isoindol-1-one | 446.58 | 447.2 |
| 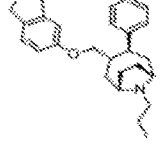 | C0084 | 6-{2-[(cis)-4-(4-methoxyphenyl)-9-propyl-9-azabicyclo[4.2.1]nonan-3-yl]ethyl}-2,3-dihydro-1H-(trans)-isoindol-1-one | 434.57 | 435.2 |
| 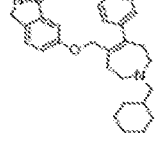 | C0085 | 6-{[1-(cyclohexylmethyl)-5-(4-methoxyphenyl)-2,3,6,7-tetrahydro-1H-azepin-4-yl]methoxy}-2,3-dihydro-1H-isoindol-1-one | 460.61 | 461.2 |
| 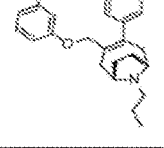 | C0086 | (±)-3-{[4-(4-methoxyphenyl)-9-propyl-9-azabicyclo[4.2.1]non-3-en-3-yl]methoxy}benzamide | 420.54 | 421.2 |
| 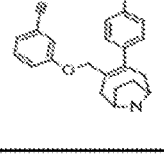 | C0087 | (±)-3-{[4-(4-methoxyphenyl)-9-azabicyclo[4.2.1]non-3-en-3-yl]methoxy}benzonitrile | 360.45 | 361.1 |
| 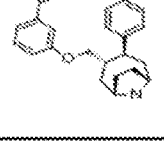 | C0088 | 1-(3-{[(trans)-4-(4-methoxyphenyl)-9-azabicyclo[4.2.1]nonan-3-yl]methoxy}phenyl)ethan-1-one | 380.48 | 381.2 |

Figure 1

| Structure | ID | Name | MW | MS |
|---|---|---|---|---|
| 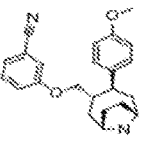 | C0089 | 3-{[(trans)-4-(4-methoxyphenyl)-9-azabicyclo[4.2.1]nonan-3-yl]methoxy}benzonitrile | 362.46 | 363.2 |
| 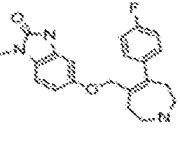 | C0090 | 5-{[5-(4-fluorophenyl)-2,3,6,7-tetrahydro-1H-azepin-4-yl]methoxy}-1-methyl-2-methylidene-2,3-dihydro-1H-1,3-benzodiazol-2-one | 367.42 | 368.1 |
| 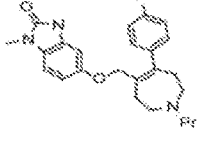 | C0091 | 5-{[5-(4-fluorophenyl)-1-propyl-2,3,6,7-tetrahydro-1H-azepin-4-yl]methoxy}-1-methyl-2,3-dihydro-1H-1,3-benzodiazol-2-one | 409.5 | 410.2 |
| 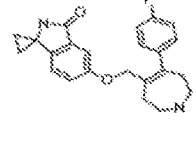 | C0092 | 5'-{[5-(4-fluorophenyl)-2,3,6,7-tetrahydro-1H-azepin-4-yl]methoxy}-2',3'-dihydrospiro[cyclopropane-1,1'-isoindole]-3'-one | 378.44 | 379.2 |
| 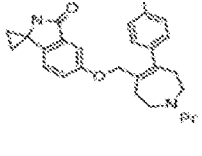 | C0093 | 5'-{[5-(4-fluorophenyl)-1-propyl-2,3,6,7-tetrahydro-1H-azepin-4-yl]methoxy}-2',3'-dihydrospiro[cyclopropane-1,1'-isoindole]-3'-one | 420.52 | 421.2 |
| 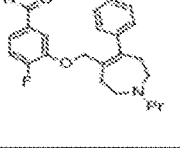 | C0094 | 4-fluoro-3-{[5-(4-fluorophenyl)-1-propyl-2,3,6,7-tetrahydro-1H-azepin-4-yl]methoxy}benzamide | 400.46 | 401.3 |
| 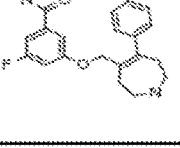 | C0095 | 3-fluoro-5-{[5-(4-fluorophenyl)-1-propyl-2,3,6,7-tetrahydro-1H-azepin-4-yl]methoxy}benzamide | 358.38 | 359 |
| 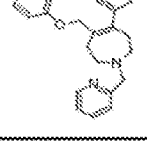 | C0096 | 6-{[5-(4-methoxyphenyl)-1-(pyridin-2-ylmethyl)-2,3,6,7-tetrahydro-1H-azepin-4-yl]methoxy}-2,3-dihydro-1H-isoindol-1-one | 455.55 | 456.2 |

Figure 1

| | | | | |
|---|---|---|---|---|
| 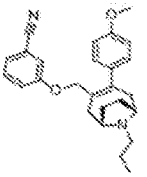 | C0097 | (±)-3-{[4-(4-methoxyphenyl)-9-propyl-9-azabicyclo[4.2.1]non-3-en-3-yl]methoxy}benzonitrile | 402.53 | 403.2 |
| 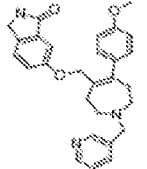 | C0098 | 6-{[5-(4-methoxyphenyl)-1-(pyridin-3-ylmethyl)-2,3,6,7-tetrahydro-1H-azepin-4-yl]methoxy}-2,3-dihydro-1H-isoindol-1-one | 455.55 | 456.2 |
| 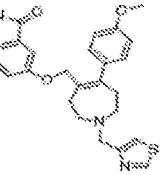 | C0099 | 6-{[5-(4-methoxyphenyl)-1-(1,3-thiazol-4-ylmethyl)-2,3,6,7-tetrahydro-1H-azepin-4-yl]methoxy}-2,3-dihydro-1H-isoindol-1-one | 461.58 | 462.2 |
| 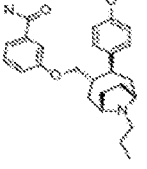 | C0100 | 3-{[(cis, trans)-4-(4-methoxyphenyl)-9-propyl-9-azabicyclo[4.2.1]nonan-3-yl]methoxy}benzamide | 422.56 | 423.2 |
| 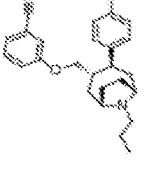 | C0101 | 3-{[(cis, trans)-4-(4-methoxyphenyl)-9-propyl-9-azabicyclo[4.2.1]nonan-3-yl]methoxy}benzonitrile | 404.54 | 405.2 |
| 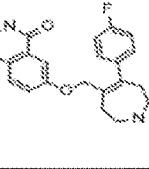 | C0102 | 7-{[5-(4-fluorophenyl)-2,3,6,7-tetrahydro-1H-azepin-4-yl]methoxy}-1,2-dihydroisoquinolin-1-one | 364.41 | 365 |
| 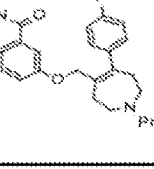 | C0103 | 7-{[5-(4-fluorophenyl)-1-propyl-2,3,6,7-tetrahydro-1H-azepin-4-yl]methoxy}-1,2-dihydroisoquinolin-1-one | 406.49 | 407.1 |
| 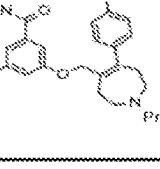 | C0104 | 3-fluoro-5-{[5-(4-fluorophenyl)-1-propyl-2,3,6,7-tetrahydro-1H-azepin-4-yl]methoxy}benzamide | 400.46 | 401.2 |

Figure 1

| | | | | |
|---|---|---|---|---|
| 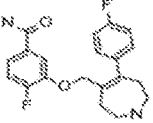 | C0105 | 4-fluoro-3-{[5-(4-fluorophenyl)-2,3,6,7-tetrahydro-1H-azepin-4-yl]methoxy}benzamide | 358.38 | 359.3 |
| 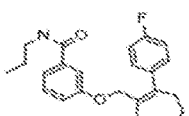 | C0106 | 3-{[5-(4-fluorophenyl)-2,3,6,7-tetrahydro-1H-azepin-4-yl]methoxy}-N-propylbenzamide | 382.47 | 383.1 |
| 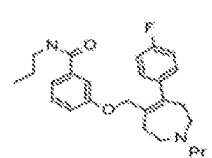 | C0107 | 3-{[5-(4-fluorophenyl)-1-propyl-2,3,6,7-tetrahydro-1H-azepin-4-yl]methoxy}-N-propylbenzamide | 424.55 | 425.2 |
| 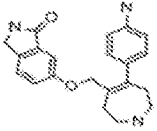 | C0108 | 6-{[5-(4-aminophenyl)-2,3,6,7-tetrahydro-1H-azepin-4-yl]methoxy}-2,3-dihydro-1H-isoindol-1-one | 349.43 | 350.4 |
| 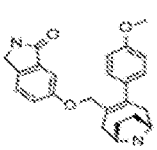 | C0109 | (+)-6-{[4-(4-methoxyphenyl)-9-azabicyclo[4.2.1]non-3-en-3-yl]methoxy}-2,3-dihydro-1H-isoindol-1-one | 390.47 | 391.2 |
| 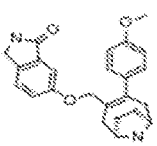 | C0110 | (−)-6-{[4-(4-methoxyphenyl)-9-azabicyclo[4.2.1]non-3-en-3-yl]methoxy}-2,3-dihydro-1H-isoindol-1-one | 390.47 | 391.2 |
| 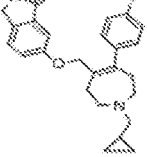 | C0111 | 6-{[1-(cyclopropylmethyl)-5-(4-methoxyphenyl)-2,3,6,7-tetrahydro-1H-azepin-4-yl]methoxy}-2,3-dihydro-1H-isoindol-1-one | 418.53 | 419.2 |
| 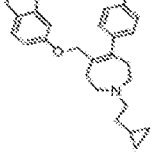 | C0112 | 6-{[1-(2-cyclopropylethyl)-5-(4-methoxyphenyl)-2,3,6,7-tetrahydro-1H-azepin-4-yl]methoxy}-2,3-dihydro-1H-isoindol-1-one | 432.55 | 433.2 |

Figure 1

| | | | | |
|---|---|---|---|---|
| 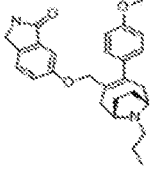 | C0113 | (+)-6-{[4-(4-methoxyphenyl)-9-propyl-9-azabicyclo[4.2.1]non-3-en-3-yl]methoxy}-2,3-dihydro-1H-isoindol-1-one | 432.55 | 433.2 |
| 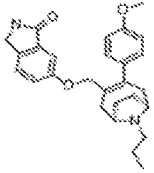 | C0114 | (-)-6-{[4-(4-methoxyphenyl)-9-propyl-9-azabicyclo[4.2.1]non-3-en-3-yl]methoxy}-2,3-dihydro-1H-isoindol-1-one | 432.55 | 433.2 |
| 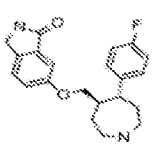 | C0115 | (-)-6-{[(trans)-5-(4-fluorophenyl)azepan-4-yl]methoxy}-2,3-dihydro-1H-isoindol-1-one | 354.42 | 355.2 |
| 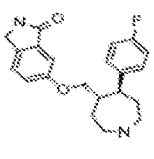 | C0116 | (+)-6-{[(trans)-5-(4-fluorophenyl)azepan-4-yl]methoxy}-2,3-dihydro-1H-isoindol-1-one | 354.42 | 355.2 |
| 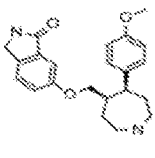 | C0117 | 6-{[(cis)-5-(4-methoxyphenyl)azepan-4-yl]methoxy}-2,3-dihydro-1H-isoindol-1-one | 366.45 | 367.2 |
| 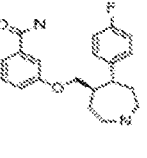 | C0118 | (-)-3-{[(trans)-5-(4-fluorophenyl)azepan-4-yl]methoxy}benzamide | 342.41 | 343.1 |
| 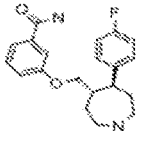 | C0119 | (+)-3-{[(trans)-5-(4-fluorophenyl)azepan-4-yl]methoxy}benzamide | 342.41 | 343.1 |
| 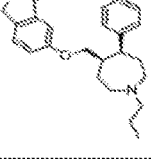 | C0120 | 6-{[(cis)-5-(4-methoxyphenyl)-1-propylazepan-4-yl]methoxy}-2,3-dihydro-1H-isoindol-1-one | 408.53 | 409.2 |

Figure 1

| | | | | |
|---|---|---|---|---|
| 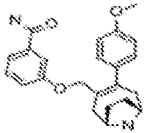 | C0121 | (+)-3-{[4-(4-methoxyphenyl)-9-azabicyclo[4.2.1]non-3-en-3-yl]methoxy}benzamide | 378.46 | 379.2 |
| 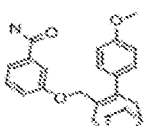 | C0122 | (−)-3-{[4-(4-methoxyphenyl)-9-azabicyclo[4.2.1]non-3-en-3-yl]methoxy}benzamide | 378.46 | 379.2 |
| 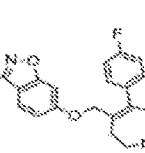 | C0123 | 6-{[5-(4-fluorophenyl)-2,3,6,7-tetrahydro-1H-azepin-4-yl]methoxy}-1,2-benzoxazol-3-amine | 353.39 | 354.3 |
| 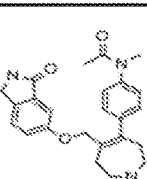 | C0124 | N-methyl-N-[4-(5-{[(3-oxo-2,3-dihydro-1H-isoindol-5-yl)oxy]methyl}-2,3,6,7-tetrahydro-1H-azepin-4-yl)phenyl]acetamide | 405.49 | 406 |
| 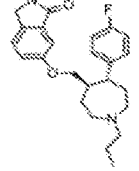 | C0125 | (−)-6-{[(trans)-5-(4-fluorophenyl)-1-propylazepan-4-yl]methoxy}-2,3-dihydro-1H-isoindol-1-one | 396.5 | 397.2 |
| 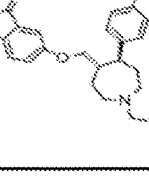 | C0126 | (+)-6-{[(trans)-5-(4-fluorophenyl)-1-propylazepan-4-yl]methoxy}-2,3-dihydro-1H-isoindol-1-one | 396.5 | 397.2 |
| 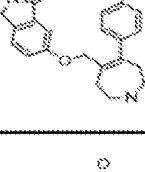 | C0127 | N-methyl-N-[4-(5-{[(3-oxo-2,3-dihydro-1H-isoindol-5-yl)oxy]methyl}-2,3,6,7-tetrahydro-1H-azepin-4-yl)phenyl]methanesulfonamide | 441.54 | 442.2 |
|  | C0128 | N-methyl-N-[4-(5-{[(3-oxo-2,3-dihydro-1H-isoindol-5-yl)oxy]methyl}-2,3,6,7-tetrahydro-1H-azepin-4-yl)phenyl]propanamide | 419.52 | 420.4 |

Figure 1

| | | | | |
|---|---|---|---|---|
| 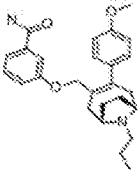 | C0129 | (+)-3-{[4-(4-methoxyphenyl)-9-propyl-9-azabicyclo[4.2.1]non-3-en-3-yl]methoxy}benzamide | 420.54 | 421.2 |
| 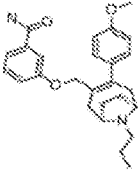 | C0130 | (-)-3-{[4-(4-methoxyphenyl)-9-propyl-9-azabicyclo[4.2.1]non-3-en-3-yl]methoxy}benzamide | 420.54 | 421.2 |
| 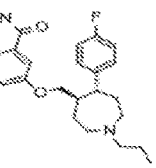 | C0131 | (-)-3-{[(trans)-5-(4-fluorophenyl)-1-propylazepan-4-yl]methoxy}benzamide | 384.49 | 385.2 |
| 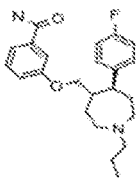 | C0132 | (+)-3-{[(trans)-5-(4-fluorophenyl)-1-propylazepan-4-yl]methoxy}benzamide | 384.49 | 385.2 |
| 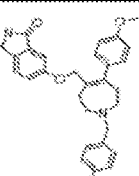 | C0133 | 6-({1-[(4-fluorophenyl)methyl]-5-(4-methoxyphenyl)-2,3,6,7-tetrahydro-1H-azepin-4-yl}methoxy)-2,3-dihydro-1H-isoindol-1-one | 472.55 | 473.2 |
| 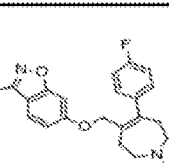 | C0134 | 6-{[5-(4-fluorophenyl)-1-propyl-2,3,6,7-tetrahydro-1H-azepin-4-yl]methoxy}-1,2-benzoxazol-3-amine | 395.47 | 396.2 |
| 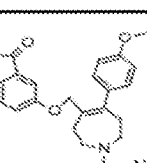 | C0135 | 6-{[5-(4-methoxyphenyl)-1-(1,3-oxazol-4-ylmethyl)-2,3,6,7-tetrahydro-1H-azepin-4-yl]methoxy}-2,3-dihydro-1H-isoindol-1-one | 445.51 | 446.2 |
| 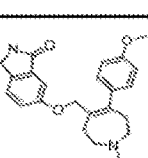 | C0136 | 6-{[5-(4-methoxyphenyl)-1-(pyridin-4-ylmethyl)-2,3,6,7-tetrahydro-1H-azepin-4-yl]methoxy}-2,3-dihydro-1H-isoindol-1-one | 455.55 | 456.2 |

Figure 1

| | | | | |
|---|---|---|---|---|
| 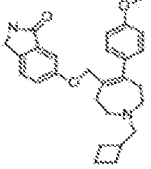 | C0137 | 6-{[1-(cyclobutylmethyl)-5-(4-methoxyphenyl)-2,3,6,7-tetrahydro-1H-azepin-4-yl]methoxy}-2,3-dihydro-1H-isoindol-1-one | 432.55 | 433.2 |
| 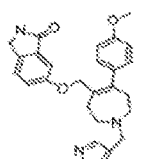 | C0138 | 6-({1-[(1,5-dimethyl-1H-pyrazol-4-yl)methyl]-5-(4-methoxyphenyl)-2,3,6,7-tetrahydro-1H-azepin-4-yl}methoxy)-2,3-dihydro-1H-isoindol-1-one | 472.58 | 473.2 |
| 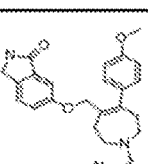 | C0139 | 6-{[5-(4-methoxyphenyl)-1-(1,3-thiazol-2-ylmethyl)-2,3,6,7-tetrahydro-1H-azepin-4-yl]methoxy}-2,3-dihydro-1H-isoindol-1-one | 461.58 | 462.2 |
| 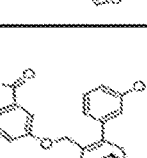 | C0140 | (±)-6-{[4-(3-methoxyphenyl)-9-azabicyclo[4.2.1]non-3-en-3-yl]methoxy}-2,3-dihydro-1H-isoindol-1-one | 390.47 | 391.2 |
| 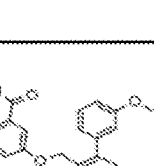 | C0141 | (±)-3-{[4-(3-methoxyphenyl)-9-azabicyclo[4.2.1]non-3-en-3-yl]methoxy}benzamide | 378.46 | 379.2 |
| 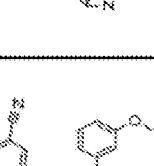 | C0142 | (±)-3-{[4-(3-methoxyphenyl)-9-azabicyclo[4.2.1]non-3-en-3-yl]methoxy}benzonitrile | 360.45 | 361.2 |
| 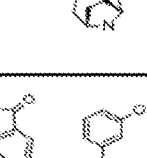 | C0143 | (±)-6-{[4-(3-methoxyphenyl)-9-propyl-9-azabicyclo[4.2.1]non-3-en-3-yl]methoxy}-2,3-dihydro-1H-isoindol-1-one | 432.55 | 433.2 |
| 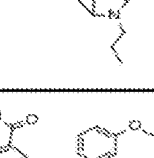 | C0144 | (±)-3-{[4-(3-methoxyphenyl)-9-propyl-9-azabicyclo[4.2.1]non-3-en-3-yl]methoxy}benzamide | 420.54 | 421.2 |

Figure 1

| | C0145 | (±)-3-{[4-(3-methoxyphenyl)-9-propyl-9-azabicyclo[4.2.1]non-3-en-3-yl]methoxy}benzonitrile | 402.53 | 403 |
|---|---|---|---|---|
| 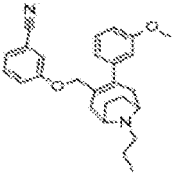 | C0145 | (±)-3-{[4-(3-methoxyphenyl)-9-propyl-9-azabicyclo[4.2.1]non-3-en-3-yl]methoxy}benzonitrile | 402.53 | 403 |
| 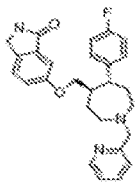 | C0146 | (+)-6-{[(trans)-5-(4-fluorophenyl)-1-(pyridin-2-ylmethyl)azepan-4-yl]methoxy}-2,3-dihydro-1H-isoindol-1-one | 445.53 | 446.2 |
| 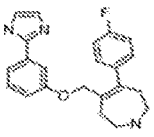 | C0147 | 4-(4-fluorophenyl)-5-[3-(1H-imidazol-2-yl)phenoxymethyl]-2,3,6,7-tetrahydro-1H-azepine | 363.43 | 364.1 |
| 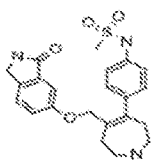 | C0148 | N-[4-(5-{[(3-oxo-2,3-dihydro-1H-isoindol-5-yl)oxy]methyl}-2,3,6,7-tetrahydro-1H-azepin-4-yl)phenyl]methanesulfonamide | 427.52 | 428.1 |
| 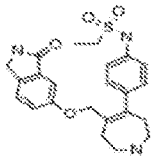 | C0149 | N-[4-(5-{[(3-oxo-2,3-dihydro-1H-isoindol-5-yl)oxy]methyl}-2,3,6,7-tetrahydro-1H-azepin-4-yl)phenyl]ethane-1-sulfonamide | 441.54 | 442.1 |
| 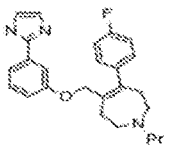 | C0150 | 4-(4-fluorophenyl)-5-[3-(1H-imidazol-2-yl)phenoxymethyl]-1-propyl-2,3,6,7-tetrahydro-1H-azepine | 405.51 | 406.2 |
| 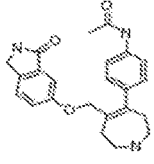 | C0151 | N-[4-(5-{[(3-oxo-2,3-dihydro-1H-isoindol-5-yl)oxy]methyl}-2,3,6,7-tetrahydro-1H-azepin-4-yl)phenyl]acetamide | 391.46 | 392.4 |
| 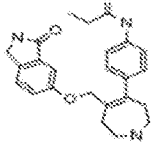 | C0152 | N-[4-(5-{[(3-oxo-2,3-dihydro-1H-isoindol-5-yl)oxy]methyl}-2,3,6,7-tetrahydro-1H-azepin-4-yl)phenyl]propanamide | 405.49 | 406.4 |

Figure 1

| | | | | |
|---|---|---|---|---|
| 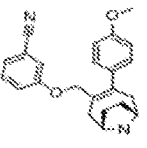 | C0153 | (+)-3-{[4-(4-methoxyphenyl)-9-azabicyclo[4.2.1]non-3-en-3-yl]methoxy}benzonitrile | 360.45 | 361 |
| 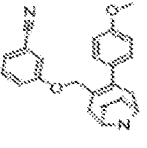 | C0154 | (-)-3-{[4-(4-methoxyphenyl)-9-azabicyclo[4.2.1]non-3-en-3-yl]methoxy}benzonitrile | 360.45 | 361 |
| 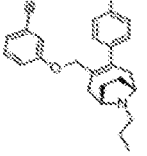 | C0155 | (+)-3-{[4-(4-methoxyphenyl)-9-propyl-9-azabicyclo[4.2.1]non-3-en-3-yl]methoxy}benzonitrile | 402.53 | 403.2 |
| 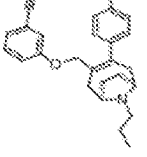 | C0156 | (-)-3-{[4-(4-methoxyphenyl)-9-propyl-9-azabicyclo[4.2.1]non-3-en-3-yl]methoxy}benzonitrile | 402.53 | 403.2 |
| 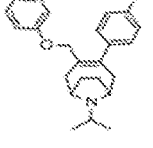 | C0157 | (±)-6-{[4-(4-methoxyphenyl)-9-(propan-2-yl)-9-azabicyclo[4.2.1]non-3-en-3-yl]methoxy}-2,3-dihydro-1H-isoindol-1-one | 432.55 | 433.2 |
| 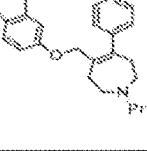 | C0158 | 6-[(5-phenyl-1-propyl-2,3,6,7-tetrahydro-1H-azepin-4-yl)methoxy]-2,3-dihydro-1H-isoindol-1-one | 376.49 | 377.1 |
| 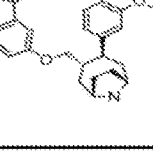 | C0159 | 6-{[(trans)-4-(3-methoxyphenyl)-9-azabicyclo[4.2.1]nonan-3-yl]methoxy}-2,3-dihydro-1H-isoindol-1-one | 392.49 | 393.2 |
| 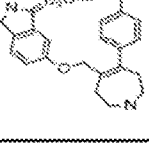 | C0160 | 2,2,2-trifluoro-N-[4-(5-{[(3-oxo-2,3-dihydro-1H-isoindol-5-yl)oxy]methyl}-2,3,6,7-tetrahydro-1H-azepin-4-yl)phenyl]ethane-1-sulfonamide | 495.51 | 496.1 |

Figure 1

| | | | | |
|---|---|---|---|---|
| 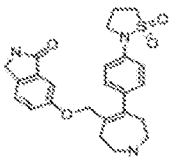 | C0161 | 2-[4-(5-{[(3-oxo-2,3-dihydro-1H-isoindol-5-yl)oxy]methyl}-2,3,6,7-tetrahydro-1H-azepin-4-yl)phenyl]-1,2-thiazolidine-1,1-dione | 453.55 | 454.3 |
| 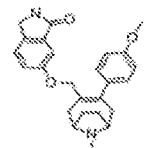 | C0162 | (±)-6-{[4-(4-methoxyphenyl)-9-(1,3-thiazol-4-ylmethyl)-9-azabicyclo[4.2.1]non-3-en-3-yl]methoxy}-2,3-dihydro-1H-isoindol-1-one | 487.61 | 488.2 |
| 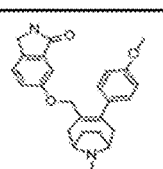 | C0163 | (±)-6-{[9-(cyclopropylmethyl)-4-(4-methoxyphenyl)-9-azabicyclo[4.2.1]non-3-en-3-yl]methoxy}-2,3-dihydro-1H-isoindol-1-one | 444.57 | 445.2 |
| 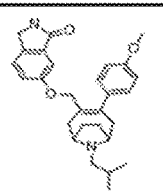 | C0164 | (±)-6-{[4-(4-methoxyphenyl)-9-(2-methylpropyl)-9-azabicyclo[4.2.1]non-3-en-3-yl]methoxy}-2,3-dihydro-1H-isoindol-1-one | 446.58 | 447.2 |
| 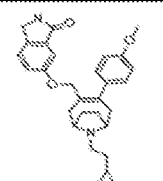 | C0165 | (±)-6-{[9-(2-cyclopropylethyl)-4-(4-methoxyphenyl)-9-azabicyclo[4.2.1]non-3-en-3-yl]methoxy}-2,3-dihydro-1H-isoindol-1-one | 458.59 | 459.2 |
| 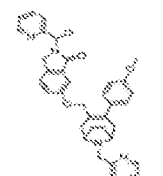 | C0166 | (±)-2-[hydroxy(pyridin-2-yl)methyl]-6-{[4-(4-methoxyphenyl)-9-(pyridin-2-ylmethyl)-9-azabicyclo[4.2.1]non-3-en-3-yl]methoxy}-2,3-dihydro-1H-isoindol-1-one | 588.7 | 589.2 |
| 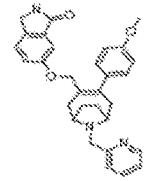 | C0167 | (±)-6-{[4-(4-methoxyphenyl)-9-(pyridin-2-ylmethyl)-9-azabicyclo[4.2.1]non-3-en-3-yl]methoxy}-2,3-dihydro-1H-isoindol-1-one | 481.59 | 482.2 |
| 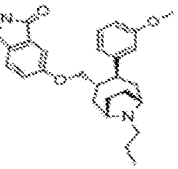 | C0168 | 6-{[(trans)-4-(3-methoxyphenyl)-9-propyl-9-azabicyclo[4.2.1]nonan-3-yl]methoxy}-2,3-dihydro-1H-isoindol-1-one | 434.57 | 435.2 |

Figure 1

| | | | | |
|---|---|---|---|---|
| 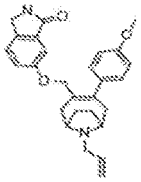 | C0169 | (±)-6-{[4-(4-methoxyphenyl)-9-(prop-2-en-1-yl)-9-azabicyclo[4.2.1]non-3-en-3-yl]methoxy}-2,3-dihydro-1H-isoindol-1-one | 430.54 | 431.2 |
| 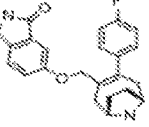 | C0170 | (+)-6-{[4-(4-fluorophenyl)-9-azabicyclo[4.2.1]non-3-en-3-yl]methoxy}-2,3-dihydro-1H-isoindol-1-one | 378.44 | 379.2 |
| 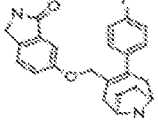 | C0171 | (-)-6-{[4-(4-fluorophenyl)-9-azabicyclo[4.2.1]non-3-en-3-yl]methoxy}-2,3-dihydro-1H-isoindol-1-one | 378.44 | 379.1 |
| 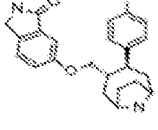 | C0172 | 6-{[(trans)-4-(4-fluorophenyl)-9-azabicyclo[4.2.1]nonan-3-yl]methoxy}-2,3-dihydro-1H-isoindol-1-one | 380.46 | 381.2 |
| 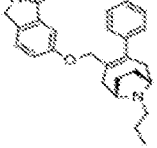 | C0173 | (+)-6-{[4-(4-fluorophenyl)-9-propyl-9-azabicyclo[4.2.1]non-3-en-3-yl]methoxy}-2,3-dihydro-1H-isoindol-1-one | 420.52 | 421.2 |
| 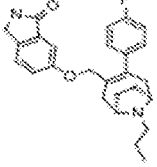 | C0174 | (-)-6-{[4-(4-fluorophenyl)-9-propyl-9-azabicyclo[4.2.1]non-3-en-3-yl]methoxy}-2,3-dihydro-1H-isoindol-1-one | 420.52 | 421.2 |
| 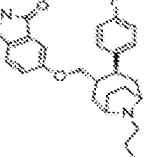 | C0175 | 6-{[(trans)-4-(4-fluorophenyl)-9-propyl-9-azabicyclo[4.2.1]nonan-3-yl]methoxy}-2,3-dihydro-1H-isoindol-1-one | 422.54 | 423.2 |
| 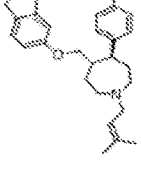 | C0176 | 6-{[(trans)-5-(4-fluorophenyl)-1-(3-methylbut-2-en-1-yl)azepan-4-yl]methoxy}-2,3-dihydro-1H-isoindol-1-one | 422.54 | 423.2 |

Figure 1

| Structure | ID | Name | MW | MS |
|---|---|---|---|---|
| 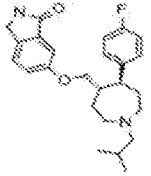 | C0177 | (-)-6-{[(trans)-5-(4-fluorophenyl)-1-(2-methylpropyl)azepan-4-yl]methoxy}-2,3-dihydro-1H-isoindol-1-one | 410.52 | 411.2 |
| 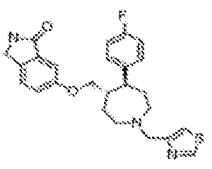 | C0178 | 6-{[(trans)-5-(4-fluorophenyl)-1-(1,3-thiazol-4-ylmethyl)azepan-4-yl]methoxy}-2,3-dihydro-1H-isoindol-1-one | 451.56 | 452.1 |
| 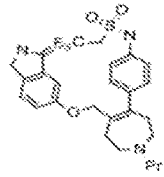 | C0179 | 2,2,2-trifluoro-N-{4-(5-{[(3-oxo-2,3-dihydro-1H-isoindol-5-yl)oxy]methyl}-1-propyl-2,3,6,7-tetrahydro-1H-azepin-4-yl)phenyl}ethane-1-sulfonamide | 537.59 | 538.1 |
| 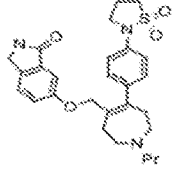 | C0180 | 2-[4-(5-{[(3-oxo-2,3-dihydro-1H-isoindol-5-yl)oxy]methyl}-1-propyl-2,3,6,7-tetrahydro-1H-azepin-4-yl)phenyl]-1,2-thiazolidine-1,1-dione | 495.63 | 496.2 |
| 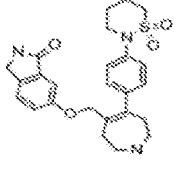 | C0181 | 2-[4-(5-{[(3-oxo-2,3-dihydro-1H-isoindol-5-yl)oxy]methyl}-2,3,6,7-tetrahydro-1H-azepin-4-yl)phenyl]-1,2-thiazinane-1,1-dione | 467.58 | 468.4 |
| 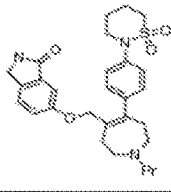 | C0182 | 2-[4-(5-{[(3-oxo-2,3-dihydro-1H-isoindol-5-yl)oxy]methyl}-1-propyl-2,3,6,7-tetrahydro-1H-azepin-4-yl)phenyl]-1,2-thiazinane-1,1-dione | 509.66 | 510.2 |
| 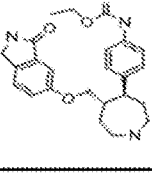 | C0183 | ethyl N-{4-[(trans)-5-{[(3-oxo-2,3-dihydro-1H-isoindol-5-yl)oxy]methyl}azepan-4-yl]phenyl}carbamate | 423.5 | 424.2 |
| 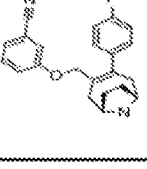 | C0184 | (+)-3-{[4-(4-fluorophenyl)-9-azabicyclo[4.2.1]non-3-en-3-yl]methoxy}benzonitrile | 348.41 | 349.1 |

Figure 1

| Structure | ID | Name | | |
|---|---|---|---|---|
| 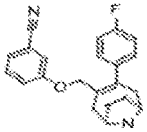 | C0185 | (-)-3-{[4-(4-fluorophenyl)-9-azabicyclo[4.2.1]non-3-en-3-yl]methoxy}benzonitrile | 348.41 | 349.1 |
| 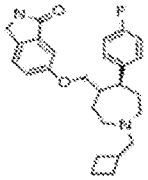 | C0186 | 6-{[(trans)-1-(cyclobutylmethyl)-5-(4-fluorophenyl)azepan-4-yl]methoxy}-2,3-dihydro-1H-isoindol-1-one | 422.54 | 423.2 |
| 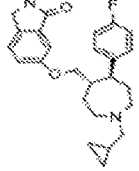 | C0187 | (-)-6-{[(trans)-1-(cyclopropylmethyl)-5-(4-fluorophenyl)azepan-4-yl]methoxy}-2,3-dihydro-1H-isoindol-1-one | 408.51 | 409.2 |
| 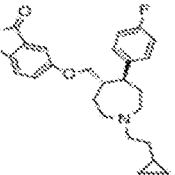 | C0188 | 6-{[(trans)-1-(2-cyclopropylethyl)-5-(4-fluorophenyl)azepan-4-yl]methoxy}-2,3-dihydro-1H-isoindol-1-one | 422.54 | 423.2 |
| 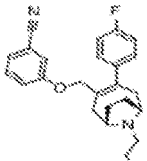 | C0189 | (+)-3-{[4-(4-fluorophenyl)-9-propyl-9-azabicyclo[4.2.1]non-3-en-3-yl]methoxy}benzonitrile | 390.49 | 391.2 |
| 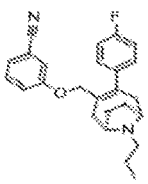 | C0190 | (-)-3-{[-4-(4-fluorophenyl)-9-propyl-9-azabicyclo[4.2.1]non-3-en-3-yl]methoxy}benzonitrile | 390.49 | 391.2 |
| 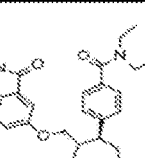 | C0191 | N,N-diethyl-4-[(trans)-5-{[(3-oxo-2,3-dihydro-1H-isoindol-5-yl)oxy]methyl}azepan-4-yl]benzamide | 435.56 | 436.2 |
| 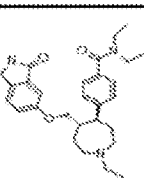 | C0192 | N,N-diethyl-4-[(trans)-5-{[(3-oxo-2,3-dihydro-1H-isoindol-5-yl)oxy]methyl}-1-propylazepanyl]benzamide | 477.64 | 478.3 |

Figure 1

| | | | | |
|---|---|---|---|---|
| 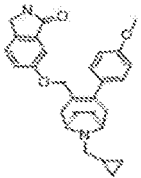 | C0193 | (-)-6-{[9-(cyclopropylmethyl)-4-(4-methoxyphenyl)-9-azabicyclo[4.2.1]non-3-en-3-yl]methoxy}-2,3-dihydro-1H-isoindol-1-one | 444.57 | 445.2 |
| 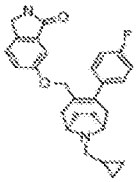 | C0194 | (-)-6-{[9-(cyclopropylmethyl)-4-(4-fluorophenyl)-9-azabicyclo[4.2.1]non-3-en-3-yl]methoxy}-2,3-dihydro-1H-isoindol-1-one | 432.53 | 433.2 |
| 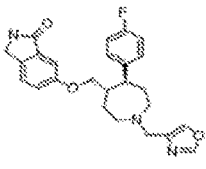 | C0195 | 6-{[(trans)-5-(4-fluorophenyl)-1-(1,3-oxazol-4-ylmethyl)azepan-4-yl]methoxy}-2,3-dihydro-1H-isoindol-1-one | 435.49 | 436.2 |
| 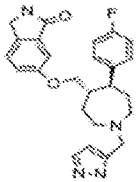 | C0196 | 6-{[(trans)-5-(4-fluorophenyl)-1-(1H-pyrazol-5-ylmethyl)azepan-4-yl]methoxy}-2,3-dihydro-1H-isoindol-1-one | 434.51 | 435.2 |
| 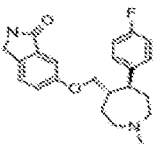 | C0197 | 6-{[(trans)-5-(4-fluorophenyl)-1-methylazepan-4-yl]methoxy}-2,3-dihydro-1H-isoindol-1-one | 368.44 | 369.2 |
| 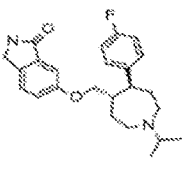 | C0198 | 6-{[(trans)-5-(4-fluorophenyl)-1-(propan-2-yl)azepan-4-yl]methoxy}-2,3-dihydro-1H-isoindol-1-one | 396.5 | 397.2 |
| 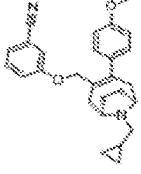 | C0199 | (-)-3-{[9-(cyclopropylmethyl)-4-(4-methoxyphenyl)-9-azabicyclo[4.2.1]non-3-en-3-yl]methoxy}benzonitrile | 414.54 | 415.2 |
| 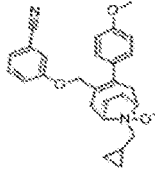 | C0200 | (-)-3-(3-cyanophenoxymethyl)-9-(cyclopropylmethyl)-4-(4-methoxyphenyl)-9-oxido-9-azabicyclo[4.2.1]non-3-en-9-ium | 430.54 | 431.2 |

Figure 1

| | | | | |
|---|---|---|---|---|
| 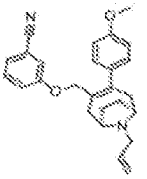 | C0201 | (-)-3-{[4-(4-methoxyphenyl)-9-(prop-2-en-1-yl)-9-azabicyclo[4.2.1]non-3-en-3-yl]methoxy}benzonitrile | 400.51 | 401.2 |
| 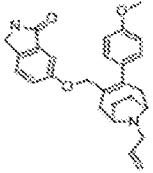 | C0202 | (-)-6-{[4-(4-methoxyphenyl)-9-(prop-2-en-1-yl)-9-azabicyclo[4.2.1]non-3-en-3-yl]methoxy}-2,3-dihydro-1H-isoindol-1-one | 430.54 | 431.2 |
| 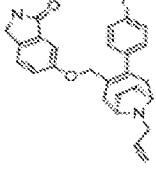 | C0203 | (-)-6-{[4-(4-fluorophenyl)-9-(prop-2-en-1-yl)-9-azabicyclo[4.2.1]non-3-en-3-yl]methoxy}-2,3-dihydro-1H-isoindol-1-one | 418.5 | 419.2 |
| 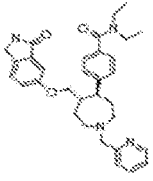 | C0204 | N,N-diethyl-4-[(trans)-5-{[(3-oxo-2,3-dihydro-1H-isoindol-5-yl)oxy]methyl}-1-(pyridin-2-ylmethyl)azepan-4-yl]benzamide | 526.67 | 527.3 |
| 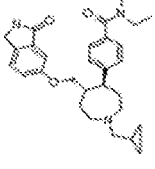 | C0205 | 4-[(trans)-1-(cyclopropylmethyl)-5-{[(3-oxo-2,3-dihydro-1H-isoindol-5-yl)oxy]methyl}azepan-4-yl]-N,N-diethylbenzamide | 489.65 | 490.3 |
| 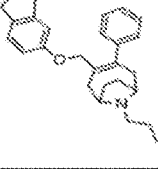 | C0206 | (±)-6-({4-phenyl-9-propyl-9-azabicyclo[4.2.1]non-3-en-3-yl}methoxy)-2,3-dihydro-1H-isoindol-1-one | 402.53 | 424.3 |
| 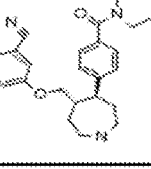 | C0207 | 4-[(trans)-5-(3-cyanophenoxymethyl)azepan-4-yl]-N,N-diethylbenzamide | 405.53 | 406.2 |
| 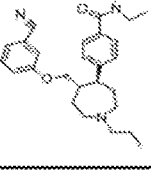 | C0208 | 4-[(trans)-5-(3-cyanophenoxymethyl)-1-propylazepan-4-yl]-N,N-diethylbenzamide | 447.61 | 448.3 |

Figure 1

| | | | | |
|---|---|---|---|---|
| 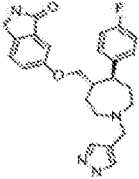 | C0209 | 6-{[(trans)-5-(4-fluorophenyl)-1-(1H-pyrazol-4-ylmethyl)azepan-4-yl]methoxy}-2,3-dihydro-1H-isoindol-1-one | 434.51 | 435.2 |
| 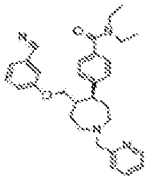 | C0210 | 4-[(trans)-5-(3-cyanophenoxymethyl)-1-(pyridin-2-ylmethyl)azepan-4-yl]-N,N-diethylbenzamide | 496.64 | 497.3 |
| 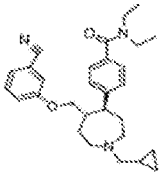 | C0211 | 4-[(trans)-5-(3-cyanophenoxymethyl)-1-(cyclopropylmethyl)azepan-4-yl]-N,N-diethylbenzamide | 459.62 | 460.3 |
| 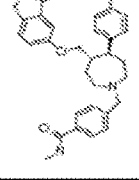 | C0212 | 4-{[(trans)-4-(4-fluorophenyl)-5-{[(3-oxo-2,3-dihydro-1H-isoindol-5-yl)oxy]methyl}azepan-1-yl]methyl}-N-methylbenzamide | 501.59 | 502.2 |
| 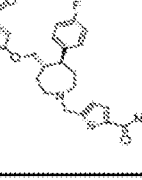 | C0213 | N-ethyl-5-{[(trans)-4-(4-fluorophenyl)-5-{[(3-oxo-2,3-dihydro-1H-isoindol-5-yl)oxy]methyl}azepan-1-yl]methyl}thiophene-2-carboxamide | 521.65 | 522.2 |
| 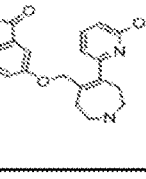 | C0214 | 6-{[5-(6-methoxypyridin-2-yl)-2,3,6,7-tetrahydro-1H-azepin-4-yl]methoxy}-2,3-dihydro-1H-isoindol-1-one | 365.43 | 366.1 |
| 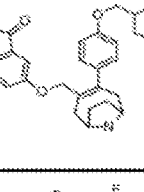 | C0215 | (±)-6-({4-[4-(oxan-4-ylmethoxy)phenyl]-9-azabicyclo[4.2.1]non-3-en-3-yl}methoxy)-2,3-dihydro-1H-isoindol-1-one | 474.59 | 475.3 |
| 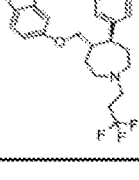 | C0216 | 6-{[(trans)-5-(4-fluorophenyl)-1-(3,3,3-trifluoropropyl)azepan-4-yl]methoxy}-2,3-dihydro-1H-isoindol-1-one | 450.47 | 451.2 |

Figure 1

| | ID | Name | MW | MS |
|---|---|---|---|---|
| 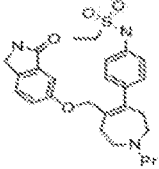 | C0217 | N-[4-(5-{[(3-oxo-2,3-dihydro-1H-isoindol-5-yl)oxy]methyl}-1-propyl-2,3,6,7-tetrahydro-1H-azepin-4-yl)phenyl]ethane-1-sulfonamide | 483.62 | 484.3 |
| 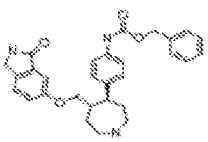 | C0218 | benzyl N-{4-[(trans)-5-{[(3-oxo-2,3-dihydro-1H-isoindol-5-yl)oxy]methyl}azepan-4-yl]phenyl}carbamate | 485.57 | 486.3 |
| 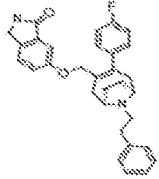 | C0219 | (–)-6-{[4-(4-fluorophenyl)-9-(2-phenylethyl)-9-azabicyclo[4.2.1]non-3-en-3-yl]methoxy}-2,3-dihydro-1H-isoindol-1-one | 482.59 | 483.2 |
| 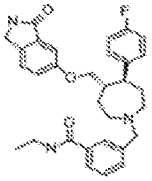 | C0220 | N-ethyl-4-{[(trans)-4-(4-fluorophenyl)-5-{[(3-oxo-2,3-dihydro-1H-isoindol-5-yl)oxy]methyl}azepan-1-yl]methyl}benzamide | 515.62 | 516.2 |
| 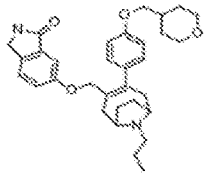 | C0221 | (±)-6-({4-[4-(oxan-4-ylmethoxy)phenyl]-9-propyl-9-azabicyclo[4.2.1]non-3-en-3-yl}methoxy)-2,3-dihydro-1H-isoindol-1-one | 516.67 | 517.3 |
| 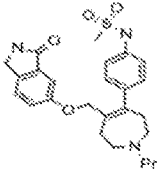 | C0222 | N-[4-(5-{[(3-oxo-2,3-dihydro-1H-isoindol-5-yl)oxy]methyl}-1-propyl-2,3,6,7-tetrahydro-1H-azepin-4-yl)phenyl]methanesulfonamide | 469.6 | 470.3 |
| 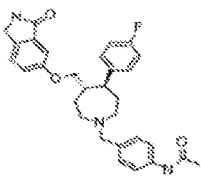 | C0223 | N-(4-{[(trans)-4-(4-fluorophenyl)-5-{[(3-oxo-2,3-dihydro-1H-isoindol-5-yl)oxy]methyl}azepan-1-yl]methyl}phenyl)acetamide | 501.59 | 502.2 |
| 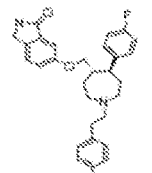 | C0224 | 6-{[(trans)-5-(4-fluorophenyl)-1-[2-(4-fluorophenyl)ethyl]azepan-4-yl]methoxy}-2,3-dihydro-1H-isoindol-1-one | 476.56 | 477.2 |

Figure 1

| | | | | |
|---|---|---|---|---|
| 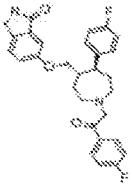 | C0225 | 6-{[(trans)-5-(4-fluorophenyl)-1-[2-(4-fluorophenyl)-2-oxoethyl]azepan-4-yl]methoxy}-2,3-dihydro-1H-isoindol-1-one | 490.54 | 491.2 |
| 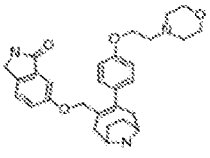 | C0226 | (±)-6-[(4-{4-[2-(morpholin-4-yl)ethoxy]phenyl}-9-azabicyclo[4.2.1]non-3-en-3-yl)methoxy]-2,3-dihydro-1H-isoindol-1-one | 489.61 | 490.3 |
| 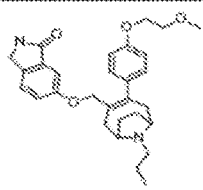 | C0227 | (±)-6-({4-[4-(2-methoxyethoxy)phenyl]-9-propyl-9-azabicyclo[4.2.1]non-3-en-3-yl}methoxy)-2,3-dihydro-1H-isoindol-1-one | 476.61 | 477.3 |
| 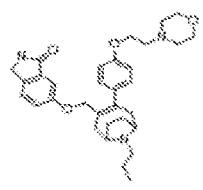 | C0228 | (±)-6-[(4-{4-[2-(morpholin-4-yl)ethoxy]phenyl}-9-propyl-9-azabicyclo[4.2.1]non-3-en-3-yl)methoxy]-2,3-dihydro-1H-isoindol-1-one | 531.69 | 532.3 |
| 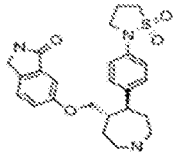 | C0229 | 2-{4-[(trans)-5-{[(3-oxo-2,3-dihydro-1H-isoindol-5-yl)oxy]methyl}azepan-4-yl]phenyl}-1,2-thiazolidine-1,1-dione | 455.57 | 456.2 |
| 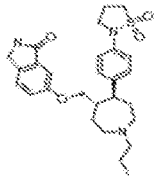 | C0230 | 2-{4-[(trans)-5-{[(3-oxo-2,3-dihydro-1H-isoindol-5-yl)oxy]methyl}-1-propylazepan-4-yl]phenyl}-1,2-thiazolidine-1,1-dione | 497.65 | 498.2 |
| 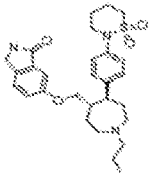 | C0231 | 2-{4-[(trans)-5-{[(3-oxo-2,3-dihydro-1H-isoindol-5-yl)oxy]methyl}-1-propylazepan-4-yl]phenyl}-1,2-thiazinane-1,1-dione | 511.68 | 512.2 |
| 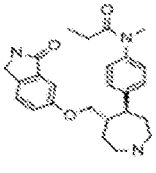 | C0232 | N-methyl-N-{4-[(trans)-5-{[(3-oxo-2,3-dihydro-1H-isoindol-5-yl)oxy]methyl}azepan-4-yl]phenyl}propanamide | 421.53 | 422.2 |

Figure 1

| | | | | |
|---|---|---|---|---|
| 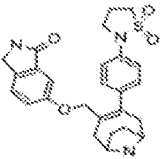 | C0233 | (±)-2-[4-(4-{[(3-oxo-2,3-dihydro-1H-isoindol-5-yl)oxy]methyl}-9-azabicyclo[4.2.1]non-3-en-3-yl)phenyl]-1,2-thiazolidine-1,1-dione | 479.59 | 480.1 |
| 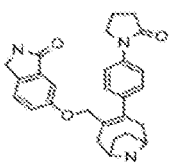 | C0234 | (±)-6-({4-[4-(2-oxopyrrolidin-1-yl)phenyl]-9-azabicyclo[4.2.1]non-3-en-3-yl}methoxy)-2,3-dihydro-1H-isoindol-1-one | 443.54 | 444.2 |
| 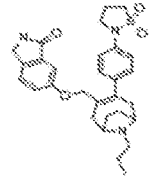 | C0235 | (±)-2-[4-(4-{[(3-oxo-2,3-dihydro-1H-isoindol-5-yl)oxy]methyl}-9-propyl-9-azabicyclo[4.2.1]non-3-en-3-yl)phenyl]-1$\lambda^6$,2-thiazolidine-1,1-dione | 521.67 | 522.2 |
| 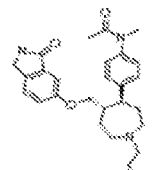 | C0236 | N-methyl-N-{4-[(trans)-5-{[(3-oxo-2,3-dihydro-1H-isoindol-5-yl)oxy]methyl}-1-propylazepan-4-yl]phenyl}acetamide | 449.59 | 450.2 |
| 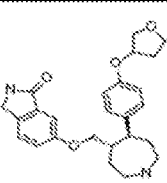 | C0237 | 6-{[(trans)-5-[4-(oxolan-3-yloxy)phenyl]azepan-4-yl]methoxy}-2,3-dihydro-1H-isoindol-1-one | 422.52 | 423.2 |
| 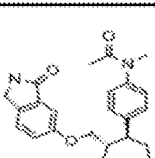 | C0238 | N-methyl-N-{4-[(trans)-5-{[(3-oxo-2,3-dihydro-1H-isoindol-5-yl)oxy]methyl}azepan-4-yl]phenyl}propanamide | 407.51 | 408.2 |
| 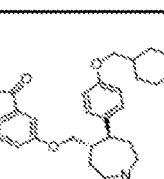 | C0239 | 6-{[(trans)-5-[4-(oxan-4-ylmethoxy)phenyl]azepan-4-yl]methoxy}-2,3-dihydro-1H-isoindol-1-one | 450.57 | 451.3 |
| 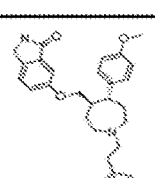 | C0240 | (-)-6-{[(trans)-5-(4-methoxyphenyl)-1-(2-phenylethyl)azepan-4-yl]methoxy}-2,3-dihydro-1H-isoindol-1-one | 470.6 | 471.3 |

Figure 1

| | | | | |
|---|---|---|---|---|
| 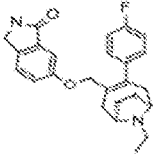 | C0241 | (-)-6-{[9-ethyl-4-(4-fluorophenyl)-9-azabicyclo[4.2.1]non-3-en-3-yl]methoxy}-2,3-dihydro-1H-isoindol-1-one | 406.49 | 407.3 |
| 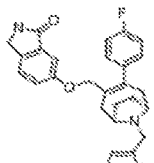 | C0242 | (-)-6-{[4-(4-fluorophenyl)-9-(1H-imidazol-4-ylmethyl)-9-azabicyclo[4.2.1]non-3-en-3-yl]methoxy}-2,3-dihydro-1H-isoindol-1-one | 458.53 | 459.2 |
| 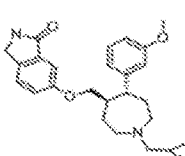 | C0243 | 6-{[(trans)-1-(cyclopropylmethyl)-5-(3-methoxyphenyl)azepan-4-yl]methoxy}-2,3-dihydro-1H-isoindol-1-one | 420.54 | 421.2 |
| 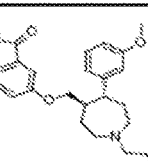 | C0244 | 6-{[(trans)-1-(2-cyclopropylethyl)-5-(3-methoxyphenyl)azepan-4-yl]methoxy}-2,3-dihydro-1H-isoindol-1-one | 434.57 | 435.2 |
| 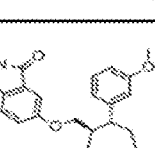 | C0245 | 6-{[(trans)-5-(3-methoxyphenyl)-1-(2-methylpropyl)azepan-4-yl]methoxy}-2,3-dihydro-1H-isoindol-1-one | 422.56 | 423.2 |
| 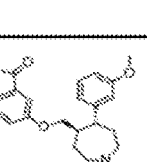 | C0246 | 6-{[5-(3-methoxyphenyl)-1-(2-phenylethyl)azepan-4-yl]methoxy}-2,3-dihydro-1H-isoindol-1-one | 470.6 | 471.2 |
| 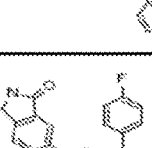 | C0247 | (-)-6-{[9-cyclobutyl-4-(4-fluorophenyl)-9-azabicyclo[4.2.1]non-3-en-3-yl]methoxy}-2,3-dihydro-1H-isoindol-1-one | 432.53 | 433.2 |
| 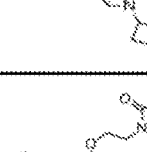 | C0248 | 1-(2-{4-[(trans)-5-{[(3-oxo-2,3-dihydro-1H-isoindol-5-yl)oxy]methyl}azepan-4-yl]phenoxy}ethyl)pyrrolidine-2,5-dione | 477.55 | 478.2 |

Figure 1

| Structure | ID | Name | | |
|---|---|---|---|---|
| 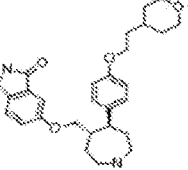 | C0249 | 6-{[(trans)-5-{4-[2-(oxan-4-yl)ethoxy]phenyl}azepan-4-yl]methoxy}-2,3-dihydro-1H-isoindol-1-one | 464.6 | 465.4 |
| 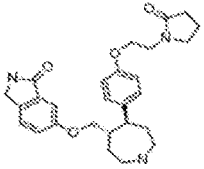 | C0250 | 6-{[(trans)-5-{4-[2-(2-oxopyrrolidin-1-yl)ethoxy]phenyl}azepan-4-yl]methoxy}-2,3-dihydro-1H-isoindol-1-one | 463.57 | 464.2 |
| 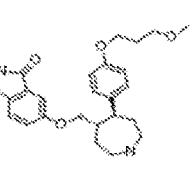 | C0251 | 6-{[(trans)-5-[4-(3-methoxypropoxy)phenyl]azepan-4-yl]methoxy}-2,3-dihydro-1H-isoindol-1-one | 424.53 | 425.2 |
| 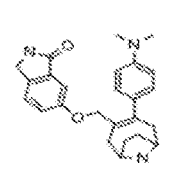 | C0252 | (±)-6-({4-[4-(dimethylamino)phenyl]-9-azabicyclo[4.2.1]non-3-en-3-yl}methoxy)-2,3-dihydro-1H-isoindol-1-one | 403.52 | 404.2 |
| 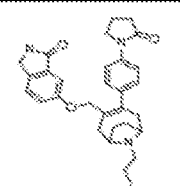 | C0253 | (±)-6-({4-[4-(2-oxopyrrolidin-1-yl)phenyl]-9-propyl-9-azabicyclo[4.2.1]non-3-en-3-yl}methoxy)-2,3-dihydro-1H-isoindol-1-one | 485.62 | 486.2 |
| 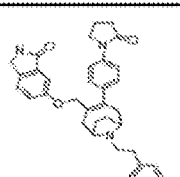 | C0254 | (±)-6-({4-[4-(2-oxopyrrolidin-1-yl)phenyl]-9-(2-phenylethyl)-9-azabicyclo[4.2.1]non-3-en-3-yl}methoxy)-2,3-dihydro-1H-isoindol-1-one | 547.69 | 548.2 |
| 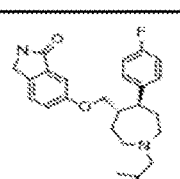 | C0255 | 6-{[(trans)-1-(2,2-dimethylpropyl)-5-(4-fluorophenyl)azepan-4-yl]methoxy}-2,3-dihydro-1H-isoindol-1-one | 424.55 | 425.2 |
| 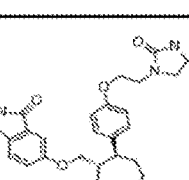 | C0256 | 6-{[(trans)-5-{4-[2-(2-oxoimidazolidin-1-yl)ethoxy]phenyl}azepan-4-yl]methoxy}-2,3-dihydro-1H-isoindol-1-one | 464.56 | 465.2 |

Figure 1

| | | | | |
|---|---|---|---|---|
| 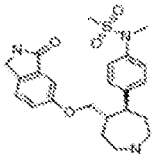 | C0257 | N-methyl-N-{4-[(trans)-5-{[(3-oxo-2,3-dihydro-1H-isoindol-5-yl)oxy]methyl}azepan-4-yl]phenyl}methanesulfonamide | 443.56 | 444.5 |
| 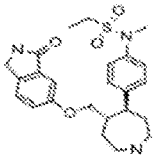 | C0258 | N-methyl-N-{4-[(trans)-5-{[(3-oxo-2,3-dihydro-1H-isoindol-5-yl)oxy]methyl}azepan-4-yl]phenyl}methanesulfonamide | 457.59 | 458.3 |
| 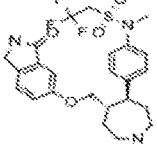 | C0259 | 2,2,2-trifluoro-N-methyl-N-{4-[(trans)-5-{[(3-oxo-2,3-dihydro-1H-isoindol-5-yl)oxy]methyl}azepan-4-yl]phenyl}ethane-1-sulfonamide | 511.56 | 512.1 |
| 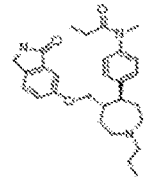 | C0260 | N-methyl-N-{4-[(trans)-5-{[(3-oxo-2,3-dihydro-1H-isoindol-5-yl)oxy]methyl}-1-propylazepan-4-yl]phenyl}propanamide | 463.61 | 464.2 |
| 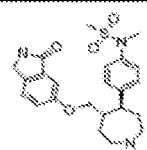 | C0261 | N-methyl-N-{4-[(trans)-5-{[(3-oxo-2,3-dihydro-1H-isoindol-5-yl)oxy]methyl}-1-propylazepan-4-yl]phenyl}methanesulfonamide | 485.64 | 486.1 |
| 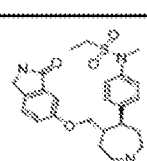 | C0262 | N-methyl-N-{4-[(trans)-5-{[(3-oxo-2,3-dihydro-1H-isoindol-5-yl)oxy]methyl}-1-propylazepan-4-yl]phenyl}ethane-1-sulfonamide | 499.67 | 500.2 |
| 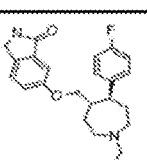 | C0263 | 6-{[(trans)-5-(4-fluorophenyl)-1-(3-methoxy-3-methylbutyl)azepan-4-yl]methoxy}-2,3-dihydro-1H-isoindol-1-one | 454.58 | 455.2 |
| 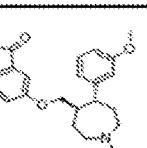 | C0264 | 6-{[(trans)-1-(3-methoxy-3-methylbutyl)-5-(3-methoxyphenyl)azepan-4-yl]methoxy}-2,3-dihydro-1H-isoindol-1-one | 466.61 | 467.2 |

Figure 1

| | | | | |
|---|---|---|---|---|
| 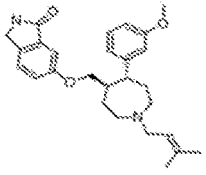 | C0265 | 6-{[(trans)-5-(3-methoxyphenyl)-1-(3-methylbut-2-en-1-yl)azepan-4-yl]methoxy}-2,3-dihydro-1H-isoindol-1-one | 434.57 | 435.2 |
| 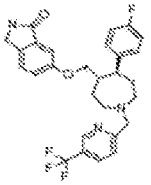 | C0266 | 6-{[(trans)-5-(4-fluorophenyl)-1-{[5-(trifluoromethyl)pyridin-2-yl]methyl}azepan-4-yl]methoxy}-2,3-dihydro-1H-isoindol-1-one | 513.53 | 514.2 |
| 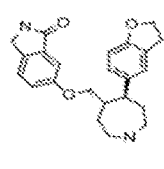 | C0267 | 6-{[(trans)-5-(2,3-dihydro-1-benzofuran-5-yl)-1-[2-(4-methoxyphenyl)ethyl]azepan-4-yl]methoxy}-2,3-dihydro-1H-isoindol-1-one | 378.46 | 379.2 |
| 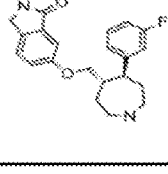 | C0268 | 6-{[(trans)-5-(3-fluorophenyl)azepan-4-yl]methoxy}-2,3-dihydro-1H-isoindol-1-one | 354.42 | 355.1 |
| 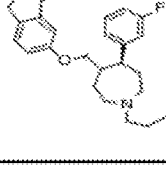 | C0269 | 6-{[(trans)-5-(3-fluorophenyl)-1-propylazepan-4-yl]methoxy}-2,3-dihydro-1H-isoindol-1-one | 396.5 | 397.2 |
| 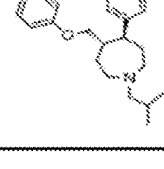 | C0270 | 6-{[(trans-5-(3-fluorophenyl)-1-(2-methylpropyl)azepan-4-yl]methoxy}-2,3-dihydro-1H-isoindol-1-one | 410.52 | 411.2 |
| 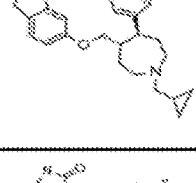 | C0271 | 6-{[1-(cyclopropylmethyl)-(trans)-5-(3-fluorophenyl)azepan-4-yl]methoxy}-2,3-dihydro-1H-isoindol-1-one | 408.51 | 409.2 |
| 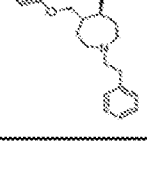 | C0272 | 6-{[(trans)-5-(3-fluorophenyl)-1-(2-phenylethyl)azepan-4-yl]methoxy}-2,3-dihydro-1H-isoindol-1-one | 458.57 | 459.2 |

Figure 1

| Structure | ID | Name | | |
|---|---|---|---|---|
| 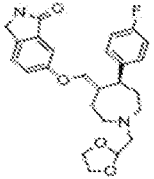 | C0273 | 6-{[(trans)-1-(1,3-dioxolan-2-ylmethyl)-5-(4-fluorophenyl)azepan-4-yl]methoxy}-2,3-dihydro-1H-isoindol-1-one | 440.51 | 441.2 |
| 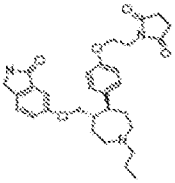 | C0274 | 1-(2-{4-[(trans)-5-{[(3-oxo-2,3-dihydro-1H-isoindol-5-yl)oxy]methyl}-1-propylazepan-4-yl]phenoxy}ethyl)pyrrolidine-2,5-dione | 519.63 | 520.2 |
| 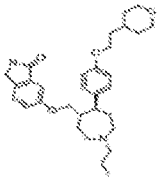 | C0275 | 6-{[(trans)-5-{4-[2-(oxan-4-yl)ethoxy]phenyl}-1-propylazepan-4-yl]methoxy}-2,3-dihydro-1H-isoindol-1-one | 506.68 | 507.3 |
| 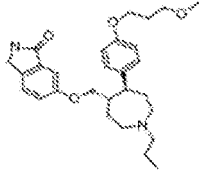 | C0276 | 6-{[(trans)-5-[4-(3-methoxypropoxy)phenyl]-1-propylazepan-4-yl]methoxy}-2,3-dihydro-1H-isoindol-1-one | 466.61 | 467.2 |
| 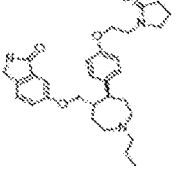 | C0277 | 6-{[(trans)-5-{4-[2-(2-oxopyrrolidin-1-yl)ethoxy]phenyl}-1-propylazepan-4-yl]methoxy}-2,3-dihydro-1H-isoindol-1-one | 505.65 | 506.3 |
| 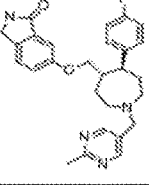 | C0278 | 6-{[(trans)-5-(4-fluorophenyl)-1-[(2-methylpyrimidin-5-yl)methyl]azepan-4-yl]methoxy}-2,3-dihydro-1H-isoindol-1-one | 460.54 | 461.3 |
| 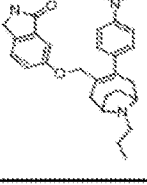 | C0279 | (±)-6-({4-[4-(dimethylamino)phenyl]-9-propyl-9-azabicyclo[4.2.1]non-3-en-3-yl}methoxy)-2,3-dihydro-1H-isoindol-1-one | 445.6 | 446.2 |
| 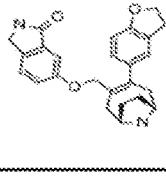 | C0280 | (±)-6-{[4-(2,3-dihydro-1-benzofuran-5-yl)-9-azabicyclo[4.2.1]non-3-en-3-yl]methoxy}-2,3-dihydro-1H-isoindol-1-one | 402.49 | 403.2 |

Figure 1

| | | | | |
|---|---|---|---|---|
| 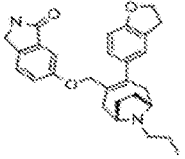 | C0281 | (±)-6-{[4-(2,3-dihydro-1-benzofuran-5-yl)-9-propyl-9-azabicyclo[4.2.1]non-3-en-3-yl]methoxy}-2,3-dihydro-1H-isoindol-1-one | 444.57 | 445.3 |
| 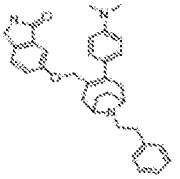 | C0282 | (±)-6-({4-[4-(dimethylamino)phenyl]-9-(2-phenylethyl)-9-azabicyclo[4.2.1]non-3-en-3-yl}methoxy)-2,3-dihydro-1H-isoindol-1-one | 507.67 | 508.3 |
| 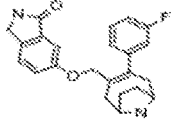 | C0283 | (±)-6-{[4-(3-fluorophenyl)-9-azabicyclo[4.2.1]non-3-en-3-yl]methoxy}-2,3-dihydro-1H-isoindol-1-one | 378.44 | 379.2 |
| 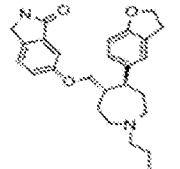 | C0284 | 6-{[(trans)-5-(2,3-dihydro-1-benzofuran-5-yl)-1-propylazepan-4-yl]methoxy}-2,3-dihydro-1H-isoindol-1-one | 420.54 | 421.3 |
| 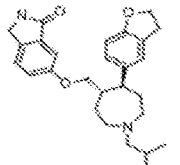 | C0285 | 6-{[(trans)-5-(2,3-dihydro-1-benzofuran-5-yl)-1-(2-methylpropyl)azepan-4-yl]methoxy}-2,3-dihydro-1H-isoindol-1-one | 434.57 | 435.3 |
| 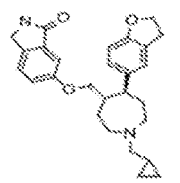 | C0286 | 6-{[1-(cyclopropylmethyl)-(trans)-5-(2,3-dihydro-1-benzofuran-5-yl)azepan-4-yl]methoxy}-2,3-dihydro-1H-isoindol-1-one | 432.55 | 433.3 |
| 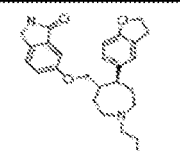 | C0287 | 6-{[(trans)-5-(2,3-dihydro-1-benzofuran-5-yl)-1-(2-phenylethyl)azepan-4-yl]methoxy}-2,3-dihydro-1H-isoindol-1-one | 482.61 | 483.3 |
| 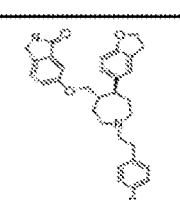 | C0288 | 6-{[(trans)-5-(2,3-dihydro-1-benzofuran-5-yl)-1-[2-(4-fluorophenyl)ethyl]azepan-4-yl]methoxy}-2,3-dihydro-1H-isoindol-1-one | 500.6 | 501.3 |

Figure 1

| | | | | |
|---|---|---|---|---|
| 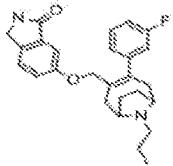 | C0289 | (±)-6-{[4-(3-fluorophenyl)-9-propyl-9-azabicyclo[4.2.1]non-3-en-3-yl]methoxy}-2,3-dihydro-1H-isoindol-1-one | 420.52 | 421.3 |
| 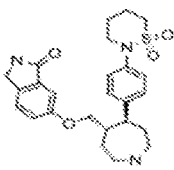 | C0290 | 2-{4-[(trans)-5-{[(3-oxo-2,3-dihydro-1H-isoindol-5-yl)oxy]methyl}azepan-4-yl]phenyl}-1,2-thiazinane-1,1-dione | 469.6 | 470.5 |
| 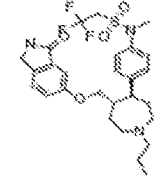 | C0291 | 2,2,2-trifluoro-N-methyl-N-{4-[(trans)-5-{[(3-oxo-2,3-dihydro-1H-isoindol-5-yl)oxy]methyl}-1-propylazepan-4-yl]phenyl}ethane-1-sulfonamide | 553.64 | 554.5 |
| 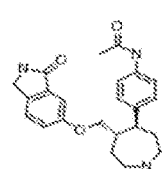 | C0292 | N-{4-[(trans)-5-{[(3-oxo-2,3-dihydro-1H-isoindol-5-yl)oxy]methyl}azepan-4-yl]phenyl}acetamide | 393.48 | 394.1 |
| 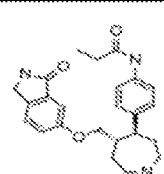 | C0293 | N-{4-[(trans)-5-{[(3-oxo-2,3-dihydro-1H-isoindol-5-yl)oxy]methyl}-1-propylazepan-4-yl]phenyl}propanamide | 407.51 | 408.3 |
| 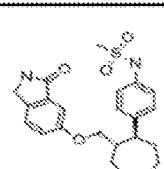 | C0294 | N-{4-[(trans)-5-{[(3-oxo-2,3-dihydro-1H-isoindol-5-yl)oxy]methyl}azepan-4-yl]phenyl}methanesulfonamide | 429.53 | 430.1 |
| 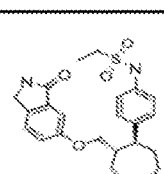 | C0295 | N-{4-[(trans)-5-{[(3-oxo-2,3-dihydro-1H-isoindol-5-yl)oxy]methyl}azepan-4-yl]phenyl}ethane-1-sulfonamide | 443.56 | 444.2 |
| 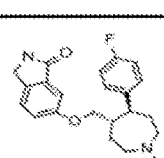 | C0296 | 2-[(trans)-4-(4-fluorophenyl)-5-{[(3-oxo-2,3-dihydro-1H-isoindol-5-yl)oxy]methyl}azepan-1-yl]acetonitrile | 393.45 | 394.2 |

Figure 1

| | | | | |
|---|---|---|---|---|
| 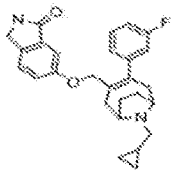 | C0297 | (±)-6-{[9-(cyclopropylmethyl)-4-(3-fluorophenyl)-9-azabicyclo[4.2.1]non-3-en-3-yl]methoxy}-2,3-dihydro-1H-isoindol-1-one | 432.53 | 433.3 |
| 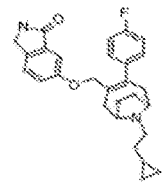 | C0298 | (-)-6-{[9-(2-cyclopropylethyl)-4-(4-fluorophenyl)-9-azabicyclo[4.2.1]non-3-en-3-yl]methoxy}-2,3-dihydro-1H-isoindol-1-one | 446.56 | 447.3 |
| 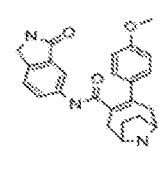 | C0299 | (±)-4-(4-methoxyphenyl)-N-(3-oxo-2,3-dihydro-1H-isoindol-5-yl)-9-azabicyclo[4.2.1]non-3-ene-3-carboxamide | 403.47 | 404.2 |
| 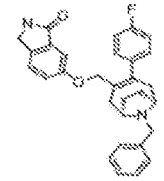 | C0300 | (-)-6-{[9-benzyl-4-(4-fluorophenyl)-9-azabicyclo[4.2.1]non-3-en-3-yl]methoxy}-2,3-dihydro-1H-isoindol-1-one | 468.56 | 469.2 |
| 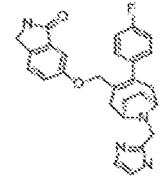 | C0301 | (-)-6-{[9-benzyl-4-(4-fluorophenyl)-9-azabicyclo[4.2.1]non-3-en-3-yl]methoxy}-2,3-dihydro-1H-isoindol-1-one | 458.53 | 459.3 |
| 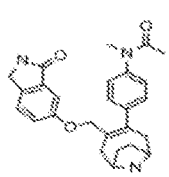 | C0302 | (±)-N-methyl-N-[4-(4-{[(3-oxo-2,3-dihydro-1H-isoindol-5-yl)oxy]methyl}-9-azabicyclo[4.2.1]non-3-en-3-yl)phenyl]acetamide | 431.53 | 432.2 |
| 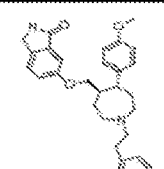 | C0303 | (-)-6-{[(trans)-5-(4-methoxyphenyl)-1-(2-phenylethyl)azepan-4-yl]methoxy}-2,3-dihydro-1H-isoindol-1-one | 470.6 | 471.3 |
| 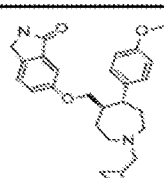 | C0304 | (-)-6-{[(trans)-1-(cyclopropylmethyl)-5-(4-methoxyphenyl)azepan-4-yl]methoxy}-2,3-dihydro-1H-isoindol-1-one | 420.54 | 421.3 |

Figure 1

| | | | | |
|---|---|---|---|---|
| 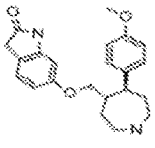 | C0305 | 6-{[(trans)-5-(4-methoxyphenyl)azepan-4-yl]methoxy}-2,3-dihydro-1H-indol-2-one | 366.45 | 367.2 |
| 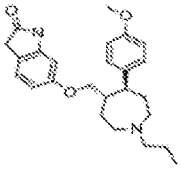 | C0306 | 6-{[(trans)-5-(4-methoxyphenyl)-1-propylazepan-4-yl]methoxy}-2,3-dihydro-1H-indol-2-one | 408.53 | 409.3 |
| 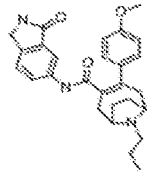 | C0307 | (±)-4-(4-methoxyphenyl)-N-(3-oxo-2,3-dihydro-1H-isoindol-5-yl)-9-propyl-9-azabicyclo[4.2.1]non-3-ene-3-carboxamide | 445.55 | 446.3 |
| 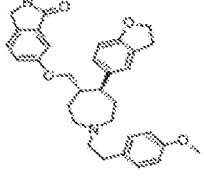 | C0308 | 6-{[(trans)-5-(2,3-dihydro-1-benzofuran-5-yl)-1-[2-(4-methoxyphenyl)ethyl]azepan-4-yl]methoxy}-2,3-dihydro-1H-isoindol-1-one | 512.64 | 513.3 |
| 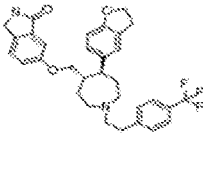 | C0309 | 6-{[(trans)-5-(2,3-dihydro-1-benzofuran-5-yl)-1-{2-[4-(trifluoromethyl)phenyl]ethyl}azepan-4-yl]methoxy}-2,3-dihydro-1H-isoindol-1-one | 550.61 | 551.3 |
| 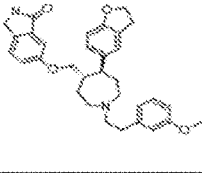 | C0310 | 6-{[(trans)-5-(2,3-dihydro-1-benzofuran-5-yl)-1-[2-(3-methoxyphenyl)ethyl]azepan-4-yl]methoxy}-2,3-dihydro-1H-isoindol-1-one | 512.64 | 513.3 |
| 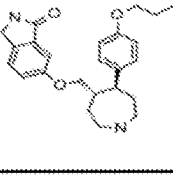 | C0311 | 6-{[(trans)-5-(4-propoxyphenyl)azepan-4-yl]methoxy}-2,3-dihydro-1H-isoindol-1-one | 394.51 | 395.2 |
| 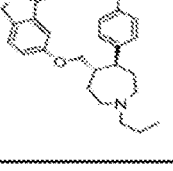 | C0312 | 6-{[(trans)-5-(4-propoxyphenyl)-1-propylazepan-4-yl]methoxy}-2,3-dihydro-1H-isoindol-1-one | 436.59 | 437.3 |

Figure 1

| | | | | |
|---|---|---|---|---|
| 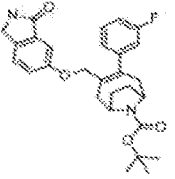 | C0313 | (±)-tert-butyl 3-(3-fluorophenyl)-4-{[(3-oxo-2,3-dihydro-1H-isoindol-5-yl)oxy]methyl}-9-azabicyclo[4.2.1]non-3-ene-9-carboxylate | 478.56 | 501.3 |
| 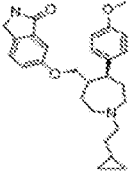 | C0314 | (−)-6-{[(trans)-1-(2-cyclopropylethyl)-5-(4-methoxyphenyl)azepan-4-yl]methoxy}-2,3-dihydro-1H-isoindol-1-one | 434.57 | 435.3 |
| 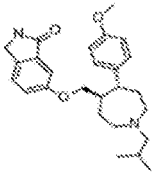 | C0315 | (−)-6-{[(trans)-5-(4-fluorophenyl)-1-(2-methylpropyl)azepan-4-yl]methoxy}-2,3-dihydro-1H-isoindol-1-one | 422.56 | 423.3 |
| 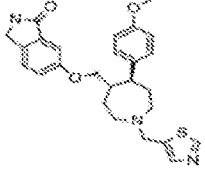 | C0316 | (−)-6-{[(trans)-5-(4-methoxyphenyl)-1-(1,3-thiazol-5-ylmethyl)azepan-4-yl]methoxy}-2,3-dihydro-1H-isoindol-1-one | 463.59 | 464.2 |
| 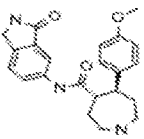 | C0317 | (trans)-5-(4-methoxyphenyl)-N-(3-oxo-2,3-dihydro-1H-isoindol-5-yl)azepane-4-carboxamide | 379.45 | 380.2 |
|  | C0318 | (−)-4-{[(trans)-4-(4-methoxyphenyl)-5-{[(3-oxo-2,3-dihydro-1H-isoindol-5-yl)oxy]methyl}azepan-1-yl]methyl}-N-methylbenzamide | 513.63 | 514.3 |
| 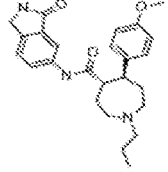 | C0319 | (trans)-5-(4-methoxyphenyl)-N-(3-oxo-2,3-dihydro-1H-isoindol-5-yl)-1-propylazepane-4-carboxamide | 421.53 | 422.3 |
| 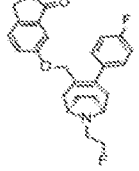 | C0320 | (−)-6-{[9-(2-fluoroethyl)-4-(4-fluorophenyl)-9-azabicyclo[4.2.1]non-3-en-3-yl]methoxy}-2,3-dihydro-1H-isoindol-1-one | 424.48 | 425.2 |

Figure 1

| | | | | |
|---|---|---|---|---|
| 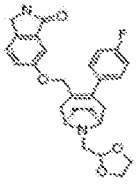 | C0321 | (-)-6-{[9-(1,3-dioxolan-2-ylmethyl)-4-(4-fluorophenyl)-9-azabicyclo[4.2.1]non-3-en-3-yl]methoxy}-2,3-dihydro-1H-isoindol-1-one | 464.53 | 465.3 |
| 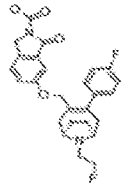 | C0322 | (-)-6-{[9-(2-fluoroethyl)-4-(4-fluorophenyl)-9-azabicyclo[4.2.1]non-3-en-3-yl]methoxy}-1-oxo-2,3-dihydro-1H-isoindole-2-carboxylic acid | 468.49 | 469.2 |
| 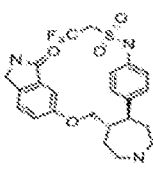 | C0323 | 2,2,2-trifluoro-N-{4-[(trans)-5-{[(3-oxo-2,3-dihydro-1H-isoindol-5-yl)oxy]methyl}azepan-4-yl]phenyl}ethane-1-sulfonamide | 497.53 | 498.1 |
| 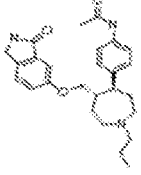 | C0324 | N-{4-[(trans)-5-{[(3-oxo-2,3-dihydro-1H-isoindol-5-yl)oxy]methyl}-1-propylazepan-4-yl]phenyl}acetamide | 435.56 | 436.2 |
| 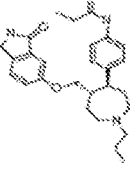 | C0325 | N-{4-[(trans)-5-{[(3-oxo-2,3-dihydro-1H-isoindol-5-yl)oxy]methyl}-1-propylazepan-4-yl]phenyl}propanamide | 449.59 | 450.3 |
| 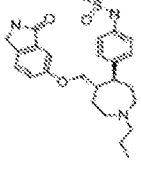 | C0326 | N-{4-[(tran)-5-{[(3-oxo-2,3-dihydro-1H-isoindol-5-yl)oxy]methyl}-1-propylazepan-4-yl]phenyl}methanesulfon-amide | 471.61 | 472.2 |
| 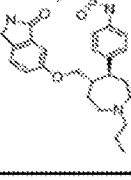 | C0327 | N-{4-[(trans)-5-{[(3-oxo-2,3-dihydro-1H-isoindol-5-yl)oxy]methyl}-1-propylazepan-4-yl]phenyl}ethane-1-sulfonamide | 485.64 | 486.3 |
| 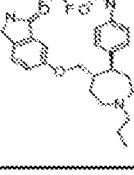 | C0328 | 2,2,2-trifluoro-N-{4-[(trans)-5-{[(3-oxo-2,3-dihydro-1H-isoindol-5-yl)oxy]methyl}-1-propylazepan-4-yl]phenyl}ethane-1-sulfonamide | 539.61 | 540.2 |

Figure 1

| | | | | |
|---|---|---|---|---|
| 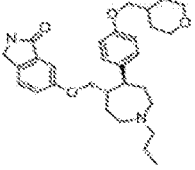 | C0329 | 6-{[(trans)-5-[4-(oxan-4-ylmethoxy)phenyl]-1-propylazepan-4-yl]methoxy}-2,3-dihydro-1H-isoindol-1-one | 492.65 | 493.3 |
| 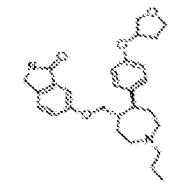 | C0330 | 6-{[(trans)-5-[4-(oxolan-3-yloxy)phenyl]-1-propylazepan-4-yl]methoxy}-2,3-dihydro-1H-isoindol-1-one | 464.6 | 465.2 |
| 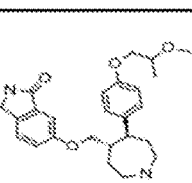 | C0331 | 6-{[(trans)-5-[4-(2-methoxypropoxy)phenyl]azepan-4-yl]methoxy}-2,3-dihydro-1H-isoindol-1-one | 424.53 | 425 |
| 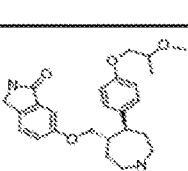 | C0332 | 6-{[(trans)-5-[4-(2-methoxypropoxy)phenyl]-1-propylazepan-4-yl]methoxy}-2,3-dihydro-1H-isoindol-1-one | 466.61 | 468.2 |
| 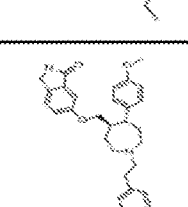 | C0333 | (-)-6-{[(trans)-1-[2-(4-fluorophenyl)ethyl]-5-(4-methoxyphenyl)azepan-4-yl]methoxy}-2,3-dihydro-1H-isoindol-1-one | 488.59 | 489.3 |
| 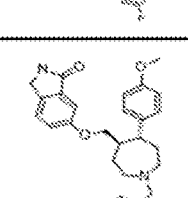 | C0334 | (-)-6-{[(trans)-5-(4-methoxyphenyl)-1-(1,3-thiazol-4-ylmethyl)azepan-4-yl]methoxy}-2,3-dihydro-1H-isoindol-1-one | 463.59 | 464.2 |
| 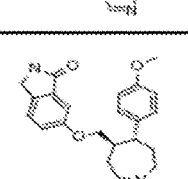 | C0335 | (-)-6-{[(trans)-5-(4-methoxyphenyl)-1-(propan-2-yl)azepan-4-yl]methoxy}-2,3-dihydro-1H-isoindol-1-one | 408.53 | 409.3 |
| 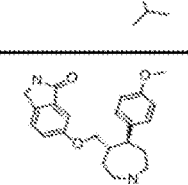 | C0336 | (-)-6-{[(trans)-5-(4-methoxyphenyl)-1-(3-methylbut-2-en-1-yl)azepan-4-yl]methoxy}-2,3-dihydro-1H-isoindol-1-one | 434.57 | 435.3 |

Figure 1

| | | | | |
|---|---|---|---|---|
| 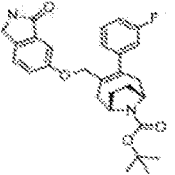 | C0337 | (+)-tert-butyl 3-(3-fluorophenyl)-4-{[(3-oxo-2,3-dihydro-1H-isoindol-5-yl)oxy]methyl}-9-azabicyclo[4.2.1]non-3-ene-9-carboxylate | 478.56 | 501.3 |
| 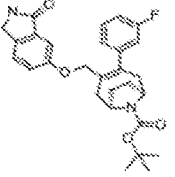 | C0338 | (−)-tert-butyl 3-(3-fluorophenyl)-4-{[(3-oxo-2,3-dihydro-1H-isoindol-5-yl)oxy]methyl}-9-azabicyclo[4.2.1]non-3-ene-9-carboxylate | 478.56 | 501.2 |
| 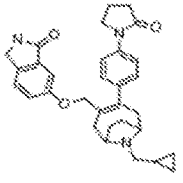 | C0339 | (±)-6-{[9-(cyclopropylmethyl)-4-[4-(2-oxopyrrolidin-1-yl)phenyl]-9-azabicyclo[4.2.1]non-3-en-3-yl]methoxy}-2,3-dihydro-1H-isoindol-1-one | 497.63 | 498.3 |
| 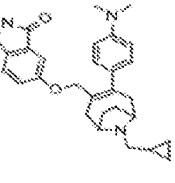 | C0340 | (±)-6-{[9-(cyclopropylmethyl)-4-[4-(dimethylamino)phenyl]-9-azabicyclo[4.2.1]non-3-en-3-yl]methoxy}-2,3-dihydro-1H-isoindol-1-one | 457.61 | 458.3 |
| 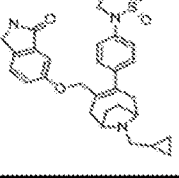 | C0341 | (±)-2-[4-(4-{[(3-oxo-2,3-dihydro-1H-isoindol-5-yl)oxy]methyl}-9-(2-phenylethyl)-9-azabicyclo[4.2.1]non-3-en-3-yl)phenyl]-1$\lambda^6$,2-thiazolidine-1,1-dione | 533.68 | 534.3 |
| 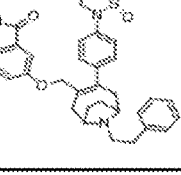 | C0342 | (±)-2-[4-(4-{[(3-oxo-2,3-dihydro-1H-isoindol-5-yl)oxy]methyl}-9-(2-phenylethyl)-9-azabicyclo[4.2.1]non-3-en-3-yl)phenyl]-1$\lambda^6$,2-thiazolidine-1,1-dione | 583.74 | 584.3 |
| 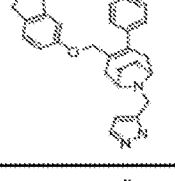 | C0343 | (−)-6-{[4-(4-fluorophenyl)-9-(1H-pyrazol-5-ylmethyl)-9-azabicyclo[4.2.1]non-3-en-3-yl]methoxy}-2,3-dihydro-1H-isoindol-1-one | 458.53 | 460.2 |
| 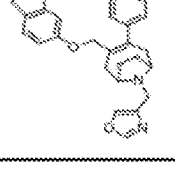 | C0344 | (−)-6-{[4-(4-fluorophenyl)-9-(1,3-oxazol-4-ylmethyl)-9-azabicyclo[4.2.1]non-3-en-3-yl]methoxy}-2,3-dihydro-1H-isoindol-1-one | 459.51 | 460.2 |

Figure 1

| | | | | |
|---|---|---|---|---|
| 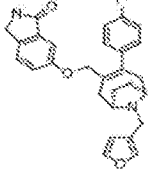 | C0345 | (-)-6-{[4-(4-fluorophenyl)-9-(furan-3-ylmethyl)-9-azabicyclo[4.2.1]non-3-en-3-yl]methoxy}-2,3-dihydro-1H-isoindol-1-one | 458.52 | 459.2 |
| 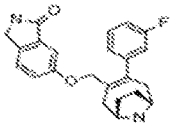 | C0346 | (+)-6-{[4-(3-fluorophenyl)-9-azabicyclo[4.2.1]non-3-en-3-yl]methoxy}-2,3-dihydro-1H-isoindol-1-one | 378.44 | 379.2 |
| 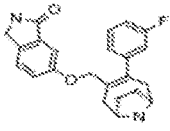 | C0347 | (-)-6-{[4-(3-fluorophenyl)-9-azabicyclo[4.2.1]non-3-en-3-yl]methoxy}-2,3-dihydro-1H-isoindol-1-one | 378.44 | 379.2 |
| 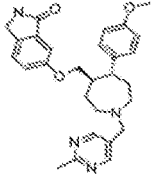 | C0348 | (-)-6-{[(trans)-5-(4-methoxyphenyl)-1-[(2-methylpyrimidin-5-yl)methyl]azepan-4-yl]methoxy}-2,3-dihydro-1H-isoindol-1-one | 472.58 | 473.3 |
| 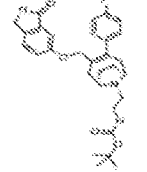 | C0349 | (-)-tert-butyl N-{2-[3-(4-fluorophenyl)-4-{[(3-oxo-2,3-dihydro-1H-isoindol-5-yl)oxy]methyl}-9-azabicyclo[4.2.1]non-3-en-9-yl]ethyl}carbamate | 521.62 | 522.3 |
| 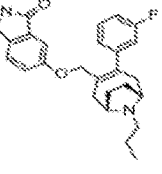 | C0350 | (+)-6-{[4-(3-fluorophenyl)-9-propyl-9-azabicyclo[4.2.1]non-3-en-3-yl]methoxy}-2,3-dihydro-1H-isoindol-1-one | 420.52 | 421.2 |
| 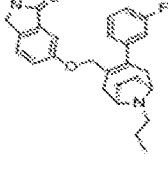 | C0351 | (-)-6-{[4-(3-fluorophenyl)-9-propyl-9-azabicyclo[4.2.1]non-3-en-3-yl]methoxy}-2,3-dihydro-1H-isoindol-1-one | 420.52 | 421.2 |
| 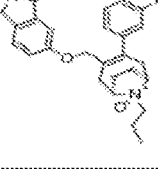 | C0352 | (-)-3-(3-fluorophenyl)-9-oxido-4-{[(3-oxo-2,3-dihydro-1H-isoindol-5-yl)oxy]methyl}-9-propyl-9-azabicyclo[4.2.1]non-3-en-9-ium | 436.52 | 437.2 |

Figure 1

| | | | | |
|---|---|---|---|---|
| 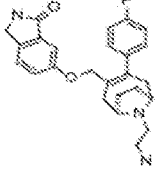 | C0353 | (-)-6-{[9-(2-aminoethyl)-4-(4-fluorophenyl)-9-azabicyclo[4.2.1]non-3-en-3-yl]methoxy}-2,3-dihydro-1H-isoindol-1-one | 421.51 | 422.3 |
| 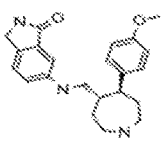 | C0354 | 6-{[(trans)-5-(4-methoxyphenyl)azepan-4-yl]methoxy}-2,3-dihydro-1H-isoindol-1-one | 365.47 | 367.3 |
| 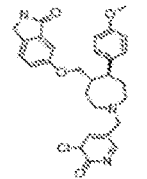 | C0355 | (-)-6-{[(trans)-1-{(5-chloro-6-oxo-5,6-dihydropyridin-3-yl)methyl}-5-(4-methoxyphenyl)azepan-4-yl]methoxy}-2,3-dihydro-1H-isoindol-1-one | 508.01 | 508.3 |
| 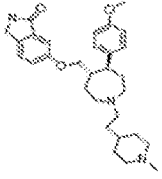 | C0356 | (-)-6-{[(trans)-5-(4-methoxyphenyl)-1-[2-(1-methylpiperidin-4-yl)ethyl]azepan-4-yl]methoxy}-2,3-dihydro-1H-isoindol-1-one | 491.66 | 492.4 |
| 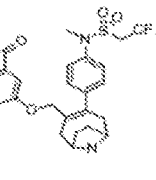 | C0357 | (±)-2,2,2-trifluoro-N-methyl-N-[4-(4-{[(3-oxo-2,3-dihydro-1H-isoindol-5-yl)oxy]methyl}-9-azabicyclo[4.2.1]non-3-en-3-yl)phenyl]ethane-1-sulfonamide | 535.58 | 536.2 |
| 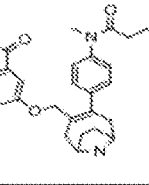 | C0358 | (±)-N-methyl-N-[4-(4-{[(3-oxo-2,3-dihydro-1H-isoindol-5-yl)oxy]methyl}-9-azabicyclo[4.2.1]non-3-en-3-yl)phenyl]butanamide | 459.58 | 460.3 |
| 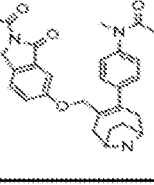 | C0359 | (±)-N-[4-(4-{[(2-acetyl-3-oxo-2,3-dihydro-1H-isoindol-5-yl)oxy]methyl}-9-azabicyclo[4.2.1]non-3-en-3-yl)phenyl]-N-methylacetamide | 473.56 | 474.3 |
| 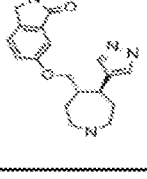 | C0360 | 6-{[(trans)-5-(1H-pyrazol-4-yl)azepan-4-yl]methoxy}-2,3-dihydro-1H-isoindol-1-one | 326.39 | 327.1 |

Figure 1

| | | | | |
|---|---|---|---|---|
| (structure) | C0361 | 6-{[(trans)-5-(1-methyl-1H-pyrazol-4-yl)azepan-4-yl]methoxy}-2,3-dihydro-1H-isoindol-1-one | 340.42 | 341.1 |
| (structure) | C0362 | 6-{[(trans)-5-(1-methyl-1H-pyrazol-4-yl)-1-propylazepan-4-yl]methoxy}-2,3-dihydro-1H-isoindol-1-one | 382.5 | 383.1 |
| (structure) | C0363 | 6-{[(trans)-5-(4-fluorophenyl)-1-[2-(2-fluorophenyl)ethyl]azepan-4-yl]methoxy}-2,3-dihydro-1H-isoindol-1-one | 476.56 | 476.2 |
| (structure) | C0364 | (-)-6-{[(trans)-1-[2-(2-fluorophenyl)ethyl]-5-(4-methoxyphenyl)azepan-4-yl]methoxy}-2,3-dihydro-1H-isoindol-1-one | 488.59 | 489.3 |
| (structure) | C0365 | (±)-N-methyl-N-[4-(4-{[(3-oxo-2,3-dihydro-1H-isoindol-5-yl)oxy]methyl}-9-propyl-9-azabicyclo[4.2.1]non-3-en-3-yl)phenyl]acetamide | 473.61 | 474.3 |
| (structure) | C0366 | (±)-N-{4-[9-(cyclopropylmethyl)-4-{[(3-oxo-2,3-dihydro-1H-isoindol-5-yl)oxy]methyl}-9-azabicyclo[4.2.1]non-3-en-3-yl]phenyl}-N-methylacetamide | 485.62 | 486.3 |
| (structure) | C0367 | (±)-N-methyl-N-[4-(4-{[(3-oxo-2,3-dihydro-1H-isoindol-5-yl)oxy]methyl}-9-(2-phenylethyl)-9-azabicyclo[4.2.1]non-3-en-3-yl)phenyl]acetamide | 535.68 | 536.3 |
| (structure) | C0368 | (±)-N-(4-{9-[2-(2-fluorophenyl)ethyl]-4-{[(3-oxo-2,3-dihydro-1H-isoindol-5-yl)oxy]methyl}-9-azabicyclo[4.2.1]non-3-en-3-yl}phenyl)-N-methylacetamide | 553.67 | 554.3 |

Figure 1

| | | | | |
|---|---|---|---|---|
| 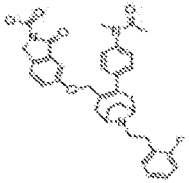 | C0369 | (±)-N-[4-(4-{[(2-acetyl-3-oxo-2,3-dihydro-1H-isoindol-5-yl)oxy]methyl}-9-[2-(2-fluorophenyl)ethyl]-9-azabicyclo[4.2.1]non-3-en-3-yl)phenyl]-N-methylacetamide | 597.68 | 598.3 |
| 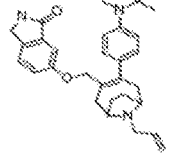 | C0370 | (±)-N-methyl-N-[4-(4-{[(3-oxo-2,3-dihydro-1H-isoindol-5-yl)oxy]methyl}-9-(prop-2-en-1-yl)-9-azabicyclo[4.2.1]non-3-en-3-yl)phenyl]acetamide | 471.59 | 472.3 |
| 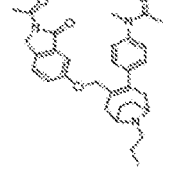 | C0371 | (±)-N-[4-(4-{[(2-acetyl-3-oxo-2,3-dihydro-1H-isoindol-5-yl)oxy]methyl}-9-propyl-9-azabicyclo[4.2.1]non-3-en-3-yl)phenyl]-N-methylacetamide | 515.64 | 516.3 |
| 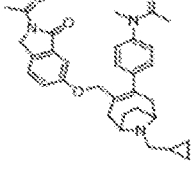 | C0372 | (±)-N-[4-(4-{[(2-acetyl-3-oxo-2,3-dihydro-1H-isoindol-5-yl)oxy]methyl}-9-(cyclopropylmethyl)-9-azabicyclo[4.2.1]non-3-en-3-yl)phenyl]-N-methylacetamide | 527.65 | 528.3 |
| 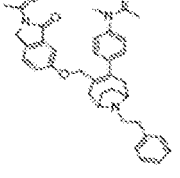 | C0373 | (±)-N-[4-(4-{[(2-acetyl-3-oxo-2,3-dihydro-1H-isoindol-5-yl)oxy]methyl}-9-(2-phenylethyl)-9-azabicyclo[4.2.1]non-3-en-3-yl)phenyl]-N-methylacetamide | 577.71 | 578.3 |
| 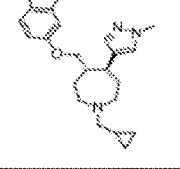 | C0374 | 6-{[(trans)-1-(cyclopropylmethyl)-5-(1-methyl-1H-pyrazol-4-yl)azepan-4-yl]methoxy}-2,3-dihydro-1H-isoindol-1-one | 394.51 | 395.2 |
| 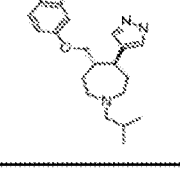 | C0375 | 6-{[(trans)-1-(2-methylpropyl)-5-(1H-pyrazol-4-yl)azepan-4-yl]methoxy}-2,3-dihydro-1H-isoindol-1-one | 382.5 | 383.3 |
| 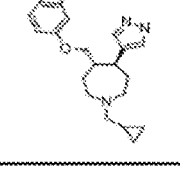 | C0376 | 6-{[(trans)-1-(cyclopropylmethyl)-5-(1H-pyrazol-4-yl)azepan-4-yl]methoxy}-2,3-dihydro-1H-isoindol-1-one | 380.48 | 381.2 |

Figure 1

| | | | | |
|---|---|---|---|---|
| 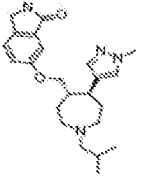 | C0377 | 6-{[(trans)-5-(1-methyl-1H-pyrazol-4-yl)-1-(2-methylpropyl)azepan-4-yl]methoxy}-2,3-dihydro-1H-isoindol-1-one | 396.53 | 397.2 |
| 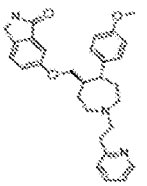 | C0378 | (-)-6-{[(trans)-5-(4-methoxyphenyl)-1-[2-(pyridin-2-yl)ethyl]azepan-4-yl]methoxy}-2,3-dihydro-1H-isoindol-1-one | 471.59 | 472.3 |
| 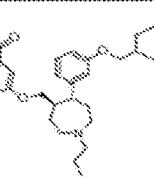 | C0379 | 6-{[(trans)-5-[3-(oxan-4-ylmethoxy)phenyl]-1-propylazepan-4-yl]methoxy}-2,3-dihydro-1H-isoindol-1-one | 492.65 | 493.3 |
| 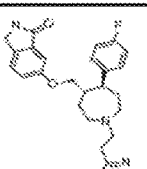 | C0380 | 6-{[(trans)-5-(4-fluorophenyl)-1-[2-(pyridin-2-yl)ethyl]azepan-4-yl]methoxy}-2,3-dihydro-1H-isoindol-1-one | 459.56 | 460.3 |
| 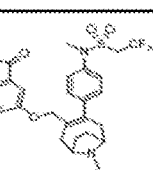 | C0381 | (±)-2,2,2-trifluoro-N-methyl-N-[4-(4-{[(3-oxo-2,3-dihydro-1H-isoindol-5-yl)oxy]methyl}-9-propyl-9-azabicyclo[4.2.1]non-3-en-3-yl)phenyl]ethane-1-sulfonamide | 577.66 | 578.3 |
| 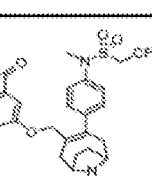 | C0382 | (±)-N-{4-[9-(cyclopropylmethyl)-4-{[(3-oxo-2,3-dihydro-1H-isoindol-5-yl)oxy]methyl}-9-azabicyclo[4.2.1]non-3-en-3-yl]phenyl}-2,2,2-trifluoro-N-methylethane-1-sulfonamide | 589.67 | 590.3 |
| 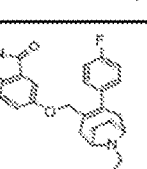 | C0383 | (-)-N-{2-[-3-(4-fluorophenyl)-4-{[(3-oxo-2,3-dihydro-1H-isoindol-5-yl)oxy]methyl}-9-azabicyclo[4.2.1]non-3-en-9-yl]ethyl}acetamide | 463.54 | 464.3 |
| 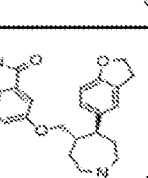 | C0384 | 6-{[(trans)-1-(2-cyclopropylethyl)-5-(2,3-dihydro-1-benzofuran-5-yl)azepan-4-yl]methoxy}-2,3-dihydro-1H-isoindol-1-one | 446.58 | 447.3 |

Figure 1

| | | | | |
|---|---|---|---|---|
| 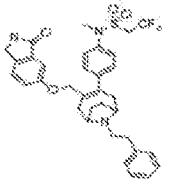 | C0385 | (±)-2,2,2-trifluoro-N-methyl-N-[4-(4-{[(3-oxo-2,3-dihydro-1H-isoindol-5-yl)oxy]methyl}-9-(2-phenylethyl)-9-azabicyclo[4.2.1]non-3-en-3-yl)phenyl]ethane-1-sulfonamide | 639.73 | 640.3 |
| 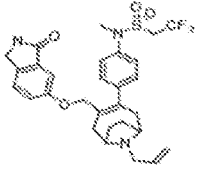 | C0386 | (±)-2,2,2-trifluoro-N-methyl-N-[4-(4-{[(3-oxo-2,3-dihydro-1H-isoindol-5-yl)oxy]methyl}-9-(prop-2-en-1-yl)-9-azabicyclo[4.2.1]non-3-en-3-yl)phenyl]ethane-1-sulfonamide | 575.64 | 576.3 |
| 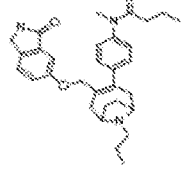 | C0387 | (±)-N-methyl-N-[4-(4-{[(3-oxo-2,3-dihydro-1H-isoindol-5-yl)oxy]methyl}-9-propyl-9-azabicyclo[4.2.1]non-3-en-3-yl)phenyl]butanamide | 501.66 | 502.3 |
| 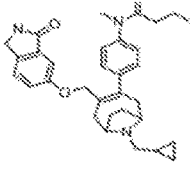 | C0388 | (±)-N-{4-[9-(cyclopropylmethyl)-4-{[(3-oxo-2,3-dihydro-1H-isoindol-5-yl)oxy]methyl}-9-azabicyclo[4.2.1]non-3-en-3-yl]phenyl}-N-methylbutanamide | 513.67 | 514.3 |
| 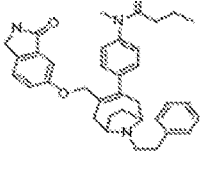 | C0389 | (±)-N-methyl-N-[4-(4-{[(3-oxo-2,3-dihydro-1H-isoindol-5-yl)oxy]methyl}-9-(2-phenylethyl)-9-azabicyclo[4.2.1]non-3-en-3-yl)phenyl]butanamide | 563.73 | 564.3 |
| 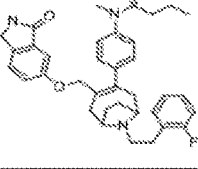 | C0390 | (±)-N-(4-{9-[2-(2-fluorophenyl)ethyl]-4-{[(3-oxo-2,3-dihydro-1H-isoindol-5-yl)oxy]methyl}-9-azabicyclo[4.2.1]non-3-en-3-yl}phenyl)-N-methylbutanamide | 581.72 | 582.2 |
| 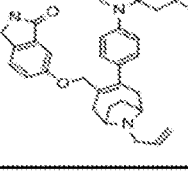 | C0391 | (±)-N-methyl-N-[4-(4-{[(3-oxo-2,3-dihydro-1H-isoindol-5-yl)oxy]methyl}-9-(prop-2-en-1-yl)-9-azabicyclo[4.2.1]non-3-en-3-yl)phenyl]butanamide | 499.64 | 500.3 |
| 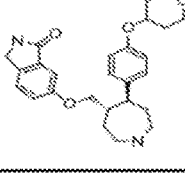 | C0392 | 6-{[(trans)-5-[4-(oxan-4-yloxy)phenyl]azepan-4-yl]methoxy}-2,3-dihydro-1H-isoindol-1-one | 436.54 | 437.3 |

Figure 1

| | | | | |
|---|---|---|---|---|
| 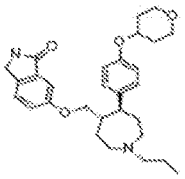 | C0393 | 6-{[(trans)-5-[4-(oxan-4-yloxy)phenyl]-1-propylazepan-4-yl]methoxy}-2,3-dihydro-1H-isoindol-1-one | 478.62 | 479.3 |
| 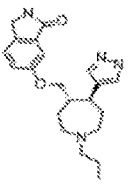 | C0394 | 6-{[(trans)-1-propyl-5-(1H-pyrazol-4-yl)azepan-4-yl]methoxy}-2,3-dihydro-1H-isoindol-1-one | 368.47 | 369.1 |
| 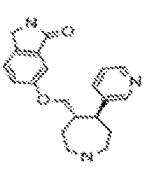 | C0395 | 6-{[(trans)-5-(pyridin-3-yl)azepan-4-yl]methoxy}-2,3-dihydro-1H-isoindol-1-one | 337.42 | 338.1 |
| 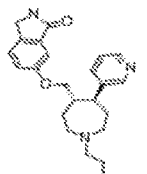 | C0396 | 6-{[(trans)-1-propyl-5-(pyridin-3-yl)azepan-4-yl]methoxy}-2,3-dihydro-1H-isoindol-1-one | 379.5 | 380.3 |
| 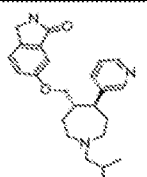 | C0397 | 6-{[(trans)-1-(2-methylpropyl)-5-(pyridin-3-yl)azepan-4-yl]methoxy}-2,3-dihydro-1H-isoindol-1-one | 393.52 | 394.2 |
| 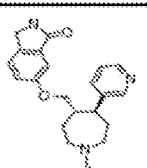 | C0398 | 6-{[(trans)-1-(cyclopropylmethyl)-5-(pyridin-3-yl)azepan-4-yl]methoxy}-2,3-dihydro-1H-isoindol-1-one | 391.51 | 392.4 |
|  | C0399 | 6-{[(trans)-5-(3,5-dimethyl-1,2-oxazol-4-yl)azepan-4-yl]methoxy}-2,3-dihydro-1H-isoindol-1-one | 355.43 | 356.3 |
| 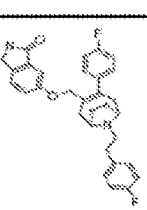 | C0400 | (-)-6-{[4-(4-fluorophenyl)-9-[2-(4-fluorophenyl)ethyl]-9-azabicyclo[4.2.1]non-3-en-3-yl]methoxy}-2,3-dihydro-1H-isoindol-1-one | 500.58 | 501.3 |

Figure 1

| | | | | |
|---|---|---|---|---|
| 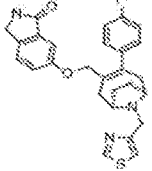 | C0401 | (-)-6-{[4-(4-fluorophenyl)-9-(1,3-thiazol-4-yl)methyl]-9-azabicyclo[4.2.1]non-3-en-3-yl]methoxy}-2,3-dihydro-1H-isoindol-1-one | 475.58 | 476.2 |
| 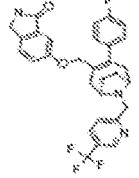 | C0402 | (-)-6-{[4-(4-fluorophenyl)-9-(1,3-thiazol-5-yl)methyl]-9-azabicyclo[4.2.1]non-3-en-3-yl]methoxy}-2,3-dihydro-1H-isoindol-1-one | 537.55 | 538.2 |
| 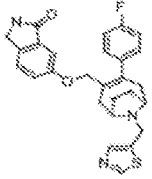 | C0403 | (-)-6-{[4-(4-fluorophenyl)-9-[(5-methylfuran-2-yl)methyl]-9-azabicyclo[4.2.1]non-3-en-3-yl]methoxy}-2,3-dihydro-1H-isoindol-1-one | 475.58 | 476.2 |
| 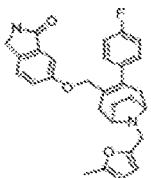 | C0404 | (-)-6-{[4-(4-fluorophenyl)-9-[(5-methylfuran-2-yl)methyl]-9-azabicyclo[4.2.1]non-3-en-3-yl]methoxy}-2,3-dihydro-1H-isoindol-1-one | 472.55 | 473.2 |
| 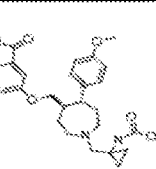 | C0405 | (-)-tert-butyl N-(1-{[4-(4-methoxyphenyl)-5-{[(trans)-(3-oxo-2,3-dihydro-1H-isoindol-5-yl)oxy]methyl}azepan-1-yl]methyl}cyclopropyl)carbamate | 535.67 | 536.3 |
|  | C0406 | (-)-6-{[(trans)-5-(4-methoxyphenyl)-1-[2-(2-oxopyrrolidin-1-yl)ethyl]azepan-4-yl]methoxy}-2,3-dihydro-1H-isoindol-1-one | 477.6 | 478.3 |
| 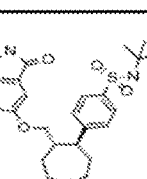 | C0407 | N-tert-butyl-4-[(trans)-5-{[(3-oxo-2,3-dihydro-1H-isoindol-5-yl)oxy]methyl}azepan-4-yl]benzene-1-sulfonamide | 471.61 | 472.3 |
| 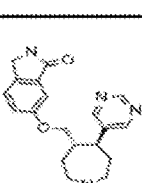 | C0408 | 6-{[(trans)-5-(pyrimidin-5-yl)azepan-4-yl]methoxy}-2,3-dihydro-1H-isoindol-1-one | 338.4 | 339.2 |

Figure 1

| | | | | |
|---|---|---|---|---|
| 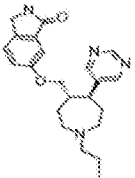 | C0409 | 6-{[(trans)-1-propyl-5-(pyrimidin-5-yl)azepan-4-yl]methoxy}-2,3-dihydro-1H-isoindol-1-one | 380.48 | 381.4 |
| 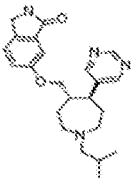 | C0410 | 6-{[(trans)-1-(2-methylpropyl)-5-(pyrimidin-5-yl)azepan-4-yl]methoxy}-2,3-dihydro-1H-isoindol-1-one | 394.51 | 395.4 |
| 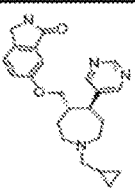 | C0411 | 6-{[(trans)-1-(cyclopropylmethyl)-5-(pyrimidin-5-yl)azepan-4-yl]methoxy}-2,3-dihydro-1H-isoindol-1-one | 392.49 | 393.3 |
| 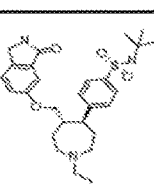 | C0412 | N-tert-butyl-4-[(trans)-5-{[(3-oxo-2,3-dihydro-1H-isoindol-5-yl)oxy]methyl}-1-propylazepan-4-yl]benzene-1-sulfonamide | 513.69 | 514.4 |
| 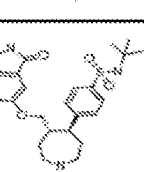 | C0413 | N-tert-butyl-4-[(trans)-1-(2-methylpropyl)-5-{[(3-oxo-2,3-dihydro-1H-isoindol-5-yl)oxy]methyl}azepan-4-yl]benzene-1-sulfonamide | 527.72 | 528.4 |
| 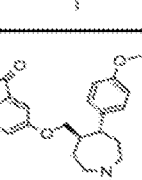 | C0414 | 6-{[(trans)-1-{(1-aminocyclopropyl)methyl}-5-(4-methoxyphenyl)azepan-4-yl]methoxy}-2,3-dihydro-1H-isoindol-1-one | 435.56 | 436.3 |
| 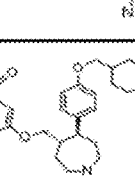 | C0415 | 6-{[(trans)-1-[2-(2-fluorophenyl)ethyl]-5-[4-(oxan-4-ylmethoxy)phenyl]azepan-4-yl]methoxy}-2,3-dihydro-1H-isoindol-1-one | 572.71 | 573.3 |
|  | C0416 | N-tert-butyl-4-[(trans)-1-(cyclopropylmethyl)-5-{[(3-oxo-2,3-dihydro-1H-isoindol-5-yl)oxy]methyl}azepan-4-yl]benzene-1-sulfonamide | 525.7 | 526.3 |

Figure 1

| | | | | |
|---|---|---|---|---|
| 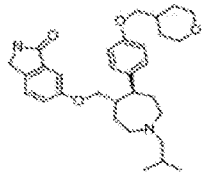 | C0417 | 6-{[(trans)-1-(2-methylpropyl)-5-[4-(oxan-4-ylmethoxy)phenyl]azepan-4-yl]methoxy}-2,3-dihydro-1H-isoindol-1-one | 506.68 | 507.7 |
| 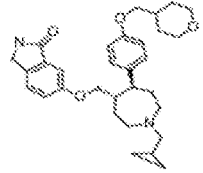 | C0418 | 6-{[(trans)-1-(cyclopropylmethyl)-5-[4-(oxan-4-ylmethoxy)phenyl]azepan-4-yl]methoxy}-2,3-dihydro-1H-isoindol-1-one | 504.66 | 505.3 |
| 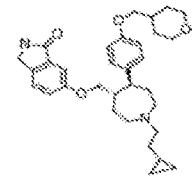 | C0419 | 6-{[(trans)-1-(2-cyclopropylethyl)-5-[4-(oxan-4-ylmethoxy)phenyl]azepan-4-yl]methoxy}-2,3-dihydro-1H-isoindol-1-one | 518.69 | 519.3 |
| 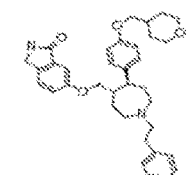 | C0420 | 6-{[(trans)-5-[4-(oxan-4-ylmethoxy)phenyl]-1-(2-phenylethyl)azepan-4-yl]methoxy}-2,3-dihydro-1H-isoindol-1-one | 554.72 | 555.3 |
| 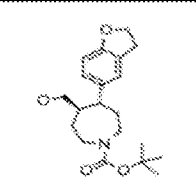 | C0421 | (-)-tert-butyl-(trans)-4-(2,3-dihydro-1-benzofuran-5-yl)-5-(hydroxymethyl)azepane-1-carboxylate | 347.45 | 370.2 |
| 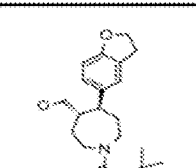 | C0422 | (+)-tert-butyl-(trans)-4-(2,3-dihydro-1-benzofuran-5-yl)-5-(hydroxymethyl)azepane-1-carboxylate | 347.45 | 370.2 |
| 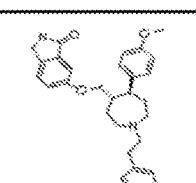 | C0423 | 6-{[(trans)-1-[2-(3-fluorophenyl)ethyl]-5-(4-methoxyphenyl)azepan-4-yl]methoxy}-2,3-dihydro-1H-isoindol-1-one | 488.59 | 489.3 |
| 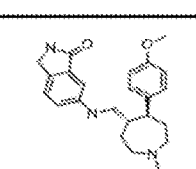 | C0424 | 6-{[(trans)-5-(4-methoxyphenyl)-1-propylazepan-4-yl]methoxy}-2,3-dihydro-1H-isoindol-1-one | 407.55 | 408.3 |

Figure 1

| | ID | Name | | |
|---|---|---|---|---|
| 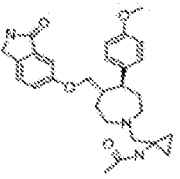 | C0425 | N-(1-{[(trans)-4-(4-methoxyphenyl)-5-{[(3-oxo-2,3-dihydro-1H-isoindol-5-yl)oxy]methyl}azepan-1-yl]methyl}cyclopropyl)acetamide | 477.6 | 478.3 |
| 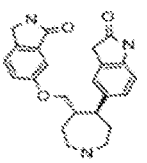 | C0426 | 5-[(trans)-5-{[(3-oxo-2,3-dihydro-1H-isoindol-5-yl)oxy]methyl}azepan-4-yl]-2,3-dihydro-1H-indol-2-one | 391.46 | 392.3 |
| 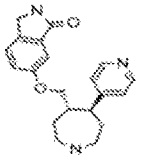 | C0427 | 6-{[(trans)-5-(pyridin-4-yl)azepan-4-yl]methoxy}-2,3-dihydro-1H-isoindol-1-one | 337.42 | 338.2 |
| 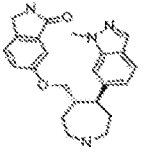 | C0428 | 6-{[(trans)-5-(1-methyl-1H-indazol-6-yl)azepan-4-yl]methoxy}-2,3-dihydro-1H-isoindol-1-one | 390.48 | 391.3 |
| 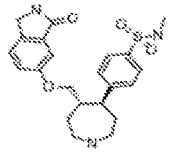 | C0429 | N-methyl-4-[(trans)-5-{[(3-oxo-2,3-dihydro-1H-isoindol-5-yl)oxy]methyl}azepan-4-yl]benzene-1-sulfonamide | 429.53 | 430.3 |
| 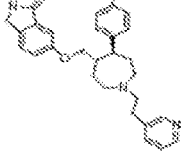 | C0430 | 6-{[(trans)-5-(4-methoxyphenyl)-1-[2-(pyridin-3-yl)ethyl]azepan-4-yl]methoxy}-2,3-dihydro-1H-isoindol-1-one | 471.59 | 472.3 |
| 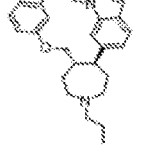 | C0431 | 6-{[(trans)-5-(1-methyl-1H-indazol-6-yl)-1-propylazepan-4-yl]methoxy}-2,3-dihydro-1H-isoindol-1-one | 432.56 | 433.4 |
| 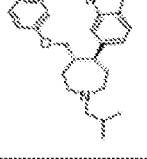 | C0432 | 6-{[(trans)-5-(1-methyl-1H-indazol-6-yl)-1-(2-methylpropyl)azepan-4-yl]methoxy}-2,3-dihydro-1H-isoindol-1-one | 446.58 | 447.4 |

Figure 1

| | | | | |
|---|---|---|---|---|
| 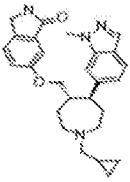 | C0433 | 6-{[(trans)-1-(cyclopropylmethyl)-5-(1-methyl-1H-indazol-6-yl)azepan-4-yl]methoxy}-2,3-dihydro-1H-isoindol-1-one | 444.57 | 445.4 |
|  | C0434 | N-methyl-4-[(trans)-5-{[(3-oxo-2,3-dihydro-1H-isoindol-5-yl)oxy]methyl}-1-propylazepan-4-yl]benzene-1-sulfonamide | 471.61 | 472.3 |
| 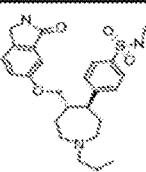 | C0435 | N-methyl-4-[(trans)-1-(2-methylpropyl)-5-{[(3-oxo-2,3-dihydro-1H-isoindol-5-yl)oxy]methyl}azepan-4-yl]benzene-1-sulfonamide | 485.64 | 486.3 |
| 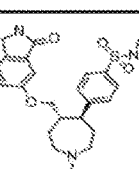 | C0436 | 4-[(trans)-1-(cyclopropylmethyl)-5-{[(3-oxo-2,3-dihydro-1H-isoindol-5-yl)oxy]methyl}azepan-4-yl]-N-methylbenzene-1-sulfonamide | 483.62 | 484.3 |
| 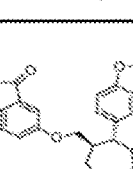 | C0437 | (-)-6-{[(trans)-5-(2,3-dihydro-1-benzofuran-5-yl)azepan-4-yl]methoxy}-2,3-dihydro-1H-isoindol-1-one | 378.46 | 379.2 |
| 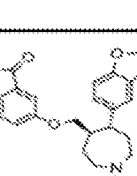 | C0438 | (+)-6-{[(trans)-5-(2,3-dihydro-1-benzofuran-5-yl)-1-propylazepan-4-yl]methoxy}-2,3-dihydro-1H-isoindol-1-one | 420.54 | 421.3 |
| 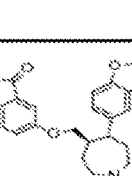 | C0439 | (+)-6-{[(trans)-1-(cyclopropylmethyl)-5-(2,3-dihydro-1-benzofuran-5-yl)azepan-4-yl]methoxy}-2,3-dihydro-1H-isoindol-1-one | 432.55 | 433.3 |
| 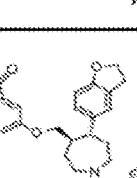 | C0440 | (+)-6-{[(trans)-5-(2,3-dihydro-1-benzofuran-5-yl)-1-(2-phenylethyl)azepan-4-yl]methoxy}-2,3-dihydro-1H-isoindol-1-one | 482.61 | 483.3 |

Figure 1

| | | | | |
|---|---|---|---|---|
| 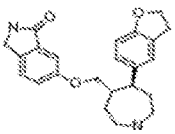 | C0441 | (-)-6-{[(trans)-5-(2,3-dihydro-1-benzofuran-5-yl)azepan-4-yl]methoxy}-2,3-dihydro-1H-isoindol-1-one | 378.46 | 379.2 |
| 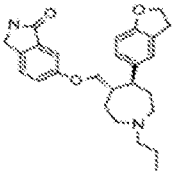 | C0442 | (-)-6-{[(trans)-5-(2,3-dihydro-1-benzofuran-5-yl)-1-propylazepan-4-yl]methoxy}-2,3-dihydro-1H-isoindol-1-one | 420.54 | 421.3 |
| 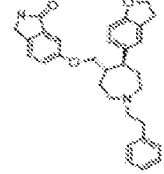 | C0443 | (-)-6-{[(trans)-5-(2,3-dihydro-1-benzofuran-5-yl)-1-(2-phenylethyl)azepan-4-yl]methoxy}-2,3-dihydro-1H-isoindol-1-one | 482.61 | 483.3 |
| 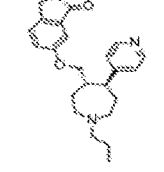 | C0444 | 6-{[(trans)-1-propyl-5-(pyridin-4-yl)azepan-4-yl]methoxy}-2,3-dihydro-1H-isoindol-1-one | 379.5 | 380.3 |
| 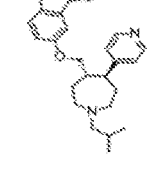 | C0445 | 6-{[(trans)-1-(2-methylpropyl)-5-(pyridin-4-yl)azepan-4-yl]methoxy}-2,3-dihydro-1H-isoindol-1-one | 393.52 | 394.4 |
| 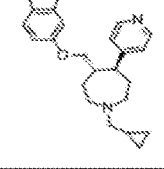 | C0446 | 6-{[(trans)-1-(cyclopropylmethyl)-5-(pyridin-4-yl)azepan-4-yl]methoxy}-2,3-dihydro-1H-isoindol-1-one | 391.51 | 392.3 |
| 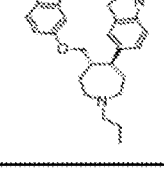 | C0447 | 5-[(trans)-5-{[(3-oxo-2,3-dihydro-1H-isoindol-5-yl)oxy]methyl}-1-propylazepan-4-yl]-2,3-dihydro-1H-isoindol-1-one | 433.54 | 434.4 |
| 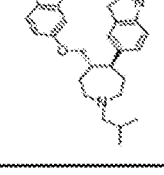 | C0448 | 5-[(trans)-1-(2-methylpropyl)-5-{[(3-oxo-2,3-dihydro-1H-isoindol-5-yl)oxy]methyl}azepan-4-yl]-2,3-dihydro-1H-isoindol-1-one | 447.57 | 448.15 |

Figure 1

| | | | | |
|---|---|---|---|---|
| 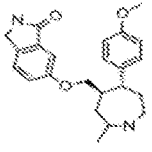 | C0449 | 6-{[(trans)-5-(4-methoxyphenyl)-2-methylazepan-4-yl]methoxy}-2,3-dihydro-1H-isoindol-1-one | 380.48 | 381.2 |
| 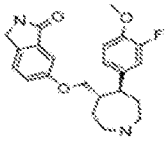 | C0450 | 6-{[(trans)-5-(3-fluoro-4-methoxyphenyl)azepan-4-yl]methoxy}-2,3-dihydro-1H-isoindol-1-one | 384.44 | 385.2 |
| 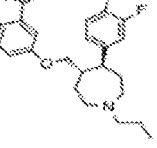 | C0451 | 6-{[(trans)-5-(3-fluoro-4-methoxyphenyl)-1-propylazepan-4-yl]methoxy}-2,3-dihydro-1H-isoindol-1-one | 426.52 | 427.3 |
| 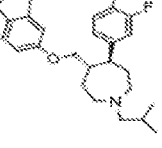 | C0452 | 6-{[(trans)-5-(3-fluoro-4-methoxyphenyl)-1-(2-methylpropyl)azepan-4-yl]methoxy}-2,3-dihydro-1H-isoindol-1-one | 440.55 | 441.3 |
| 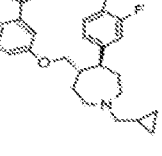 | C0453 | 6-{[(trans)-1-(cyclopropylmethyl)-5-(3-fluoro-4-methoxyphenyl)azepan-4-yl]methoxy}-2,3-dihydro-1H-isoindol-1-one | 438.53 | 439.2 |
| 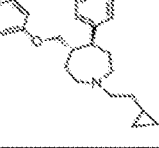 | C0454 | 6-{[(trans)-1-(2-cyclopropylethyl)-5-(3-fluoro-4-methoxyphenyl)azepan-4-yl]methoxy}-2,3-dihydro-1H-isoindol-1-one | 452.56 | 453.3 |
| 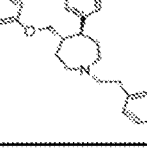 | C0455 | 6-{[(trans)-5-(3-fluoro-4-methoxyphenyl)-1-(2-phenylethyl)azepan-4-yl]methoxy}-2,3-dihydro-1H-isoindol-1-one | 488.59 | 489.3 |
| 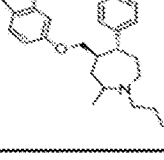 | C0456 | 6-{[(trans)-5-(4-methoxyphenyl)-2-methyl-1-propylazepan-4-yl]methoxy}-2,3-dihydro-1H-isoindol-1-one | 422.56 | 423.3 |

Figure 1

| | ID | Name | | |
|---|---|---|---|---|
| 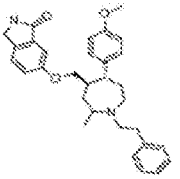 | C0457 | 6-{[(trans)-5-(4-methoxyphenyl)-2-methyl-1-(2-phenylethyl)azepan-4-yl]methoxy}-2,3-dihydro-1H-isoindol-1-one | 484.63 | 485.3 |
| 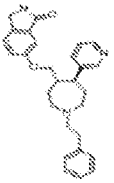 | C0458 | 6-{[(trans)-1-(2-phenylethyl)-5-(pyridin-3-yl)azepan-4-yl]methoxy}-2,3-dihydro-1H-isoindol-1-one | 441.56 | 442.3 |
| 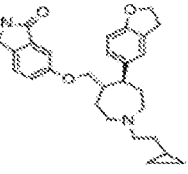 | C0459 | (-)-6-{[(trans)-1-(2-cyclopropylethyl)-5-(2,3-dihydro-1-benzofuran-5-yl)azepan-4-yl]methoxy}-2,3-dihydro-1H-isoindol-1-one | 446.58 | 447.3 |
| 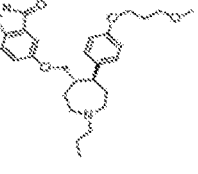 | C0460 | (-)-6-{[(trans)-5-[4-(3-methoxypropoxy)phenyl]-1-propylazepan-4-yl]methoxy}-2,3-dihydro-1H-isoindol-1-one | 466.61 | 467.3 |
| 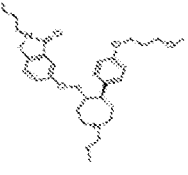 | C0461 | (-)-6-{[(trans)-5-[4-(3-methoxypropoxy)phenyl]-1-propylazepan-4-yl]methoxy}-2-(3-methoxypropyl)-2,3-dihydro-1H-isoindol-1-one | 538.72 | 539.4 |
| 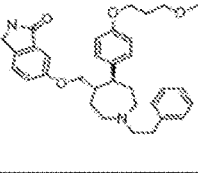 | C0462 | (-)-6-{[(trans)-5-[4-(3-methoxypropoxy)phenyl]-1-(2-phenylethyl)azepan-4-yl]methoxy}-2,3-dihydro-1H-isoindol-1-one | 528.68 | 529.3 |
| 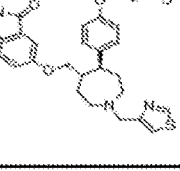 | C0463 | (-)-6-{[(trans)-5-[4-(3-methoxypropoxy)phenyl]-1-(1,3-thiazol-4-ylmethyl)azepan-4-yl]methoxy}-2,3-dihydro-1H-isoindol-1-one | 521.67 | 522.3 |
| 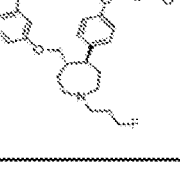 | C0464 | (-)-6-{[(trans)-1-(3-fluoropropyl)-5-[4-(3-methoxypropoxy)phenyl]azepan-4-yl]methoxy}-2,3-dihydro-1H-isoindol-1-one | 484.6 | 485.3 |

Figure 1

| | | | | |
|---|---|---|---|---|
| 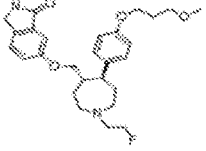 | C0465 | (-)-6-{[(trans)-1-(2-fluoroethyl)-5-[4-(3-methoxypropoxy)phenyl]azepan-4-yl]methoxy}-2,3-dihydro-1H-isoindol-1-one | 470.58 | 471.3 |
| 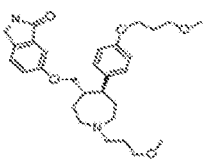 | C0466 | 6-{[(trans)-5-[4-(3-methoxypropoxy)phenyl]-1-(3-methoxypropyl)azepan-4-yl]methoxy}-2,3-dihydro-1H-isoindol-1-one | 496.64 | 497.3 |
| 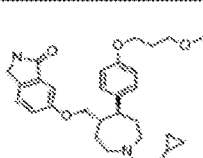 | C0467 | 6-{[(trans)-1-(2-cyclopropylethyl)-5-[4-(3-methoxypropoxy)phenyl]azepan-4-yl]methoxy}-2,3-dihydro-1Hisoindol-1-one | 492.65 | 493.3 |
| 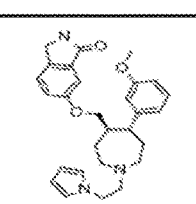 | C0468 | 6-{[(trans)-5-(3-methoxyphenyl)-1-[2-(1H-pyrrol-1-yl)ethyl]azepan-4-yl]methoxy}-2,3-dihydro-1H-isoindol-1-one | 459.58 | 460.25 |
| 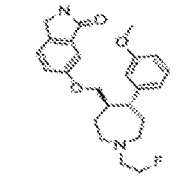 | C0469 | 6-{[(trans)-1-(2-fluoroethyl)-5-(3-methoxyphenyl)azepan-4-yl]methoxy}-2,3-dihydro-1H-isoindol-1-one | 412.5 | 413.2 |
| 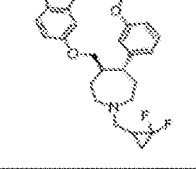 | C0470 | 6-{[(trans)-1-[(2,2-difluorocyclopropyl)methyl]-5-(3-methoxyphenyl)azepan-4-yl]methoxy}-2,3-dihydro-1H-isoindol-1-one | 456.52 | 457.25 |
| 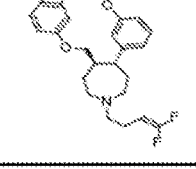 | C0471 | 6-{[(trans)-1-(4,4-difluorobut-3-en-1-yl)-5-(3-methoxyphenyl)azepan-4-yl]methoxy}-2,3-dihydro-1H-isoindol-1-one | 456.52 | 457.2 |
| 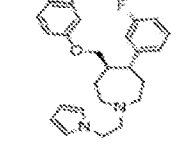 | C0472 | 6-{[(trans)-5-(3-fluorophenyl)-1-[2-(1H-pyrrol-1-yl)ethyl]azepan-4-yl]methoxy}-2,3-dihydro-1H-isoindol-1-one | 447.54 | 448.25 |

Figure 1

| Structure | ID | Name | | |
|---|---|---|---|---|
| 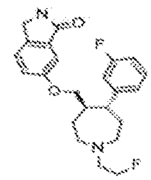 | C0473 | 6-{[(trans)-1-(2-fluoroethyl)-5-(3-fluorophenyl)azepan-4-yl]methoxy}-2,3-dihydro-1H-isoindol-1-one | 400.46 | 401.2 |
| 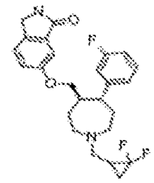 | C0474 | 6-{[(trans)-1-{(2,2-difluorocyclopropyl)methyl]-5-(3-fluorophenyl)azepan-4-yl]methoxy}-2,3-dihydro-1H-isoindol-1-one | 444.49 | 445.2 |
| 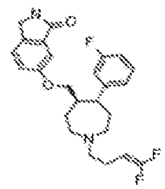 | C0475 | 6-{[(trans)-1-(4,4-difluorobut-3-en-1-yl)-5-(3-fluorophenyl)azepan-4-yl]methoxy}-2,3-dihydro-1H-isoindol-1-one | 444.49 | 445.2 |
| 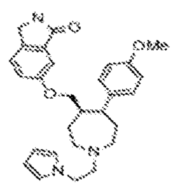 | C0476 | 6-{[(trans)-5-(4-methoxyphenyl)-1-[2-(1H-pyrrol-1-yl)ethyl]azepan-4-yl]methoxy}-2,3-dihydro-1H-isoindol-1-one | 459.58 | 460.3 |
| 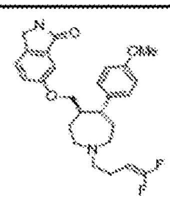 | C0477 | 6-{[(trans)-1-(4,4-difluorobut-3-en-1-yl)-5-(4-methoxyphenyl)azepan-4-yl]methoxy}-2,3-dihydro-1H-isoindol-1-one | 456.52 | 457.2 |
| 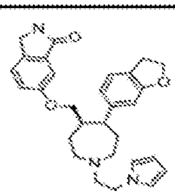 | C0478 | 6-{[(trans)-5-(2,3-dihydro-1-benzofuran-6-yl)-1-[2-(1H-pyrrol-1-yl)ethyl]azepan-4-yl]methoxy}-2,3-dihydro-1H-isoindol-1-one | 471.59 | 472.15 |
| 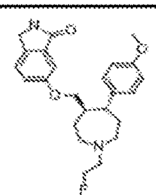 | C0479 | 6-{[(trans)-1-(2-fluoroethyl)-5-(4-methoxyphenyl)azepan-4-yl]methoxy}-2,3-dihydro-1H-isoindol-1-one | 412.5 | 413.1 |
| 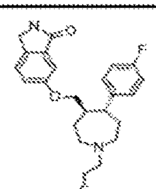 | C0480 | 6-{[(trans)-1-(2-fluoroethyl)-5-(4-fluorophenyl)azepan-4-yl]methoxy}-2,3-dihydro-1H-isoindol-1-one | 400.46 | 401.3 |

Figure 1

| | | | | |
|---|---|---|---|---|
| 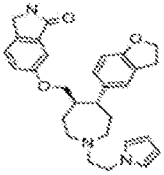 | C0481 | 6-{[(trans)-5-(2,3-dihydro-1-benzofuran-5-yl)-1-[2-(1H-pyrrol-1-yl)ethyl]azepan-4-yl]methoxy}-2,3-dihydro-1H-isoindol-1-one | 471.59 | 472.1 |
| 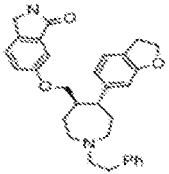 | C0482 | 6-{[(trans)-5-(2,3-dihydro-1-benzofuran-6-yl)-1-(2-phenylethyl)azepan-4-yl]methoxy}-2,3-dihydro-1H-isoindol-1-one | 482.61 | 483.3 |
| 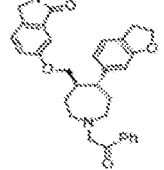 | C0483 | 6-{[(trans)-5-(2,3-dihydro-1-benzofuran-6-yl)-1-(2-oxo-2-phenylethyl)azepan-4-yl]methoxy}-2,3-dihydro-1H-isoindol-1-one | 496.6 | 497.2 |
| 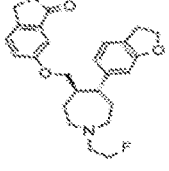 | C0484 | 6-{[(trans)-5-(2,3-dihydro-1-benzofuran-6-yl)-1-(2-fluoroethyl)azepan-4-yl]methoxy}-2,3-dihydro-1H-isoindol-1-one | 424.51 | 425.2 |
| 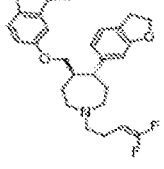 | C0485 | 6-{[(trans)-1-(4,4-difluorobut-3-en-1-yl)-5-(2,3-dihydro-1-benzofuran-6-yl)azepan-4-yl]methoxy}-2,3-dihydro-1H-isoindol-1-one | 468.54 | 469.25 |
| 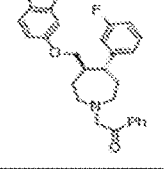 | C0486 | 6-{[(trans)-5-(3-fluorophenyl)-1-(2-oxo-2-phenylethyl)azepan-4-yl]methoxy}-2,3-dihydro-1H-isoindol-1-one | 472.55 | 473.3 |
| 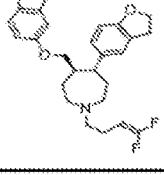 | C0487 | 6-{[(trans)-1-(4,4-difluorobut-3-en-1-yl)-5-(2,3-dihydro-1-benzofuran-5-yl)azepan-4-yl]methoxy}-2,3-dihydro-1H-isoindol-1-one | 468.54 | 469.25 |
| 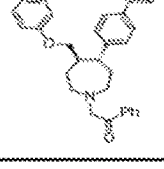 | C0488 | 6-{[(trans)-5-(4-methoxyphenyl)-1-(2-oxo-2-phenylethyl)azepan-4-yl]methoxy}-2,3-dihydro-1H-isoindol-1-one | 484.59 | 485.3 |

Figure 1

| | | | | |
|---|---|---|---|---|
| 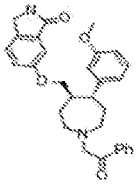 | C0489 | 6-{[(trans)-5-(3-methoxyphenyl)-1-(2-oxo-2-phenylethyl)azepan-4-yl]methoxy}-2,3-dihydro-1H-isoindol-1-one | 484.59 | 485.3 |
| 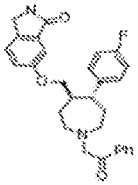 | C0490 | 6-{[(trans)-5-(4-fluorophenyl)-1-(2-oxo-2-phenylethyl)azepan-4-yl]methoxy}-2,3-dihydro-1H-isoindol-1-one | 472.55 | 473.3 |
| 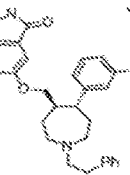 | C0491 | 6-{[(trans)-5-[3-(2-methoxyethoxy)phenyl]-1-(2-phenylethyl)azepan-4-yl]methoxy}-2,3-dihydro-1H-isoindol-1-one | 514.66 | 515.5 |
| 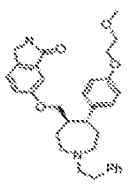 | C0492 | 6-{[(trans)-5-[4-(2-methoxyethoxy)phenyl]-1-(2-phenylethyl)azepan-4-yl]methoxy}-2,3-dihydro-1H-isoindol-1-one | 514.66 | 515.5 |
| 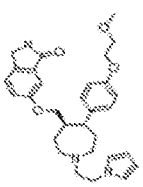 | C0493 | 6-{[(trans)-5-[4-(2-methoxyethoxy)phenyl]-1-[2-(1H-pyrrol-1-yl)ethyl]azepan-4-yl]methoxy}-2,3-dihydro-1H-isoindol-1-one | 503.63 | 504.4 |
| 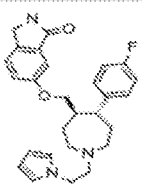 | C0494 | 6-{[(trans)-5-(4-fluorophenyl)-1-[2-(1H-pyrrol-1-yl)ethyl]azepan-4-yl]methoxy}-2,3-dihydro-1H-isoindol-1-one | 447.54 | 448.3 |
| 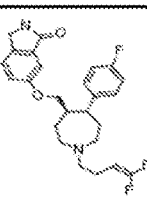 | C0495 | 6-{[(trans)-1-(4,4-difluorobut-3-en-1-yl)-5-(4-fluorophenyl)azepan-4-yl]methoxy}-2,3-dihydro-1H-isoindol-1-one | 444.49 | 446.2 |
| 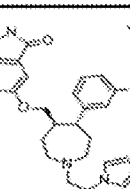 | C0496 | 6-{[(trans)-5-[3-(2-methoxyethoxy)phenyl]-1-[2-(1H-pyrrol-1-yl)ethyl]azepan-4-yl]methoxy}-2,3-dihydro-1H-isoindol-1-one | 503.63 | 504.25 |

Figure 1

| | | | | |
|---|---|---|---|---|
| 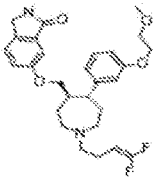 | C0497 | 6-{[(trans)-1-(4,4-difluorobut-3-en-1-yl)-5-[3-(2-methoxyethoxy)phenyl]azepan-4-yl]methoxy}-2,3-dihydro-1H-isoindol-1-one | 500.58 | 501.2 |
| 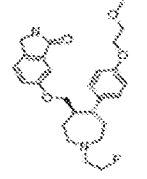 | C0498 | 6-{[(trans)-1-(2-fluoroethyl)-5-[4-(2-methoxyethoxy)phenyl]azepan-4-yl]methoxy}-2,3-dihydro-1H-isoindol-1-one | 456.55 | 457.2 |
| 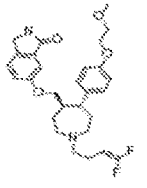 | C0499 | 6-{[(trans)-1-(4,4-difluorobut-3-en-1-yl)-5-[4-(2-methoxyethoxy)phenyl]azepan-4-yl]methoxy}-2,3-dihydro-1H-isoindol-1-one | 500.58 | 501.25 |
| 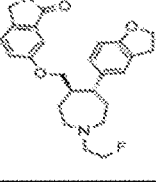 | C0500 | 6-{[(trans)-5-(2,3-dihydro-1-benzofuran-5-yl)-1-(2-fluoroethyl)azepan-4-yl]methoxy}-2,3-dihydro-1H-isoindol-1-one | 424.51 | 425.1 |
| 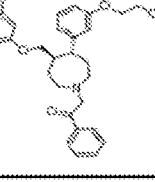 | C0501 | 6-{[(trans)-5-[3-(2-methoxyethoxy)phenyl]-1-(2-oxo-2-phenylethyl)azepan-4-yl]methoxy}-2,3-dihydro-1H-isoindol-1-one | 528.64 | 529.3 |
| 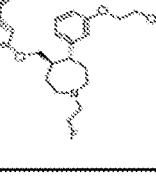 | C0502 | 6-{[(trans)-1-(2-fluoroethyl)-5-[3-(2-methoxyethoxy)phenyl]azepan-4-yl]methoxy}-2,3-dihydro-1H-isoindol-1-one | 456.55 | 457.2 |
| 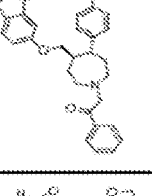 | C0503 | 6-{[(trans)-5-[4-(2-methoxyethoxy)phenyl]-1-(2-oxo-2-phenylethyl)azepan-4-yl]methoxy}-2,3-dihydro-1H-isoindol-1-one | 528.64 | 529.25 |
| 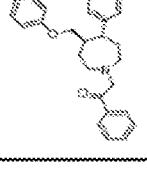 | C0504 | 6-{[(trans)-5-(2,3-dihydro-1-benzofuran-5-yl)-1-(2-oxo-2-phenylethyl)azepan-4-yl]methoxy}-2,3-dihydro-1H-isoindol-1-one | 496.6 | 497.2 |

Figure 1

| | | | | |
|---|---|---|---|---|
| 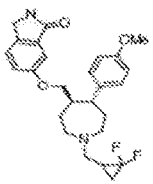 | C0505 | 6-{[(trans)-1-[(2,2-difluorocyclopropyl)methyl]-5-(4-methoxyphenyl)azepan-4-yl]methoxy}-2,3-dihydro-1H-isoindol-1-one | 456.52 | 457.2 |
| 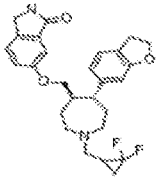 | C0506 | 6-{[(trans)-1-[(2,2-difluorocyclopropyl)methyl]-5-(2,3-dihydro-1-benzofuran-6-yl)azepan-4-yl]methoxy}-2,3-dihydro-1H-isoindol-1-one | 468.54 | 469.15 |
| 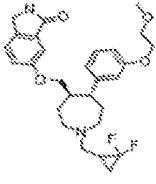 | C0507 | 6-{[(trans)-1-[(2,2-difluorocyclopropyl)methyl]-5-[3-(2-methoxyethoxy)phenyl]azepan-4-yl]methoxy}-2,3-dihydro-1H-isoindol-1-one | 500.58 | 501.3 |
| 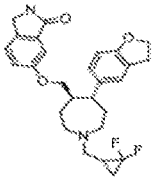 | C0508 | 6-{[(trans)-1-[(2,2-difluorocyclopropyl)methyl]-5-(2,3-dihydro-1-benzofuran-5-yl)azepan-4-yl]methoxy}-2,3-dihydro-1H-isoindol-1-one | 468.54 | 469.5 |
| 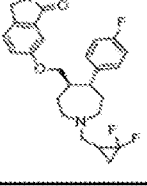 | C0509 | 6-{[(trans)-1-[(2,2-difluorocyclopropyl)methyl]-5-(4-fluorophenyl)azepan-4-yl]methoxy}-2,3-dihydro-1H-isoindol-1-one | 444.49 | 445.1 |

Figure 2

| Compd. | hDOR | | | | hMOR | | | | hKOR | | | |
|---|---|---|---|---|---|---|---|---|---|---|---|---|
| | G-protein $pEC_{50}$ | G-protein %eff | βarr2 $pEC_{50}$ | βarr2 %eff | G-protein $pEC_{50}$ | G-protein %eff | βarr2 $pEC_{50}$ | βarr2 %eff | G-protein $pEC_{50}$ | G-protein %eff | βarr2 $pEC_{50}$ | βarr2 %eff |
| C0001 | < 7 | ≥ 50 | < 7 | < 50 | < 7 | ≥ 50 | < 7 | < 50 | < 7 | ≥ 50 | < 7 | < 50 |
| C0002 | ≥ 7 | ≥ 50 | < 7 | < 50 | < 7 | < 50 | < 7 | < 50 | < 7 | ≥ 50 | < 7 | < 50 |
| C0003 | < 7 | ≥ 50 | < 7 | < 50 | < 7 | < 50 | < 7 | < 50 | < 7 | ≥ 50 | < 7 | < 50 |
| C0004 | ≥ 7 | ≥ 50 | < 7 | < 50 | < 7 | < 50 | < 7 | < 50 | < 7 | ≥ 50 | < 7 | < 50 |
| C0005 | < 7 | ≥ 50 | < 7 | < 50 | < 7 | ≥ 50 | < 7 | < 50 | < 7 | < 50 | < 7 | < 50 |
| C0006 | < 7 | ≥ 50 | < 7 | < 50 | < 7 | ≥ 50 | < 7 | < 50 | < 7 | < 50 | < 7 | < 50 |
| C0007 | < 7 | ≥ 50 | < 7 | < 50 | < 7 | < 50 | < 7 | < 50 | < 7 | < 50 | < 7 | < 50 |
| C0008 | < 7 | ≥ 50 | < 7 | < 50 | < 7 | < 50 | < 7 | < 50 | < 7 | < 50 | < 7 | < 50 |
| C0009 | < 7 | ≥ 50 | < 7 | < 50 | < 7 | < 50 | < 7 | < 50 | < 7 | ≥ 50 | < 7 | < 50 |
| C0010 | < 7 | < 50 | < 7 | < 50 | < 7 | < 50 | < 7 | < 50 | < 7 | < 50 | < 7 | < 50 |
| C0011 | < 7 | ≥ 50 | < 7 | < 50 | < 7 | < 50 | < 7 | < 50 | < 7 | < 50 | < 7 | < 50 |
| C0012 | < 7 | ≥ 50 | < 7 | < 50 | < 7 | ≥ 50 | < 7 | < 50 | < 7 | < 50 | < 7 | < 50 |
| C0013 | < 7 | ≥ 50 | < 7 | < 50 | < 7 | < 50 | < 7 | < 50 | < 7 | ≥ 50 | < 7 | < 50 |
| C0014 | < 7 | < 50 | < 7 | < 50 | < 7 | < 50 | < 7 | < 50 | < 7 | < 50 | < 7 | < 50 |
| C0015 | < 7 | ≥ 50 | < 7 | < 50 | < 7 | < 50 | < 7 | < 50 | < 7 | < 50 | < 7 | < 50 |
| C0016 | < 7 | ≥ 50 | < 7 | < 50 | < 7 | < 50 | < 7 | < 50 | < 7 | < 50 | < 7 | < 50 |
| C0017 | < 7 | ≥ 50 | < 7 | < 50 | < 7 | < 50 | < 7 | < 50 | < 7 | ≥ 50 | < 7 | < 50 |
| C0018 | ≥ 7 | ≥ 50 | < 7 | < 50 | < 7 | < 50 | < 7 | < 50 | < 7 | < 50 | < 7 | < 50 |
| C0019 | ≥ 7 | ≥ 50 | < 7 | ≥ 50 | < 7 | < 50 | < 7 | < 50 | < 7 | ≥ 50 | < 7 | < 50 |
| C0020 | < 7 | ≥ 50 | < 7 | < 50 | < 7 | < 50 | < 7 | < 50 | < 7 | < 50 | < 7 | < 50 |
| C0021 | < 7 | ≥ 50 | < 7 | < 50 | < 7 | < 50 | < 7 | < 50 | < 7 | < 50 | < 7 | < 50 |
| C0022 | < 7 | ≥ 50 | < 7 | < 50 | < 7 | < 50 | < 7 | < 50 | < 7 | < 50 | < 7 | < 50 |
| C0023 | ≥ 7 | ≥ 50 | < 7 | ≥ 50 | < 7 | < 50 | < 7 | < 50 | < 7 | ≥ 50 | < 7 | < 50 |
| C0024 | ≥ 7 | ≥ 50 | < 7 | < 50 | < 7 | < 50 | < 7 | < 50 | < 7 | < 50 | < 7 | < 50 |
| C0025 | < 7 | ≥ 50 | < 7 | < 50 | < 7 | < 50 | < 7 | < 50 | < 7 | ≥ 50 | < 7 | < 50 |
| C0026 | < 7 | ≥ 50 | < 7 | < 50 | < 7 | < 50 | < 7 | < 50 | < 7 | < 50 | < 7 | < 50 |
| C0027 | < 7 | ≥ 50 | < 7 | < 50 | < 7 | < 50 | < 7 | < 50 | < 7 | < 50 | < 7 | < 50 |
| C0028 | < 7 | ≥ 50 | < 7 | < 50 | < 7 | < 50 | < 7 | < 50 | < 7 | < 50 | < 7 | < 50 |
| C0029 | < 7 | ≥ 50 | < 7 | < 50 | < 7 | < 50 | < 7 | < 50 | < 7 | < 50 | < 7 | < 50 |
| C0030 | < 7 | ≥ 50 | < 7 | < 50 | < 7 | < 50 | < 7 | < 50 | < 7 | < 50 | < 7 | < 50 |
| C0031 | < 7 | ≥ 50 | < 7 | < 50 | < 7 | < 50 | < 7 | < 50 | < 7 | < 50 | < 7 | < 50 |
| C0032 | ≥ 7 | ≥ 50 | < 7 | < 50 | < 7 | < 50 | < 7 | < 50 | < 7 | < 50 | < 7 | < 50 |
| C0033 | ≥ 7 | ≥ 50 | < 7 | < 50 | < 7 | < 50 | < 7 | < 50 | < 7 | < 50 | < 7 | < 50 |
| C0034 | < 7 | ≥ 50 | < 7 | < 50 | < 7 | ≥ 50 | < 7 | < 50 | < 7 | < 50 | < 7 | < 50 |
| C0035 | ≥ 7 | ≥ 50 | < 7 | ≥ 50 | < 7 | < 50 | < 7 | < 50 | < 7 | < 50 | < 7 | < 50 |
| C0036 | < 7 | ≥ 50 | < 7 | < 50 | < 7 | < 50 | < 7 | < 50 | < 7 | < 50 | < 7 | < 50 |
| C0037 | < 7 | ≥ 50 | < 7 | < 50 | < 7 | < 50 | < 7 | < 50 | < 7 | ≥ 50 | < 7 | < 50 |
| C0038 | ≥ 7 | ≥ 50 | < 7 | < 50 | < 7 | < 50 | < 7 | < 50 | < 7 | ≥ 50 | < 7 | < 50 |
| C0039 | < 7 | ≥ 50 | < 7 | < 50 | < 7 | ≥ 50 | < 7 | < 50 | < 7 | < 50 | < 7 | < 50 |
| C0040 | < 7 | ≥ 50 | < 7 | < 50 | < 7 | ≥ 50 | < 7 | < 50 | < 7 | ≥ 50 | < 7 | < 50 |
| C0041 | < 7 | ≥ 50 | < 7 | < 50 | < 7 | < 50 | < 7 | < 50 | < 7 | < 50 | < 7 | < 50 |
| C0042 | < 7 | ≥ 50 | < 7 | < 50 | < 7 | ≥ 50 | < 7 | < 50 | < 7 | < 50 | < 7 | < 50 |
| C0043 | < 7 | ≥ 50 | < 7 | < 50 | < 7 | < 50 | < 7 | < 50 | < 7 | < 50 | < 7 | < 50 |
| C0044 | < 7 | ≥ 50 | < 7 | < 50 | < 7 | < 50 | < 7 | < 50 | < 7 | < 50 | < 7 | < 50 |
| C0045 | < 7 | ≥ 50 | < 7 | < 50 | < 7 | < 50 | < 7 | < 50 | < 7 | < 50 | < 7 | < 50 |
| C0046 | ≥ 7 | ≥ 50 | < 7 | ≥ 50 | < 7 | ≥ 50 | < 7 | < 50 | < 7 | ≥ 50 | < 7 | < 50 |
| C0047 | < 7 | ≥ 50 | < 7 | < 50 | < 7 | < 50 | < 7 | < 50 | < 7 | < 50 | < 7 | < 50 |
| C0048 | ≥ 7 | ≥ 50 | < 7 | < 50 | < 7 | < 50 | < 7 | < 50 | < 7 | ≥ 50 | < 7 | < 50 |
| C0049 | < 7 | ≥ 50 | < 7 | < 50 | < 7 | < 50 | < 7 | < 50 | < 7 | < 50 | < 7 | < 50 |
| C0050 | ≥ 7 | ≥ 50 | < 7 | < 50 | < 7 | < 50 | < 7 | < 50 | < 7 | < 50 | < 7 | < 50 |
| C0051 | < 7 | ≥ 50 | < 7 | < 50 | < 7 | < 50 | < 7 | < 50 | < 7 | < 50 | < 7 | < 50 |

Figure 2

| | | | | | | | | | | | |
|---|---|---|---|---|---|---|---|---|---|---|---|
| C0052 | ≥ 7 | ≥ 50 | < 7 | < 50 | < 7 | < 50 | < 7 | < 50 | < 7 | < 50 | < 7 | < 50 |
| C0053 | ≥ 7 | ≥ 50 | < 7 | ≥ 50 | < 7 | ≥ 50 | < 7 | < 50 | < 7 | ≥ 50 | < 7 | < 50 |
| C0054 | < 7 | ≥ 50 | < 7 | < 50 | < 7 | < 50 | < 7 | < 50 | < 7 | < 50 | < 7 | < 50 |
| C0055 | < 7 | ≥ 50 | < 7 | < 50 | < 7 | < 50 | < 7 | < 50 | < 7 | < 50 | < 7 | < 50 |
| C0056 | ≥ 7 | ≥ 50 | < 7 | ≥ 50 | < 7 | < 50 | < 7 | < 50 | < 7 | ≥ 50 | < 7 | < 50 |
| C0057 | < 7 | ≥ 50 | < 7 | < 50 | < 7 | ≥ 50 | < 7 | < 50 | < 7 | < 50 | < 7 | < 50 |
| C0058 | < 7 | ≥ 50 | < 7 | < 50 | < 7 | ≥ 50 | < 7 | < 50 | < 7 | < 50 | < 7 | < 50 |
| C0059 | < 7 | ≥ 50 | < 7 | < 50 | < 7 | < 50 | < 7 | < 50 | < 7 | < 50 | < 7 | < 50 |
| C0060 | < 7 | ≥ 50 | < 7 | < 50 | < 7 | < 50 | < 7 | < 50 | < 7 | < 50 | < 7 | < 50 |
| C0061 | ≥ 7 | ≥ 50 | < 7 | < 50 | < 7 | < 50 | < 7 | < 50 | < 7 | < 50 | < 7 | < 50 |
| C0062 | < 7 | < 50 | < 7 | < 50 | < 7 | < 50 | < 7 | < 50 | < 7 | < 50 | < 7 | < 50 |
| C0063 | < 7 | ≥ 50 | < 7 | < 50 | < 7 | < 50 | < 7 | < 50 | < 7 | < 50 | < 7 | < 50 |
| C0064 | < 7 | ≥ 50 | < 7 | < 50 | < 7 | ≥ 50 | < 7 | < 50 | < 7 | < 50 | < 7 | < 50 |
| C0065 | ≥ 7 | ≥ 50 | < 7 | ≥ 50 | < 7 | < 50 | < 7 | < 50 | < 7 | < 50 | < 7 | < 50 |
| C0066 | ≥ 7 | ≥ 50 | < 7 | < 50 | < 7 | < 50 | < 7 | < 50 | < 7 | ≥ 50 | < 7 | < 50 |
| C0067 | ≥ 7 | ≥ 50 | < 7 | < 50 | < 7 | < 50 | < 7 | < 50 | < 7 | ≥ 50 | < 7 | < 50 |
| C0068 | < 7 | ≥ 50 | < 7 | < 50 | < 7 | ≥ 50 | < 7 | < 50 | < 7 | < 50 | < 7 | < 50 |
| C0069 | < 7 | ≥ 50 | < 7 | < 50 | < 7 | ≥ 50 | < 7 | < 50 | < 7 | < 50 | < 7 | < 50 |
| C0070 | < 7 | ≥ 50 | < 7 | < 50 | < 7 | < 50 | < 7 | < 50 | < 7 | < 50 | < 7 | < 50 |
| C0071 | < 7 | ≥ 50 | < 7 | < 50 | < 7 | < 50 | < 7 | < 50 | < 7 | < 50 | < 7 | < 50 |
| C0072 | < 7 | ≥ 50 | < 7 | < 50 | < 7 | ≥ 50 | < 7 | < 50 | < 7 | < 50 | < 7 | < 50 |
| C0073 | < 7 | ≥ 50 | < 7 | < 50 | < 7 | < 50 | < 7 | < 50 | < 7 | < 50 | < 7 | < 50 |
| C0074 | < 7 | ≥ 50 | < 7 | < 50 | < 7 | ≥ 50 | < 7 | < 50 | < 7 | < 50 | < 7 | < 50 |
| C0075 | < 7 | ≥ 50 | < 7 | < 50 | < 7 | < 50 | < 7 | < 50 | < 7 | < 50 | < 7 | < 50 |
| C0076 | ≥ 7 | ≥ 50 | < 7 | < 50 | < 7 | < 50 | < 7 | < 50 | < 7 | ≥ 50 | < 7 | < 50 |
| C0077 | < 7 | ≥ 50 | < 7 | < 50 | < 7 | < 50 | < 7 | < 50 | < 7 | < 50 | < 7 | < 50 |
| C0078 | < 7 | ≥ 50 | < 7 | ≥ 50 | < 7 | ≥ 50 | < 7 | < 50 | < 7 | < 50 | < 7 | < 50 |
| C0079 | < 7 | ≥ 50 | < 7 | < 50 | < 7 | < 50 | < 7 | < 50 | < 7 | < 50 | < 7 | < 50 |
| C0080 | < 7 | ≥ 50 | < 7 | < 50 | < 7 | ≥ 50 | < 7 | < 50 | < 7 | < 50 | < 7 | < 50 |
| C0081 | < 7 | ≥ 50 | < 7 | < 50 | < 7 | < 50 | < 7 | < 50 | < 7 | < 50 | < 7 | < 50 |
| C0082 | ≥ 7 | ≥ 50 | < 7 | < 50 | < 7 | < 50 | < 7 | < 50 | < 7 | < 50 | < 7 | < 50 |
| C0083 | < 7 | < 50 | < 7 | < 50 | < 7 | < 50 | < 7 | < 50 | < 7 | < 50 | < 7 | < 50 |
| C0084 | ≥ 7 | ≥ 50 | < 7 | < 50 | < 7 | < 50 | < 7 | < 50 | < 7 | ≥ 50 | < 7 | < 50 |
| C0085 | < 7 | < 50 | < 7 | < 50 | < 7 | ≥ 50 | < 7 | < 50 | < 7 | < 50 | < 7 | < 50 |
| C0086 | ≥ 7 | ≥ 50 | < 7 | < 50 | < 7 | < 50 | < 7 | < 50 | < 7 | ≥ 50 | < 7 | < 50 |
| C0087 | < 7 | ≥ 50 | < 7 | < 50 | < 7 | ≥ 50 | < 7 | < 50 | < 7 | ≥ 50 | < 7 | < 50 |
| C0088 | < 7 | ≥ 50 | < 7 | < 50 | < 7 | < 50 | < 7 | < 50 | < 7 | < 50 | < 7 | < 50 |
| C0089 | < 7 | ≥ 50 | < 7 | < 50 | < 7 | ≥ 50 | < 7 | < 50 | < 7 | < 50 | < 7 | < 50 |
| C0090 | < 7 | ≥ 50 | < 7 | < 50 | < 7 | ≥ 50 | < 7 | < 50 | < 7 | < 50 | < 7 | < 50 |
| C0091 | < 7 | ≥ 50 | < 7 | < 50 | < 7 | < 50 | < 7 | < 50 | < 7 | < 50 | < 7 | < 50 |
| C0092 | < 7 | ≥ 50 | < 7 | < 50 | < 7 | < 50 | < 7 | < 50 | < 7 | < 50 | < 7 | < 50 |
| C0093 | < 7 | ≥ 50 | < 7 | < 50 | < 7 | < 50 | < 7 | < 50 | < 7 | < 50 | < 7 | < 50 |
| C0094 | < 7 | < 50 | < 7 | < 50 | < 7 | < 50 | < 7 | < 50 | < 7 | < 50 | < 7 | < 50 |
| C0095 | < 7 | < 50 | < 7 | < 50 | < 7 | < 50 | < 7 | < 50 | < 7 | < 50 | < 7 | < 50 |
| C0096 | ≥ 7 | ≥ 50 | < 7 | ≥ 50 | < 7 | ≥ 50 | < 7 | < 50 | < 7 | < 50 | < 7 | < 50 |
| C0097 | ≥ 7 | ≥ 50 | < 7 | < 50 | < 7 | ≥ 50 | < 7 | < 50 | < 7 | ≥ 50 | < 7 | ≥ 50 |
| C0098 | < 7 | ≥ 50 | < 7 | < 50 | < 7 | < 50 | < 7 | < 50 | < 7 | < 50 | < 7 | < 50 |
| C0099 | ≥ 7 | ≥ 50 | < 7 | < 50 | < 7 | ≥ 50 | < 7 | < 50 | < 7 | ≥ 50 | < 7 | < 50 |
| C0100 | ≥ 7 | ≥ 50 | < 7 | < 50 | < 7 | < 50 | < 7 | < 50 | ≥ 7 | ≥ 50 | < 7 | < 50 |
| C0101 | ≥ 7 | ≥ 50 | < 7 | < 50 | < 7 | ≥ 50 | < 7 | < 50 | < 7 | ≥ 50 | < 7 | < 50 |
| C0102 | < 7 | ≥ 50 | < 7 | < 50 | < 7 | ≥ 50 | < 7 | < 50 | < 7 | < 50 | < 7 | < 50 |
| C0103 | < 7 | < 50 | < 7 | < 50 | < 7 | < 50 | < 7 | < 50 | < 7 | < 50 | < 7 | < 50 |
| C0104 | < 7 | < 50 | < 7 | < 50 | < 7 | < 50 | < 7 | < 50 | < 7 | < 50 | < 7 | < 50 |
| C0105 | < 7 | ≥ 50 | < 7 | < 50 | < 7 | < 50 | < 7 | < 50 | < 7 | < 50 | < 7 | < 50 |
| C0106 | < 7 | ≥ 50 | < 7 | < 50 | < 7 | ≥ 50 | < 7 | < 50 | < 7 | ≥ 50 | < 7 | < 50 |

Figure 2

| | | | | | | | | | | | | |
|---|---|---|---|---|---|---|---|---|---|---|---|---|
| C0107 | < 7 | ≥ 50 | < 7 | < 50 | < 7 | ≥ 50 | < 7 | < 50 | < 7 | ≥ 50 | < 7 | < 50 |
| C0108 | < 7 | ≥ 50 | < 7 | < 50 | < 7 | < 50 | < 7 | < 50 | < 7 | < 50 | < 7 | < 50 |
| C0109 | < 7 | ≥ 50 | < 7 | < 50 | < 7 | < 50 | < 7 | < 50 | < 7 | < 50 | < 7 | < 50 |
| C0110 | ≥ 7 | ≥ 50 | < 7 | ≥ 50 | < 7 | ≥ 50 | < 7 | < 50 | < 7 | ≥ 50 | < 7 | < 50 |
| C0111 | ≥ 7 | ≥ 50 | < 7 | < 50 | < 7 | < 50 | < 7 | < 50 | < 7 | < 50 | < 7 | < 50 |
| C0112 | ≥ 7 | ≥ 50 | < 7 | < 50 | < 7 | < 50 | < 7 | < 50 | < 7 | < 50 | < 7 | < 50 |
| C0113 | ≥ 7 | ≥ 50 | < 7 | < 50 | < 7 | ≥ 50 | < 7 | < 50 | < 7 | ≥ 50 | < 7 | < 50 |
| C0114 | ≥ 7 | ≥ 50 | < 7 | < 50 | < 7 | < 50 | < 7 | < 50 | < 7 | ≥ 50 | < 7 | < 50 |
| C0115 | ≥ 7 | ≥ 50 | < 7 | ≥ 50 | < 7 | ≥ 50 | < 7 | < 50 | < 7 | ≥ 50 | < 7 | < 50 |
| C0116 | < 7 | ≥ 50 | < 7 | < 50 | < 7 | < 50 | < 7 | < 50 | < 7 | < 50 | < 7 | < 50 |
| C0117 | < 7 | ≥ 50 | < 7 | < 50 | < 7 | < 50 | < 7 | < 50 | < 7 | < 50 | < 7 | < 50 |
| C0118 | < 7 | ≥ 50 | < 7 | < 50 | < 7 | < 50 | < 7 | < 50 | < 7 | < 50 | < 7 | < 50 |
| C0119 | < 7 | < 50 | < 7 | < 50 | < 7 | < 50 | < 7 | < 50 | < 7 | < 50 | < 7 | < 50 |
| C0120 | ≥ 7 | ≥ 50 | < 7 | < 50 | < 7 | ≥ 50 | < 7 | < 50 | < 7 | < 50 | < 7 | < 50 |
| C0121 | ≥ 7 | ≥ 50 | < 7 | < 50 | < 7 | < 50 | < 7 | < 50 | < 7 | ≥ 50 | < 7 | < 50 |
| C0122 | ≥ 7 | ≥ 50 | < 7 | < 50 | < 7 | < 50 | < 7 | < 50 | < 7 | < 50 | < 7 | < 50 |
| C0123 | ≥ 7 | ≥ 50 | < 7 | ≥ 50 | < 7 | ≥ 50 | < 7 | < 50 | < 7 | ≥ 50 | < 7 | < 50 |
| C0124 | ≥ 7 | ≥ 50 | < 7 | ≥ 50 | < 7 | < 50 | < 7 | < 50 | < 7 | ≥ 50 | < 7 | < 50 |
| C0125 | ≥ 7 | ≥ 50 | < 7 | < 50 | < 7 | < 50 | < 7 | < 50 | < 7 | ≥ 50 | < 7 | < 50 |
| C0126 | < 7 | ≥ 50 | < 7 | < 50 | < 7 | ≥ 50 | < 7 | < 50 | < 7 | < 50 | < 7 | < 50 |
| C0127 | ≥ 7 | ≥ 50 | < 7 | < 50 | < 7 | < 50 | < 7 | < 50 | < 7 | < 50 | < 7 | < 50 |
| C0128 | ≥ 7 | ≥ 50 | < 7 | ≥ 50 | < 7 | < 50 | < 7 | < 50 | < 7 | ≥ 50 | < 7 | < 50 |
| C0129 | ≥ 7 | ≥ 50 | < 7 | < 50 | < 7 | ≥ 50 | < 7 | < 50 | < 7 | ≥ 50 | < 7 | < 50 |
| C0130 | ≥ 7 | ≥ 50 | < 7 | < 50 | < 7 | < 50 | < 7 | < 50 | < 7 | ≥ 50 | < 7 | < 50 |
| C0131 | < 7 | < 50 | < 7 | < 50 | < 7 | < 50 | < 7 | < 50 | < 7 | < 50 | < 7 | < 50 |
| C0132 | < 7 | < 50 | < 7 | < 50 | < 7 | < 50 | < 7 | < 50 | < 7 | < 50 | < 7 | < 50 |
| C0133 | < 7 | ≥ 50 | < 7 | < 50 | < 7 | < 50 | < 7 | < 50 | < 7 | < 50 | < 7 | < 50 |
| C0134 | < 7 | ≥ 50 | < 7 | < 50 | < 7 | < 50 | < 7 | < 50 | < 7 | < 50 | < 7 | < 50 |
| C0135 | ≥ 7 | ≥ 50 | < 7 | ≥ 50 | < 7 | < 50 | < 7 | < 50 | < 7 | < 50 | < 7 | < 50 |
| C0136 | < 7 | ≥ 50 | < 7 | < 50 | < 7 | < 50 | < 7 | < 50 | < 7 | < 50 | < 7 | < 50 |
| C0137 | ≥ 7 | ≥ 50 | < 7 | < 50 | < 7 | < 50 | < 7 | < 50 | < 7 | < 50 | < 7 | < 50 |
| C0138 | < 7 | < 50 | < 7 | < 50 | < 7 | < 50 | < 7 | < 50 | < 7 | < 50 | < 7 | < 50 |
| C0139 | < 7 | ≥ 50 | < 7 | < 50 | < 7 | < 50 | < 7 | < 50 | < 7 | ≥ 50 | < 7 | < 50 |
| C0140 | ≥ 7 | ≥ 50 | < 7 | ≥ 50 | < 7 | ≥ 50 | < 7 | < 50 | < 7 | ≥ 50 | < 7 | < 50 |
| C0141 | ≥ 7 | ≥ 50 | < 7 | < 50 | < 7 | < 50 | < 7 | < 50 | < 7 | ≥ 50 | < 7 | < 50 |
| C0142 | < 7 | ≥ 50 | < 7 | < 50 | < 7 | ≥ 50 | < 7 | < 50 | < 7 | ≥ 50 | < 7 | < 50 |
| C0143 | < 7 | ≥ 50 | < 7 | < 50 | < 7 | < 50 | < 7 | < 50 | < 7 | ≥ 50 | < 7 | < 50 |
| C0144 | < 7 | ≥ 50 | < 7 | < 50 | < 7 | < 50 | < 7 | < 50 | < 7 | ≥ 50 | < 7 | < 50 |
| C0145 | < 7 | ≥ 50 | < 7 | < 50 | < 7 | < 50 | < 7 | < 50 | < 7 | ≥ 50 | < 7 | < 50 |
| C0146 | < 7 | ≥ 50 | < 7 | < 50 | < 7 | < 50 | < 7 | < 50 | < 7 | < 50 | < 7 | < 50 |
| C0147 | ≥ 7 | ≥ 50 | < 7 | ≥ 50 | < 7 | < 50 | < 7 | < 50 | < 7 | < 50 | < 7 | < 50 |
| C0148 | ≥ 7 | ≥ 50 | < 7 | ≥ 50 | < 7 | < 50 | < 7 | < 50 | < 7 | ≥ 50 | < 7 | < 50 |
| C0149 | ≥ 7 | ≥ 50 | < 7 | ≥ 50 | < 7 | < 50 | < 7 | < 50 | < 7 | < 50 | < 7 | < 50 |
| C0150 | < 7 | ≥ 50 | < 7 | < 50 | < 7 | < 50 | < 7 | < 50 | < 7 | < 50 | < 7 | < 50 |
| C0151 | ≥ 7 | ≥ 50 | < 7 | ≥ 50 | < 7 | < 50 | < 7 | < 50 | < 7 | < 50 | < 7 | < 50 |
| C0152 | ≥ 7 | ≥ 50 | < 7 | ≥ 50 | < 7 | < 50 | < 7 | < 50 | < 7 | < 50 | < 7 | < 50 |
| C0153 | < 7 | ≥ 50 | < 7 | < 50 | < 7 | < 50 | < 7 | < 50 | < 7 | < 50 | < 7 | < 50 |
| C0154 | < 7 | ≥ 50 | < 7 | ≥ 50 | < 7 | ≥ 50 | < 7 | < 50 | < 7 | ≥ 50 | < 7 | < 50 |
| C0155 | < 7 | ≥ 50 | < 7 | < 50 | < 7 | < 50 | < 7 | < 50 | < 7 | ≥ 50 | < 7 | < 50 |
| C0156 | ≥ 7 | ≥ 50 | < 7 | < 50 | < 7 | < 50 | < 7 | < 50 | < 7 | ≥ 50 | < 7 | ≥ 50 |
| C0157 | ≥ 7 | ≥ 50 | < 7 | < 50 | < 7 | < 50 | < 7 | < 50 | < 7 | ≥ 50 | < 7 | < 50 |
| C0158 | < 7 | ≥ 50 | < 7 | < 50 | < 7 | < 50 | < 7 | < 50 | < 7 | ≥ 50 | < 7 | < 50 |
| C0159 | ≥ 7 | ≥ 50 | < 7 | < 50 | < 7 | ≥ 50 | < 7 | < 50 | < 7 | ≥ 50 | < 7 | < 50 |
| C0160 | ≥ 7 | ≥ 50 | < 7 | ≥ 50 | < 7 | < 50 | < 7 | < 50 | < 7 | ≥ 50 | < 7 | < 50 |
| C0161 | ≥ 7 | ≥ 50 | < 7 | < 50 | < 7 | < 50 | < 7 | < 50 | < 7 | ≥ 50 | < 7 | < 50 |

Figure 2

| | | | | | | | | | | | | |
|---|---|---|---|---|---|---|---|---|---|---|---|---|
| C0162 | ≥ 7 | ≥ 50 | ≥ 7 | ≥ 50 | < 7 | ≥ 50 | < 7 | < 50 | < 7 | ≥ 50 | < 7 | < 50 |
| C0163 | ≥ 7 | ≥ 50 | < 7 | ≥ 50 | < 7 | < 50 | < 7 | < 50 | < 7 | ≥ 50 | < 7 | < 50 |
| C0164 | ≥ 7 | ≥ 50 | < 7 | ≥ 50 | < 7 | ≥ 50 | < 7 | < 50 | ≥ 7 | ≥ 50 | < 7 | < 50 |
| C0165 | ≥ 7 | ≥ 50 | < 7 | < 50 | < 7 | ≥ 50 | < 7 | < 50 | < 7 | ≥ 50 | < 7 | < 50 |
| C0166 | ≥ 7 | ≥ 50 | ≥ 7 | ≥ 50 | < 7 | ≥ 50 | < 7 | < 50 | < 7 | ≥ 50 | < 7 | < 50 |
| C0167 | ≥ 7 | ≥ 50 | ≥ 7 | ≥ 50 | < 7 | ≥ 50 | < 7 | < 50 | < 7 | ≥ 50 | < 7 | < 50 |
| C0168 | ≥ 7 | ≥ 50 | < 7 | ≥ 50 | < 7 | < 50 | < 7 | < 50 | < 7 | ≥ 50 | < 7 | < 50 |
| C0169 | ≥ 7 | ≥ 50 | < 7 | ≥ 50 | < 7 | < 50 | < 7 | < 50 | < 7 | ≥ 50 | < 7 | < 50 |
| C0170 | < 7 | ≥ 50 | < 7 | < 50 | < 7 | < 50 | < 7 | < 50 | < 7 | ≥ 50 | < 7 | < 50 |
| C0171 | ≥ 7 | ≥ 50 | < 7 | ≥ 50 | < 7 | ≥ 50 | < 7 | < 50 | < 7 | ≥ 50 | < 7 | < 50 |
| C0172 | < 7 | ≥ 50 | < 7 | < 50 | < 7 | < 50 | < 7 | < 50 | < 7 | ≥ 50 | < 7 | < 50 |
| C0173 | < 7 | ≥ 50 | < 7 | < 50 | < 7 | ≥ 50 | < 7 | < 50 | < 7 | ≥ 50 | < 7 | < 50 |
| C0174 | ≥ 7 | ≥ 50 | < 7 | < 50 | < 7 | ≥ 50 | < 7 | < 50 | < 7 | ≥ 50 | < 7 | < 50 |
| C0175 | < 7 | ≥ 50 | < 7 | < 50 | < 7 | < 50 | < 7 | < 50 | < 7 | ≥ 50 | < 7 | < 50 |
| C0176 | < 7 | ≥ 50 | < 7 | < 50 | < 7 | ≥ 50 | < 7 | < 50 | < 7 | < 50 | < 7 | < 50 |
| C0177 | ≥ 7 | ≥ 50 | < 7 | < 50 | < 7 | ≥ 50 | < 7 | < 50 | < 7 | ≥ 50 | < 7 | < 50 |
| C0178 | < 7 | ≥ 50 | < 7 | < 50 | < 7 | < 50 | < 7 | < 50 | < 7 | < 50 | < 7 | < 50 |
| C0179 | ≥ 7 | ≥ 50 | < 7 | < 50 | < 7 | < 50 | < 7 | < 50 | < 7 | ≥ 50 | < 7 | < 50 |
| C0180 | ≥ 7 | ≥ 50 | < 7 | < 50 | < 7 | < 50 | < 7 | < 50 | < 7 | < 50 | < 7 | < 50 |
| C0181 | ≥ 7 | ≥ 50 | < 7 | < 50 | < 7 | < 50 | < 7 | < 50 | < 7 | ≥ 50 | < 7 | < 50 |
| C0182 | ≥ 7 | ≥ 50 | < 7 | < 50 | < 7 | < 50 | < 7 | < 50 | < 7 | ≥ 50 | < 7 | < 50 |
| C0183 | ≥ 7 | ≥ 50 | < 7 | ≥ 50 | < 7 | ≥ 50 | < 7 | < 50 | < 7 | ≥ 50 | < 7 | < 50 |
| C0184 | < 7 | ≥ 50 | < 7 | < 50 | < 7 | < 50 | < 7 | < 50 | < 7 | ≥ 50 | < 7 | < 50 |
| C0185 | < 7 | ≥ 50 | < 7 | ≥ 50 | < 7 | ≥ 50 | < 7 | < 50 | < 7 | ≥ 50 | < 7 | < 50 |
| C0186 | < 7 | ≥ 50 | < 7 | < 50 | < 7 | ≥ 50 | < 7 | < 50 | < 7 | ≥ 50 | < 7 | < 50 |
| C0187 | ≥ 7 | ≥ 50 | < 7 | ≥ 50 | < 7 | < 50 | < 7 | < 50 | < 7 | ≥ 50 | < 7 | < 50 |
| C0188 | ≥ 7 | ≥ 50 | < 7 | < 50 | < 7 | ≥ 50 | < 7 | < 50 | < 7 | ≥ 50 | < 7 | < 50 |
| C0189 | < 7 | ≥ 50 | < 7 | < 50 | < 7 | ≥ 50 | < 7 | < 50 | < 7 | ≥ 50 | < 7 | < 50 |
| C0190 | < 7 | ≥ 50 | < 7 | < 50 | < 7 | < 50 | < 7 | < 50 | < 7 | ≥ 50 | < 7 | < 50 |
| C0191 | ≥ 7 | ≥ 50 | ≥ 7 | ≥ 50 | < 7 | < 50 | < 7 | < 50 | < 7 | ≥ 50 | < 7 | < 50 |
| C0192 | ≥ 7 | ≥ 50 | < 7 | ≥ 50 | < 7 | < 50 | < 7 | < 50 | < 7 | ≥ 50 | < 7 | < 50 |
| C0193 | ≥ 7 | ≥ 50 | < 7 | ≥ 50 | < 7 | < 50 | < 7 | < 50 | < 7 | ≥ 50 | < 7 | < 50 |
| C0194 | ≥ 7 | ≥ 50 | < 7 | ≥ 50 | < 7 | < 50 | < 7 | < 50 | < 7 | ≥ 50 | < 7 | < 50 |
| C0195 | ≥ 7 | ≥ 50 | < 7 | < 50 | < 7 | < 50 | < 7 | < 50 | < 7 | ≥ 50 | < 7 | < 50 |
| C0196 | < 7 | ≥ 50 | < 7 | < 50 | < 7 | < 50 | < 7 | < 50 | < 7 | < 50 | < 7 | < 50 |
| C0197 | < 7 | ≥ 50 | < 7 | < 50 | < 7 | ≥ 50 | < 7 | < 50 | < 7 | ≥ 50 | < 7 | < 50 |
| C0198 | ≥ 7 | ≥ 50 | < 7 | < 50 | < 7 | < 50 | < 7 | < 50 | < 7 | ≥ 50 | < 7 | < 50 |
| C0199 | < 7 | ≥ 50 | < 7 | ≥ 50 | < 7 | ≥ 50 | < 7 | < 50 | < 7 | ≥ 50 | < 7 | < 50 |
| C0200 | < 7 | ≥ 50 | < 7 | < 50 | < 7 | < 50 | < 7 | < 50 | < 7 | ≥ 50 | < 7 | < 50 |
| C0201 | ≥ 7 | ≥ 50 | < 7 | < 50 | < 7 | ≥ 50 | < 7 | < 50 | < 7 | ≥ 50 | < 7 | < 50 |
| C0202 | ≥ 7 | ≥ 50 | < 7 | ≥ 50 | < 7 | ≥ 50 | < 7 | < 50 | < 7 | ≥ 50 | < 7 | < 50 |
| C0203 | ≥ 7 | ≥ 50 | < 7 | ≥ 50 | < 7 | ≥ 50 | < 7 | < 50 | < 7 | ≥ 50 | < 7 | < 50 |
| C0204 | ≥ 7 | ≥ 50 | < 7 | ≥ 50 | < 7 | < 50 | < 7 | < 50 | < 7 | < 50 | < 7 | < 50 |
| C0205 | ≥ 7 | ≥ 50 | ≥ 7 | ≥ 50 | < 7 | < 50 | < 7 | < 50 | < 7 | ≥ 50 | < 7 | < 50 |
| C0206 | < 7 | ≥ 50 | < 7 | ≥ 50 | < 7 | ≥ 50 | < 7 | < 50 | < 7 | ≥ 50 | < 7 | < 50 |
| C0207 | < 7 | ≥ 50 | < 7 | ≥ 50 | < 7 | < 50 | < 7 | < 50 | < 7 | < 50 | < 7 | < 50 |
| C0208 | < 7 | ≥ 50 | < 7 | ≥ 50 | < 7 | < 50 | < 7 | < 50 | < 7 | < 50 | < 7 | < 50 |
| C0209 | < 7 | ≥ 50 | < 7 | < 50 | < 7 | ≥ 50 | < 7 | < 50 | < 7 | < 50 | < 7 | < 50 |
| C0210 | < 7 | ≥ 50 | < 7 | ≥ 50 | < 7 | < 50 | < 7 | < 50 | < 7 | < 50 | < 7 | < 50 |
| C0211 | < 7 | ≥ 50 | < 7 | ≥ 50 | < 7 | < 50 | < 7 | < 50 | < 7 | < 50 | < 7 | < 50 |
| C0212 | < 7 | ≥ 50 | < 7 | < 50 | < 7 | < 50 | < 7 | < 50 | < 7 | < 50 | < 7 | < 50 |
| C0213 | < 7 | ≥ 50 | < 7 | < 50 | < 7 | < 50 | < 7 | < 50 | < 7 | < 50 | < 7 | < 50 |
| C0214 | < 7 | ≥ 50 | < 7 | < 50 | < 7 | < 50 | < 7 | < 50 | < 7 | ≥ 50 | < 7 | < 50 |
| C0215 | ≥ 7 | ≥ 50 | < 7 | ≥ 50 | < 7 | ≥ 50 | < 7 | < 50 | < 7 | ≥ 50 | < 7 | < 50 |
| C0216 | < 7 | ≥ 50 | < 7 | < 50 | < 7 | ≥ 50 | < 7 | < 50 | < 7 | ≥ 50 | < 7 | < 50 |

Figure 2

| | | | | | | | | | | | | |
|---|---|---|---|---|---|---|---|---|---|---|---|---|
| C0217 | ≥ 7 | ≥ 50 | < 7 | < 50 | < 7 | < 50 | < 7 | < 50 | < 7 | ≥ 50 | < 7 | < 50 |
| C0218 | ≥ 7 | ≥ 50 | < 7 | ≥ 50 | < 7 | ≥ 50 | < 7 | < 50 | < 7 | ≥ 50 | < 7 | < 50 |
| C0219 | < 7 | ≥ 50 | < 7 | < 50 | < 7 | ≥ 50 | < 7 | < 50 | < 7 | ≥ 50 | < 7 | < 50 |
| C0220 | < 7 | ≥ 50 | < 7 | < 50 | < 7 | ≥ 50 | < 7 | < 50 | < 7 | < 50 | < 7 | < 50 |
| C0221 | ≥ 7 | ≥ 50 | < 7 | ≥ 50 | < 7 | < 50 | < 7 | < 50 | < 7 | ≥ 50 | < 7 | < 50 |
| C0222 | ≥ 7 | ≥ 50 | < 7 | < 50 | < 7 | < 50 | < 7 | < 50 | < 7 | < 50 | < 7 | < 50 |
| C0223 | ≥ 7 | ≥ 50 | < 7 | < 50 | < 7 | < 50 | < 7 | < 50 | < 7 | < 50 | < 7 | < 50 |
| C0224 | < 7 | ≥ 50 | < 7 | < 50 | < 7 | ≥ 50 | < 7 | < 50 | < 7 | ≥ 50 | < 7 | < 50 |
| C0225 | < 7 | ≥ 50 | < 7 | < 50 | < 7 | ≥ 50 | < 7 | < 50 | < 7 | ≥ 50 | < 7 | < 50 |
| C0226 | ≥ 7 | ≥ 50 | < 7 | ≥ 50 | < 7 | ≥ 50 | < 7 | < 50 | < 7 | ≥ 50 | < 7 | < 50 |
| C0227 | ≥ 7 | ≥ 50 | < 7 | ≥ 50 | < 7 | ≥ 50 | < 7 | < 50 | < 7 | ≥ 50 | < 7 | < 50 |
| C0228 | ≥ 7 | ≥ 50 | < 7 | ≥ 50 | < 7 | ≥ 50 | < 7 | < 50 | < 7 | ≥ 50 | < 7 | < 50 |
| C0229 | ≥ 7 | ≥ 50 | < 7 | ≥ 50 | < 7 | < 50 | < 7 | < 50 | < 7 | ≥ 50 | < 7 | < 50 |
| C0230 | ≥ 7 | ≥ 50 | < 7 | < 50 | < 7 | < 50 | < 7 | < 50 | < 7 | ≥ 50 | < 7 | < 50 |
| C0231 | ≥ 7 | ≥ 50 | < 7 | < 50 | < 7 | < 50 | < 7 | < 50 | < 7 | ≥ 50 | < 7 | < 50 |
| C0232 | ≥ 7 | ≥ 50 | < 7 | ≥ 50 | < 7 | < 50 | < 7 | < 50 | < 7 | ≥ 50 | < 7 | < 50 |
| C0233 | ≥ 7 | ≥ 50 | < 7 | ≥ 50 | < 7 | ≥ 50 | < 7 | < 50 | < 7 | ≥ 50 | < 7 | < 50 |
| C0234 | ≥ 7 | ≥ 50 | < 7 | ≥ 50 | < 7 | ≥ 50 | < 7 | < 50 | < 7 | ≥ 50 | < 7 | < 50 |
| C0235 | ≥ 7 | ≥ 50 | < 7 | < 50 | < 7 | < 50 | < 7 | < 50 | < 7 | ≥ 50 | < 7 | < 50 |
| C0236 | ≥ 7 | ≥ 50 | < 7 | ≥ 50 | < 7 | < 50 | < 7 | < 50 | < 7 | ≥ 50 | < 7 | < 50 |
| C0237 | ≥ 7 | ≥ 50 | < 7 | ≥ 50 | < 7 | < 50 | < 7 | < 50 | < 7 | ≥ 50 | < 7 | < 50 |
| C0238 | ≥ 7 | ≥ 50 | < 7 | ≥ 50 | < 7 | ≥ 50 | < 7 | < 50 | < 7 | ≥ 50 | < 7 | < 50 |
| C0239 | ≥ 7 | ≥ 50 | < 7 | ≥ 50 | < 7 | < 50 | < 7 | < 50 | < 7 | ≥ 50 | < 7 | < 50 |
| C0240 | ≥ 7 | ≥ 50 | < 7 | < 50 | < 7 | ≥ 50 | < 7 | < 50 | < 7 | ≥ 50 | < 7 | < 50 |
| C0241 | < 7 | ≥ 50 | < 7 | < 50 | < 7 | ≥ 50 | < 7 | < 50 | < 7 | ≥ 50 | < 7 | < 50 |
| C0242 | ≥ 7 | ≥ 50 | < 7 | ≥ 50 | < 7 | ≥ 50 | < 7 | < 50 | < 7 | ≥ 50 | < 7 | < 50 |
| C0243 | ≥ 7 | ≥ 50 | < 7 | ≥ 50 | < 7 | < 50 | < 7 | < 50 | < 7 | ≥ 50 | < 7 | < 50 |
| C0244 | ≥ 7 | ≥ 50 | < 7 | < 50 | < 7 | ≥ 50 | < 7 | < 50 | < 7 | < 50 | < 7 | < 50 |
| C0245 | ≥ 7 | ≥ 50 | < 7 | ≥ 50 | < 7 | < 50 | < 7 | < 50 | < 7 | ≥ 50 | < 7 | < 50 |
| C0246 | ≥ 7 | ≥ 50 | < 7 | < 50 | < 7 | ≥ 50 | < 7 | < 50 | < 7 | < 50 | < 7 | < 50 |
| C0247 | < 7 | ≥ 50 | < 7 | < 50 | < 7 | ≥ 50 | < 7 | < 50 | < 7 | ≥ 50 | < 7 | < 50 |
| C0248 | ≥ 7 | ≥ 50 | < 7 | ≥ 50 | < 7 | ≥ 50 | < 7 | < 50 | < 7 | ≥ 50 | < 7 | < 50 |
| C0249 | ≥ 7 | ≥ 50 | < 7 | ≥ 50 | < 7 | < 50 | < 7 | < 50 | < 7 | ≥ 50 | < 7 | < 50 |
| C0250 | ≥ 7 | ≥ 50 | < 7 | ≥ 50 | < 7 | < 50 | < 7 | < 50 | < 7 | ≥ 50 | < 7 | < 50 |
| C0251 | ≥ 7 | ≥ 50 | < 7 | ≥ 50 | < 7 | < 50 | < 7 | < 50 | < 7 | ≥ 50 | < 7 | < 50 |
| C0252 | ≥ 7 | ≥ 50 | < 7 | ≥ 50 | < 7 | ≥ 50 | < 7 | < 50 | < 7 | ≥ 50 | < 7 | < 50 |
| C0253 | ≥ 7 | ≥ 50 | < 7 | ≥ 50 | < 7 | < 50 | < 7 | < 50 | < 7 | ≥ 50 | < 7 | < 50 |
| C0254 | ≥ 7 | ≥ 50 | < 7 | < 50 | < 7 | < 50 | < 7 | < 50 | < 7 | < 50 | < 7 | < 50 |
| C0255 | < 7 | ≥ 50 | < 7 | < 50 | < 7 | ≥ 50 | < 7 | < 50 | < 7 | < 50 | < 7 | < 50 |
| C0256 | ≥ 7 | ≥ 50 | < 7 | ≥ 50 | < 7 | < 50 | < 7 | < 50 | < 7 | ≥ 50 | < 7 | < 50 |
| C0257 | ≥ 7 | ≥ 50 | < 7 | ≥ 50 | < 7 | ≥ 50 | < 7 | < 50 | < 7 | ≥ 50 | < 7 | < 50 |
| C0258 | ≥ 7 | ≥ 50 | < 7 | ≥ 50 | < 7 | ≥ 50 | < 7 | < 50 | < 7 | ≥ 50 | < 7 | < 50 |
| C0259 | ≥ 7 | ≥ 50 | < 7 | ≥ 50 | < 7 | < 50 | < 7 | < 50 | < 7 | ≥ 50 | < 7 | < 50 |
| C0260 | ≥ 7 | ≥ 50 | < 7 | ≥ 50 | < 7 | ≥ 50 | < 7 | < 50 | < 7 | ≥ 50 | < 7 | < 50 |
| C0261 | ≥ 7 | ≥ 50 | < 7 | < 50 | < 7 | < 50 | < 7 | < 50 | < 7 | ≥ 50 | < 7 | < 50 |
| C0262 | ≥ 7 | ≥ 50 | < 7 | < 50 | < 7 | < 50 | < 7 | < 50 | < 7 | ≥ 50 | < 7 | < 50 |
| C0263 | < 7 | ≥ 50 | < 7 | < 50 | < 7 | ≥ 50 | < 7 | < 50 | < 7 | ≥ 50 | < 7 | < 50 |
| C0264 | < 7 | ≥ 50 | < 7 | < 50 | < 7 | ≥ 50 | < 7 | < 50 | < 7 | ≥ 50 | < 7 | < 50 |
| C0265 | < 7 | ≥ 50 | < 7 | < 50 | < 7 | ≥ 50 | < 7 | < 50 | < 7 | < 50 | < 7 | < 50 |
| C0266 | < 7 | ≥ 50 | < 7 | < 50 | < 7 | ≥ 50 | < 7 | < 50 | < 7 | ≥ 50 | < 7 | < 50 |
| C0267 | ≥ 7 | ≥ 50 | < 7 | < 50 | < 7 | ≥ 50 | < 7 | < 50 | < 7 | ≥ 50 | < 7 | < 50 |
| C0268 | ≥ 7 | ≥ 50 | < 7 | ≥ 50 | < 7 | ≥ 50 | < 7 | < 50 | < 7 | ≥ 50 | < 7 | < 50 |
| C0269 | ≥ 7 | ≥ 50 | < 7 | < 50 | < 7 | ≥ 50 | < 7 | < 50 | < 7 | ≥ 50 | < 7 | < 50 |
| C0270 | ≥ 7 | ≥ 50 | < 7 | < 50 | < 7 | ≥ 50 | < 7 | < 50 | < 7 | ≥ 50 | < 7 | < 50 |
| C0271 | ≥ 7 | ≥ 50 | < 7 | ≥ 50 | < 7 | ≥ 50 | < 7 | < 50 | < 7 | ≥ 50 | < 7 | < 50 |

Figure 2

| | | | | | | | | | | | |
|---|---|---|---|---|---|---|---|---|---|---|---|
| C0272 | < 7 | ≥ 50 | < 7 | < 50 | < 7 | ≥ 50 | < 7 | < 50 | < 7 | < 50 | < 7 | < 50 |
| C0273 | < 7 | ≥ 50 | < 7 | < 50 | < 7 | ≥ 50 | < 7 | < 50 | < 7 | ≥ 50 | < 7 | < 50 |
| C0274 | ≥ 7 | ≥ 50 | < 7 | ≥ 50 | < 7 | < 50 | < 7 | < 50 | < 7 | ≥ 50 | < 7 | < 50 |
| C0275 | ≥ 7 | ≥ 50 | < 7 | ≥ 50 | < 7 | ≥ 50 | < 7 | < 50 | < 7 | ≥ 50 | < 7 | < 50 |
| C0276 | ≥ 7 | ≥ 50 | < 7 | ≥ 50 | < 7 | ≥ 50 | < 7 | < 50 | < 7 | ≥ 50 | < 7 | < 50 |
| C0277 | ≥ 7 | ≥ 50 | < 7 | ≥ 50 | < 7 | ≥ 50 | < 7 | < 50 | < 7 | ≥ 50 | < 7 | < 50 |
| C0278 | < 7 | ≥ 50 | < 7 | < 50 | < 7 | ≥ 50 | < 7 | < 50 | < 7 | ≥ 50 | < 7 | < 50 |
| C0279 | ≥ 7 | ≥ 50 | < 7 | < 50 | < 7 | ≥ 50 | < 7 | < 50 | < 7 | ≥ 50 | < 7 | < 50 |
| C0280 | ≥ 7 | ≥ 50 | < 7 | ≥ 50 | < 7 | ≥ 50 | < 7 | < 50 | < 7 | ≥ 50 | < 7 | < 50 |
| C0281 | < 7 | ≥ 50 | < 7 | < 50 | < 7 | ≥ 50 | < 7 | < 50 | < 7 | ≥ 50 | < 7 | < 50 |
| C0282 | < 7 | ≥ 50 | < 7 | < 50 | < 7 | ≥ 50 | < 7 | < 50 | < 7 | ≥ 50 | < 7 | < 50 |
| C0283 | ≥ 7 | ≥ 50 | < 7 | ≥ 50 | < 7 | ≥ 50 | < 7 | < 50 | < 7 | ≥ 50 | < 7 | < 50 |
| C0284 | ≥ 7 | ≥ 50 | < 7 | < 50 | < 7 | ≥ 50 | < 7 | < 50 | < 7 | ≥ 50 | < 7 | < 50 |
| C0285 | ≥ 7 | ≥ 50 | < 7 | < 50 | < 7 | ≥ 50 | < 7 | < 50 | < 7 | ≥ 50 | < 7 | < 50 |
| C0286 | ≥ 7 | ≥ 50 | < 7 | < 50 | < 7 | ≥ 50 | < 7 | < 50 | < 7 | ≥ 50 | < 7 | < 50 |
| C0287 | < 7 | ≥ 50 | < 7 | < 50 | < 7 | ≥ 50 | < 7 | < 50 | < 7 | < 50 | < 7 | < 50 |
| C0288 | < 7 | ≥ 50 | < 7 | < 50 | < 7 | ≥ 50 | < 7 | < 50 | < 7 | < 50 | < 7 | < 50 |
| C0289 | ≥ 7 | ≥ 50 | < 7 | < 50 | < 7 | ≥ 50 | < 7 | < 50 | < 7 | ≥ 50 | < 7 | < 50 |
| C0290 | ≥ 7 | ≥ 50 | < 7 | ≥ 50 | < 7 | ≥ 50 | < 7 | < 50 | < 7 | ≥ 50 | < 7 | < 50 |
| C0291 | ≥ 7 | ≥ 50 | < 7 | < 50 | < 7 | < 50 | < 7 | < 50 | < 7 | ≥ 50 | < 7 | < 50 |
| C0292 | ≥ 7 | ≥ 50 | < 7 | ≥ 50 | < 7 | ≥ 50 | < 7 | < 50 | < 7 | ≥ 50 | < 7 | < 50 |
| C0293 | ≥ 7 | ≥ 50 | < 7 | ≥ 50 | < 7 | ≥ 50 | < 7 | < 50 | < 7 | ≥ 50 | < 7 | < 50 |
| C0294 | ≥ 7 | ≥ 50 | < 7 | ≥ 50 | < 7 | ≥ 50 | < 7 | < 50 | < 7 | ≥ 50 | < 7 | < 50 |
| C0295 | ≥ 7 | ≥ 50 | < 7 | ≥ 50 | < 7 | ≥ 50 | < 7 | < 50 | < 7 | ≥ 50 | < 7 | < 50 |
| C0296 | ≥ 7 | ≥ 50 | N.D. | N.D. | < 7 | ≥ 50 | < 7 | < 50 | < 7 | ≥ 50 | < 7 | < 50 |
| C0297 | < 7 | ≥ 50 | < 7 | < 50 | < 7 | ≥ 50 | < 7 | < 50 | < 7 | ≥ 50 | < 7 | < 50 |
| C0298 | < 7 | ≥ 50 | < 7 | < 50 | < 7 | ≥ 50 | < 7 | < 50 | < 7 | ≥ 50 | < 7 | < 50 |
| C0299 | < 7 | ≥ 50 | < 7 | < 50 | < 7 | < 50 | < 7 | < 50 | < 7 | < 50 | < 7 | < 50 |
| C0300 | ≥ 7 | ≥ 50 | < 7 | ≥ 50 | < 7 | ≥ 50 | < 7 | < 50 | < 7 | ≥ 50 | < 7 | < 50 |
| C0301 | ≥ 7 | ≥ 50 | < 7 | ≥ 50 | < 7 | ≥ 50 | < 7 | < 50 | < 7 | ≥ 50 | < 7 | < 50 |
| C0302 | ≥ 7 | ≥ 50 | < 7 | ≥ 50 | < 7 | ≥ 50 | < 7 | < 50 | < 7 | ≥ 50 | < 7 | < 50 |
| C0303 | ≥ 7 | ≥ 50 | < 7 | < 50 | < 7 | ≥ 50 | < 7 | < 50 | < 7 | ≥ 50 | < 7 | < 50 |
| C0304 | ≥ 7 | ≥ 50 | < 7 | ≥ 50 | < 7 | ≥ 50 | < 7 | < 50 | < 7 | ≥ 50 | < 7 | < 50 |
| C0305 | < 7 | ≥ 50 | < 7 | < 50 | < 7 | ≥ 50 | < 7 | < 50 | < 7 | < 50 | < 7 | < 50 |
| C0306 | < 7 | ≥ 50 | < 7 | < 50 | < 7 | < 50 | < 7 | < 50 | < 7 | ≥ 50 | < 7 | < 50 |
| C0307 | < 7 | ≥ 50 | < 7 | < 50 | < 7 | < 50 | < 7 | < 50 | < 7 | < 50 | < 7 | < 50 |
| C0308 | < 7 | ≥ 50 | < 7 | < 50 | < 7 | ≥ 50 | < 7 | < 50 | < 7 | < 50 | < 7 | < 50 |
| C0309 | < 7 | ≥ 50 | < 7 | < 50 | < 7 | < 50 | < 7 | < 50 | < 7 | < 50 | < 7 | < 50 |
| C0310 | < 7 | < 50 | < 7 | < 50 | < 7 | ≥ 50 | < 7 | < 50 | < 7 | < 50 | < 7 | < 50 |
| C0311 | ≥ 7 | ≥ 50 | < 7 | ≥ 50 | < 7 | ≥ 50 | < 7 | < 50 | < 7 | ≥ 50 | < 7 | < 50 |
| C0312 | ≥ 7 | ≥ 50 | < 7 | ≥ 50 | < 7 | < 50 | < 7 | < 50 | < 7 | ≥ 50 | < 7 | < 50 |
| C0313 | N.D. | N.D. | N.D. | N.D. | N.D. | N.D. | N.D. | N.D. | N.D. | N.D. | N.D. | N.D. |
| C0314 | ≥ 7 | ≥ 50 | < 7 | < 50 | < 7 | ≥ 50 | < 7 | < 50 | < 7 | ≥ 50 | < 7 | < 50 |
| C0315 | ≥ 7 | ≥ 50 | < 7 | ≥ 50 | < 7 | ≥ 50 | < 7 | < 50 | < 7 | ≥ 50 | < 7 | < 50 |
| C0316 | ≥ 7 | ≥ 50 | < 7 | < 50 | < 7 | < 50 | < 7 | < 50 | < 7 | < 50 | < 7 | < 50 |
| C0317 | < 7 | ≥ 50 | < 7 | < 50 | < 7 | < 50 | < 7 | < 50 | < 7 | ≥ 50 | < 7 | < 50 |
| C0318 | < 7 | ≥ 50 | < 7 | < 50 | < 7 | < 50 | < 7 | < 50 | < 7 | < 50 | < 7 | < 50 |
| C0319 | < 7 | ≥ 50 | < 7 | < 50 | < 7 | < 50 | < 7 | < 50 | < 7 | < 50 | < 7 | < 50 |
| C0320 | < 7 | ≥ 50 | < 7 | < 50 | < 7 | ≥ 50 | < 7 | < 50 | < 7 | ≥ 50 | < 7 | < 50 |
| C0321 | < 7 | ≥ 50 | < 7 | < 50 | < 7 | ≥ 50 | < 7 | < 50 | < 7 | ≥ 50 | < 7 | < 50 |
| C0322 | < 7 | ≥ 50 | < 7 | < 50 | < 7 | < 50 | < 7 | < 50 | < 7 | ≥ 50 | < 7 | < 50 |
| C0323 | ≥ 7 | ≥ 50 | < 7 | ≥ 50 | < 7 | ≥ 50 | < 7 | < 50 | < 7 | ≥ 50 | < 7 | < 50 |
| C0324 | ≥ 7 | ≥ 50 | < 7 | ≥ 50 | < 7 | ≥ 50 | < 7 | < 50 | < 7 | ≥ 50 | < 7 | < 50 |
| C0325 | ≥ 7 | ≥ 50 | < 7 | ≥ 50 | < 7 | ≥ 50 | < 7 | < 50 | < 7 | ≥ 50 | < 7 | < 50 |
| C0326 | ≥ 7 | ≥ 50 | < 7 | ≥ 50 | < 7 | < 50 | < 7 | < 50 | < 7 | ≥ 50 | < 7 | < 50 |

Figure 2

| | | | | | | | | | | | |
|---|---|---|---|---|---|---|---|---|---|---|---|
| C0327 | ≥ 7 | ≥ 50 | < 7 | < 50 | < 7 | < 50 | < 7 | < 50 | < 7 | ≥ 50 | < 7 | < 50 |
| C0328 | ≥ 7 | ≥ 50 | < 7 | ≥ 50 | < 7 | < 50 | < 7 | < 50 | < 7 | ≥ 50 | < 7 | < 50 |
| C0329 | ≥ 7 | ≥ 50 | < 7 | ≥ 50 | < 7 | < 50 | < 7 | < 50 | < 7 | ≥ 50 | < 7 | < 50 |
| C0330 | ≥ 7 | ≥ 50 | < 7 | ≥ 50 | < 7 | ≥ 50 | < 7 | < 50 | < 7 | ≥ 50 | < 7 | < 50 |
| C0331 | ≥ 7 | ≥ 50 | < 7 | ≥ 50 | < 7 | < 50 | < 7 | < 50 | < 7 | ≥ 50 | < 7 | < 50 |
| C0332 | ≥ 7 | ≥ 50 | < 7 | ≥ 50 | < 7 | ≥ 50 | < 7 | < 50 | < 7 | ≥ 50 | < 7 | < 50 |
| C0333 | ≥ 7 | ≥ 50 | < 7 | < 50 | < 7 | ≥ 50 | < 7 | < 50 | < 7 | ≥ 50 | < 7 | < 50 |
| C0334 | ≥ 7 | ≥ 50 | < 7 | ≥ 50 | < 7 | ≥ 50 | < 7 | < 50 | < 7 | ≥ 50 | < 7 | < 50 |
| C0335 | ≥ 7 | ≥ 50 | < 7 | ≥ 50 | < 7 | ≥ 50 | < 7 | < 50 | < 7 | ≥ 50 | < 7 | < 50 |
| C0336 | ≥ 7 | ≥ 50 | < 7 | < 50 | < 7 | ≥ 50 | < 7 | < 50 | < 7 | ≥ 50 | < 7 | < 50 |
| C0337 | N.D. | N.D. | N.D. | N.D. | N.D. | N.D. | N.D. | N.D. | N.D. | N.D. | N.D. | N.D. |
| C0338 | N.D. | N.D. | N.D. | N.D. | N.D. | N.D. | N.D. | N.D. | N.D. | N.D. | N.D. | N.D. |
| C0339 | ≥ 7 | ≥ 50 | < 7 | ≥ 50 | < 7 | < 50 | < 7 | < 50 | < 7 | ≥ 50 | < 7 | < 50 |
| C0340 | ≥ 7 | ≥ 50 | < 7 | < 50 | < 7 | ≥ 50 | < 7 | < 50 | < 7 | ≥ 50 | < 7 | < 50 |
| C0341 | ≥ 7 | ≥ 50 | < 7 | ≥ 50 | < 7 | ≥ 50 | < 7 | < 50 | < 7 | ≥ 50 | < 7 | < 50 |
| C0342 | < 7 | ≥ 50 | < 7 | < 50 | < 7 | < 50 | < 7 | < 50 | < 7 | < 50 | < 7 | < 50 |
| C0343 | ≥ 7 | ≥ 50 | < 7 | ≥ 50 | < 7 | ≥ 50 | < 7 | < 50 | < 7 | ≥ 50 | < 7 | < 50 |
| C0344 | ≥ 7 | ≥ 50 | < 7 | ≥ 50 | < 7 | ≥ 50 | < 7 | < 50 | < 7 | ≥ 50 | < 7 | < 50 |
| C0345 | ≥ 7 | ≥ 50 | < 7 | ≥ 50 | < 7 | ≥ 50 | < 7 | < 50 | < 7 | ≥ 50 | < 7 | < 50 |
| C0346 | ≥ 7 | ≥ 50 | < 7 | ≥ 50 | < 7 | ≥ 50 | < 7 | < 50 | < 7 | ≥ 50 | < 7 | < 50 |
| C0347 | < 7 | ≥ 50 | < 7 | < 50 | < 7 | < 50 | < 7 | < 50 | < 7 | ≥ 50 | < 7 | < 50 |
| C0348 | < 7 | ≥ 50 | < 7 | < 50 | < 7 | < 50 | < 7 | < 50 | < 7 | < 50 | < 7 | < 50 |
| C0349 | < 7 | < 50 | < 7 | < 50 | < 7 | < 50 | < 7 | < 50 | < 7 | < 50 | < 7 | < 50 |
| C0350 | < 7 | ≥ 50 | < 7 | < 50 | < 7 | ≥ 50 | < 7 | < 50 | < 7 | ≥ 50 | < 7 | < 50 |
| C0351 | < 7 | ≥ 50 | < 7 | < 50 | < 7 | ≥ 50 | < 7 | < 50 | < 7 | ≥ 50 | < 7 | < 50 |
| C0352 | < 7 | ≥ 50 | < 7 | < 50 | < 7 | ≥ 50 | < 7 | < 50 | < 7 | ≥ 50 | < 7 | < 50 |
| C0353 | ≥ 7 | ≥ 50 | < 7 | ≥ 50 | < 7 | ≥ 50 | < 7 | < 50 | < 7 | ≥ 50 | < 7 | < 50 |
| C0354 | < 7 | ≥ 50 | < 7 | < 50 | < 7 | < 50 | < 7 | < 50 | < 7 | < 50 | < 7 | < 50 |
| C0355 | ≥ 7 | ≥ 50 | < 7 | < 50 | < 7 | < 50 | < 7 | < 50 | < 7 | < 50 | < 7 | < 50 |
| C0356 | < 7 | ≥ 50 | < 7 | < 50 | < 7 | < 50 | < 7 | < 50 | < 7 | < 50 | < 7 | < 50 |
| C0357 | ≥ 7 | ≥ 50 | < 7 | ≥ 50 | < 7 | ≥ 50 | < 7 | < 50 | < 7 | ≥ 50 | < 7 | < 50 |
| C0358 | ≥ 7 | ≥ 50 | < 7 | ≥ 50 | < 7 | ≥ 50 | < 7 | < 50 | < 7 | ≥ 50 | < 7 | < 50 |
| C0359 | < 7 | ≥ 50 | < 7 | < 50 | < 7 | ≥ 50 | < 7 | < 50 | < 7 | ≥ 50 | < 7 | < 50 |
| C0360 | < 7 | ≥ 50 | < 7 | < 50 | < 7 | < 50 | < 7 | < 50 | < 7 | ≥ 50 | < 7 | < 50 |
| C0361 | < 7 | ≥ 50 | < 7 | < 50 | < 7 | < 50 | < 7 | < 50 | < 7 | ≥ 50 | < 7 | < 50 |
| C0362 | < 7 | ≥ 50 | < 7 | < 50 | < 7 | < 50 | < 7 | < 50 | < 7 | ≥ 50 | < 7 | < 50 |
| C0363 | < 7 | ≥ 50 | < 7 | < 50 | < 7 | < 50 | < 7 | < 50 | < 7 | ≥ 50 | < 7 | < 50 |
| C0364 | ≥ 7 | ≥ 50 | < 7 | < 50 | < 7 | ≥ 50 | < 7 | < 50 | < 7 | ≥ 50 | < 7 | < 50 |
| C0365 | < 7 | ≥ 50 | < 7 | ≥ 50 | < 7 | ≥ 50 | < 7 | < 50 | < 7 | ≥ 50 | < 7 | < 50 |
| C0366 | < 7 | ≥ 50 | < 7 | ≥ 50 | < 7 | ≥ 50 | < 7 | < 50 | < 7 | ≥ 50 | < 7 | < 50 |
| C0367 | < 7 | ≥ 50 | < 7 | < 50 | < 7 | < 50 | < 7 | < 50 | < 7 | ≥ 50 | < 7 | < 50 |
| C0368 | < 7 | ≥ 50 | < 7 | < 50 | < 7 | < 50 | < 7 | < 50 | < 7 | < 50 | < 7 | < 50 |
| C0369 | < 7 | ≥ 50 | < 7 | < 50 | < 7 | < 50 | < 7 | < 50 | < 7 | ≥ 50 | < 7 | < 50 |
| C0370 | ≥ 7 | ≥ 50 | < 7 | ≥ 50 | < 7 | ≥ 50 | < 7 | < 50 | < 7 | ≥ 50 | < 7 | < 50 |
| C0371 | < 7 | ≥ 50 | < 7 | < 50 | < 7 | < 50 | < 7 | < 50 | < 7 | ≥ 50 | < 7 | < 50 |
| C0372 | < 7 | ≥ 50 | < 7 | < 50 | < 7 | < 50 | < 7 | < 50 | < 7 | ≥ 50 | < 7 | < 50 |
| C0373 | < 7 | ≥ 50 | < 7 | < 50 | < 7 | < 50 | < 7 | < 50 | < 7 | ≥ 50 | < 7 | < 50 |
| C0374 | < 7 | ≥ 50 | < 7 | < 50 | < 7 | < 50 | < 7 | < 50 | < 7 | ≥ 50 | < 7 | < 50 |
| C0375 | < 7 | ≥ 50 | < 7 | ≥ 50 | < 7 | < 50 | < 7 | < 50 | < 7 | ≥ 50 | < 7 | < 50 |
| C0376 | < 7 | ≥ 50 | < 7 | ≥ 50 | < 7 | < 50 | < 7 | < 50 | < 7 | ≥ 50 | < 7 | < 50 |
| C0377 | < 7 | ≥ 50 | < 7 | < 50 | < 7 | < 50 | < 7 | < 50 | < 7 | ≥ 50 | < 7 | < 50 |
| C0378 | < 7 | ≥ 50 | < 7 | < 50 | < 7 | ≥ 50 | < 7 | < 50 | < 7 | < 50 | < 7 | < 50 |
| C0379 | ≥ 7 | ≥ 50 | < 7 | ≥ 50 | < 7 | ≥ 50 | < 7 | < 50 | < 7 | ≥ 50 | < 7 | < 50 |
| C0380 | < 7 | ≥ 50 | < 7 | < 50 | < 7 | ≥ 50 | < 7 | < 50 | < 7 | < 50 | < 7 | < 50 |
| C0381 | ≥ 7 | ≥ 50 | < 7 | ≥ 50 | < 7 | ≥ 50 | < 7 | < 50 | < 7 | ≥ 50 | < 7 | < 50 |

Figure 2

| | | | | | | | | | | | | |
|---|---|---|---|---|---|---|---|---|---|---|---|---|
| C0382 | ≥ 7 | ≥ 50 | < 7 | ≥ 50 | < 7 | ≥ 50 | < 7 | < 50 | < 7 | < 50 | < 7 | < 50 |
| C0383 | < 7 | ≥ 50 | < 7 | < 50 | < 7 | < 50 | < 7 | < 50 | < 7 | ≥ 50 | < 7 | < 50 |
| C0384 | ≥ 7 | ≥ 50 | < 7 | < 50 | < 7 | ≥ 50 | < 7 | < 50 | < 7 | ≥ 50 | < 7 | < 50 |
| C0385 | < 7 | ≥ 50 | < 7 | < 50 | < 7 | < 50 | < 7 | < 50 | < 7 | < 50 | < 7 | < 50 |
| C0386 | ≥ 7 | ≥ 50 | < 7 | ≥ 50 | < 7 | ≥ 50 | < 7 | < 50 | < 7 | ≥ 50 | < 7 | < 50 |
| C0387 | ≥ 7 | ≥ 50 | < 7 | ≥ 50 | < 7 | ≥ 50 | < 7 | < 50 | < 7 | ≥ 50 | < 7 | < 50 |
| C0388 | ≥ 7 | ≥ 50 | < 7 | ≥ 50 | < 7 | ≥ 50 | < 7 | < 50 | < 7 | ≥ 50 | < 7 | < 50 |
| C0389 | < 7 | ≥ 50 | < 7 | < 50 | < 7 | < 50 | < 7 | < 50 | < 7 | < 50 | < 7 | < 50 |
| C0390 | < 7 | ≥ 50 | < 7 | ≥ 50 | < 7 | ≥ 50 | < 7 | < 50 | < 7 | ≥ 50 | < 7 | < 50 |
| C0391 | ≥ 7 | ≥ 50 | < 7 | ≥ 50 | < 7 | ≥ 50 | < 7 | < 50 | < 7 | ≥ 50 | < 7 | < 50 |
| C0392 | ≥ 7 | ≥ 50 | < 7 | ≥ 50 | < 7 | < 50 | < 7 | < 50 | < 7 | ≥ 50 | < 7 | < 50 |
| C0393 | ≥ 7 | ≥ 50 | < 7 | ≥ 50 | < 7 | < 50 | < 7 | < 50 | < 7 | ≥ 50 | < 7 | < 50 |
| C0394 | < 7 | ≥ 50 | < 7 | < 50 | < 7 | < 50 | < 7 | < 50 | < 7 | ≥ 50 | < 7 | < 50 |
| C0395 | N.D. | N.D. | N.D. | N.D. | N.D. | N.D. | N.D. | N.D. | N.D. | N.D. | N.D. | N.D. |
| C0396 | < 7 | ≥ 50 | < 7 | ≥ 50 | < 7 | < 50 | < 7 | < 50 | < 7 | ≥ 50 | < 7 | < 50 |
| C0397 | < 7 | ≥ 50 | < 7 | ≥ 50 | < 7 | < 50 | < 7 | < 50 | < 7 | ≥ 50 | < 7 | < 50 |
| C0398 | ≥ 7 | ≥ 50 | < 7 | ≥ 50 | < 7 | < 50 | < 7 | < 50 | < 7 | ≥ 50 | < 7 | < 50 |
| C0399 | ≥ 7 | ≥ 50 | < 7 | ≥ 50 | < 7 | ≥ 50 | < 7 | < 50 | < 7 | ≥ 50 | < 7 | < 50 |
| C0400 | < 7 | ≥ 50 | < 7 | < 50 | < 7 | ≥ 50 | < 7 | < 50 | < 7 | ≥ 50 | < 7 | < 50 |
| C0401 | ≥ 7 | ≥ 50 | < 7 | ≥ 50 | < 7 | ≥ 50 | < 7 | < 50 | < 7 | ≥ 50 | < 7 | < 50 |
| C0402 | < 7 | ≥ 50 | < 7 | < 50 | < 7 | ≥ 50 | < 7 | < 50 | < 7 | ≥ 50 | < 7 | < 50 |
| C0403 | < 7 | ≥ 50 | < 7 | < 50 | < 7 | ≥ 50 | < 7 | < 50 | < 7 | ≥ 50 | < 7 | < 50 |
| C0404 | < 7 | ≥ 50 | < 7 | < 50 | < 7 | ≥ 50 | < 7 | < 50 | < 7 | ≥ 50 | < 7 | < 50 |
| C0405 | < 7 | ≥ 50 | < 7 | < 50 | < 7 | < 50 | < 7 | < 50 | < 7 | ≥ 50 | < 7 | < 50 |
| C0406 | < 7 | ≥ 50 | < 7 | < 50 | < 7 | < 50 | < 7 | < 50 | < 7 | < 50 | < 7 | < 50 |
| C0407 | ≥ 7 | ≥ 50 | < 7 | ≥ 50 | < 7 | < 50 | < 7 | < 50 | < 7 | ≥ 50 | < 7 | < 50 |
| C0408 | < 7 | ≥ 50 | < 7 | < 50 | < 7 | < 50 | < 7 | < 50 | < 7 | ≥ 50 | < 7 | < 50 |
| C0409 | < 7 | ≥ 50 | < 7 | < 50 | < 7 | < 50 | < 7 | < 50 | < 7 | ≥ 50 | < 7 | < 50 |
| C0410 | < 7 | ≥ 50 | < 7 | < 50 | < 7 | < 50 | < 7 | < 50 | < 7 | ≥ 50 | < 7 | < 50 |
| C0411 | < 7 | ≥ 50 | < 7 | ≥ 50 | < 7 | < 50 | < 7 | < 50 | < 7 | ≥ 50 | < 7 | < 50 |
| C0412 | ≥ 7 | ≥ 50 | < 7 | ≥ 50 | < 7 | < 50 | < 7 | < 50 | < 7 | ≥ 50 | < 7 | < 50 |
| C0413 | ≥ 7 | ≥ 50 | < 7 | ≥ 50 | < 7 | < 50 | < 7 | < 50 | < 7 | ≥ 50 | < 7 | < 50 |
| C0414 | < 7 | ≥ 50 | < 7 | < 50 | < 7 | < 50 | < 7 | < 50 | < 7 | ≥ 50 | < 7 | < 50 |
| C0415 | < 7 | ≥ 50 | < 7 | < 50 | < 7 | < 50 | < 7 | < 50 | < 7 | < 50 | < 7 | < 50 |
| C0416 | ≥ 7 | ≥ 50 | < 7 | ≥ 50 | < 7 | < 50 | < 7 | < 50 | < 7 | ≥ 50 | < 7 | < 50 |
| C0417 | ≥ 7 | ≥ 50 | < 7 | ≥ 50 | < 7 | ≥ 50 | < 7 | < 50 | < 7 | ≥ 50 | < 7 | < 50 |
| C0418 | ≥ 7 | ≥ 50 | < 7 | ≥ 50 | < 7 | < 50 | < 7 | < 50 | < 7 | ≥ 50 | < 7 | < 50 |
| C0419 | ≥ 7 | ≥ 50 | < 7 | < 50 | < 7 | ≥ 50 | < 7 | < 50 | < 7 | ≥ 50 | < 7 | < 50 |
| C0420 | ≥ 7 | ≥ 50 | < 7 | < 50 | < 7 | ≥ 50 | < 7 | < 50 | < 7 | ≥ 50 | < 7 | < 50 |
| C0421 | N.D. | N.D. | N.D. | N.D. | N.D. | N.D. | N.D. | N.D. | N.D. | N.D. | N.D. | N.D. |
| C0422 | N.D. | N.D. | N.D. | N.D. | N.D. | N.D. | N.D. | N.D. | N.D. | N.D. | N.D. | N.D. |
| C0423 | ≥ 7 | ≥ 50 | < 7 | < 50 | < 7 | ≥ 50 | < 7 | < 50 | < 7 | ≥ 50 | < 7 | < 50 |
| C0424 | ≥ 7 | ≥ 50 | < 7 | < 50 | < 7 | ≥ 50 | < 7 | < 50 | < 7 | ≥ 50 | < 7 | < 50 |
| C0425 | < 7 | ≥ 50 | < 7 | < 50 | < 7 | < 50 | < 7 | < 50 | < 7 | < 50 | < 7 | < 50 |
| C0426 | < 7 | ≥ 50 | < 7 | ≥ 50 | < 7 | ≥ 50 | < 7 | < 50 | < 7 | ≥ 50 | < 7 | < 50 |
| C0427 | < 7 | ≥ 50 | < 7 | ≥ 50 | < 7 | ≥ 50 | < 7 | < 50 | < 7 | ≥ 50 | < 7 | < 50 |
| C0428 | < 7 | ≥ 50 | < 7 | < 50 | < 7 | ≥ 50 | < 7 | < 50 | < 7 | ≥ 50 | < 7 | < 50 |
| C0429 | ≥ 7 | ≥ 50 | < 7 | ≥ 50 | < 7 | ≥ 50 | < 7 | < 50 | < 7 | ≥ 50 | < 7 | < 50 |
| C0430 | ≥ 7 | ≥ 50 | < 7 | < 50 | < 7 | ≥ 50 | < 7 | < 50 | < 7 | < 50 | < 7 | < 50 |
| C0431 | < 7 | ≥ 50 | < 7 | < 50 | < 7 | ≥ 50 | < 7 | < 50 | < 7 | ≥ 50 | < 7 | < 50 |
| C0432 | < 7 | ≥ 50 | < 7 | < 50 | < 7 | ≥ 50 | < 7 | < 50 | < 7 | ≥ 50 | < 7 | < 50 |
| C0433 | < 7 | ≥ 50 | < 7 | < 50 | < 7 | ≥ 50 | < 7 | < 50 | < 7 | ≥ 50 | < 7 | < 50 |
| C0434 | ≥ 7 | ≥ 50 | < 7 | < 50 | < 7 | < 50 | < 7 | < 50 | < 7 | ≥ 50 | < 7 | < 50 |
| C0435 | ≥ 7 | ≥ 50 | < 7 | ≥ 50 | < 7 | < 50 | < 7 | < 50 | < 7 | ≥ 50 | < 7 | < 50 |
| C0436 | ≥ 7 | ≥ 50 | < 7 | ≥ 50 | < 7 | < 50 | < 7 | < 50 | < 7 | ≥ 50 | < 7 | < 50 |

Figure 2

| | | | | | | | | | | | | |
|---|---|---|---|---|---|---|---|---|---|---|---|---|
| C0437 | < 7 | < 50 | < 7 | < 50 | < 7 | < 50 | < 7 | < 50 | < 7 | ≥ 50 | < 7 | < 50 |
| C0438 | < 7 | < 50 | < 7 | < 50 | < 7 | ≥ 50 | < 7 | < 50 | < 7 | ≥ 50 | < 7 | < 50 |
| C0439 | < 7 | ≥ 50 | < 7 | < 50 | < 7 | ≥ 50 | < 7 | < 50 | < 7 | < 50 | < 7 | < 50 |
| C0440 | < 7 | < 50 | < 7 | < 50 | < 7 | ≥ 50 | < 7 | < 50 | < 7 | < 50 | < 7 | < 50 |
| C0441 | ≥ 7 | ≥ 50 | < 7 | ≥ 50 | < 7 | ≥ 50 | < 7 | < 50 | < 7 | ≥ 50 | < 7 | < 50 |
| C0442 | ≥ 7 | ≥ 50 | < 7 | ≥ 50 | < 7 | < 50 | < 7 | < 50 | < 7 | ≥ 50 | < 7 | < 50 |
| C0443 | < 7 | ≥ 50 | < 7 | < 50 | < 7 | ≥ 50 | < 7 | < 50 | < 7 | < 50 | < 7 | < 50 |
| C0444 | ≥ 7 | ≥ 50 | < 7 | < 50 | < 7 | < 50 | < 7 | < 50 | < 7 | ≥ 50 | < 7 | < 50 |
| C0445 | < 7 | ≥ 50 | < 7 | ≥ 50 | < 7 | < 50 | < 7 | < 50 | < 7 | ≥ 50 | < 7 | < 50 |
| C0446 | ≥ 7 | ≥ 50 | < 7 | ≥ 50 | < 7 | < 50 | < 7 | < 50 | < 7 | ≥ 50 | < 7 | < 50 |
| C0447 | ≥ 7 | ≥ 50 | < 7 | ≥ 50 | < 7 | < 50 | < 7 | < 50 | < 7 | ≥ 50 | < 7 | < 50 |
| C0448 | ≥ 7 | ≥ 50 | < 7 | ≥ 50 | < 7 | < 50 | < 7 | < 50 | < 7 | ≥ 50 | < 7 | < 50 |
| C0449 | ≥ 7 | ≥ 50 | < 7 | ≥ 50 | < 7 | ≥ 50 | < 7 | < 50 | < 7 | ≥ 50 | < 7 | < 50 |
| C0450 | ≥ 7 | ≥ 50 | < 7 | ≥ 50 | < 7 | ≥ 50 | < 7 | < 50 | < 7 | ≥ 50 | < 7 | < 50 |
| C0451 | ≥ 7 | ≥ 50 | < 7 | < 50 | < 7 | < 50 | < 7 | < 50 | < 7 | ≥ 50 | < 7 | < 50 |
| C0452 | ≥ 7 | ≥ 50 | < 7 | < 50 | < 7 | ≥ 50 | < 7 | < 50 | < 7 | ≥ 50 | < 7 | < 50 |
| C0453 | ≥ 7 | ≥ 50 | < 7 | ≥ 50 | < 7 | ≥ 50 | < 7 | < 50 | < 7 | ≥ 50 | < 7 | < 50 |
| C0454 | ≥ 7 | ≥ 50 | < 7 | < 50 | < 7 | ≥ 50 | < 7 | < 50 | < 7 | ≥ 50 | < 7 | < 50 |
| C0455 | ≥ 7 | ≥ 50 | < 7 | < 50 | < 7 | ≥ 50 | < 7 | < 50 | < 7 | ≥ 50 | < 7 | < 50 |
| C0456 | ≥ 7 | ≥ 50 | < 7 | ≥ 50 | < 7 | ≥ 50 | < 7 | < 50 | < 7 | ≥ 50 | < 7 | < 50 |
| C0457 | ≥ 7 | ≥ 50 | < 7 | < 50 | < 7 | ≥ 50 | < 7 | < 50 | < 7 | ≥ 50 | < 7 | < 50 |
| C0458 | < 7 | ≥ 50 | < 7 | < 50 | < 7 | ≥ 50 | < 7 | < 50 | < 7 | < 50 | < 7 | < 50 |
| C0459 | ≥ 7 | ≥ 50 | < 7 | < 50 | < 7 | ≥ 50 | < 7 | < 50 | < 7 | ≥ 50 | < 7 | < 50 |
| C0460 | ≥ 7 | ≥ 50 | < 7 | ≥ 50 | < 7 | < 50 | < 7 | < 50 | < 7 | ≥ 50 | < 7 | < 50 |
| C0461 | < 7 | ≥ 50 | N.D. | N.D. | < 7 | ≥ 50 | < 7 | < 50 | < 7 | ≥ 50 | < 7 | < 50 |
| C0462 | < 7 | ≥ 50 | < 7 | < 50 | < 7 | ≥ 50 | < 7 | < 50 | < 7 | < 50 | < 7 | < 50 |
| C0463 | ≥ 7 | ≥ 50 | < 7 | < 50 | < 7 | ≥ 50 | < 7 | < 50 | < 7 | ≥ 50 | < 7 | < 50 |
| C0464 | ≥ 7 | ≥ 50 | < 7 | ≥ 50 | < 7 | < 50 | < 7 | < 50 | < 7 | ≥ 50 | < 7 | < 50 |
| C0465 | ≥ 7 | ≥ 50 | < 7 | ≥ 50 | < 7 | ≥ 50 | < 7 | < 50 | < 7 | ≥ 50 | < 7 | < 50 |
| C0466 | ≥ 7 | ≥ 50 | < 7 | ≥ 50 | < 7 | ≥ 50 | < 7 | < 50 | < 7 | ≥ 50 | < 7 | < 50 |
| C0467 | ≥ 7 | ≥ 50 | < 7 | < 50 | < 7 | ≥ 50 | < 7 | < 50 | < 7 | ≥ 50 | < 7 | < 50 |
| C0468 | < 7 | ≥ 50 | < 7 | < 50 | < 7 | ≥ 50 | < 7 | < 50 | < 7 | ≥ 50 | < 7 | < 50 |
| C0469 | ≥ 7 | ≥ 50 | < 7 | ≥ 50 | < 7 | < 50 | < 7 | < 50 | < 7 | ≥ 50 | < 7 | < 50 |
| C0470 | ≥ 7 | ≥ 50 | < 7 | ≥ 50 | < 7 | < 50 | < 7 | < 50 | < 7 | ≥ 50 | < 7 | < 50 |
| C0471 | ≥ 7 | ≥ 50 | < 7 | < 50 | < 7 | ≥ 50 | < 7 | < 50 | < 7 | ≥ 50 | < 7 | < 50 |
| C0472 | < 7 | ≥ 50 | < 7 | < 50 | < 7 | ≥ 50 | < 7 | < 50 | < 7 | ≥ 50 | < 7 | < 50 |
| C0473 | ≥ 7 | ≥ 50 | < 7 | ≥ 50 | < 7 | ≥ 50 | < 7 | < 50 | < 7 | ≥ 50 | < 7 | < 50 |
| C0474 | ≥ 7 | ≥ 50 | < 7 | < 50 | < 7 | ≥ 50 | < 7 | < 50 | < 7 | ≥ 50 | < 7 | < 50 |
| C0475 | < 7 | ≥ 50 | < 7 | < 50 | < 7 | ≥ 50 | < 7 | < 50 | < 7 | ≥ 50 | < 7 | < 50 |
| C0476 | ≥ 7 | ≥ 50 | < 7 | < 50 | < 7 | ≥ 50 | < 7 | < 50 | < 7 | ≥ 50 | < 7 | < 50 |
| C0477 | ≥ 7 | ≥ 50 | < 7 | < 50 | < 7 | ≥ 50 | < 7 | < 50 | < 7 | ≥ 50 | < 7 | < 50 |
| C0478 | ≥ 7 | ≥ 50 | < 7 | < 50 | < 7 | ≥ 50 | < 7 | < 50 | < 7 | ≥ 50 | < 7 | < 50 |
| C0479 | ≥ 7 | ≥ 50 | < 7 | ≥ 50 | < 7 | < 50 | < 7 | < 50 | < 7 | ≥ 50 | < 7 | < 50 |
| C0480 | ≥ 7 | ≥ 50 | < 7 | ≥ 50 | < 7 | ≥ 50 | < 7 | < 50 | < 7 | ≥ 50 | < 7 | < 50 |
| C0481 | < 7 | ≥ 50 | < 7 | < 50 | < 7 | ≥ 50 | < 7 | < 50 | < 7 | ≥ 50 | < 7 | < 50 |
| C0482 | ≥ 7 | ≥ 50 | ≥ 7 | < 50 | < 7 | ≥ 50 | ≥ 7 | < 50 | < 7 | ≥ 50 | < 7 | < 50 |
| C0483 | N.D. | N.D. | N.D. | N.D. | N.D. | N.D. | N.D. | N.D. | N.D. | N.D. | N.D. | N.D. |
| C0484 | ≥ 7 | ≥ 50 | < 7 | ≥ 50 | < 7 | < 50 | < 7 | < 50 | < 7 | ≥ 50 | < 7 | < 50 |
| C0485 | ≥ 7 | ≥ 50 | < 7 | < 50 | < 7 | < 50 | < 7 | < 50 | < 7 | ≥ 50 | < 7 | < 50 |
| C0486 | < 7 | ≥ 50 | < 7 | < 50 | < 7 | ≥ 50 | < 7 | < 50 | < 7 | ≥ 50 | < 7 | < 50 |
| C0487 | < 7 | ≥ 50 | < 7 | < 50 | < 7 | ≥ 50 | < 7 | < 50 | < 7 | ≥ 50 | < 7 | < 50 |
| C0488 | ≥ 7 | < 50 | < 7 | < 50 | < 7 | < 50 | < 7 | < 50 | < 7 | < 50 | < 7 | < 50 |
| C0489 | < 7 | ≥ 50 | < 7 | < 50 | < 7 | ≥ 50 | < 7 | < 50 | < 7 | < 50 | < 7 | < 50 |
| C0490 | < 7 | ≥ 50 | < 7 | < 50 | < 7 | ≥ 50 | < 7 | < 50 | < 7 | ≥ 50 | < 7 | < 50 |
| C0491 | < 7 | ≥ 50 | < 7 | < 50 | < 7 | ≥ 50 | < 7 | < 50 | < 7 | < 50 | < 7 | < 50 |

Figure 2

| | | | | | | | | | | | | |
|---|---|---|---|---|---|---|---|---|---|---|---|---|
| C0492 | < 7 | ≥ 50 | < 7 | < 50 | < 7 | ≥ 50 | < 7 | < 50 | < 7 | ≥ 50 | < 7 | < 50 |
| C0493 | ≥ 7 | ≥ 50 | < 7 | < 50 | < 7 | ≥ 50 | < 7 | < 50 | < 7 | ≥ 50 | < 7 | < 50 |
| C0494 | < 7 | ≥ 50 | < 7 | < 50 | < 7 | ≥ 50 | < 7 | < 50 | < 7 | ≥ 50 | < 7 | < 50 |
| C0495 | < 7 | ≥ 50 | < 7 | < 50 | < 7 | ≥ 50 | < 7 | < 50 | < 7 | ≥ 50 | < 7 | < 50 |
| C0496 | ≥ 7 | ≥ 50 | < 7 | < 50 | N.D. | N.D. | < 7 | < 50 | < 7 | ≥ 50 | < 7 | < 50 |
| C0497 | ≥ 7 | ≥ 50 | < 7 | < 50 | N.D. | N.D. | < 7 | < 50 | < 7 | ≥ 50 | < 7 | < 50 |
| C0498 | ≥ 7 | ≥ 50 | < 7 | ≥ 50 | N.D. | N.D. | < 7 | < 50 | < 7 | ≥ 50 | < 7 | < 50 |
| C0499 | ≥ 7 | ≥ 50 | < 7 | < 50 | N.D. | N.D. | < 7 | < 50 | < 7 | ≥ 50 | < 7 | < 50 |
| C0500 | ≥ 7 | ≥ 50 | < 7 | ≥ 50 | N.D. | N.D. | < 7 | < 50 | < 7 | ≥ 50 | < 7 | < 50 |
| C0501 | ≥ 7 | ≥ 50 | < 7 | < 50 | N.D. | N.D. | < 7 | < 50 | < 7 | ≥ 50 | < 7 | < 50 |
| C0502 | ≥ 7 | ≥ 50 | < 7 | ≥ 50 | N.D. | N.D. | < 7 | < 50 | < 7 | ≥ 50 | < 7 | < 50 |
| C0503 | ≥ 7 | ≥ 50 | < 7 | < 50 | N.D. | N.D. | < 7 | < 50 | < 7 | < 50 | < 7 | < 50 |
| C0504 | ≥ 7 | ≥ 50 | < 7 | < 50 | N.D. | N.D. | < 7 | < 50 | < 7 | < 50 | < 7 | < 50 |
| C0505 | ≥ 7 | ≥ 50 | < 7 | < 50 | < 7 | ≥ 50 | < 7 | < 50 | < 7 | ≥ 50 | < 7 | < 50 |
| C0506 | ≥ 7 | ≥ 50 | < 7 | < 50 | < 7 | < 50 | < 7 | < 50 | < 7 | ≥ 50 | < 7 | < 50 |
| C0507 | ≥ 7 | ≥ 50 | < 7 | ≥ 50 | < 7 | ≥ 50 | < 7 | < 50 | < 7 | ≥ 50 | < 7 | < 50 |
| C0508 | ≥ 7 | ≥ 50 | < 7 | < 50 | < 7 | ≥ 50 | < 7 | < 50 | < 7 | ≥ 50 | < 7 | < 50 |
| C0509 | ≥ 7 | ≥ 50 | < 7 | < 50 | < 7 | ≥ 50 | < 7 | < 50 | < 7 | ≥ 50 | < 7 | < 50 |

7-MEMBERED AZA-HETEROCYCLIC CONTAINING δ-OPIOID RECEPTOR MODULATING COMPOUNDS, METHODS OF USING AND MAKING THE SAME

CROSS REFERENCE TO RELATED APPLICATIONS

This application is a National Phase Entry of International Patent Application No. PCT/US2018/018303, filed Feb. 15, 2018, which claims priority to U.S. Provisional Application No. 61/460,386, filed Feb. 17, 2017, each of which is hereby incorporated by reference in its entirety.

REFERENCE TO GOVERNMENT RIGHTS

This invention was made with government support under Grant No. U01NS074480-02 awarded by the National Institutes of Health. The government has certain rights in the invention.

FIELD

Embodiments disclosed herein are directed, in part, to compounds, or pharmaceutically acceptable salts thereof, for modulating the activity of delta opioid receptor and/or methods for treating pain, (e.g., neuropathic pain), migraines (e.g. episodic, chronic or acute), headaches (e.g., episodic, chronic, or acute), depression, Parkinsons Disease, PTSD, anxiety, and/or overactive bladder, or any combination thereof.

BACKGROUND

Opioid receptors (ORs) mediate the actions of morphine and morphine-like opioids, including most clinical analgesics. Three molecularly and pharmacologically distinct opioid receptor types have been described: δ, κ and μ. Furthermore, each type is believed to have sub-types. All three of these opioid receptor types appear to share the same functional mechanisms at a cellular level. For example, certain activation of the opioid receptors causes inhibition of adenylate cyclase, and recruits β-arrestin.

The delta opioid receptor (DOR) has long been of interest as a target for potentially non-addictive treatments for a variety of CNS disorders. Recent evidence suggests that DOR activation may be beneficial in the treatment of migraine, neuropathic pain, Parkinson's disease, depression, anxiety and several other indications. However, some DOR agonists have caused seizure in preclinical species, hindering the development of selective drugs targeting the DOR. Thus there is a need to identify a DOR modulator for the treatment of these and other conditions. The present embodiments described herein fulfill these needs and others.

SUMMARY

In some embodiments, one or more compounds as described herein, or a pharmaceutically acceptable salt thereof, are provided. In some embodiments, a compound of one or more formula as described herein, or a pharmaceutically acceptable salt thereof, are provided.

In some embodiments, the present invention provides pharmaceutical compositions comprising one or more compounds described herein or a pharmaceutically acceptable salt thereof of.

In some embodiments, the present embodiments provide methods of treating pain, migraines (e.g. episodic, chronic or acute), headaches (e.g., episodic, chronic, or acute), depression, anxiety, and/or overactive bladder in a subject are provided. In some embodiments, the methods comprise administering to the subject one or more compounds described herein, or a salt thereof or a pharmaceutical composition comprising one or more compounds, or salt thereof of a compound described herein. In some embodiments, methods of preventing migraines or headaches are provided. In some embodiments, methods for treating major depressive disorder, treatment resistant anxiety, post traumatic stress disorder, neuropathic pain, including, diabetic peripheral neuropathy, post-herpetic neuralgia, chemotherapy induced neuropathic pain, prevention of chemotherapy-induced neuropathy, prevention of chemotherapy-induced neuropathic pain, trigeminal neuralgia, inflammatory pain, including, osteoarthritis, rheumatoid arthritis, Rett Syndrome, Autism spectrum disorders, migraine, cluster headaches, acute abortive treatment, prophylaxis of acute intermittent migraine, prophylaxis of chronic migraine, treatment of episodic and chronic cluster headache, prevention of episodic and chronic cluster headache, Charcot-Marie Tooth disease, Traumatic brain injury, fibromyalgia, stroke, acute ischemic syndrome, ischemia/reperfusion injury, substance abuse intervention, and/or treatment of alcohol abuse in a subject are provided. In some embodiments, the methods comprise administering to the subject one or more compounds described herein, or a salt thereof or a pharmaceutical composition comprising one or more compounds, or salt thereof of a compound described herein. In some embodiments the subject is a mammal. In some embodiments, the subject is a subject in need thereof.

BRIEF DESCRIPTION OF THE DRAWINGS

FIG. 1 illustrates compounds prepared according to the examples, which includes the LCMS data.

FIG. 2 illustrates the in vitro data for the compounds described herein and as referenced in the examples.

DESCRIPTION OF EMBODIMENTS

Unless defined otherwise, all technical and scientific terms have the same meaning as is commonly understood by one of ordinary skill in the art to which the embodiments disclosed belongs.

As used herein, the terms "a" or "an" means that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by 10% and remain within the scope of the disclosed embodiments.

As used herein, the term "acylamino" means an amino group substituted by an acyl group (e.g., —O—C(=O)—H or —O—C(=O)-alkyl). An example of an acylamino is —NHC(=O)H or —NHC(=O)CH$_3$. The term "lower acylamino" refers to an amino group substituted by a loweracyl group (e.g., —O—C(=O)—H or —O—C(=O)—C$_{1-6}$alkyl). An example of a lower acylamino is —NHC(=O)H or —NHC(=O)CH$_3$.

As used herein, the term "alkenyl" means a straight or branched alkyl group having one or more double carbon-carbon bonds and 2-20 carbon atoms, including, but not limited to, ethenyl, 1-propenyl, 2-propenyl, 2-methyl-1-propenyl, 1-butenyl, 2-butenyl, and the like. In some embodiments, the alkenyl chain is from 2 to 10 carbon atoms in length, from 2 to 8 carbon atoms in length, from 2 to 6 carbon atoms in length, or from 2 to 4 carbon atoms in length.

The terms "alkoxy", "phenyloxy", "benzoxy" and "pyrimidinyloxy" refer to an alkyl group, phenyl group, benzyl group, or pyrimidinyl group, respectively, each optionally substituted, that is bonded through an oxygen atom. For example, the term "alkoxy" means a straight or branched —O-alkyl group of 1 to 20 carbon atoms, including, but not limited to, methoxy, ethoxy, n-propoxy, iso-propoxy, t-butoxy, and the like. In some embodiments, the alkoxy chain is from 1 to 10 carbon atoms in length, from 1 to 8 carbon atoms in length, from 1 to 6 carbon atoms in length, from 1 to 4 carbon atoms in length, from 2 to 10 carbon atoms in length, from 2 to 8 carbon atoms in length, from 2 to 6 carbon atoms in length, or from 2 to 4 carbon atoms in length.

As used herein, the term "alkyl" means a saturated hydrocarbon group which is straight-chained or branched. An alkyl group can contain from 1 to 20, from 2 to 20, from 1 to 10, from 2 to 10, from 1 to 8, from 2 to 8, from 1 to 6, from 2 to 6, from 1 to 4, from 2 to 4, from 1 to 3, or 2 or 3 carbon atoms. Examples of alkyl groups include, but are not limited to, methyl (Me), ethyl (Et), propyl (e.g., n-propyl and isopropyl), butyl (e.g., n-butyl, t-butyl, isobutyl), pentyl (e.g., n-pentyl, isopentyl, neopentyl), hexyl, isohexyl, heptyl, 4,4-dimethylpentyl, octyl, 2,2,4-trimethylpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

As used herein, the term "alkylamino" means an amino group substituted by an alkyl group having from 1 to 6 carbon atoms. An example of an alkylamino is —NHCH$_2$CH$_3$.

As used herein, the term "alkylene" or "alkylenyl" means a divalent alkyl linking group. An example of an alkylene (or alkylenyl) is methylene or methylenyl (—CH$_2$—).

As used herein, the term "alkylthio" means an —S-alkyl group having from 1 to 6 carbon atoms. An example of an alkylthio group is —SCH$_2$CH$_3$.

As used herein, the term "alkynyl" means a straight or branched alkyl group having one or more triple carbon-carbon bonds and 2-20 carbon atoms, including, but not limited to, acetylene, 1-propylene, 2-propylene, and the like. In some embodiments, the alkynyl chain is 2 to 10 carbon atoms in length, from 2 to 8 carbon atoms in length, from 2 to 6 carbon atoms in length, or from 2 to 4 carbon atoms in length.

As used herein, the term "amidino" means —C(=NH)NH$_2$.

As used herein, the term "amino" means —NH$_2$.

As used herein, the term "aminoalkoxy" means an alkoxy group substituted by an amino group. An example of an aminoalkoxy is —OCH$_2$CH$_2$NH$_2$.

As used herein, the term "aminoalkyl" means an alkyl group substituted by an amino group. An example of an aminoalkyl is —CH$_2$CH$_2$NH$_2$.

As used herein, the term "aminosulfonyl" means —S(=O)$_2$NH$_2$.

As used herein, the term "aminoalkylthio" means an alkylthio group substituted by an amino group. An example of an aminoalkylthio is —SCH$_2$CH$_2$NH$_2$.

As used herein, the term "amphiphilic" means a three-dimensional structure having discrete hydrophobic and hydrophilic regions. An amphiphilic compound suitably has the presence of both hydrophobic and hydrophilic elements.

As used herein, the term "animal" includes, but is not limited to, humans and non-human vertebrates such as wild, domestic, and farm animals.

As used herein, the term "antagonize" or "antagonizing" means reducing or completely eliminating an effect, such as an activity of the delta opioid receptor.

As used herein, the phrase "anti-recetpor effective amount" of a compound can be measured by the anti-receptor effectiveness of the compound. In some embodiments, an anti-receptor effective amount inhibits an activity of the receptor by at least 10%, by at least 20%, by at least 30%, by at least 40%, by at least 50%, by at least 60%, by at least 70%, by at least 80%, by at least 90%, or by at least 95%. In some embodiments, an "anti-receptor effective amount" is also a "therapeutically effective amount" whereby the compound reduces or eliminates at least one effect of a delta opioid receptor. In some embodiments, the effect is the Beta-arrestin effect. In some embodiments, the effect is the G-protein mediated effect.

As used herein, the term "aryl" means a monocyclic, bicyclic, or polycyclic (e.g., having 2, 3 or 4 fused rings) aromatic hydrocarbons. In some embodiments, aryl groups have from 6 to 20 carbon atoms or from 6 to 10 carbon atoms. Examples of aryl groups include, but are not limited to, phenyl, naphthyl, anthracenyl, phenanthrenyl, indanyl, indenyl, tetrahydronaphthyl, and the like. Examples of aryl groups include, but are not limited to:

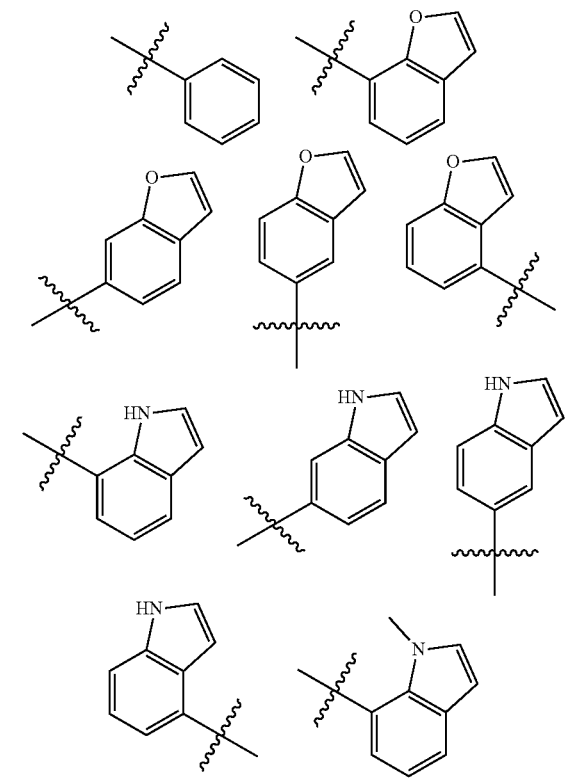

-continued

-continued
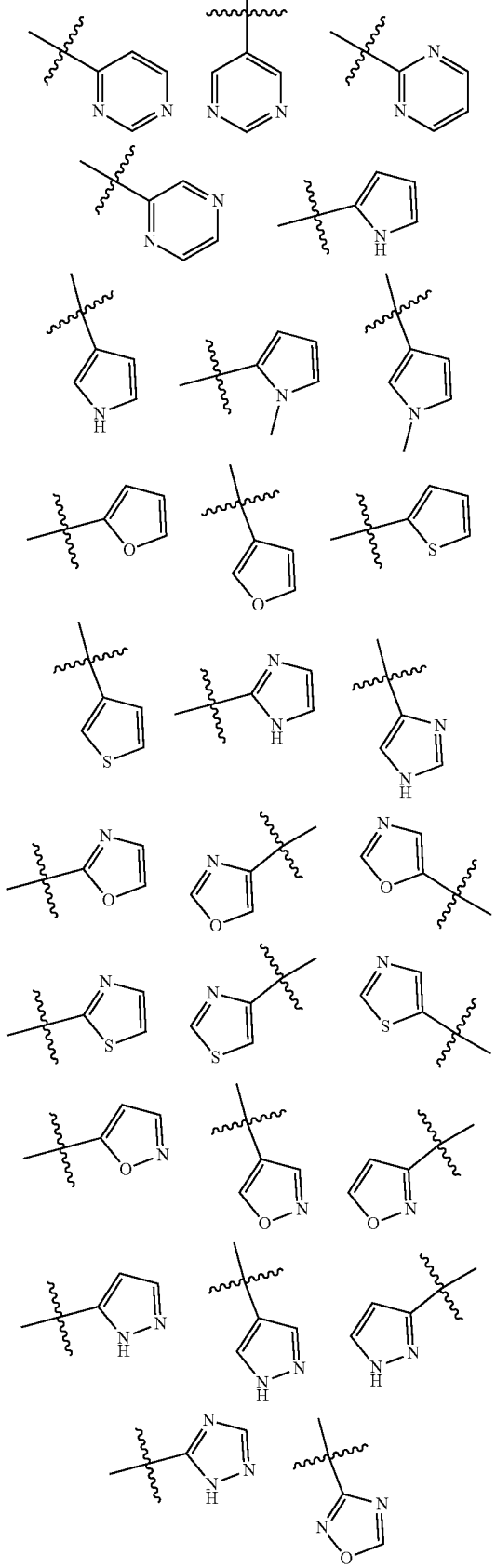
-continued
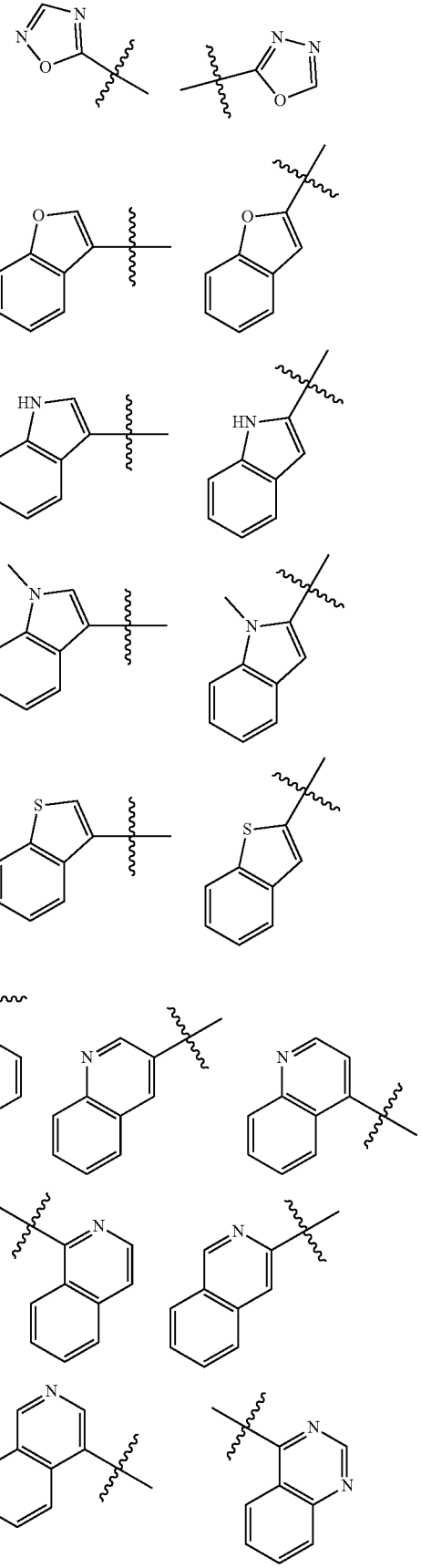

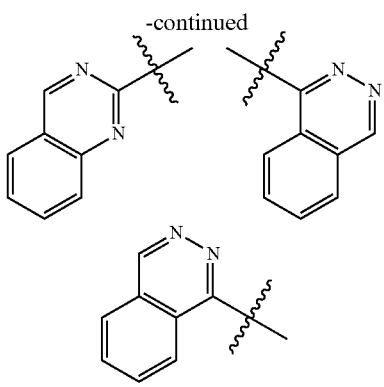

As used herein, the term "arylalkyl" means a $C_{1-6}$alkyl substituted by aryl.

As used herein, the term "arylamino" means an amino group substituted by an aryl group. An example of an arylamino is —NH(phenyl).

As used herein, the term "arylene" means an aryl linking group, i.e., an aryl group that links one group to another group in a molecule.

As used herein, the term "cancer" means a spectrum of pathological symptoms associated with the initiation or progression, as well as metastasis, of malignant tumors.

As used herein, the term "carbamoyl" means —C(O)—NH$_2$.

As used herein, the term "carbocycle" means a 5- or 6-membered, saturated or unsaturated cyclic ring, optionally containing O, S, or N atoms as part of the ring. Examples of carbocycles include, but are not limited to, cyclopentyl, cyclohexyl, cyclopenta-1,3-diene, phenyl, and any of the heterocycles recited above.

As used herein, the term "carrier" means a diluent, adjuvant, or excipient with which a compound is administered. Pharmaceutical carriers can be liquids, such as water and oils, including those of petroleum, animal, vegetable or synthetic origin, such as peanut oil, soybean oil, mineral oil, sesame oil and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used.

As used herein, the term, "compound" means all stereoisomers, tautomers, and isotopes of the compounds described herein.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "contacting" means bringing together of two elements in an in vitro system or an in vivo system. For example, "contacting" a δ-opioid compound with a δ-opioid receptor with an individual or patient or cell includes the administration of the compound to an individual or patient, such as a human, as well as, for example, introducing a compound into a sample containing a cellular or purified preparation containing the δ-opioid receptor.

As used herein, the term "cyano" means —CN.

As used herein, the term "cycloalkyl" means non-aromatic cyclic hydrocarbons including cyclized alkyl, alkenyl, and alkynyl groups that contain up to 20 ring-forming carbon atoms. Cycloalkyl groups can include mono- or polycyclic ring systems such as fused ring systems, bridged ring systems, and spiro ring systems. In some embodiments, polycyclic ring systems include 2, 3, or 4 fused rings. A cycloalkyl group can contain from 3 to 15, from 3 to 10, from 3 to 8, from 3 to 6, from 4 to 6, from 3 to 5, or 5 or 6 ring-forming carbon atoms. Ring-forming carbon atoms of a cycloalkyl group can be optionally substituted by oxo or sulfido. Examples of cycloalkyl groups include, but are not limited to, cyclopropyl, cyclobutyl, cyclopentyl, cyclohexyl, cycloheptyl, cyclooctyl, cyclononyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (having a bond in common with) to the cycloalkyl ring, for example, benzo or thienyl derivatives of pentane, pentene, hexane, and the like (e.g., 2,3-dihydro-H-indene-1-yl, or 1H-inden-2(3H)-one-1-yl).

As used herein, the term "cycloalkylalkyl" means a $C_{1-6}$alkyl substituted by cycloalkyl.

As used herein, the term "dialkylamino" means an amino group substituted by two alkyl groups, each having from 1 to 6 carbon atoms.

As used herein, the term "diazamino" means —N(NH$_2$)$_2$.

As used herein, the term "facially amphiphilic" or "facial amphiphilicity" means compounds with polar (hydrophilic) and nonpolar (hydrophobic) side chains that adopt conformation(s) leading to segregation of polar and nonpolar side chains to opposite faces or separate regions of the structure or molecule.

As used herein, the term "guanidino" means —NH(=NH)NH$_2$.

As used herein, the term "halo" means halogen groups including, but not limited to fluoro, chloro, bromo, and iodo.

As used herein, the term "haloalkoxy" means an —O-haloalkyl group. An example of an haloalkoxy group is OCF$_3$.

As used herein, the term "haloalkyl" means a $C_{1-6}$alkyl group having one or more halogen substituents. Examples of haloalkyl groups include, but are not limited to, CF$_3$, C$_2$F$_5$, CH$_2$F, CHF$_2$, CCl$_3$, CHCl$_2$, CH$_2$CF$_3$, and the like.

As used herein, the term "heteroaryl" means an aromatic heterocycle having up to 20 ring-forming atoms (e.g., C) and having at least one heteroatom ring member (ring-forming atom) such as sulfur, oxygen, or nitrogen. In some embodiments, the heteroaryl group has at least one or more heteroatom ring-forming atoms, each of which are, independently, sulfur, oxygen, or nitrogen. In some embodiments, the heteroaryl group has from 3 to 20 ring-forming atoms, from 3 to 10 ring-forming atoms, from 3 to 6 ring-forming atoms, or from 3 to 5 ring-forming atoms. In some embodiments, the heteroaryl group contains 2 to 14 carbon atoms, from 2 to 7 carbon atoms, or 5 or 6 carbon atoms. In some embodiments, the heteroaryl group has 1 to 4 heteroatoms, 1 to 3 heteroatoms, or 1 or 2 heteroatoms. Heteroaryl groups include monocyclic and polycyclic (e.g., having 2, 3 or 4 fused rings) systems. Examples of heteroaryl groups include, but are not limited to, pyridyl, pyrimidinyl, pyrazinyl, pyridazinyl, triazinyl, furyl, quinolyl, isoquinolyl, thienyl, imidazolyl, thiazolyl, indolyl (such as indol-3-yl), pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, pyranyl, oxadiazolyl, isoxazolyl, triazolyl, thianthrenyl, pyrazolyl, indolizinyl, isoindolyl, isobenzofuranyl, benzoxazolyl, xanthenyl, 2H-pyrrolyl, pyrrolyl, 3H-indolyl, 4H-quinolizinyl, phthalazinyl, naphthyridinyl, quinazolinyl, phenanthridinyl, acridinyl, perimidinyl, phenanthrolinyl, phenazinyl, isothiazolyl, phenothiazinyl, isoxazolyl, furanyl, phenoxazinyl groups, and the like. Suitable heteroaryl groups include 1,2,3-triazole, 1,2,4-triazole, 5-amino-1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, and 2-aminopyridine.

As used herein, the term "heteroarylalkyl" means a $C_{1-6}$alkyl group substituted by a heteroaryl group.

As used herein, the term "heteroarylamino" means an amino group substituted by a heteroaryl group. An example of a heteroarylamino is —NH-(2-pyridyl).

As used herein, the term "heteroarylene" means a heteroaryl linking group, i.e., a heteroaryl group that links one group to another group in a molecule.

As used herein, the term "heterocycle" or "heterocyclic ring" means a 5- to 7-membered mono- or bicyclic or 7- to 10-membered bicyclic heterocyclic ring system any ring of which may be saturated or unsaturated, and which consists of carbon atoms and from one to three heteroatoms chosen from N, O and S, and wherein the N and S heteroatoms may optionally be oxidized, and the N heteroatom may optionally be quaternized, and including any bicyclic group in which any of the above-defined heterocyclic rings is fused to a benzene ring. Particularly useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of heterocyclic groups include, but are not limited to, piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

As used herein, the term "heterocycloalkyl" means non-aromatic heterocycles having up to 20 ring-forming atoms including cyclized alkyl, alkenyl, and alkynyl groups, where one or more of the ring-forming carbon atoms is replaced by a heteroatom such as an O, N, or S atom. Hetercycloalkyl groups can be mono or polycyclic (e.g., fused, bridged, or spiro systems). In some embodiments, the heterocycloalkyl group has from 1 to 20 carbon atoms, or from 3 to 20 carbon atoms. In some embodiments, the heterocycloalkyl group contains 3 to 14 ring-forming atoms, 3 to 7 ring-forming atoms, or 5 or 6 ring-forming atoms. In some embodiments, the heterocycloalkyl group has 1 to 4 heteroatoms, 1 to 3 heteroatoms, or 1 or 2 heteroatoms. In some embodiments, the heterocycloalkyl group contains 0 to 3 double bonds. In some embodiments, the heterocycloalkyl group contains 0 to 2 triple bonds. Examples of heterocycloalkyl groups include, but are not limited to, morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, oxazolidinyl, isothiazolidinyl, pyrazolidinyl, thiazolidinyl, imidazolidinyl, pyrrolidin-2-one-3-yl, and the like. In addition, ring-forming carbon atoms and heteroatoms of a heterocycloalkyl group can be optionally substituted by oxo or sulfido. For example, a ring-forming S atom can be substituted by 1 or 2 oxo (form a S(O) or S(O)$_2$). For another example, a ring-forming C atom can be substituted by oxo (form carbonyl). Also included in the definition of heterocycloalkyl are moieties that have one or more aromatic rings fused (having a bond in common with) to the nonaromatic heterocyclic ring including, but not limited to, pyridinyl, thiophenyl, phthalimidyl, naphthalimidyl, and benzo derivatives of heterocycles such as indolene, isoindolene, 4,5,6,7-tetrahydrothieno[2,3-c]pyridine-5-yl, 5,6-dihydrothieno[2,3-c]pyridin-7(4H)-one-5-yl, isoindolin-1-one-3-yl, and 3,4-dihydroisoquinolin-1(2H)-one-3yl groups. Ring-forming carbon atoms and heteroatoms of the heterocycloalkyl group can be optionally substituted by oxo or sulfido.

As used herein, the term "heterocycloalkylalkyl" refers to a $C_{1-6}$alkyl substituted by heterocycloalkyl.

As used herein, the term "hydoxy" or "hydroxyl" means an —OH group.

As used herein, the term "hydroxyalkyl" or "hydroxylalkyl" means an alkyl group substituted by a hydroxyl group. Examples of a hydroxylalkyl include, but are not limited to, —CH$_2$OH and —CH$_2$CH$_2$OH.

As used herein, the term "individual" or "patient," used interchangeably, means any animal, including mammals, such as mice, rats, other rodents, rabbits, dogs, cats, swine, cattle, sheep, horses, or primates, such as humans.

As used herein, the phrase "inhibiting activity," such as enzymatic or receptor activity means reducing by any measurable amount the activity of an enzyme or receptor, such as the δ-opioid receptor.

As used herein, the phrase "in need thereof" means that the animal or mammal has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent.

As used herein, the phrase "in situ gellable" means embracing not only liquids of low viscosity that form gels upon contact with the eye or with lacrimal fluid in the exterior of the eye, but also more viscous liquids such as semi-fluid and thixotropic gels that exhibit substantially increased viscosity or gel stiffness upon administration to the eye.

As used herein, the phrase "integer from X to Y" means any integer that includes the endpoints. For example, the phrase "integer from X to Y" means 1, 2, 3, 4, or 5.

As used herein, the term "isolated" means that the compounds described herein are separated from other components of either (a) a natural source, such as a plant or cell, or (b) a synthetic organic chemical reaction mixture, such as by conventional techniques.

As used herein, the term "mammal" means a rodent (i.e., a mouse, a rat, or a guinea pig), a monkey, a cat, a dog, a cow, a horse, a pig, or a human. In some embodiments, the mammal is a human.

As used herein, the term "N-alkyl" refers to a alkyl chain that is substituted with an amine group. Non-limiting examples, include, but are not limited to

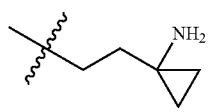 [SMILES: *CCC1(N)CC1]

and the like. The alkyl chain can be linear, branched, cyclic, or any combination thereof. In some embodiments, the alkyl comprises 1-10, 1-9, 1-8, 1-7, 1-6, 1-5, 1-4, 1-3, or 1-2 carbons.

As used herein, the term "nitro" means $-NO_2$.

As used herein, the term "n-membered", where n is an integer, typically describes the number of ring-forming atoms in a moiety, where the number of ring-forming atoms is n. For example, pyridine is an example of a 6-membered heteroaryl ring and thiophene is an example of a 5-membered heteroaryl ring.

As used herein, the phrase "ophthalmically acceptable" means having no persistent detrimental effect on the treated eye or the functioning thereof, or on the general health of the subject being treated. However, it will be recognized that transient effects such as minor irritation or a "stinging" sensation are common with topical ophthalmic administration of drugs and the existence of such transient effects is not inconsistent with the composition, formulation, or ingredient (e.g., excipient) in question being "ophthalmically acceptable" as herein defined.

As used herein, the phrase "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent groups, provided that the normal valency of the designated atom or moiety is not exceeded, and that the substitution results in a stable compound. For example, if a methyl group is optionally substituted, then 3 hydrogen atoms on the carbon atom can be replaced with substituent groups.

As used herein, the phrase "pharmaceutically acceptable" means those compounds, materials, compositions, and/or dosage forms which are, within the scope of sound medical judgment, suitable for use in contact with tissues of humans and animals. In some embodiments, "pharmaceutically acceptable" means approved by a regulatory agency of the Federal or a state government or listed in the U.S. Pharmacopeia or other generally recognized pharmacopeia for use in animals, and more particularly in humans.

As used herein, the phrase "pharmaceutically acceptable salt(s)," includes, but is not limited to, salts of acidic or basic groups. Compounds that are basic in nature are capable of forming a wide variety of salts with various inorganic and organic acids. Acids that may be used to prepare pharmaceutically acceptable acid addition salts of such basic compounds are those that form non-toxic acid addition salts, i.e., salts containing pharmacologically acceptable anions including, but not limited to, sulfuric, thiosulfuric, citric, maleic, acetic, oxalic, hydrochloride, hydrobromide, hydroiodide, nitrate, sulfate, bisulfate, bisulfite, phosphate, acid phosphate, isonicotinate, borate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, bicarbonate, malonate, mesylate, esylate, napsydisylate, tosylate, besylate, orthophosphate, trifluoroacetate, and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include, but are not limited to, alkali metal or alkaline earth metal salts and, particularly, calcium, magnesium, ammonium, sodium, lithium, zinc, potassium, and iron salts. The present invention also includes quaternary ammonium salts of the compounds described herein, where the compounds have one or more tertiary amine moiety.

As used herein, the term "phenyl" means $-C_6H_5$. A phenyl group can be unsubstituted or substituted with one, two, or three suitable substituents.

As used herein, the term "prodrug" means a derivative of a known direct acting drug, which derivative has enhanced delivery characteristics and therapeutic value as compared to the drug, and is transformed into the active drug by an enzymatic or chemical process.

As used herein, the term "purified" means that when isolated, the isolate contains at least 90%, at least 95%, at least 98%, or at least 99% of a compound described herein by weight of the isolate.

As used herein, the phrase "quaternary ammonium salts" means derivatives of the disclosed compounds with one or more tertiary amine moieties wherein at least one of the tertiary amine moieties in the parent compound is modified by converting the tertiary amine moiety to a quaternary ammonium cation via alkylation (and the cations are balanced by anions such as $Cl^-$, $CH_3COO^-$, and $CF_3COO^-$), for example methylation or ethylation.

As used herein, the term "semicarbazone" means $=NNHC(=O)NH_2$.

As used herein, the phrase "solubilizing agent" means agents that result in formation of a micellar solution or a true solution of the drug.

As used herein, the term "solution/suspension" means a liquid composition wherein a first portion of the active agent is present in solution and a second portion of the active agent is present in particulate form, in suspension in a liquid matrix.

As used herein, the phrase "substantially isolated" means a compound that is at least partially or substantially separated from the environment in which it is formed or detected.

As used herein, the phrase "suitable substituent" or "substituent" means a group that does not nullify the synthetic or pharmaceutical utility of the compounds described herein or the intermediates useful for preparing them. Examples of suitable substituents include, but are not limited to: $C_1$-$C_6$alkyl, $C_1$-$C_6$alkenyl, $C_1$-$C_6$alkynyl, $C_5$-$C_6$aryl, $C_1$-$C_6$alkoxy, $C_3$-$C_5$heteroaryl, $C_3$-$C_6$cycloalkyl, $C_5$-$C_6$aryloxy, $-CN$, $-OH$, oxo, halo, haloalkyl, $-NO_2$, $-CO_2H$, $-NH_2$, $-NH(C_1$-$C_8$alkyl), $-N(C_1$-$C_8$alkyl)$_2$, $-NH(C_6$aryl), $-N(C_5$-$C_6$aryl)$_2$, $-CHO$, $-CO(C_1$-$C_6$alkyl), $-CO((C_5$-$C_6)$aryl), $-CO_2((C_1$-$C_6)$alkyl), and $-CO_2((C_5$-$C_6)$aryl). One of skill in art can readily choose a suitable substituent based on the stability and pharmacological and synthetic activity of the compounds described herein.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, elimination of a disorder, or side-effects. The amount needed to elicit the therapeutic response can be determined based on the age, health, size and sex of the subject. Optimal amounts can also be determined based on monitoring of the subject's response to treatment.

As used herein, the terms "treat," "treated," or "treating" mean both therapeutic treatment and prophylactic measures wherein the object is to ameliorate slow down (lessen) an undesired physiological condition, disorder or disease, or obtain beneficial or desired clinical results. For purposes of this invention, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response without excessive levels of side effects. Treatment also includes prolonging survival as compared to expected survival if not receiving treatment. Thus, "treatment of pain" or "treating pain" means an activity that alleviates or ameliorates any of the primary phenomena or secondary symptoms associated with the pain or other condition described herein.

As used herein, the term "ureido" means —NHC(=O)—NH$_2$.

At various places in the present specification, substituents of compounds may be disclosed in groups or in ranges. It is specifically intended that embodiments include each and every individual subcombination of the members of such groups and ranges. For example, the term "C$_{1-6}$alkyl" is specifically intended to individually disclose methyl, ethyl, propyl, C$_4$alkyl, C$_5$alkyl, and C$_6$alkyl.

For compounds in which a variable appears more than once, each variable can be a different moiety selected from the Markush group defining the variable. For example, where a structure is described having two R groups that are simultaneously present on the same compound, the two R groups can represent different moieties selected from the Markush groups defined for R. In another example, when an optionally multiple substituent is designated in the form, for example,

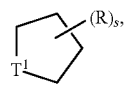

then it is understood that substituent R can occur s number of times on the ring, and R can be a different moiety at each occurrence. Further, in the above example, where the variable T$^1$ is defined to include hydrogens, such as when T$^1$ is CH$_2$, NH, etc., any H can be replaced with a substituent.

It is further appreciated that certain features described herein, which are, for clarity, described in the context of separate embodiments, can also be provided in combination in a single embodiment. Conversely, various features which are, for brevity, described in the context of a single embodiment, can also be provided separately or in any suitable subcombination.

It is understood that the present invention encompasses the use, where applicable, of stereoisomers, diastereomers and optical stereoisomers of the compounds of the invention, as well as mixtures thereof. Additionally, it is understood that stereoisomers, diastereomers, and optical stereoisomers of the compounds of the invention, and mixtures thereof, are within the scope of the invention. By way of non-limiting example, the mixture may be a racemate or the mixture may comprise unequal proportions of one particular stereoisomer over the other. Additionally, the compounds can be provided as a substantially pure stereoisomers, diastereomers and optical stereoisomers (such as epimers).

The compounds described herein can be asymmetric (e.g., having one or more stereocenters). All stereoisomers, such as enantiomers and diastereomers, are intended to be included within the scope of the invention unless otherwise indicated. Compounds that contain asymmetrically substituted carbon atoms can be isolated in optically active or racemic forms. Methods of preparation of optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds are also included within the scope of the invention and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art, including, for example, chiral HPLC, fractional recrystallization using a chiral resolving acid which is an optically active, salt-forming organic acid. Suitable resolving agents for fractional recrystallization methods include, but are not limited to, optically active acids, such as the D and L forms of tartaric acid, diacetyltartaric acid, dibenzoyltartaric acid, mandelic acid, malic acid, lactic acid, and the various optically active camphorsulfonic acids such as β-camphorsulfonic acid. Other resolving agents suitable for fractional crystallization methods include, but are not limited to, stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent compositions can be determined by one skilled in the art.

Compounds may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds also include hydrates and solvates, as well as anhydrous and non-solvated forms.

Compounds can also include all isotopes of atoms occurring in the intermediates or final compounds. Isotopes include those atoms having the same atomic number but different mass numbers. For example, isotopes of hydrogen include tritium and deuterium.

In some embodiments, the compounds, or salts thereof, are substantially isolated. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

Although the disclosed compounds are suitable, other functional groups can be incorporated into the compound with an expectation of similar results. In particular, thioamides and thioesters are anticipated to have very similar properties. The distance between aromatic rings can impact the geometrical pattern of the compound and this distance can be altered by incorporating aliphatic chains of varying length, which can be optionally substituted or can comprise an amino acid, a dicarboxylic acid or a diamine. The distance between and the relative orientation of monomers within the compounds can also be altered by replacing the amide bond with a surrogate having additional atoms. Thus, replacing a carbonyl group with a dicarbonyl alters the distance between the monomers and the propensity of dicarbonyl unit to adopt an anti arrangement of the two carbonyl moiety and alter the periodicity of the compound. Pyromellitic anhydride represents still another alternative to simple amide linkages which can alter the conformation and physical properties of the compound. Modern methods of solid phase organic chemistry (E. Atherton and R. C. Sheppard, Solid Phase Peptide Synthesis A Practical Approach IRL Press Oxford 1989) now allow the synthesis of homodisperse compounds with molecular weights approaching 5,000 Daltons. Other substitution patterns are equally effective.

The compounds also include derivatives referred to as prodrugs.

Compounds containing an amine function can also form N-oxides. A reference herein to a compound that contains an amine function also includes the N-oxide. Where a compound contains several amine functions, one or more than one nitrogen atom can be oxidized to form an N-oxide. Examples of N-oxides include N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g., a peroxycarboxylic acid) (see, Advanced Organic Chemistry, by Jerry March, 4th Edition, Wiley Interscience).

Embodiments of various compounds and salts thereof are provided. Where a variable is not specifically recited, the variable can be any option described herein, except as otherwise noted or dictated by context.

In some embodiments, the present subject matter provides compounds having Formula I Ia, Ia-1, or Ia-2, or pharmaceutically acceptable salt thereof,

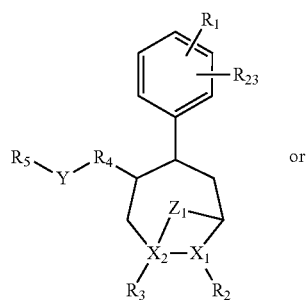

I

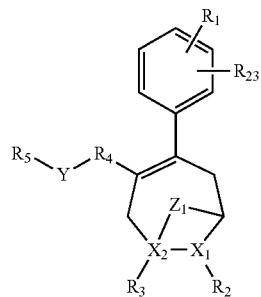

Ia

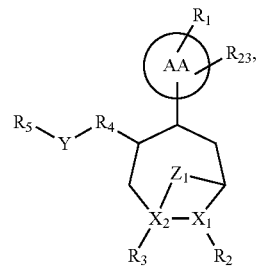

Ia-1

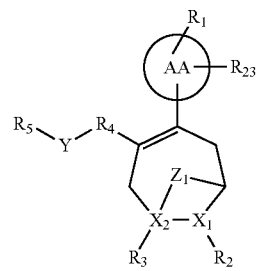

Ia-2 wherein:

(AA) is independently, optionally substituted cycloalkyl, optionally substituted heterocycle, optionally substituted imidazole,

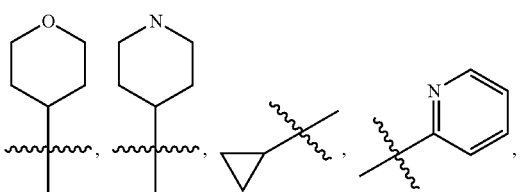

-continued

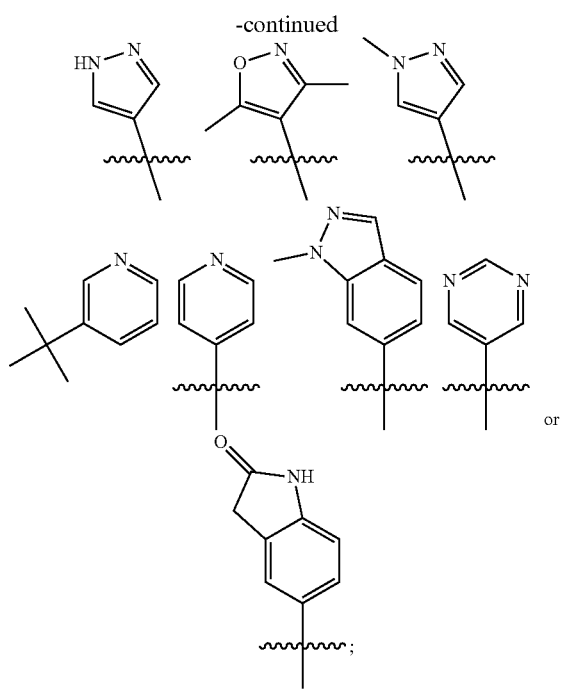

$X_1$ and $X_2$ are each, independently, C or N provided that both $X_1$ and $X_2$ are not the same;

Y is O or N, $R_1$ is H, halo, —SO$_2$C$_1$-C$_6$alkyl, —OCF$_3$, —NR$_{30}$R$_{31}$, —NH—(CH$_2$)$_y$—R$_{17}$, —S—(CH$_2$)$_y$—R$_{17}$, —(CH$_2$)$_y$—R$_{17}$, —O—CH$_2$)$_y$—R$_{17}$, —OR$_8$, or

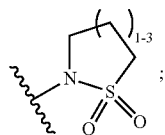

$R_{17}$ is H, C$_1$-C$_6$ haloalkyl, —OR$_{18}$,

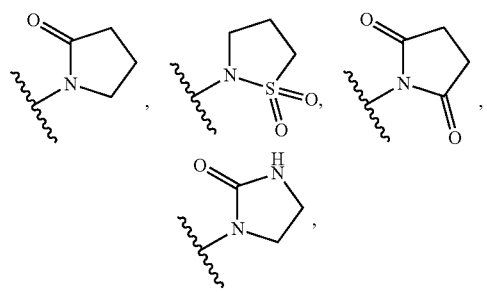

—C(=O)N(R$_{18}$)$_2$, optionally substituted cycloalkyl, —(CH$_2$)$_p$R$_{19}$, or optionally substituted heterocycle;

$R_{23}$ is H, —SO$_2$C$_1$-C$_6$alkyl, —OCF$_3$, halo, optionally substituted C$_1$-C$_6$ alkyl, optionally substituted sulfonamide, optionally substituted cyclic sulfonamide, C(=O)R$_8$;

y is an integer from 0-6;

or when $R_1$ is —(CH$_2$)$_y$—R$_{17}$, $R_1$ and $R_{23}$ form a heterocycle that is fused to the phenyl ring;

$R_2$ and $R_3$ are each, independently, is a protecting group, C(=O)OR81$_b$, H, optionally substituted aryl, optionally substituted C$_1$-C$_6$ haloalkyl, —R$_{20}$R$_{21}$, —NR$_{20}$R$_{21}$, optionally substituted C$_1$-C$_8$ branched or unbranched alkyl, optionally substituted C$_2$-C$_6$ alkenyl, optionally substituted C$_2$-C$_6$ haloalkenyl, —(CH$_2$)$_n$R$_{19}$, optionally substituted cycloalkyl, including but not limited to cyclopropyl, optionally substituted C$_1$-C$_6$ alkoxy, optionally substituted pyrrolinyl, optionally substituted morpholinyl, optionally substituted pyridyl, optionally substituted piperidyl, C$_3$-C$_6$ cyclic ether, or —CH$_2$C(=O)R$_{70A}$, wherein R$_{70A}$ is phenyl or C$_1$-C$_6$; such that when $X_1$ is C, $R_2$ is H or when $X_2$ is C, $R_3$ is H; provided that $R_2$ is not —NR$_{20}$R$_{21}$ when $X_1$ is N and $R_3$ is not —NR$_{20}$R$_{21}$ when $X_2$ is N;

—$Z_1$— is absent or $Z_1$ is C$_1$-C$_3$ alkyl, provided that when $Z_1$ is C$_1$-C$_3$ alkyl, $X_2$ is C;

R4 is a bond, optionally substituted C1-C6 branched or unbranched alkyl or —C=O;

$R_5$ is

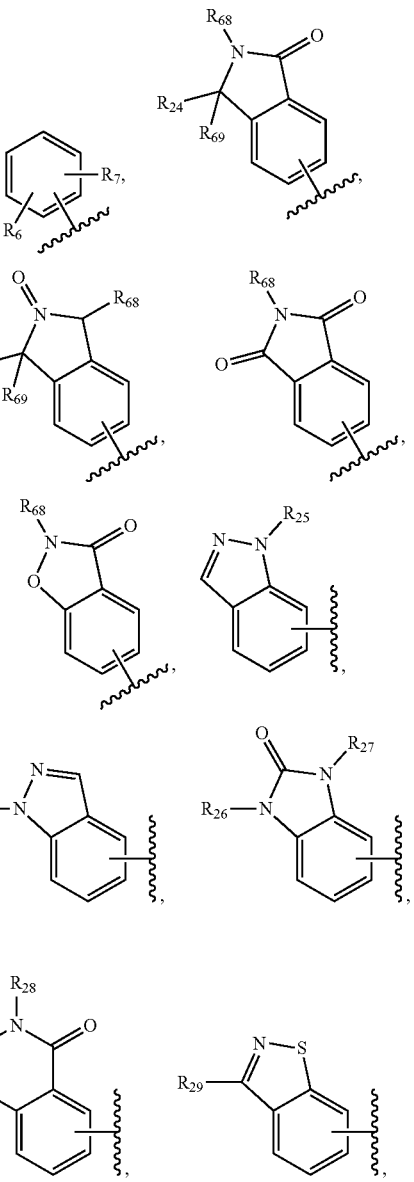

-continued

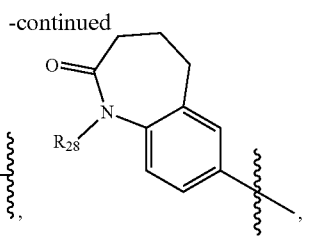

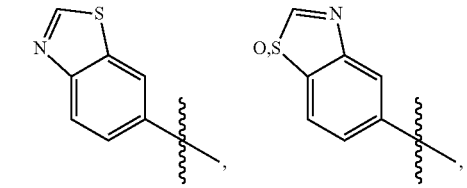

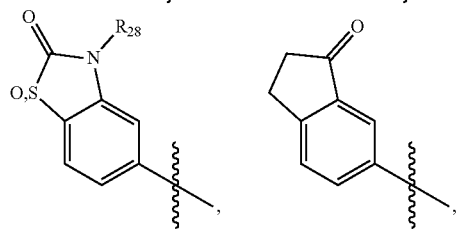

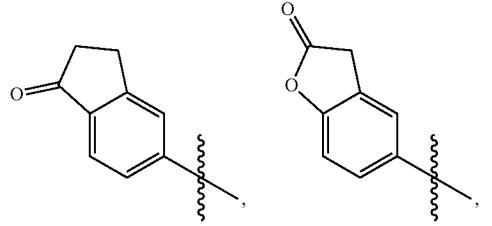

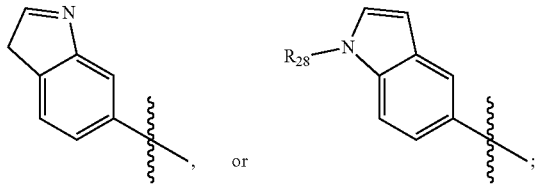

wherein:

$R_6$ and $R_7$ are each, independently, H, halo, cyano, —C(=O)N($R_{10}$)$_2$, —NHC(=O)$R_{11}$, or

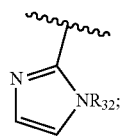

$R_8$ is H, halo, $C_1$-$C_6$ haloalkyl, —C(=O)$C_1$-$C_6$ alkyl, —O$_{8A}$, S(O)$_2R_{8B}$, —(CH$_2$)$_pR_{8C}$, optionally substituted heterocycle, or optionally substituted $C_1$-$C_6$ branched or unbranched alkyl or —(CH$_2$)$_i$OR$_9$, wherein $R_{8A}$, $R_{8B}$, $R_{8C}$ is, independently, H, optionally substituted aryl, optionally substituted $C_1$-$C_6$ haloalkyl, —NR$_{20}$R$_{21}$, optionally substituted $C_1$-$C_6$ branched or unbranched alkyl, optionally substituted $C_2$-$C_6$ alkenyl, —(CH$_2$)$_qR_{8D}$, optionally substituted cycloalkyl, —OH, optionally substituted alkoxy, optionally substituted pyrrolinyl, optionally substituted morpholinyl, or optionally substituted piperidyl, wherein $R_{8D}$ is independently, H, —C(=O)$R_{8E}$, optionally substituted C1-C6 haloalkyl, optionally substituted nitrogen, optionally substituted $C_1$-$C_6$ branched or unbranched alkyl, optionally substituted aryl, optionally substituted heteroaryl, optionally substituted $C_2$-$C_6$ alkenyl, optionally substituted cycloalkyl, optionally substituted heterocycle, —OH, optionally substituted alkoxy, optionally substituted pyrrolinyl, optionally substituted phenyl, optionally substituted pyrrolidinyl, optionally substituted imidazolidinyl, optionally substituted morpholinyl, or optionally substituted piperidyl;

$R_{8E}$ is phenyl or $C_1$-$C_6$ branched or unbranched alkyl;

$R_9$ is optionally substituted $C_1$-$C_6$ branched or unbranched alkyl;

each $R_{10}$ is, independently, H or optionally substituted $C_1$-$C_6$ branched or unbranched alkyl;

each $R_{11}$ is, independently, optionally substituted $C_1$-$C_6$ branched or unbranched alkyl;

each $R_{18}$ is independently, H, optionally substituted aryl, optionally substituted $C_1$-$C_6$ haloalkyl, —NR$_{20}$R$_{21}$, optionally substituted $C_1$-$C_6$ branched or unbranched alkyl, optionally substituted $C_2$-$C_6$ alkenyl, —(CH$_2$)$_vR_{19}$, optionally substituted cycloalkyl, —OH, optionally substituted alkoxy, optionally substituted pyrrolinyl, optionally substituted morpholinyl, or optionally substituted piperidyl;

each $R_{19}$ is, independently, H, cyano, optionally substituted $C_1$-$C_6$ haloalkyl, —NR$_{20}$R$_{21}$, optionally substituted $C_1$-$C_6$ branched or unbranched alkyl, optionally substituted aryl, optionally substituted heteroaryl, optionally substituted $C_2$-$C_6$ alkenyl, optionally substituted cycloalkyl, optionally substituted heterocycle, —OH, optionally substituted alkoxy, optionally substituted pyrrolinyl, optionally substituted morpholinyl, optionally substituted pyrazole, optionally substituted ketone, optionally substituted oxazole, optionally substituted thiazole, or optionally substituted piperidyl;

$R_{20}$ and $R_{21}$ are, each, independently, H, optionally substituted aryl, optionally substituted $C_1$-$C_6$ haloalkyl, optionally substituted $C_1$-$C_6$ branched or unbranched alkyl, optionally substituted $C_2$-$C_6$ alkenyl, —(CH$_2$)$_wR_{19}$, optionally substituted cycloalkyl, —OH, optionally substituted alkoxy, optionally substituted pyrrolinyl, optionally substituted morpholinyl, optionally substituted piperidyl; or $R_{20}$ and $R_{21}$ together form a 5-10 membered optionally substituted heterocycle or a 5-10 membered optionally substituted heteroaryl with the atom to which $R_{20}$ and $R_{21}$ are bonded to;

$R_{24}$ is H, halo, optionally substituted $C_1$-$C_6$ alkyl;

$R_{68}$ is H or optionally substituted $C_1$-$C_6$ alkyl;

$R_{69}$ is H or optionally substituted $C_1$-$C_6$ alkyl or $R_{24}$ or $R_{69}$ form a $C_3$-$C_6$ cycloalkyl including the carbon to which $R_{24}$ or $R_{69}$ are bound to;

$R_{25}$ is H or optionally substituted $C_1$-$C_6$ alkyl;

$R_{26}$ is H or optionally substituted $C_1$-$C_6$ alkyl;

$R_{27}$ is H or optionally substituted $C_1$-$C_6$ alkyl;

$R_{28}$ is H or optionally substituted $C_1$-$C_6$ alkyl;

$R_{29}$ is H, —NR$_{20}$R$_{21}$ or optionally substituted $C_1$-$C_6$ alkyl;

$R_{30}$ and $R_{31}$ are each, independently, H, $C_1$-$C_6$ alkyl, —C(=O)$C_1$-$C_6$ alkyl, —S(=O)$_2C_1$-$C_6$ alkyl; —S(=O)$_2$(CH$_2$)$_{1-4}$CF$_3$; —C(=O)O(CH$_2$)$_{1-4}$Ph; or —C(=O)N($C_1$-$C_6$ alkyl)$_2$;

$R_{32}$ is H or optionally substituted $C_1$-$C_6$ alkyl;

$R_{81b}$ is H or optionally substituted branched or unbranched $C_1$-$C_6$ alkyl; and each i, n, p, q, v, and w is, independently, an integer from 0-6.

In some embodiments, $R_{81b}$ is t-butyl.

In some embodiments, the bond that $Z_1$ forms can have one of the following orientations

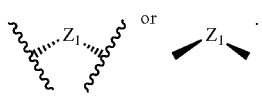

These orientations can be applied to wherever $Z_1$ is seen a formula described herein.

In some embodiments, $R_2$ and $R_3$ are each independently is H or —$CH_2CH_2R_{2A}$, wherein $R_{2A}$ is an optionally substituted aryl, heteroaryl or heterocycle. In some embodiments, $R_{2A}$ is phenyl. In some embodiments, one of $R_2$ and $R_3$ is optionally substituted $C_1$-$C_6$ branched or unbranched alkyl, —$CH_2R_{2B}$ or —$CH_2CH_2R_{2B}$, wherein $R_{2B}$ is optionally substituted aryl, optionally substituted ketone, optionally substituted cycloalkyl, optionally substituted $C_2$-$C_6$ alkenyl, optionally substituted $C_2$-$C_6$ haloalkenyl, or optionally substituted heteroaryl. In some embodiments, $R_{2B}$ is optionally substituted cyclopropyl. In some embodiments, $R_{2B}$ is diflourocyclopropyl. In some embodiments, $R_{2B}$ is 2,2-diflourocyclopropyl. In some embodiments $R_{2B}$ is $C_2$ halo-substituted alkenyl. The substitution can be mono- or di-substituted. In some embodiments, $R_{2B}$ is —C=$CF_2$. In some embodiments, $R_{2B}$ is optionally substituted pyrrole or optionally substituted alkenyl. In some embodiments, $R_{2B}$ is

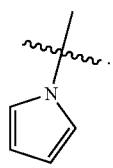

In some embodiments, $R_{2B}$ is cyclopropyl, halo substituted cylcopropyl, phenyl, —C(=O)$R_{XA}$, wherein $R_{XA}$ is optionally substituted phenyl or optionally substituted $C_1$-$C_6$ branched or unbranched alkyl. In some embodiments, one of R2 and R3 is H. In some embodiments $R_2$ is H and $R_3$ is as defined above. In some embodiments, $R_3$ is H and $R_2$ is as defined above.

As used herein, the phrase "$R_1$ and $R_{23}$ form a heterocycle that is fused to the phenyl ring" refers to a structure that results in a fused ring structure. Non-limiting examples of such a structure include

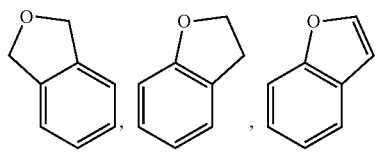

and the like. In some embodiments, the fused ring is a 6 membered ring with or without the oxygen shown here. In some embodiments, the fused ring is aromatic. In some embodiments, the fused ring is not aromatic. For example, the fused ring can form a structure including, but not limited

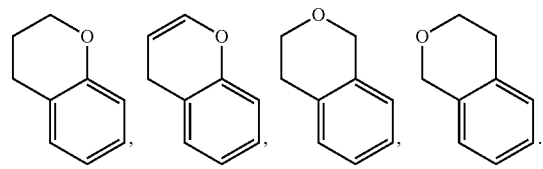

Other non-limiting examples include benzofuran and benzopyran. The structure can also be represented using the following formula in context with the remaining compound:

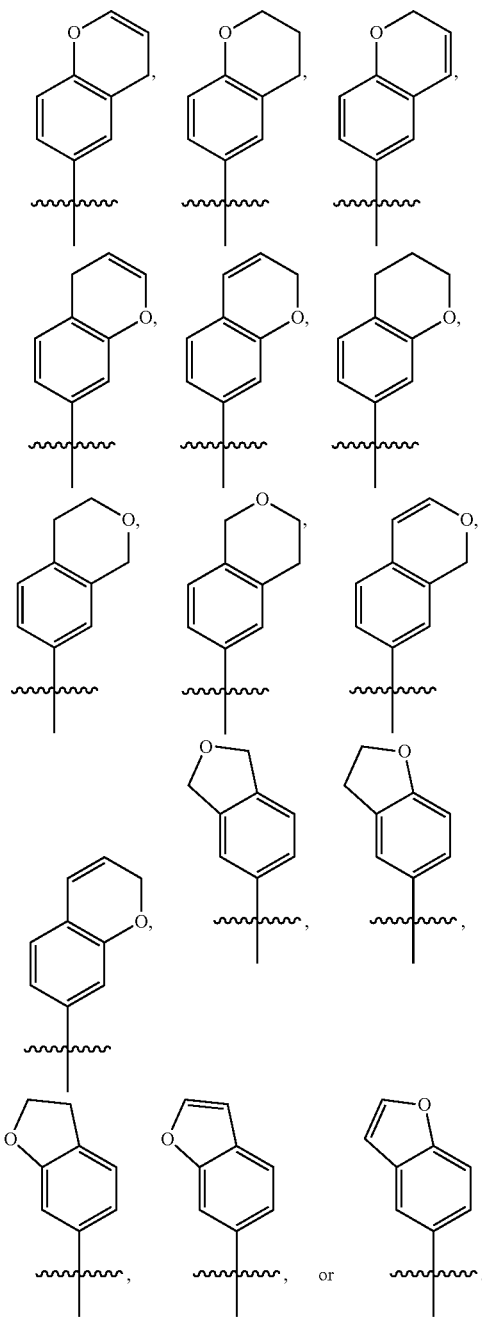

These are non-limiting examples. Examples of such fused structures are also shown in FIG. 1. The location of the fusion can change as can the heteroatom. For example, the oxygen atom shown in this example can also be a nitrogen. Additionally, the ring structures can be substituted.

In some embodiments, the compound or a pharmaceutically acceptable salt thereof. Formula I has a Formula of Formula Ib, Ic, or Id

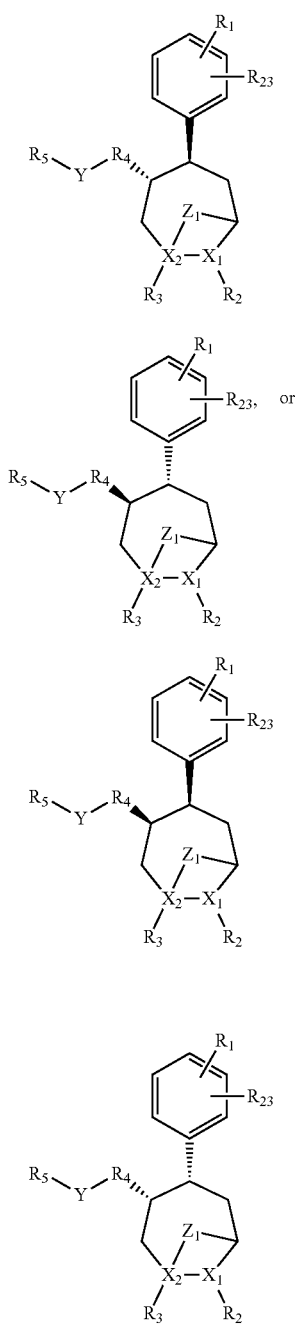

In some embodiments, the compound of Formula I, Ia, Ib, Ic, Id, Ig, or a pharmaceutically acceptable salt thereof $Z_1$ is ethyl. As discussed above, $Z_1$ can also be absent such that no carbon bridge is present. Accordingly, in some embodiments, the present disclosure provides compounds of Formulas Ie or If

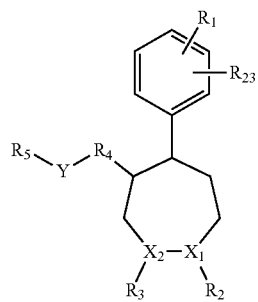

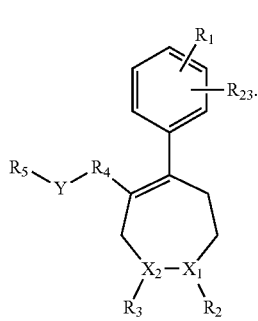

In some embodiments, the compounds of Formula I, Ia, Ib, Ic, Id, Ie, If, or a pharmaceutically acceptable salt thereof $X_1$ is N and $X_2$ is C. In some embodiments, $X_1$ is C and $X_2$ is N.

In some embodiments, the formula of Ie includes the stereoisomers having a formula of:

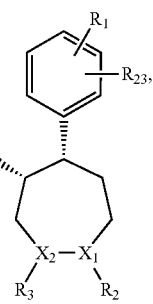 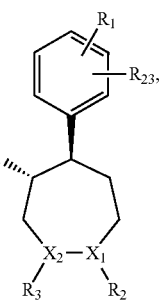

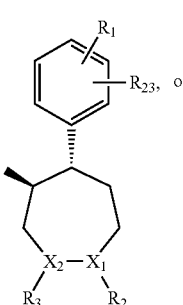 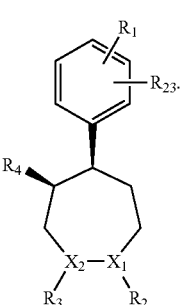

In some embodiments, a compound of formula Ig is provided

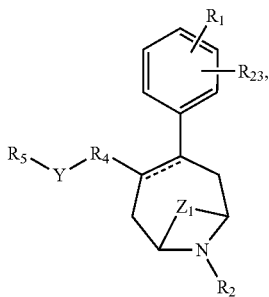

with the variables defined with reference to Formula I. The presence of a dotted line in a structure indicated that in some embodiments, the bond is present and in other embodiments, the bond is absent. For example, with regards to Formula Ig, the presence of the bond where the dotted line is shown would indicate a double bond. The absence of the dotted line would indicate a single bond with the valences being filled with hydrogens or in accordance with the embodiments described herein. When the double bond is not present, there exists for specific stereochemistry at the carbons connected by the single bond. The different cis and trans permutations are provided by the compounds disclosed herein.

In some embodiments, of a compound of Formula I, Ia, Ib, Ic, Id, Ie, If, Ig, or a pharmaceutically acceptable salt thereof, $R_2$ is H.

In some embodiments, of a compound of Formula I, Ia, Ib, Ic, Id, Ie, If, Ig, or a pharmaceutically acceptable salt thereof, Y is O. In some embodiments, when Y is O, $R_4$ is optionally substituted $C_1$-$C_6$ branched or unbranched alkyl. In some embodiments, when Y is O, $R_4$ is a bond. In some embodiments, when Y is O, $R_4$ is a —C(=O).

In some embodiments, of a compound of Formula I, Ia, Ib, Ic, Id, Ie, If, Ig, or a pharmaceutically acceptable salt thereof, Y is N. In some embodiments, when Y is N, $R_4$ is optionally substituted $C_1$-$C_6$ branched or unbranched alkyl. In some embodiments, when Y is N, $R_4$ is a bond. In some embodiments, when Y is N, $R_4$ is a —C(=O).

In some embodiments, of a compound of Formula I, Ia, Ib, Ic, Id, Ie, If, Ig, or a pharmaceutically acceptable salt thereof, $R_2$ is optionally substituted $C_1$-$C_6$ branched or unbranched alkyl. In some embodiments the substitution is aryl or heteroaryl, which can also be further substituted. In some embodiments, $R_2$ is optionally substituted $C_1$-$C_6$ branched or unbranched alkyl, —CH$_2$R$_{70}$ or —CH$_2$CH$_2$R$_{70}$, wherein $R_{70}$ is optionally substituted aryl, optionally substituted ketone, optionally substituted cycloalkyl, optionally substituted haloalkyl (e.g. $C_1$-$C_6$ branched or unbranched haloalkyl) optionally substituted $C_2$-$C_6$ alkenyl, optionally substituted $C_2$-$C_6$ haloalkenyl, or optionally substituted heteroaryl. In some embodiments, $R_{70}$ is cyclopropyl. In some embodiments, $R_{70}$ is diflourocyclopropyl. In some embodiments, $R_{70}$ is 2,2-diflourocyclopropyl. In some embodiments, $R_{70}$ is —CH=CF$_2$. In some embodiments, $R_{70}$ is —C(=O)R$_{70A}$, wherein $R_{70A}$ is phenyl or $C_1$-$C_6$ branched or unbranched alkyl. In some embodiments, $R_2$ is as described above.

In some embodiments, of a compound of Formula I, Ia, Ib, Ic, Id, Ie, If, Ig, or a pharmaceutically acceptable salt thereof, $R_3$ is H.

In some embodiments, of a compound of Formula I, Ia, Ib, Ic, Id, Ie, If, Ig, or a pharmaceutically acceptable salt thereof, $R_3$ is optionally substituted $C_1$-$C_6$ branched or unbranched alkyl. In some embodiments, $R_3$ is optionally substituted $C_1$-$C_6$ branched or unbranched alkyl, —CH$_2$R$_{70}$ or —CH$_2$CH$_2$R$_{80}$, wherein $R_{80}$ is optionally substituted aryl, optionally substituted ketone, optionally substituted cycloalkyl, optionally substituted haloalkyl (e.g. $C_1$-$C_6$ branched or unbranched haloalkyl), optionally substituted $C_2$-$C_6$ alkenyl, optionally substituted $C_2$-$C_6$ haloalkenyl, or optionally substituted heteroaryl. In some embodiments, $R_{80}$ is cyclopropyl. In some embodiments, $R_{80}$ is diflourocyclopropyl. In some embodiments, $R_{80}$ is 2,2-diflourocyclopropyl. In some embodiments, $R_{80}$ is —CH=CF$_2$. In some embodiments, $R_{80}$ is —C(=O)R$_{80A}$, wherein $R_{80A}$ is phenyl or $C_1$-$C_6$ branched or unbranched alkyl. In some embodiments, $R_3$ is as described above.

In some embodiments, of a compound of Formula I, Ia, Ib, Ic, Id, Ie, If, Ig, or a pharmaceutically acceptable salt thereof, $R_5$ is

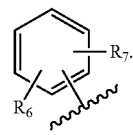

In some embodiments, of a compound of Formula I, Ia, Ib, Ic, Id, Ie, If, Ig, or a pharmaceutically acceptable salt thereof, $R_6$ is halo and $R_7$ is cyano.

In some embodiments, of a compound of Formula I, Ia, Ib, Ic, Id, Ie, If, Ig, or a pharmaceutically acceptable salt thereof, $R_6$ is halo and $R_7$ is H.

In some embodiments, of a compound of Formula I, Ia, Ib, Ic, Id, Ie, If, Ig, or a pharmaceutically acceptable salt thereof, $R_6$ is cyano and $R_7$ is H.

In some embodiments, of a compound of Formula I, Ia, Ib, Ic, Id, Ie, If, Ig, or a pharmaceutically acceptable salt thereof, $R_6$ is —C(=O)N(R$_{10}$)$_2$ and $R_7$ is H.

In some embodiments, of a compound of Formula I, Ia, Ib, Ic, Id, Ie, If, Ig, or a pharmaceutically acceptable salt thereof, $R_6$ is —C(=O)N(R$_{10}$)$_2$ and $R_7$ is halo.

In some embodiments, of a compound of Formula I, Ia, Ib, Ic, Id, Ie, If, Ig, or a pharmaceutically acceptable salt thereof, $R_6$ is —NHC(=O)R$_{11}$ and $R_7$ is H.

In some embodiments, of a compound of Formula I, Ia, Ib, Ic, Id, Ie, If, Ig, or a pharmaceutically acceptable salt thereof, $R_5$ is

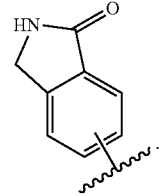

In some embodiments, In some $R_5$ is

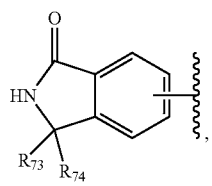

wherein $R_{73}$ and $R_{74}$ are each independently H or $C_1$-$C_6$ alkyl, or $R_{73}$ and $R_{74}$ form a $C_3$-$C_6$ cycloalkyl including the carbon that $R_{73}$ and $R_{74}$ are bound to.

In some embodiments, of a compound of Formula I, Ia, Ib, Ic, Id, Ie, If, Ig, or a pharmaceutically acceptable salt thereof, $R_1$ is H.

In some embodiments, of a compound of Formula I, Ia, Ib, Ic, Id, Ie, If, Ig, or a pharmaceutically acceptable salt thereof, $R_1$ is halo.

In some embodiments, of a compound of Formula I, Ia, Ib, Ic, Id, Ie, If, Ig, or a pharmaceutically acceptable salt thereof, $R_1$ is —$OR_8$.

In some embodiments, of a compound of Formula I, Ia, Ib, Ic, Id, Ie, If, Ig, or a pharmaceutically acceptable salt thereof, the compound is selected from the group consisting of a compound described herein.

In some embodiments, of a compound of Formula I, Ia, Ib, Ic, Id, Ie, If, Ig, or a pharmaceutically acceptable salt thereof, $Z_1$ is $C_2$ alkyl and $R_2$ is H.

The compounds described herein can be prepared according to any method. Examples of methods used to prepare the compounds described herein are provided herein. One of skill in the art can modify the procedures to yield compounds not specifically exemplified in the present disclosure without undue experimentation based upon the present disclosure.

In some embodiments, a compound or salt thereof is chosen from a compound of FIG. 1 or any compound described herein or in the Examples section of the present disclosure. The compounds can be prepared according to schemes and examples provided herein.

Although the compounds depicted herein shown with specific stereochemistries around certain atoms, such as cis or trans, the compounds can also be made in the opposite orientation or in a racemic mixture. The embodiments disclosed herein are intended to encompass such mixtures or isomers.

In some embodiments, the present invention provides pharmaceutical compositions comprising a compound or pharmaceutically salt thereof of any compound described herein.

The compounds described herein can be made by can be made according to the methods described herein and in the examples. The methods described herein can be adapted based upon the compounds desired and described herein. In some embodiments, the method is made according to the following schemes, wherein Q and L are the substituents as shown and described herein and would be apparent to one of skill in the art based upon the present disclosure. In some embodiments, this method can be used to make one or more compounds as described herein and will be apparent to one of skill in the art which compounds can be made according to the methods described herein.

In some embodiments, the compounds made according to the schemes described herein. The conditions and temperatures can be varied, or the synthesis can be performed according to the examples described herein. These schemes are non-limiting synthetic schemes and the synthetic routes can be modified as would be apparent to one of skill in the art reading the present specification.

The compounds can be used to modulate the δ-opioid receptor. Thus, in some embodiments, the compounds can be referred to as δ-opioid receptor modulating compounds Although the compounds in the tables above or in the examples section are shown with specific stereochemistries around certain atoms, such as cis or trans, the compounds can also be made in the opposite orientation or in a racemic mixture.

In some embodiments, the present invention provides pharmaceutical compositions comprising a compound or pharmaceutically salt thereof any compound described herein.

The compounds described herein can be made by can be made according to the methods described herein and in the examples. The methods described herein can be adapted based upon the compounds desired and described herein. In some embodiments, the method is made according to the following schemes, wherein Q and L are the substituents as shown and described herein and would be apparent to one of skill in the art based upon the present disclosure. In some embodiments, this method can be used to make one or more compounds as described herein and will be apparent to one of skill in the art which compounds can be made according to the methods described herein.

In some embodiments, the compounds are made according to schemes described in the examples. The schemes can be used to prepare the compounds and compositions described herein. The conditions and temperatures can be varied, or the synthesis can be performed according to the examples described herein with modifications that are readily apparent based upon the compound being synthesized.

The conditions and temperatures can be varied, such as shown in the examples described herein. These schemes are non-limiting synthetic schemes and the synthetic routes can be modified as would be apparent to one of skill in the art reading the present specification.

The compounds described herein can be administered in any conventional manner by any route where they are active. Administration can be systemic, topical, or oral. For example, administration can be, but is not limited to, parenteral, subcutaneous, intravenous, intramuscular, intraperitoneal, transdermal, oral, buccal, sublingual, or ocular routes, or intravaginally, by inhalation, by depot injections, or by implants. The mode of administration can depend on the conditions or disease to be targeted or treated. The selection of the specific route of administration can be selected or adjusted by the clinician according to methods known to the clinician to obtain the desired clinical response.

In some embodiments, it may be desirable to administer one or more compounds, or a pharmaceutically acceptable salt thereof, locally to an area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, wherein the implant is of a porous, non-porous, or gelatinous material, including membranes, such as sialastic membranes, or fibers.

The compounds described herein can be administered either alone or in combination (concurrently or serially) with other pharmaceuticals. For example, the compounds can be administered in combination with other analgesics, antidepressants, anti-anxiety compounds, anti-overactive bladder compounds, compounds for the treatment of Parkinsons, and the like. In some embodiments, the compounds can be administered in combination with other PTSD therapeutics. Examples of other pharmaceuticals or medicaments are known to one of skill in the art and include, but are not limited to those described herein.

The means and methods for administration are known in the art and an artisan can refer to various pharmacologic references for guidance (see, for example, Modem Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980)).

The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). The standard dosing for protamine can be used and adjusted (i.e., increased or decreased) depending upon the the factors described above. The selection of the specific dose regimen can be selected or adjusted or titrated by the clinician according to methods known to the clinician to obtain the desired clinical response.

The amount of a compound described herein that will be effective in the treatment and/or prevention of a particular disease, condition, or disorder will depend on the nature and extent of the disease, condition, or disorder, and can be determined by standard clinical techniques. In addition, in vitro or in vivo assays may optionally be employed to help identify optimal dosage ranges. The precise dose to be employed in the compositions will also depend on the route of administration, and the seriousness of the disorder, and should be decided according to the judgment of the practitioner and each patient's circumstances. However, a suitable dosage range for oral administration is, generally, from about 0.001 milligram to about 200 milligrams per kilogram body weight, from about 0.01 milligram to about 100 milligrams per kilogram body weight, from about 0.01 milligram to about 70 milligrams per kilogram body weight, from about 0.1 milligram to about 50 milligrams per kilogram body weight, from 0.5 milligram to about 20 milligrams per kilogram body weight, or from about 1 milligram to about 10 milligrams per kilogram body weight. In some embodiments, the oral dose is about 5 milligrams per kilogram body weight.

In some embodiments, suitable dosage ranges for intravenous (i.v.) administration are from about 0.01 mg to about 500 mg per kg body weight, from about 0.1 mg to about 100 mg per kg body weight, from about 1 mg to about 50 mg per kg body weight, or from about 10 mg to about 35 mg per kg body weight. Suitable dosage ranges for other modes of administration can be calculated based on the forgoing dosages as known by those skilled in the art. For example, recommended dosages for intranasal, transmucosal, intradermal, intramuscular, intraperitoneal, subcutaneous, epidural, sublingual, intracerebral, intravaginal, transdermal administration or administration by inhalation are in the range of from about 0.001 mg to about 200 mg per kg of body weight, from about 0.01 mg to about 100 mg per kg of body weight, from about 0.1 mg to about 50 mg per kg of body weight, or from about 1 mg to about 20 mg per kg of body weight. Effective doses may be extrapolated from dose-response curves derived from in vitro or animal model test systems. Such animal models and systems are well known in the art.

The compounds described herein can be formulated for parenteral administration by injection, such as by bolus injection or continuous infusion. The compounds can be administered by continuous infusion subcutaneously over a period of about 15 minutes to about 24 hours. Formulations for injection can be presented in unit dosage form, such as in ampoules or in multi-dose containers, with an optionally added preservative. The compositions can take such forms as suspensions, solutions or emulsions in oily or aqueous vehicles, and can contain formulatory agents such as suspending, stabilizing and/or dispersing agents. In some embodiments, the injectable is in the form of short-acting, depot, or implant and pellet forms injected subcutaneously or intramuscularly. In some embodiments, the parenteral dosage form is the form of a solution, suspension, emulsion, or dry powder.

For oral administration, the compounds described herein can be formulated by combining the compounds with pharmaceutically acceptable carriers well known in the art. Such carriers enable the compounds to be formulated as tablets, pills, dragees, capsules, emulsions, liquids, gels, syrups, caches, pellets, powders, granules, slurries, lozenges, aqueous or oily suspensions, and the like, for oral ingestion by a patient to be treated. Pharmaceutical preparations for oral use can be obtained by, for example, adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethylcellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds. Oral compositions can include standard vehicles such as mannitol, lactose, starch, magnesium stearate, sodium saccharine, cellulose, magnesium carbonate, etc. Such vehicles are suitably of pharmaceutical grade.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added.

For buccal administration, the compositions can take the form of, such as, tablets or lozenges formulated in a conventional manner.

For administration by inhalation, the compounds described herein can be delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, such as gelatin for use in an inhaler or insufflator can be formulated containing a powder mix of the compound and a suitable powder base such as lactose or starch.

The compounds described herein can also be formulated in rectal compositions such as suppositories or retention enemas, such as containing conventional suppository bases such as cocoa butter or other glycerides. The compounds described herein can also be formulated in vaginal compositions such as vaginal creams, suppositories, pessaries, vaginal rings, and intrauterine devices.

In transdermal administration, the compounds can be applied to a plaster, or can be applied by transdermal, therapeutic systems that are consequently supplied to the organism. In some embodiments, the compounds are present in creams, solutions, powders, fluid emulsions, fluid suspensions, semi-solids, ointments, pastes, gels, jellies, and foams, or in patches containing any of the same.

The compounds described herein can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In some embodiments, the compounds can be delivered in a controlled release system. In one embodiment, a pump may be used (see Langer, supra; Sefton, CRC Crit. Ref. Biomed. Eng., 1987, 14, 201; Buchwald et al., Surgery, 1980, 88, 507 Saudek et al., N. Engl. J. Med., 1989, 321, 574). In some embodiments, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger et al., J. Macromol. Sci. Rev. Macromol. Chem., 1983, 23, 61; see, also Levy et al., Science, 1985, 228, 190; During et al., Ann. Neurol., 1989, 25, 351; Howard et al., J. Neurosurg., 1989, 71, 105). In yet another embodiment, a controlled-release system can be placed in proximity of the target of the compounds described herein, such as the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, Science, 1990, 249, 1527-1533) may be used.

It is also known in the art that the compounds can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols. In some embodiments, the compounds described herein can be used with agents including, but not limited to, topical analgesics (e.g., lidocaine), barrier devices (e.g., GelClair), or rinses (e.g., Caphosol).

In some embodiments, the compounds described herein can be delivered in a vesicle, in particular a liposome (see, Langer, Science, 1990, 249, 1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

Suitable compositions include, but are not limited to, oral non-absorbed compositions. Suitable compositions also include, but are not limited to saline, water, cyclodextrin solutions, and buffered solutions of pH 3-9.

The compounds described herein, or pharmaceutically acceptable salts thereof, can be formulated with numerous excipients including, but not limited to, purified water, propylene glycol, PEG 400, glycerin, DMA, ethanol, benzyl alcohol, citric acid/sodium citrate (pH3), citric acid/sodium citrate (pH5), tris(hydroxymethyl)amino methane HCl (pH7.0), 0.9% saline, and 1.2% saline, and any combination thereof. In some embodiments, excipient is chosen from propylene glycol, purified water, and glycerin.

In some embodiments, the formulation can be lyophilized to a solid and reconstituted with, for example, water prior to use.

When administered to a mammal (e.g., to an animal for veterinary use or to a human for clinical use) the compounds can be administered in isolated form.

When administered to a human, the compounds can be sterile. Water is a suitable carrier when the compound of Formula I is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions described herein can take the form of a solution, suspension, emulsion, tablet, pill, pellet, capsule, capsule containing a liquid, powder, sustained-release formulation, suppository, aerosol, spray, or any other form suitable for use. Examples of suitable pharmaceutical carriers are described in Remington's Pharmaceutical Sciences, A. R. Gennaro (Editor) Mack Publishing Co.

In some embodiments, the compounds are formulated in accordance with routine procedures as a pharmaceutical composition adapted for administration to humans. Typically, compounds are solutions in sterile isotonic aqueous buffer. Where necessary, the compositions can also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound is to be administered by infusion, it can be dispensed, for example, with an infusion bottle containing sterile pharmaceutical grade water or saline. Where the compound is administered by injection, an ampoule of sterile water for injection or saline can be provided so that the ingredients may be mixed prior to administration.

The pharmaceutical compositions can be in unit dosage form. In such form, the composition can be divided into unit doses containing appropriate quantities of the active component. The unit dosage form can be a packaged preparation, the package containing discrete quantities of the preparations, for example, packeted tablets, capsules, and powders in vials or ampules. The unit dosage form can also be a capsule, cachet, or tablet itself, or it can be the appropriate number of any of these packaged forms.

In some embodiments, a composition of the present invention is in the form of a liquid wherein the active agent (i.e., one of the facially amphiphilic polymers or oligomers disclosed herein) is present in solution, in suspension, as an emulsion, or as a solution/suspension. In some embodiments, the liquid composition is in the form of a gel. In other embodiments, the liquid composition is aqueous. In other embodiments, the composition is in the form of an ointment.

In some embodiments, the composition is in the form of a solid article. For example, in some embodiments, the ophthalmic composition is a solid article that can be inserted in a suitable location in the eye, such as between the eye and eyelid or in the conjunctival sac, where it releases the active agent as described, for example, U.S. Pat. Nos. 3,863,633; 3,867,519; 3,868,445; 3,960,150; 3,963,025; 4,186,184; 4,303,637; 5,443,505; and 5,869,079. Release from such an article is usually to the cornea, either via the lacrimal fluid that bathes the surface of the cornea, or directly to the cornea itself, with which the solid article is generally in intimate contact. Solid articles suitable for implantation in the eye in such fashion are generally composed primarily of polymers and can be bioerodible or non-bioerodible. Bioerodible polymers that can be used in the preparation of ocular implants carrying one or more of the anti-microbial, facially amphiphilic polymer or oligomer active agents in accordance with the present invention include, but are not limited to, aliphatic polyesters such as polymers and copolymers of poly(glycolide), poly(lactide), poly(epsilon-caprolactone), poly-(hydroxybutyrate) and poly(hydroxyvalerate), polyamino acids, polyorthoesters, polyanhydrides, aliphatic polycarbonates and polyether lactones. Suitable non-bioerodible polymers include silicone elastomers.

The compositions described herein can contain preservatives. Suitable preservatives include, but are not limited to, mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof.

Optionally one or more stabilizers can be included in the compositions to enhance chemical stability where required. Suitable stabilizers include, but are not limited to, chelating agents or complexing agents, such as, for example, the calcium complexing agent ethylene diamine tetraacetic acid (EDTA). For example, an appropriate amount of EDTA or a salt thereof, e.g., the disodium salt, can be included in the composition to complex excess calcium ions and prevent gel formation during storage. EDTA or a salt thereof can suitably be included in an amount of about 0.01% to about 0.5%. In those embodiments containing a preservative other than EDTA, the EDTA or a salt thereof, more particularly disodium EDTA, can be present in an amount of about 0.025% to about 0.1% by weight.

One or more antioxidants can also be included in the compositions. Suitable antioxidants include, but are not limited to, ascorbic acid, sodium metabisulfite, sodium bisulfite, acetylcysteine, polyquaternium-1, benzalkonium chloride, thimerosal, chlorobutanol, methyl paraben, propyl paraben, phenylethyl alcohol, edetate disodium, sorbic acid, or other agents know to those of skill in the art. Such preservatives are typically employed at a level of from about 0.001% to about 1.0% by weight.

In some embodiments, the compounds are solubilized at least in part by an acceptable solubilizing agent. Certain acceptable nonionic surfactants, for example polysorbate 80, can be useful as solubilizing agents, as can ophthalmically acceptable glycols, polyglycols, e.g., polyethylene glycol 400 (PEG-400), and glycol ethers.

Suitable solubilizing agents for solution and solution/suspension compositions are cyclodextrins. Suitable cyclodextrins can be chosen from α-cyclodextrin, β-cyclodextrin, γ-cyclodextrin, alkylcyclodextrins (e.g., methyl-β-cyclodextrin, dimethyl-β-cyclodextrin, diethyl-β-cyclodextrin), hydroxyalkylcyclodextrins (e.g., hydroxyethyl-β-cyclodextrin, hydroxypropyl-β-cyclodextrin), carboxy-alkylcyclodextrins (e.g., carboxymethyl-β-cyclodextrin), sulfoalkylether cyclodextrins (e.g., sulfobutylether-β-cyclodextrin), and the like. Ophthalmic applications of cyclodextrins have been reviewed in Rajewski et al., Journal of Pharmaceutical Sciences, 1996, 85, 1155-1159.

In some embodiments, the composition optionally contains a suspending agent. For example, in those embodiments in which the composition is an aqueous suspension or solution/suspension, the composition can contain one or more polymers as suspending agents. Useful polymers include, but are not limited to, water-soluble polymers such as cellulosic polymers, for example, hydroxypropyl methylcellulose, and water-insoluble polymers such as cross-linked carboxyl-containing polymers.

One or more acceptable pH adjusting agents and/or buffering agents can be included in the compositions, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

One or more acceptable salts can be included in the compositions of the invention in an amount required to bring osmolality of the composition into an acceptable range. Such salts include, but are not limited to, those having sodium, potassium or ammonium cations and chloride, citrate, ascorbate, borate, phosphate, bicarbonate, sulfate, thiosulfate or bisulfite anions. In some embodiments, salts include sodium chloride, potassium chloride, sodium thiosulfate, sodium bisulfite and ammonium sulfate. In some embodiments, the salt is sodium chloride.

Optionally one or more acceptable surfactants, preferably nonionic surfactants, or co-solvents can be included in the compositions to enhance solubility of the components of the compositions or to impart physical stability, or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40; polysorbate 20, 60 and 80; polyoxyethylene/polyoxypropylene surfactants (e.g., Pluronic® F-68, F84 and P-103); cyclodextrin; or other agents known to those of skill in the art. Typically, such co-solvents or surfactants are employed in the compositions at a level of from about 0.01% to about 2% by weight.

The present invention also provides pharmaceutical packs or kits comprising one or more containers filled with one or more compounds described herein. Optionally associated with such container(s) can be a notice in the form prescribed by a governmental agency regulating the manufacture, use or sale of pharmaceuticals or biological products, which notice reflects approval by the agency of manufacture, use or sale for human administration for treating a condition, disease, or disorder described herein. In some embodiments, the kit contains more than one compound described herein. In some embodiments, the kit comprises a compound described herein in a single injectable dosage form, such as a single dose within an injectable device such as a syringe with a needle.

Modulation of the δ-opioid receptor has been found to be a target for the treatment of brain disorders. (Trends Pharmacol Sci. 2011 October; 32(10):581-90. Epub 2011 Sep. 17). Specifically, preclinical data has confirmed that delta opioid receptor activation reduces persistent pain and improves negative emotional states. (Id.). δ-opioid receptor modulating compounds have also been found to have anxiolytic activities. (J Pharmacol Exp Ther. 2011 July; 338(1):195-204. Epub 2011 Mar. 28.) Therefore, the compounds described herein can be used to treat brain disorders, such as depression, Parkinsons, or anxiety. The compounds can be also used to treat pain. The compounds can also be used to treat overactive bladder.

The present invention also provides methods of treating pain, including, but not limited to neuropathic pain, migraines (chronic or acute), headaches (e.g., chronic, acute, cluster, and the like) Parkinsons, depression, anxiety, overactive bladder, including, but not limited to, major depressive disorder, treatment resistant depression, anxiety, post traumatic stress disorder, neuropathic pain, including, diabetic peripheral neuropathy, post-herpetic neuralgia, chemotherapy induced neuropathic pain, prevention of chemotherapy-induced neuropathy, prevention of chemotherapy-induced neuropathic pain, trigeminal neuralgia, inflammatory pain, including, osteoarthritis, rheumatoid arthritis, Rett Syndrome, Autism spectrum disorders, migraine, cluster headaches, acute abortive treatment, prophylaxis of acute intermittent migraine, prophylaxis of chronic migraine, treatment of episodic and chronic cluster headache, prevention of episodic and chronic cluster headache, Charcot-Marie Tooth disease, Traumatic brain injury, fibromyalgia, stroke, acute ischemic syndrome, ischemia/reperfusion injury, substance abuse intervention, and/or treatment of alcohol abuse in a subject comprising administering to the subject one or more compounds described herein or a pharmaceutically acceptable salt thereof, or a pharmaceutical composition of the same. In some embodiments, the subject is a subject in need of such treatment. As described herein, in some embodiments, the subject is a mammal, such as, but not limited to, a human.

The present invention also provides one or more compounds described above, or a pharmaceutically acceptable salt thereof, or a pharmaceutical composition comprising one or more compounds described above, for the treatment of methods of treating pain, including, but not limited to neuropathic pain, migraines (chronic or acute), headaches (e.g., chronic, acute, cluster, and the like) Parkinsons, depression, anxiety, overactive bladder, including, but not limited to, major depressive disorder, treatment resistant depression, anxiety, post traumatic stress disorder, neuropathic pain, including, diabetic peripheral neuropathy, post-herpetic neuralgia, chemotherapy induced neuropathic pain, prevention of chemotherapy-induced neuropathy, prevention of chemotherapy-induced neuropathic pain, trigeminal neuralgia, inflammatory pain, including, osteoarthritis, rheumatoid arthritis, Rett Syndrome, Autism spectrum disorders, migraine, cluster headaches, acute abortive treatment, prophylaxis of acute intermittent migraine, prophylaxis of chronic migraine, treatment of episodic and chronic cluster headache, prevention of episodic and chronic cluster headache, Charcot-Marie Tooth disease, Traumatic brain injury, fibromyalgia, stroke, acute ischemic syndrome, ischemia/reperfusion injury, substance abuse intervention, and/or treatment of alcohol abuse in a subject, such as a mammal or human. In some embodiments, the compounds are for the treatment of methods of treating pain, including, but not limited to neuropathic pain, migraines (chronic or acute), headaches (e.g., chronic, acute, cluster, and the like) Parkinsons, depression, anxiety, overactive bladder, including, but not limited to, major depressive disorder, treatment resistant depression, anxiety, post traumatic stress disorder, neuropathic pain, including, diabetic peripheral neuropathy, post-herpetic neuralgia, chemotherapy induced neuropathic pain, prevention of chemotherapy-induced neuropathy, prevention of chemotherapy-induced neuropathic pain, trigeminal neuralgia, inflammatory pain, including, osteoarthritis, rheumatoid arthritis, Rett Syndrome, Autism spectrum disorders, migraine, cluster headaches, acute abortive treatment, prophylaxis of acute intermittent migraine, prophylaxis of chronic migraine, treatment of episodic and chronic cluster headache, prevention of episodic and chronic cluster headache, Charcot-Marie Tooth disease, Traumatic brain injury, fibromyalgia, stroke, acute ischemic syndrome, ischemia/reperfusion injury, substance abuse intervention, and/or treatment of alcohol abuse in a subject (e.g. mammal or human and others described herein) in need thereof.

The present invention also provides one or more compounds described above, or a pharmaceutically acceptable salt thereof, or a pharmaceutical composition comprising one or more compounds described above, for use in the manufacture of a medicament for the treatment of methods of treating pain, including, but not limited to neuropathic pain, migraines (chronic or acute), headaches (e.g., chronic, acute, cluster, and the like) Parkinsons, depression, anxiety, overactive bladder, including, but not limited to, major depressive disorder, treatment resistant depression, anxiety, post traumatic stress disorder, neuropathic pain, including, diabetic peripheral neuropathy, post-herpetic neuralgia, chemotherapy induced neuropathic pain, prevention of chemotherapy-induced neuropathy, prevention of chemotherapy-induced neuropathic pain, trigeminal neuralgia, inflammatory pain, including, osteoarthritis, rheumatoid arthritis, Rett Syndrome, Autism spectrum disorders, migraine, cluster headaches, acute abortive treatment, prophylaxis of acute intermittent migraine, prophylaxis of chronic migraine, treatment of episodic and chronic cluster headache, prevention of episodic and chronic cluster headache, Charcot-Marie Tooth disease, Traumatic brain injury, fibromyalgia, stroke, acute ischemic syndrome, ischemia/reperfusion injury, substance abuse intervention, and/or treatment of alcohol abuse in a subject, such as those described herein. In some embodiments, the mammal is a mammal in need thereof.

The present invention also provides the use of one or more compounds described above, or a pharmaceutically acceptable salt thereof, or a pharmaceutical composition comprising one or more compounds described above, in the modulation of a d-opioid receptor. In some embodiments, the compounds, pharmaceutically acceptable salt thereof, or a pharmaceutical composition of the same modulate the Beta-arrestin modulated pathway of the δ-opioid receptor. In some embodiments, the compounds, pharmaceutically acceptable salt thereof, or a pharmaceutical composition of the same modulate the G-protein modulated pathway of the δ-opioid receptor.

As used herein, "modulation" can refer to either inhibition or enhancement of a specific activity. For example, the modulation of the δ-opioid receptor can refer to the inhibition and/or activation of the G-protein mediated pathway of the δ-opioid receptor. In some embodiments, the modulation refers to the inhibition or activation of the Beta-arrestin mediated pathway of the δ-opioid receptor. The activity of a δ-opioid receptor can be measured by any method including but not limited to the methods described herein.

The compounds described herein are agonists or antagonists of the delta opioid receptors (DORs). The ability of the compounds to stimulate or inhibit DOR mediated signaling may be measured using any assay known in the art used to detect DOR mediated signaling or DOR activity, or the absence of such signaling/activity. "DOR activity" refers to the ability of an DOR to transduce a signal. Such activity can be measured, e.g., in a heterologous cell, by coupling an DOR (or a chimeric DOR) to a downstream effector such as adenylate cyclase.

A "natural ligand-induced activity" as used herein, refers to activation of the DOR by a natural ligand of the DOR. Activity can be assessed using any number of endpoints to measure DOR activity.

Generally, assays for testing compounds that modulate DOR-mediated signal transduction include the determination of any parameter that is indirectly or directly under the influence of a DOR, e.g., a functional, physical, or chemical effect.

Samples or assays comprising DORs that are treated with a potential activator, inhibitor, or modulator are compared to control samples without the inhibitor, activator, or modulator to examine the extent of inhibition. Control samples (untreated with inhibitors) are assigned a relative DOR activity value of 100%. Inhibition of an DOR is achieved when the DOR activity value relative to the control is about 80%, 50%, or 25%. Activation of an DOR is achieved when the DOR activity value relative to the control (untreated with activators) is 110%, 150%, or 200-500% (i.e., two to five fold higher relative to the control), or 1000-3000% or higher.

The effects of the compounds upon the function of an DOR can be measured by examining any of the parameters described above. Any suitable physiological change that affects DOR activity can be used to assess the influence of a compound on the DORs and natural ligand-mediated DOR activity. When the functional consequences are determined using intact cells or animals, one can also measure a variety of effects such as changes in intracellular second messengers such as cAMP.

In some embodiments, the compound or salt thereof selectively inhibits the Beta-arrestin mediated pathway of the delta-opioid receptor. In some embodiments, the compound or salt thereof selectively inhibits the cAMP mediated pathway of the delta-opioid receptor.

In some embodiments, the compound or salt thereof selectively activates the Beta-arrestin mediated pathway of the delta-opioid receptor. In some embodiments, the compound or salt thereof selectively activates the cAMP mediated pathway of the delta-opioid receptor.

Modulators of DOR activity can be tested using DOR polypeptides as described herein, either recombinant or naturally occurring. The protein can be isolated, expressed in a cell, expressed in a membrane derived from a cell, expressed in tissue or in an animal. For example, neuronal cells, cells of the immune system, transformed cells, or membranes can be used to test the GPCR polypeptides described above. Modulation is tested using one of the in vitro or in vivo assays described herein. Signal transduction can also be examined in vitro with soluble or solid state reactions, using a chimeric molecule such as an extracellular domain of a receptor covalently linked to a heterologous signal transduction domain, or a heterologous extracellular domain covalently linked to the transmembrane and or cytoplasmic domain of a receptor. Furthermore, ligand-binding domains of the protein of interest can be used in vitro in soluble or solid state reactions to assay for ligand binding.

Ligand binding to an DOR, a domain, or chimeric protein can be tested in a number of formats. Binding can be performed in solution, in a bilayer membrane, attached to a solid phase, in a lipid monolayer, or in vesicles. For example, in an assay, the binding of the natural ligand to its receptor is measured in the presence of a candidate modulator, such as the compound described herein. Alternatively, the binding of the candidate modulator may be measured in the presence of the natural ligand. Often, competitive assays that measure the ability of a compound to compete with binding of the natural ligand to the receptor are used. Binding can be tested by measuring, e.g., changes in spectroscopic characteristics (e.g., fluorescence, absorbance, refractive index), hydrodynamic (e.g., shape) changes, or changes in chromatographic or solubility properties.

The activity of the compounds can also be measured using assays involving β-arrestin recruitment. β-arrestin serves as a regulatory protein that is distributed throughout the cytoplasm in unactivated cells. Ligand binding to an appropriate DOR is associated with redistribution of β-arrestin from the cytoplasm to the cell surface, where it associates with the DOR. Thus, receptor activation and the effect of candidate modulators on ligand-induced receptor activation, can be assessed by monitoring β-arrestin recruitment to the cell surface. This is frequently performed by transfecting a labeled β-arrestin fusion protein (e.g., β-arrestin-green fluorescent protein (GFP)) into cells and monitoring its distribution using confocal microscopy (see, e.g., Groarke et al., J. Biol. Chem. 274(33):23263 69 (1999)).

Another technology that can be used to evaluate DOR-protein interactions in living cells involves bioluminescence resonance energy transfer (BRET). A detailed discussion regarding BRET can be found in Kroeger et al., J. Biol. Chem., 276(16):12736 43 (2001).

Other assays can involve determining the activity of receptors which, when activated by ligand binding, result in a change in the level of intracellular cyclic nucleotides, e.g., cAMP, by activating or inhibiting downstream effectors such as adenylate cyclase. In one embodiment, changes in intracellular cAMP can be measured using immunoassays. The method described in Offermanns & Simon, J. Biol. Chem. 270:15175 15180 (1995) may be used to determine the level of cAMP. Also, the method described in Felley-Bosco et al., Am. J. Resp. Cell and Mol. Biol. 11:159 164 (1994) may be used to determine the level of cGMP. Further, an assay kit for measuring cAMP a is described in U.S. Pat. No. 4,115,538, herein incorporated by reference.

In another embodiment, transcription levels can be measured to assess the effects of a test compound on ligand-induced signal transduction. A host cell containing the protein of interest is contacted with a test compound in the presence of the natural ligand for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using reporter genes may be used as described in U.S. Pat. No. 5,436,128, herein incorporated by reference. The reporter genes can be, e.g., chloramphenicol acetyltransferase, firefly luciferase, bacterial luciferase, β-galactosidase and alkaline phosphatase. Furthermore, the protein of interest can be used as an indirect reporter via attachment to a second reporter such as green fluorescent protein (see, e.g., Mistili & Spector, Nature Biotechnology 15:961 964 (1997)).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

Additional assays can also be used. For example, the activity of the compound can be measured in a cell based assay. For example a nucleic acid molecule encoding the delta-opioid receptor (Accession NP_000902) can be incorporated into an expression vector and transfected or transformed into a cell. I some embodiments, the expression vector is a plasmid or virus. In some embodiments, the expression of the nucleic acid molecule is operably linked to a promoter. The promoter can be constitutive or respond to a drug or other response element so that the expression can be controlled. The type of expression vector is not critical and any expression vector can be used that is suitable for the cell type. In some embodiments, the plasmid is pCMV-Prolink. In some embodiments, the cell is a mammalian cell. In some embodiments, the cell is a Chinese Hamster Ovary (CHO-1) cell. In some embodiments, the cell is an EA-arrestin parental line CHO-1 cell, which is available from DiscoveRx Corporation (Fremont, Calif.). The expression of the receptor can be stable so that that stable cell lines can be selected. The selection of stably expressing receptor cell lines can be done to routine methods, such as selecting for expression under G418 (Geneticin). The expression of the receptor can also be transient.

After the receptor is expressed in a cell the cells can be grown in appropriate media in the appropriate cell plate. The cells can be plated, for example at 5000-10000 cells per well in a 384 well plate. In some embodiments, the cells are plated at about 1000, 2000, 3000, 4000, 5000, 6000, 7000, 8000, 9000, or 10000 cells/per well. The plates can have any number of wells and the number of cells can be modified accordingly.

In some embodiments, to measure cAMP activity that is mediated by the receptor, responses can be determined by measuring changes in intracellular cAMP using. cAMP can be measured by any known method or kit. Examples of a kit that can be used, include but are not limited to, CisBio HTRF cAMP HiRange kit (cat #62AM6PEJ) based on time-resolved fluorescence resonance energy transfer (TR-FRET). The compounds (e.g. test or control) can be contacted with the cells for a period of time and then cAMP can be measured.

In some embodiments, a compound's effect on beta-arrestin activity of the receptor is measured. The activity can be measured by any method or kit. For example, the beta-arrestin recruitment or activity was determined using the DiscoveRx beta-arrestin PathHunter Detection kit (cat #93-0001). In this system, beta-Arrestin is fused to an N-terminal deletion mutant of beta-galactosidase (termed the enzyme acceptor of EA) and the GPCR of interest is fused to a smaller (42 amino acids), weakly complementing fragment termed ProLink™. In cells that stably express these fusion proteins, ligand stimulation results in the interaction of beta-arrestin and the Prolink-tagged GPCR, forcing the complementation of the two beta-galactosidase fragments and resulting in the formation of a functional enzyme that converts substrate to detectable signal. Compounds that enhance this activity will lead to an increase in functional enzyme and an increase in the detectable signal. Compounds that inhibit this activity will decrease the detectable signal. Compounds may also have no effect on the beta-arrestin recruitment.

The present invention also provides the use of one or more compounds described above, or a pharmaceutically acceptable salt thereof, or a pharmaceutical composition comprising one or more compounds described above, in the treatment of methods of treating pain, including, but not limited to neuropathic pain, migraines (chronic or acute), headaches (e.g., chronic, acute, cluster, and the like) Parkinsons, depression, anxiety, overactive bladder, including, but not limited to, major depressive disorder, treatment resistant depression, anxiety, post traumatic stress disorder, neuropathic pain, including, diabetic peripheral neuropathy, postherpetic neuralgia, chemotherapy induced neuropathic pain, prevention of chemotherapy-induced neuropathy, prevention of chemotherapy-induced neuropathic pain, trigeminal neuralgia, inflammatory pain, including, osteoarthritis, rheumatoid arthritis, Rett Syndrome, Autism spectrum disorders, migraine, cluster headaches, acute abortive treatment, prophylaxis of acute intermittent migraine, prophylaxis of chronic migraine, treatment of episodic and chronic cluster headache, prevention of episodic and chronic cluster headache, Charcot-Marie Tooth disease, Traumatic brain injury, fibromyalgia, stroke, acute ischemic syndrome, ischemia/reperfusion injury, substance abuse intervention, and/or treatment of alcohol abuse in a subject or a subject in need thereof, such as those described herein.

Any medicament having utility in an application described herein can be used in co-therapy, co-administration or co-formulation with a composition as described above. Such additional medicaments include, medicines for Parkinsons, such as but not limited to levodopa, carbidopa, Catechol-O-methyl Transferase Inhibitors (e.g. Entacapone or Tolcapone), dopamine agonists, ropinirole, bromocriptine, pramipexole, Monoamine Oxidase Inhibitors (MAOi) (e.g. rasagiline or selegiline), anti-cholinergics (e.g. Benztropine or Trihexyphenidyl), and amantadine. Examples of medicaments for overactive bladder include, but are not limited to, tolterodine (Detrol), oxybutynin (Ditropan), an oxybutynin skin patch (Oxytrol), trospium (Sanctura), solifenacin (Vesicare) and darifenacin (Enablex). Examples of medicaments for the treatment of depression and/or anxiety include, but are not limited to, selective serotonin reuptake inhibitors (SSRIs), such as fluoxetine (Prozac), paroxetine (Paxil), and sertraline (Zoloft); tricyclic and tetracyclic antidepressants, such as doxepin (Sinequan) and nortriptyline (Aventyl, Pamelor); other antidepressants, such as bupropion (Wellbutrin, Wellbutrin SR), mirtazapine (Remeron) and trazodone, and venlafaxine (Effexor, Effexor XR); monoamine oxidase inhibitors (MAOIs), such as isocarboxazid (Marplan), phenelzine sulfate (Nardil), and selegiline (Emsam), Ativan, Celexa, Cymbalta, Klonopin, Lexapro, Luvox CR, Norpramin, Paxil, Remeron, Tofranil, Valium, and Xanax.

Examples of pain medications include, but are not limited to non-steroidal anti-inflammaotry agents, opioids, non-narcotic analgesics, topical analgesics, topical anesthetics. Examples of suitable non-steroidal anti-inflammatory agents include, but are not limited to, prostaglandin H synthetase inhibitors (Cos I or Cox II), also referred to as cyclooxygenase type I and type II inhibitors, such as diclofenac, flurbiprofen, ketorolac, suprofen, nepafenac, amfenac, indomethacin, naproxen, ibuprofen, bromfenac, ketoprofen, meclofenamate, piroxicam, sulindac, mefanamic acid, diflusinal, oxaprozin, tolmetin, fenoprofen, benoxaprofen, nabumetome, etodolac, phenylbutazone, aspirin, oxyphenbutazone, tenoxicam and carprofen; cyclooxygenase type II selective inhibitors, such as vioxx, celecoxib, etodolac; PAF antagonists, such as apafant, bepafant, minopafant, nupafant and modipafant; PDE IV inhibitors, such as ariflo, torbafylline, rolipram, filaminast, piclamilast, cipamfylline, and roflumilast; inhibitors of cytokine production, such as inhibitors of the NFkB transcription factor; or other anti-inflammatory agents know to those skilled in the art. Other examples of pain medicaments include, but are not limited to, acetaminophen, buprenorphine, butorphanol, codeine, hydrocodone, hydromorphone, levorphanol, meperidine, methadone, morphine, nalbuphine, oxycodone, oxymorphone, pentazocine, propoxyphene, tramadol, butalbital, capsaicin, benzocaine, dibucaine, prilocaine and lidocaine.

The additional medicament can be administered in co-therapy (including co-formulation) with the one or more of the compounds described herein.

In some embodiments, the response of the disease or disorder to the treatment is monitored and the treatment regimen is adjusted if necessary in light of such monitoring.

Frequency of administration is typically such that the dosing interval, for example, the period of time between one dose and the next, during waking hours is from about 2 to about 12 hours, from about 3 to about 8 hours, or from about 4 to about 6 hours. It will be understood by those of skill in the art that an appropriate dosing interval is dependent to some degree on the length of time for which the selected composition is capable of maintaining a concentration of the compound(s) in the subject and/or in the target tissue (e.g., above the $EC_{50}$ (the minimum concentration of the compound which modulates the receptor's activity by 90%). Ideally the concentration remains above the $EC_{50}$ for at least 100% of the dosing interval. Where this is not achievable it is desired that the concentration should remain above the $EC_{50}$ for at least about 60% of the dosing interval, or should remain above the $EC_{50}$ for at least about 40% of the dosing interval.

In order that the invention disclosed herein may be more efficiently understood, examples are provided below. It should be understood that these examples are for illustrative purposes only and are not to be construed as limiting the invention in any manner. Throughout these examples, there may be molecular cloning reactions, and other standard recombinant DNA techniques described and these were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1. Preparation of Compounds

General Procedure C1: Preparation of 4,5-Azepine Intermediate

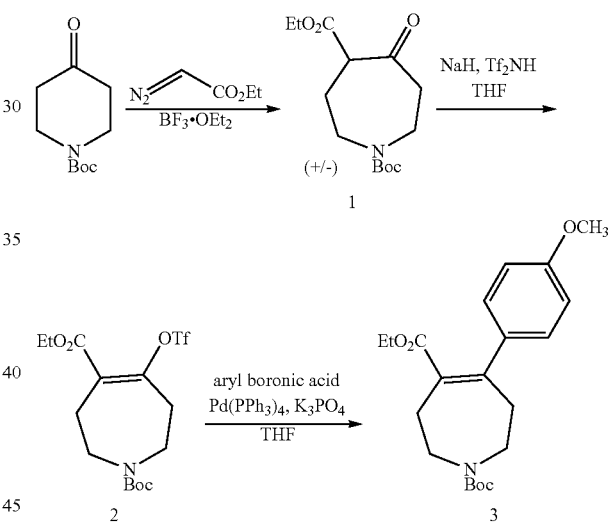

1-tert-butyl 4-ethyl 5-oxoazepane-1,4-dicarboxylate
(1)

To a −40° C. solution of tert-butyl piperidinone (10.0 g, 50.2 mmol) in diethyl ether (100 mL) was added $BF_3$-$Et_2O$ (8.6 g, 60.23 mmol), followed by dropwise addition of ethyl diazoacetate (8.1 g, 71.3 mmol). The reaction mixture was stirred at −40° C. for 1 h and then quenched at −40° C. with saturated $NaHCO_3$ (50 mL) and the mixture was allowed to warm to room temperature. The layers were separated, and the organics were washed with saturated $NaHCO_3$ until the combined aqueous portion was basic by pH paper. The aqueous mixture was extracted with EtOAc for three times (3×). The combined organic layers were washed once with brine, filtered through cotton, and concentrated under reduced pressure to yield a light orange oil 1. The crude product may be purified by flash column chromatography using EtOAc/hexanes or may be used without purification in the next step. LCMS of product peak ([M+Na]=308).

1-tert-butyl 4-ethyl 5-((trifluoromethane)sulfonyloxy]-2,3,6,7-tetrahydro-1H-azepine-1,4-dicarboxylate (2)

To a mixture of 1 (14.3 g, 50.1 mmol) in THF (200 mL) at 0° C., was added NaH (60% in oil; 2.4 g, 100.2 mmol). The reaction was stirred cold for 10 minutes, and then the ice bath was removed and the reaction mixture was stirred at room temperature for 30 minutes. The mixture as heated to 45° C. for 15 minutes and then chilled to 0° C. Tf$_2$NPh (22.4 g, 62.6 mmol) was added. The reaction mixture was heated at 60° C. overnight, cooled to room temperature and then 0° C., and was quenched by slow addition of NH$_4$Cl solution (50 mL). The aqueous phase was extracted with EtOAc (3×). The combined organic layers were washed with saturated NaHCO$_3$ (3×), brine (3×), filtered through cotton, dried (Na$_2$SO$_4$), filtered, and concentrated under reduced pressure to provide a gummy yellow semi-solid 2. The crude product may be purified by flash column chromatography using EtOAc/hexanes or may be used without purification in the next step. LCMS of product peak ([M+Na]=440).

1-tert-butyl 4-ethyl 5-(4-methoxyphenyl)-2,3,6,7-tetrahydro-1H-azepine-1,4-dicarboxylate (3)

A mixture of 2 (20.9 g, 50.1 mmol), 4-methoxy phenyl boronic acid (9.1 g, 60.1 mmol), and potassium phosphate (16.0 g, 75.2 mmol) is suspended in anhydrous THF (200 mL) and sparged with nitrogen for 75 minutes. To this mixture was added Pd(PPh$_3$)$_4$ (1.5 g, 1.3 mmol) and the reaction was heated at 60° C. overnight. The reaction mixture was cooled to room temperature and concentrated. The crude material was partitioned between EtOAc and saturated NH$_4$Cl. The layers were separated and the organic portion washed once with saturated NH$_4$Cl, once with saturated NaHCO$_3$, once with brine, filtered through Celite and concentrated to a brown oil. The crude product was purified by flash column chromatography (340 g column; 3%-24% EtOAc/hexanes) to yield 3 (88% purity). LCMS of product peak ([M+Na]=398).

General Procedure C2: Preparation of 4,5-Azepane N—H Compounds

Scheme 2

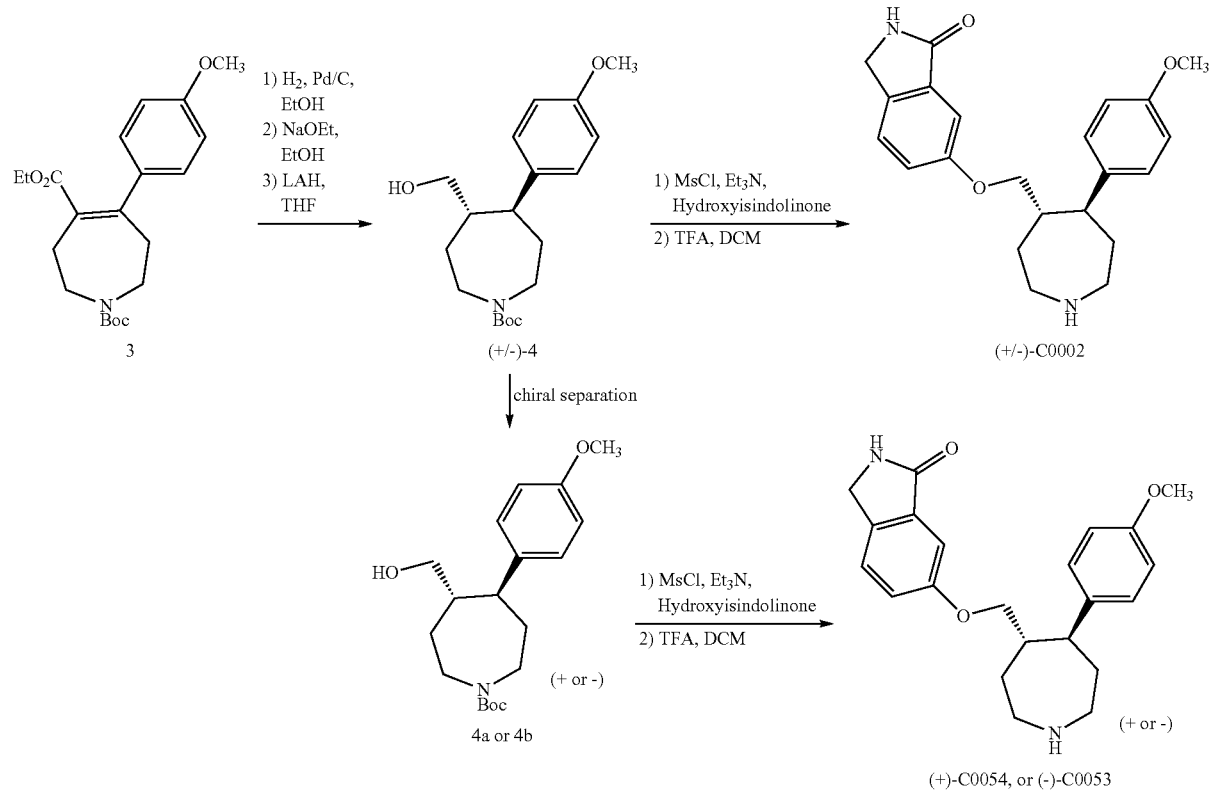

(±)-tert-butyl trans-4-(hydroxymethyl)-5-(4-methoxyphenyl)azepane-1-carboxylate ((+/−)-4)

To a Parr hydrogenation bottle purged with nitrogen was added 5% Pd—C (1.3 g) and the catalyst was dampened with EtOH. A solution of 3 (7.2 g, 19.2 mmol) in EtOH (100 mL) was added. The bottle was placed on a Parr hydrogenator, evacuated and filled with N$_2$ three time, then twice with H$_2$ before being placed under 50 psi H2 and shaken overnight. The reaction mixture was filtered through a pad of Celite and the filtrate was concentrated to provide a colorless oil. The crude product (LCMS ([M+Na]=400) was dissolved in EtOH (80 mL). To this solution was added 21 wt % NaOEt in EtOH (23 mL) and the reaction mixture was stirred at 60° C. overnight. The reaction was cooled to room temperature and then to 0° C. and quenched with saturated NH$_4$Cl (60 mL). The mixture was extracted with EtOAc (3×), and the combined organics were washed with brine (5×), filtered through cotton, and concentrated under reduced pressure to provide a clear orange gum (LCMS ([M+Na]=400), which was dissolved in THF (90 mL) under nitrogen. To this solution was added LAH (1M/THF; 35 mL, 35 mmol) dropwise via syringe. The reaction was allowed to warm to room temperature and stirred for two hours. The reaction was placed in an ice bath and water (1.4 mL) was carefully added, followed by 3N NaOH (1.4 mL) and finally water (4.1 mL). The ice bath was removed and the suspension was stirred for one hour, then filtered through Celite. The crude product was concentrated and purified by flash column chromatography, 10%-80% EtOAc/hexanes to yield 4.9 g of (+/−)-4 as a off-white crystalline solid. LCMS [M+Na]=358.

(±)-tert-Butyl Trans-4-(Hydroxymethyl)-5-(4-methoxyphenyl)azepane-1-carboxylate ((+)-C4) and (−)-tert-Butyl Trans-4-(Hydroxymethyl)-5-(4-methoxyphenyl)azepane-1-carboxylate ((−)-4)

A solution of (+/−)-4 in methanol was separated by chiral preparative HPLC (10 μM CHIRALPAK AD, 2 cm×25 cm, 5 mL/min flow rate, 3 mg/injection), eluting with 0.1% diethylamine in methanol, to provide (+)-4a as the first eluting isomer: $[\alpha]_D^{25}$=+18.2° (c 0.05, methanol). The later eluting isomer provided (−)-4b: $[\alpha]_D^{25}$=−29.8° (c 0.05, methanol). Also (+/−)-4 may be separated by supercritical fluid chromatography using a ChiralPak AS-H column and an EtOH gradient to yield the individual enantiomers.

(±)-6-{((trans)-5-(4-methoxyphenyl)azepan-4-yl]methoxy}-2,3-dihydro-1H-isoindol-1-one Hydrochloride ((+/−)-C0002)

Methanesulfonyl chloride (1.5 mL, 13.4 mmol) was added dropwise to a solution of (+/−)-4 (3.0 g, 8.9 mmol) and triethylamine (1.9 mL, 13.4 mmol) in anhydrous methylene chloride (50 mL) at 0° C. under nitrogen, after which the mixture was slowly warmed to room temperature, stirring for a total of 5 h. The mixture was treated with brine solution (150 mL) and extracted with ethyl acetate (2×150 mL). The combined organic extracts were washed with brine solution (100 mL), dried over sodium sulfate and filtered. The solvents were removed under reduced pressure to afford the mesylate adduct as a yellow oil that was suitable for use without further purification (2.5 g, 68%).

A mixture of the crude mesylate (200 mg, 0.48 mmol), 6-hydroxyisoindolin-1-one (216 mg, 1.45 mmol) and potassium carbonate (200 mg, 1.45 mmol) in anhydrous DMF (17 mL) was heated at 80° C. under nitrogen for 12 h. The mixture was cooled to room temperature and treated with saturated aqueous ammonium chloride solution (10 mL) and 2N NaOH (30 mL) and extracted with ethyl acetate (3×50 mL). The organic extracts were combined and the solvent was removed under reduced pressure. The residue was purified by flash column chromatography on silica gel, eluting with ethyl acetate/hexanes (1:1), to afford the coupling reaction adduct as a yellow semi-solid (180 mg, 80%): LCMS (M+H) 467.

Trifluoroacetic acid (8.0 mL) was added dropwise to a solution of the coupling reaction adduct (180 mg, 0.42 mmol) in anhydrous methylene chloride (10 mL) at 0° C. under nitrogen, after which the mixture was slowly warmed to room temperature, stirring for a total of 1 h. The solvents were removed under reduced pressure and the residue was dissolved in methanol for purification by reversed-phase preparative HPLC, eluting with 0.05% TFA in acetonitrile/water (gradient from 2% to 60%, Phenomenex Luna column). The isolated residue was acidified with HCl (2 mL, 2M in diethyl ether), diluted with acetonitrile/water and lyophilized to afford (+/−)-C0002 as a off-white solid (82 mg, 51%): $^1$H NMR (500 MHz, CD$_3$OD) δ 7.42 (d, J=8.5 Hz, 1H), 7.17 (d, J=8.5 Hz, 2H), 7.10 (s, 1H), 7.06 (d, J=2.5 Hz, 1H), 6.86 (d, J=8.0 Hz, 2H), 4.35 (s, 2H), 3.77 (s, 1H), 3.75 (s, 3H), 3.67-3.64 (m, 1H), 3.55-3.51 (m, 1H), 3.48-3.44 (m, 1H), 3.41-3.64 (m, 1H), 2.86 (t, J=11 Hz, 1H), 2.35-2.18 (m, 3H), 2.15-2.03 (m, 2H); LCMS (M+H) 367.

(+)-6-{((trans)-5-(4-methoxyphenyl)azepan-4-yl]methoxy}-2,3-dihydro-1H-isoindol-1-one Hydrochloride ((+)-C0054)

Prepared according to General Procedure C2 from (−)-4a]. LCMS (M+H) 367; $[\alpha]_D^{25}$=+72.9° (c 0.05, methanol).

6-{(((−)-trans)-5-(4-methoxyphenyl)azepan-4-yl]methoxy}-2,3-dihydro-1H-isoindol-1-one Hydrochloride ((−)-C0053]

Prepared according to General Procedure C2 from (+)-4b. LCMS (M+H) 367; $[\alpha]_D^{25}$=−48.9° (c 0.05, methanol).
General Procedure C3: Preparation of 4,5-Azepine N—H Compounds

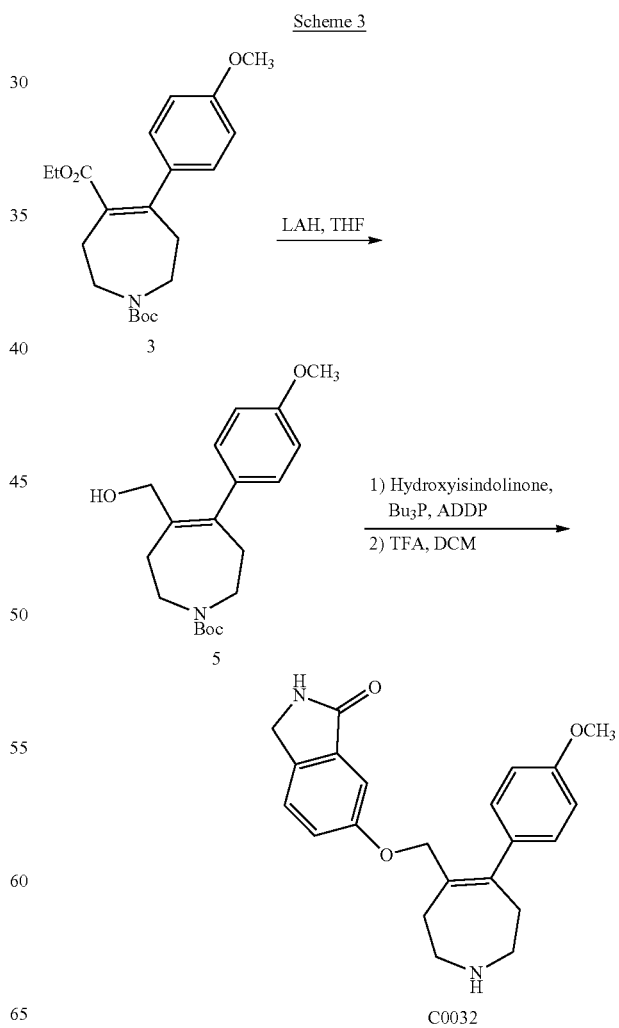

Scheme 3

Tert-butyl-4-(hydroxymethyl)-5-(4-methoxyphenyl)-2,3,6,7-tetrahydro-1H-azepine-1-carboxylate (5)

To a solution of 3 (6.4 g, 17.05 mmol) in THF (45 mL) under nitrogen was added LAH (1M/THF; 34 mL, 34 mmol) dropwise via syringe. The reaction was allowed to warm to room temperature and stirred for one hour. The reaction was placed in an ice bath and water (0.8 mL) was carefully added, followed by 3N NaOH (0.8 mL) and finally water (2.4 mL). The ice bath was removed and the suspension was stirred for one hour, then filtered through Celite. The crude product was concentrated and purified by flash column chromatography, 7%-60% EtOAc/hexanes to yield 4.1 g (72%) of 5 as a clear oil. LCMS [M+Na]=356.

6-{[5-(4-methoxyphenyl)-2,3,6,7-tetrahydro-1H-azepin-4-yl]methoxy}-2,3-dihydro-1H-isoindol-1-one (C0032)

Tributylphosphine (0.37 mL, 1.5 mmol) was added to a solution of 5 (167 mg, 0.5 mmol) and 6-hydroxyisoindolin-1-one (90 mg, 0.6 mmol) in anhydrous THF (12 mL) at 0° C. under nitrogen, followed by 1,1'-(azodicarbonyl)dipiperidine (252 mg, 1.0 mmol). The mixture was slowly warmed to room temperature, stirring for a total of 12 h. The mixture was then cooled to 0° C. and the solids were removed by filtration under reduced pressure. The filtrate solvents were removed under reduced pressure and the residue was purified by flash column chromatography on silica gel, eluting with methylene chloride/methanol (gradient from 100:0 to 9:1), to afford the semi-purified coupling product. This compound was dissolved in methylene chloride (12 mL) and cooled to 0° C. under nitrogen, after which trifluoroacetic acid (3 mL) was added. The mixture was slowly warmed to room temperature, stirring for a total of one hour. The solvents were removed under reduced pressure and the residue was dissolved in methanol for purification by reversed-phase preparative HPLC, eluting with 0.05% TFA in acetonitrile/water (gradient from 2% to 60%, Phenomenex Luna column). The isolated residue was acidified with HCl (1 mL, 2M in diethyl ether), diluted with acetonitrile/water and lyophilized to provide C0032 as a hygroscopic off-white semi-solid (41 mg, 20% over two steps). $^1$H NMR (500 MHz, CD3OD) δ ppm 2.71-2.83 (m, 4H), 3.18-3.25 (m, 4H), 3.69 (s, 3H), 4.26 (s, 2H), 4.41 (s, 2H), 6.82-6.85 (m, 2H), 6.97-7.02 (m, 2H), 7.06-7.09 (m, 2H), 7.33-7.34 (m, 1H); LCMS (M+H) 365.

General Procedure C4: Preparation of 3,4-Azepane N—H Compounds

Scheme 4

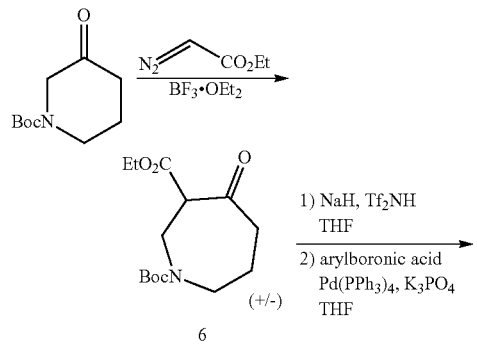

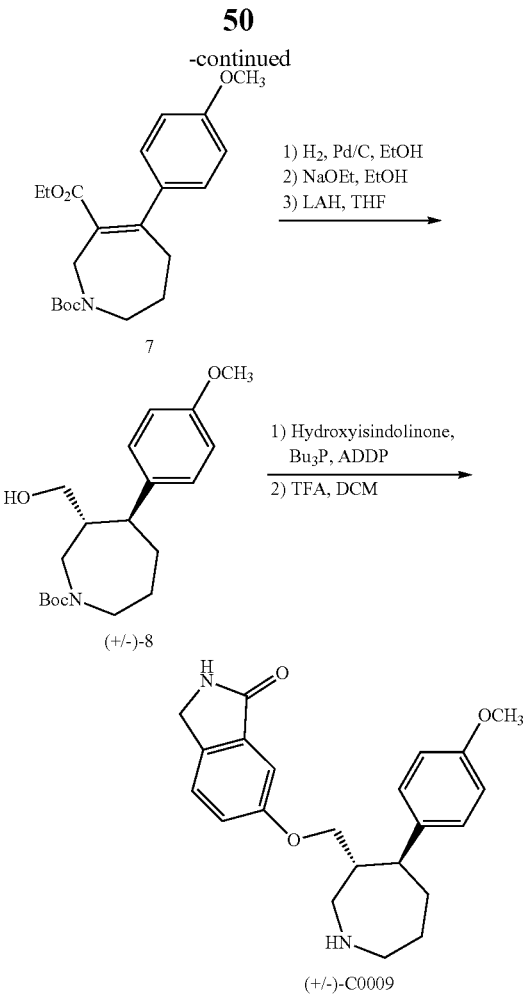

(+/−)-1-tert-butyl 3-ethyl 4-oxoazepane-1,3-dicarboxylate ((+/−)-6)

Prepared according to General Procedure C1 from commercial available tert-butyl 3-oxopiperidine-1-carboxylate. LCMS (M+H) 286.

1-tert-butyl 3-ethyl 4-(4-methoxyphenyl)-2,5,6,7-tetrahydro-1H-azepine-1,3-dicarboxylate (7)

Prepared according to General Procedure C1 from (+/−)-6. LCMS (M+H) 376.

(±)-(trans)-3-(hydroxymethyl)-4-(4-methoxyphenyl)azepane-1-carboxylate (8)

Prepared according to General Procedure C2 from 7. LCMS [M−H] 334.

(±)-6-{((trans)-4-(4-methoxyphenyl)azepan-3-yl]methoxy}-2,3-dihydro-1H-isoindol-1-one ((+/−)-C0009)

Prepared according to General Procedure C3 from 8. $^1$H NMR (500 MHz, CD$_3$OD) δ ppm 1.82-2.07 (m, 4H), 2.36-2.42 (m, 1H), 2.71-2.76 (m, 1H), 3.28-3.38 (m, 3H), 3.53-3.57 (m, 1H), 3.60-3.69 (m, 4H), 3.72-3.74 (m, 1H), 4.26 (s, 2H), 6.76-6.78 (m, 2H), 6.99-7.08 (m, 4H), 7.33-7.35 (d, J=8.50 Hz, 1H); LCMS (M+H) 367.

General Procedure C5: Preparation of Bicyclic 4,5-Azepine Intermediate

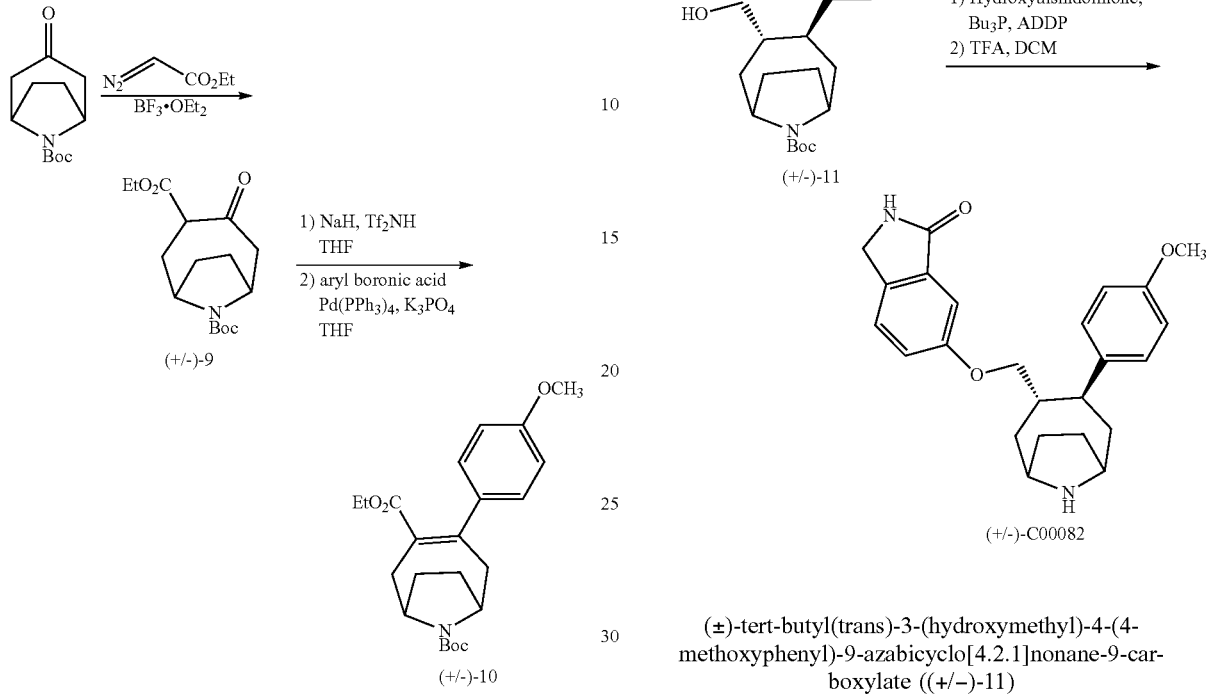

9-tert-butyl 3-ethyl 4-oxo-9-azabicyclo[4.2.1]nonane-3,9-dicarboxylate ((+/−)-9)

Prepared according to General Procedure C1 from the commercial available Boc-nortropinone. LCMS of product peak ([M+Na]=334).

9-tert-butyl 3-ethyl-4-(4-methoxyphenyl)-9-azabicyclo[4.2.1]non-3-ene-3,9-dicarboxylate ((+/−)-10)

Prepared according to General Procedure C1 from (+/−)-9. LCMS of product peak ([M+Na]=424).

General Procedure C6: Preparation of Bicyclic 4,5-Azepane N—H Compounds

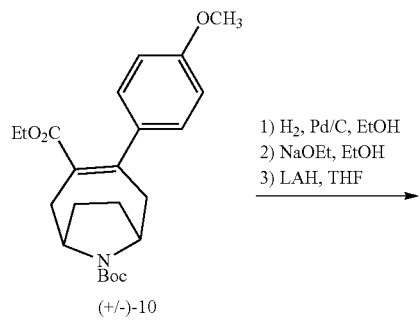

(±)-tert-butyl(trans)-3-(hydroxymethyl)-4-(4-methoxyphenyl)-9-azabicyclo[4.2.1]nonane-9-carboxylate ((+/−)-11)

Prepared according to General Procedure C2 from (+/−)-10. LCMS of product peak ([M+Na]=384).

(±)-6-{((trans)-4-(4-methoxyphenyl)-9-azabicyclo[4.2.1]nonan-3-yl]methoxy}-2,3-dihydro-1H-isoindol-1-one ((+/−)-C0082)

Prepared according to General Procedure C2 from (+/−)-11. LCMS [M+H]=393.
$^1$H NMR (400 MHz, DMSO) δ 9.05 (s, 1H), 8.70 (d, J=11.7, 1H), 8.51 (s, 1H), 7.40 (d, J=8.3, 1H), 7.14 (d, J=8.8, 2H), 6.97 (dd, J=8.3, 2.4, 1H), 6.83 (dd, J=5.4, 3.0, 2H), 4.24 (s, 2H), 4.15 (s, 1H), 4.06 (s, 1H), 3.68 (s, 2H), 3.53 (d, J=7.2, 1H), 3.40 (dd, J=9.2, 5.6, 1H), 3.03 (s, 1H), 2.47 (m, 2H), 2.30 (s, 1H), 2.17 (s, 1H), 2.05 (d, J=14.3, 3H), 1.76 (m, 2H).

General Procedure C7: Preparation of Bicyclic 4,5-Azepine N—H Compounds

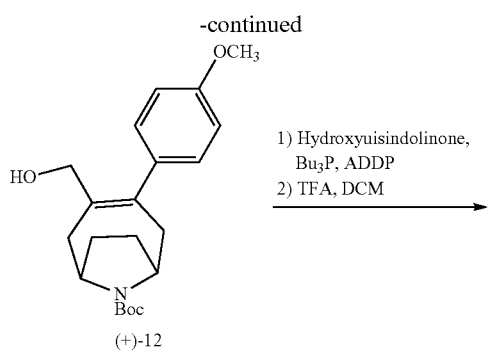

1) Hydroxyuisindolinone, Bu₃P, ADDP
2) TFA, DCM (+)-12

General Procedure C8: Preparation of 4,5-Azepane and 3,-4-Azepane N-Alkyl Compounds Scheme 8

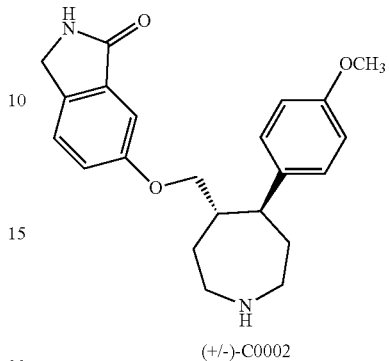

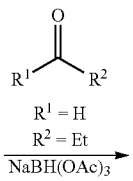

$R^1 = H$
$R^2 = Et$

NaBH(OAc)₃

(+/-)-C0002

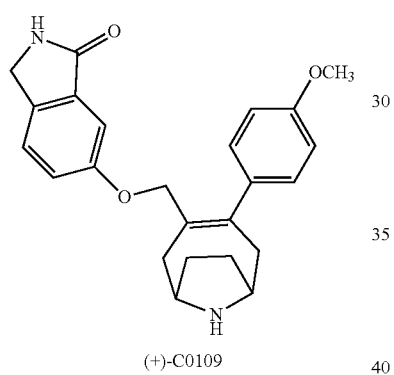

(+)-C0109

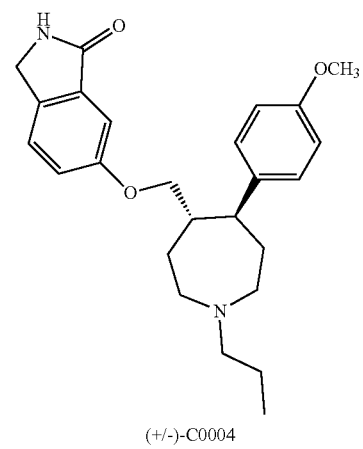

(+/-)-C0004

Tert-butyl 3-(hydroxymethyl)-4-(4-methoxyphenyl)-9-azabicyclo[4.2.1]non-3-ene-9-carboxylate ((+/−)-12)

Prepared according to General Procedure C3 and General Procedure C2 (chiral separation) from (+/−)-10 to yield 4.3 g (77%) of (+/−)-12 as a white solid. LCMS [M+Na]=382.1. The early eluting isomer provided (+)-12: $[\alpha]_D^{25}$=+27° (c=0.1, DCM).

6-{[4-(4-methoxyphenyl)-9-azabicyclo[4.2.1]non-3-en-3-yl]methoxy}-2,3-dihydro-1H-isoindol-1-one ((+)-C0109)

Prepared according to General Procedure C3 from (+/−)-12 to yield 89 mg (63%) of (+)-C0109 as a white solid. LCMS [M+H]=391. ¹H NMR (400 MHz, DMSO) δ 9.13 (s, 1H), 8.82 (d, J=10.8, 1H), 8.52 (s, 1H), 7.43 (d, J=8.4, 1H), 7.14 (m, 2H), 7.05 (dd, J=8.3, 2.4, 1H), 6.95 (dd, J=13.1, 5.6, 3H), 4.40 (dd, J=26.5, 10.7, 2H), 4.27 (s, 2H), 4.11 (m, 2H), 3.76 (s, 3H), 3.02 (d, J=17.6, 1H), 2.66 (m, 3H), 2.01 (dd, J=20.5, 8.1, 2H), 1.74 (d, J=8.5, 2H).

Example Preparation of (±)-6-{((trans)-5-(4-methoxyphenyl)-1-propylazepan-4-yl]methoxy}-2,3-dihydro-1H-isoindol-1-one ((+/−)-C0004)

To a mixture of azepane (+/−)-C0002 (45 mg, 0.12 mmol) in 6 ml DCM and propionaldehyde (0.11 mL, 0.16 mmol) was stirred for 5 minutes. NaBH(OAc)₃ (33 mg, 0.16 mmol) was added and the reaction stirred overnight, after which it was quenched with water, and the solvent was concentrated. The residue was passed through a Gilson reverse phase HPLC twice with a gradient of 10 to 60% acetonitrile for 15 min to yield 59.6 mg (91%) of (+/−)-C0004. ¹H NMR (400 MHz, CD3OD) d 7.33 (m, OH), 7.05 (m, 1H), 6.77 (d, J=8.7, 1H), 4.76 (s, 4H), 4.26 (s, 1H), 3.65 (s, 3H), 3.04 (m, 1H), 2.76 (m, OH), 2.20 (m, 1H), 1.94 (dt, J=21.9, 11.1, OH), 1.71 (m, 1H), 0.95 (t, J=7.4, 1H). LCMS (M+H) 409.3.

General Procedure C9: Preparation of 4,5-Azepine N-Alkyl Compounds

General Procedure C10: Preparation of Bicyclic 4,5-Azepane N-Alkyl Compounds

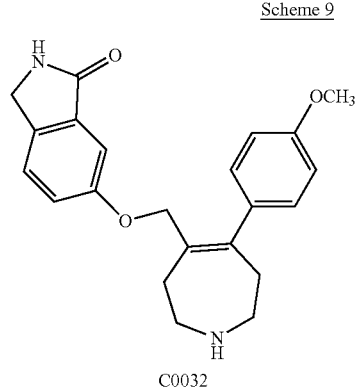

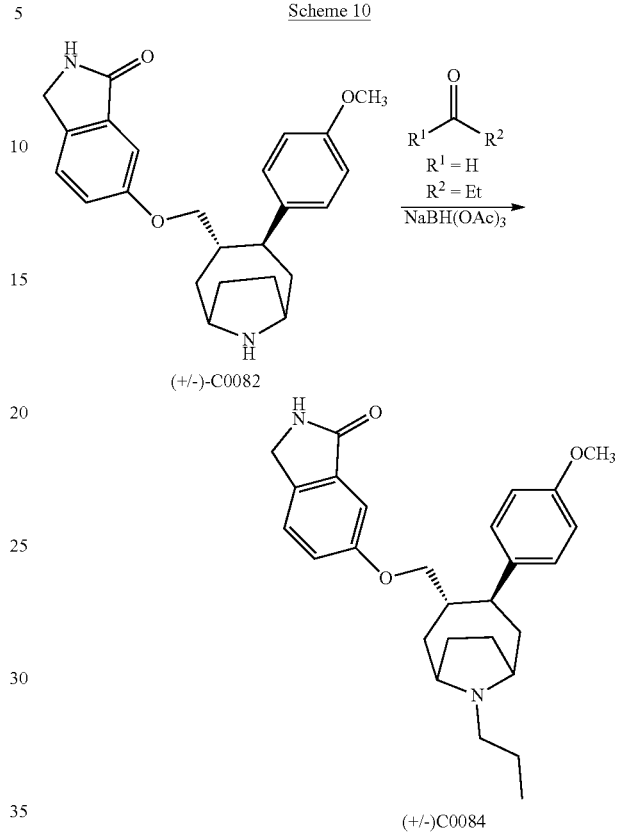

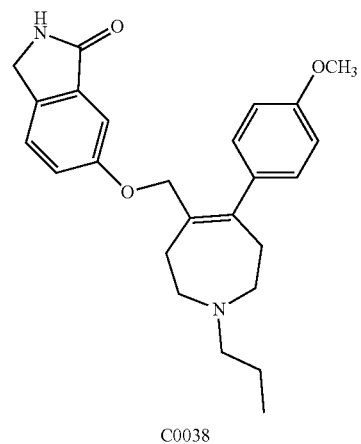

Example Preparation of 6-{[5-(4-methoxyphenyl)-1-propyl-2,3,6,7-tetrahydro-1H-azepin-4-yl]methoxy}-2,3-dihydro-1H-isoindol-1-one (C0038)

Prepared according to General Procedure C8 from C0032 to yield 150 mg (16%) of C0038 as a white solid. $^1$H NMR (400 MHz, CDCl3) δ 7.28 (m, OH), 7.19 (d, J=2.3, OH), 7.08 (m, 1H), 6.83 (m, 1H), 4.39 (d, J=24.8, 1H), 3.79 (m, 1H), 3.32 (m, OH), 2.92 (ddd, J=10.5, 9.2, 3.2, OH), 2.65 (m, 2H), 2.52 (dd, J=6.5, 3.8, OH), 2.44 (m, OH), 1.55 (m, 1H), 0.93 (dp, J=23.1, 7.6, 1H). LCMS (m/z) [M+1] 407.2.

Example Preparation of 6-{2-((cis)-4-(4-methoxyphenyl)-9-propyl-9-azabicyclo[4.2.1]nonan-3-yl]ethyl}-2,3-dihydro-1H-(trans)-isoindol-1-one ((+/−) C0084)

Prepared according to General Procedure C8 from (+/−)-C0082 to yield 44 mg (90%) of (+/−)-C0084 as a white solid. LCMS [M+H]=435. $^1$H NMR (400 MHz, DMSO) δ 9.11 (s, 1H), 8.51 (s, 1H), 7.41 (d, J=8.3, 1H), 7.14 (d, J=8.8, 2H), 7.01 (m, 1H), 6.85 (m, 3H), 4.25 (s, 2H), 4.06 (m, 2H), 3.69 (s, 3H), 3.54 (t, J=10.7, 1H), 3.40 (m, 1H), 3.09 (m, 3H), 2.30 (m, 3H), 2.09 (m, 3H), 1.78 (m, 5H), 0.97 (m, 3H).

General Procedure C11: Preparation of Bicyclic 4,5-Azepine N-Alkyl Compounds

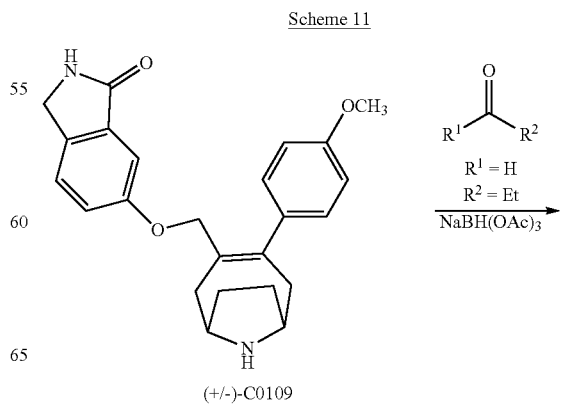

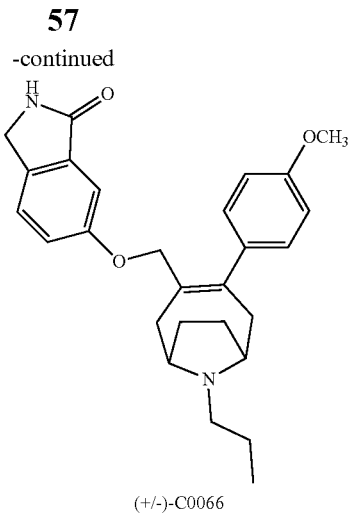

(+/−)-C0066

Example Preparation of 6-{[4-(4-methoxyphenyl)-9-propyl-9-azabicyclo[4.2.1]non-3-en-3-yl]methoxy}-2,3-dihydro-1H-isoindol-1-one ((+/−)-C0066)

Prepared according to General Procedure C8 from (+/−)-C0109 to yield to yield 24 mg (89%) of (+/−)-C0066 as a white solid. LCMS [M+H]=433. $^1$H NMR (400 MHz, DMSO) δ 9.11 (s, 1H), 8.51 (s, 1H), 7.41 (d, J=8.3, 1H), 7.14 (d, J=8.8, 2H), 7.01 (m, 1H), 6.85 (m, 3H), 4.25 (s, 2H), 4.06 (m, 2H), 3.69 (s, 3H), 3.54 (t, J=10.7, 1H), 3.40 (m, 1H), 3.09 (m, 3H), 2.09 (m, 6H), 1.78 (m, 5H), 0.97 (m, 3H).

General Procedure C12: Preparation of 4,5-cis Azepane N—H and N-alkyl Compounds

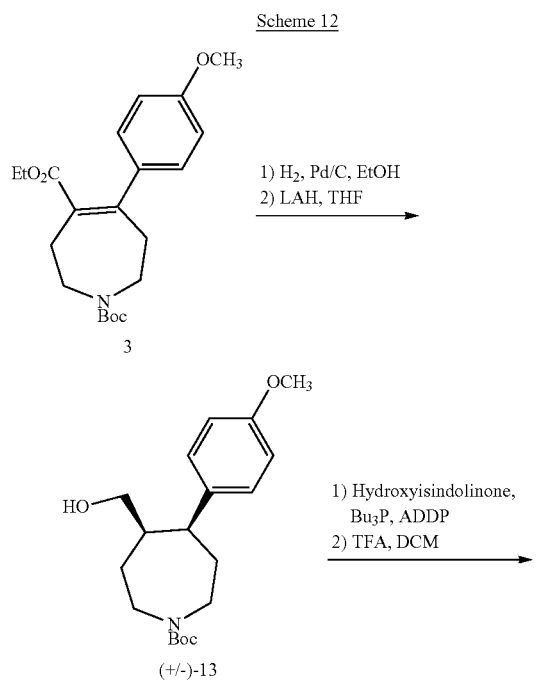

Scheme 12

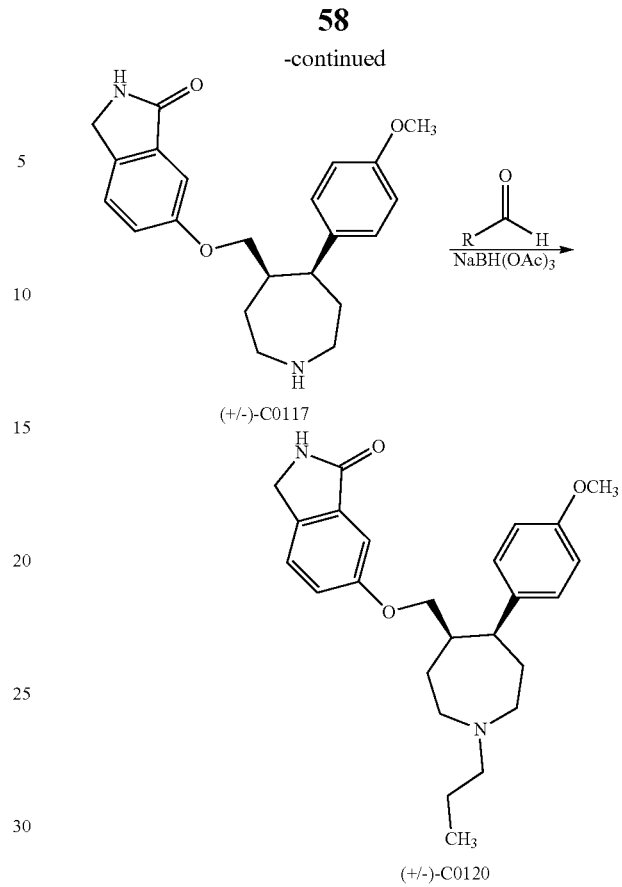

(+/−)-C0117

(+/−)-C0120

Tert-butyl(±)-cis-4-(hydroxymethyl)-5-(4-methoxyphenyl)azepane-1-carboxylate ((+/−)-13)

To a Parr hydrogenation bottle purged with nitrogen was added 5% Pd—C (0.4 g) and the catalyst was dampened with EtOH. A solution of C3 (2.25 g, 5.99 mmol in EtOH (50 mL) was added. The bottle was placed on a Parr hydrogenator, evacuated and filled with N$_2$ three time, then twice with H2 before being placed under 51 psi H2 and shaken overnight. The reaction mixture was filtered through a pad of Celite and the filtrate was concentrated to provide an amber oil. The crude ester product was dissolved in THF (35 mL). To this solution, chilled to 0° C., was added LAH (2M/THF; 6.0 mL, 12 mmol) dropwise via syringe. The reaction was allowed to warm to room temperature and stirred for one hour. The reaction was placed in an ice bath and water (0.48 mL) was carefully added, followed by 3N NaOH (0.48 mL) and finally water (1.43 mL). The ice bath was removed and the suspension was stirred for three hours, then filtered through Celite. The crude product was concentrated and purified by flash column chromatography, 10%-80% EtOAc/hexanes to yield 1.68 g of (+/−) 13 as an oil. LCMS [M+Na]=358.

(±)-6-{(cis-5-(4-methoxyphenyl)azepan-4-yl]methoxy}-2,3-dihydro-1H-isoindol-1-one ((+/−) C0117)

Prepared according to General Procedure C3 from (+/−)-13 to yield 20 mg (10%) of ((+/−)-C0117) as a white solid. $^1$H NMR (400 MHz, DMSO) δ 8.78 (m, 1H), 8.53 (s, 1H), 8.44 (m, 1H), 7.43 (d, J=8.3, 1H), 7.21 (d, J=8.7, 2H), 7.03

(dd, J=8.3, 2.4, 1H), 6.98 (d, J=2.3, 1H), 6.86 (d, J=8.7, 2H), 4.26 (s, 2H), 3.71 (s, 3H), 3.65 (m, 1H), 3.57 (m, 1H), 3.33 (m, 3H), 3.17 (m, 2H), 2.32 (m, 1H), 2.08 (m, 2H), 1.97 (m, 1H). LCMS (M+H=367).

(±)-6-{(cis-5-(4-methoxyphenyl)-1-propylazepan-4-yl]methoxy}-2,3-dihydro-1H-isoindol-1-one ((+/−)-C0120)

Prepared according to General Procedure C8 from (+/−)-C0109 to yield 16 mg (44%) of ((+/−)-C0120). $^1$H NMR (400 MHz, DMSO) δ 7.43 (d, J=8.2, 1H), 7.17 (m, 2H), 6.99 (m, 2H), 6.87 (m, 2H), 4.26 (s, 2H), 3.72 (m, 3H), 3.52 (m, 3H), 3.17 (m, 4H), 2.10 (m, 4H), 1.70 (m, 2H), 0.93 (m, 3H). LCMS (M+H=409).

General Procedure C13: Preparation of O-Substituted 4,5-Azepane N—H Compounds

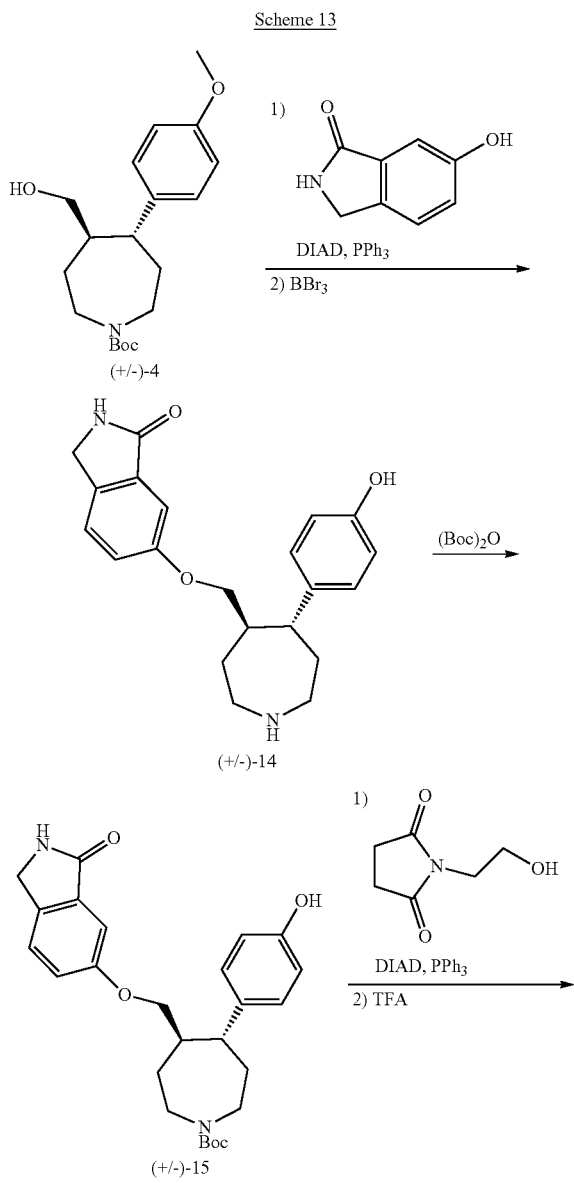

Scheme 13

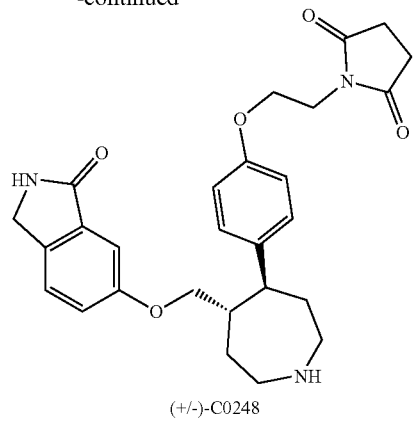

(+/−)-C0248

6-[((trans)-5-(4-hydroxyphenyl)azepan-4-yl]methoxy]-2,3-dihydro-1H-isoindol-1-one ((+/−)-14)

Into a 50-mL 3-necked round-bottom flask purged and maintained with an inert atmosphere of nitrogen, was placed a solution of tert-butyl (trans)-4-(hydroxymethyl)-5-(4-methoxyphenyl)azepane-1-carboxylate (+/−)-4 (500 mg, 1.49 mmol, 1.00 equiv) in tetrahydrofuran (20 mL), PPh$_3$ (443 mg, 1.69 mmol, 1.20 equiv), 6-hydroxy-2,3-dihydro-1H-isoindol-1-one (209.9 mg, 1.41 mmol, 1.00 equiv). This was followed by the addition of DIAD (341.4 mg, 1.69 mmol, 1.20 equiv) dropwise with stirring at 0° C. The resulting solution was stirred for 1 h at 0° C. The resulting mixture was concentrated under vacuum. The crude product (500 mg) was purified by Flash-Prep-HPLC with the following conditions (IntelFlash-1): Column, silica gel; mobile phase, PE:EA=100% PE increasing to PE:EA=100% EA within 40 min; Detector, UV 254 nm. 137 mg product was obtained. This resulted in 137 mg (20%) of tert-butyl (trans)-4-(4-methoxyphenyl)-5-[((3-oxo-2,3-dihydro-1H-isoindol-5-yl)oxy]methyl]azepane-1-carboxylate as a off-white solid. Into a 100-mL 3-necked round-bottom flask purged and maintained with an inert atmosphere of nitrogen, was placed a solution of tert-butyl (trans)-4-(4-methoxyphenyl)-5-[((3-oxo-2,3-dihydro-1H-isoindol-5-yl)oxy]methyl] azepane-1-carboxylate (2.5 g, 5.36 mmol, 1.00 equiv) in dichloromethane (25 mL). This was followed by the addition of BBr$_3$ (3.35 g, 13.40 mmol, 2.50 equiv) dropwise with stirring at −75° C. The resulting solution was stirred for 1 h at 0° C. The reaction was then quenched by the addition of 100 mL of water. The pH value of the solution was adjusted to 7 with 10% NaHCO$_3$(aq). The resulting mixture was concentrated under vacuum. This resulted in 1.6 g (85%) of (+/−)-14 as a off-white solid. LC-MS: (ES, m/z): 352 [M+H]

Tert-butyl (cis)-4-(4-hydroxyphenyl)-5-[((3-oxo-2,3-dihydro-1H-isoindol-5-yl)oxy]methyl]azepane-1-carboxylate ((+/−)-15)

Into a 25-mL round-bottom flask, was placed a solution of (+/−)-14 (370 mg, 1.05 mmol, 1.00 equiv) in dichloromethane (5 mL), TEA (1.1 g, 10.87 mmol, 10.00 equiv). This was followed by the addition of (Boc)$_2$O (372.4 mg, 1.61 mmol, 1.50 equiv). The mixture was stirred for 2 h at room temperature. The resulting mixture was concentrated under vacuum. The residue was dissolved in 30/2.14 mL of methanol/NaOH (2M). The resulting solution was stirred for 1 h at room temperature. The pH value of the solution was adjusted to 5 with hydrogen chloride (12 mol/L). The resulting solution was extracted with 3×30 mL of dichloromethane and the organic layers combined and concentrated under vacuum. The crude product (400 mg) was purified by Flash-Prep-HPLC with the following conditions (IntelFlash-1): Column, silica gel; mobile phase, methanol in DCM=100% DCM increasing to methanol in DCM=100% MeOH within 30 min; Detector, UV 254 nm. 300 mg product was obtained. This resulted in 300 mg (63%) of (+/−)-15 as a off-white solid. LC-MS: (ES, m/z): 452 [M+H]

Tert-butyl (cis)-4-[4-[2-(2,5-dioxopyrrolidin-1-yl)ethoxy]phenyl]-5-[((3-oxo-2,3-dihydro-1H-isoindol-5-yl)oxy]methyl]azepane-1-carboxylate ((+/−)-C0248)

Into a 25-mL round-bottom flask purged and maintained with an inert atmosphere of nitrogen, was placed a solution of $PPh_3$ (288.2 mg, 1.10 mmol, 5.00 equiv) in tetrahydrofuran (5 mL). This was followed by the addition of DIAD (222.2 mg, 1.10 mmol, 5.00 equiv) dropwise with stirring at 0° C. To this was added 1-(2-hydroxyethyl)pyrrolidine-2,5-dione (157.3 g, 1.10 mol, 5.00 equiv) at 0° C. The mixture was stirred for 1 h at 0° C. To the mixture was added (+/−)C15 (100 mg, 0.22 mmol, 1.00 equiv) at 0° C. The resulting solution was stirred overnight at 50° C. The resulting mixture was concentrated under vacuum. The residue was applied onto a silica gel column with DCM:MeOH (1:0-9:1). This resulted in 20 mg (16%) of tert-butyl (4R,5R)-4-[4-[2-(2,5-dioxopyrrolidin-1-yl)ethoxy]phenyl]-5-[((3-oxo-2,3-dihydro-1H-isoindol-5-yl)oxy]methyl]azepane-1-carboxylate (+/−)-C0248 as colorless oil. (400 MHz, CD3OD): 7.40 (d, 1H), 7.17 (d, 2H), 7.10 (m, 2H), 6.80 (d, 2H), 4.80 (s, 2H), 4.20 (t, 2H), 3.80 (t, 2H), 3.70 (m, 1H), 3.60 (m, 1H), 3.40 (m, 4H), 2.80 (d, 1H), 2.6 (m, 4H), 2.10-2.30 (m, 5H). LC-MS: (ES, m/z): 478.2 [M+H]

Into a 25-mL round-bottom flask, was placed a solution of tert-butyl (4R,5R)-4-[4-[2-(2,5-dioxopyrrolidin-1-yl)ethoxy]phenyl]-5-[((3-oxo-2,3-dihydro-1H-isoindol-5-yl)oxy]methyl]azepane-1-carboxylate (60 mg, 0.10 mmol, 1.00 equiv) in dichloromethane (4 mL), trifluoroacetic acid (2 mL). The resulting solution was stirred for 30 min at room temperature. The resulting mixture was concentrated under vacuum. The crude product (60 mg) was purified by Prep-HPLC with the following conditions (Prep-HPLC-010): Column, SunFire Prep C18 OBD Column, 5 um, 19*150 mm; mobile phase, WATER WITH 0.05% TFA and MeCN (10.0% MeCN up to 30.0% in 8 min, up to 95.0% in 2 min, down to 10.0% in 2 min); Detector, Waters2545 UvDector 254&220 nm. This resulted in 18.2 mg (37%) of (+/−)-C0248 as a off-white solid. LC-MS: (ES, m/z): 478 [M+H] $^1$H-NMR: (400 MHz, CD3OD): 7.40 (d, 1H), 7.17 (d, 2H), 7.10 (m, 2H), 6.80 (d, 2H), 4.80 (s, 2H), 4.20 (t, 2H), 3.80 (t, 2H), 3.70 (m, 1H), 3.60 (m, 1H), 3.40 (m, 4H), 2.80 (d, 1H), 2.6 (m, 4H), 2.10-2.30 (m, 5H).

General Procedure C14: Preparation of O-Substituted 4,5-Azepane N-Alkyl Compounds
Scheme 14

1-(2-[4-((4S,5S)-5-[((3-oxo-2,3-dihydro-1H-isoindol-5-yl)oxy]methyl]-1-propylazepan-4-yl]phenoxy]ethyl)pyrrolidine-2,5-dione((+/−)-C0274)

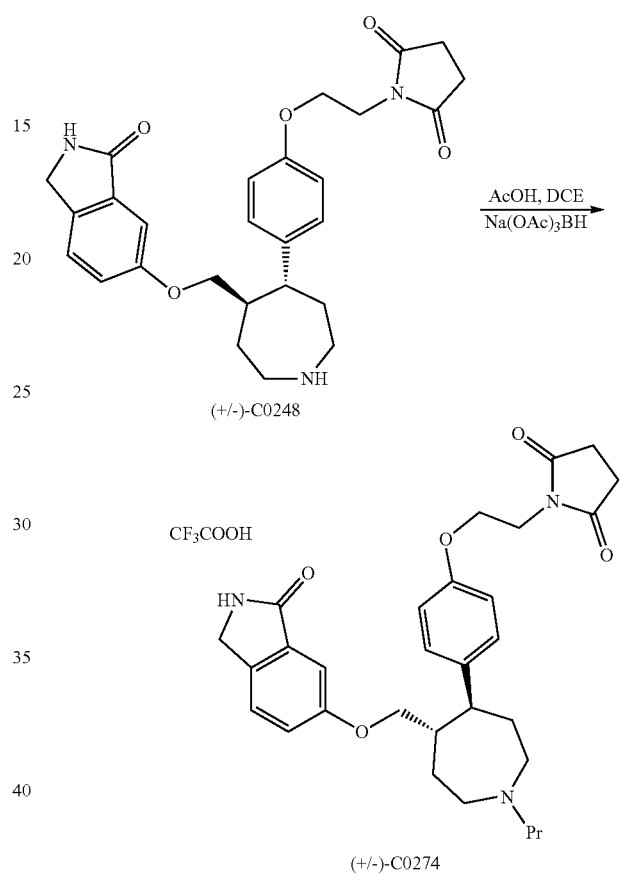

Prepared according to General Procedure C8 from (+/−)-C0248 to yield 33.1 mg (12%) of (+/−)-C0274 as a off-white solid. LC-MS: (ES, m/z): 520 [M-CF3COOH+H]. $^1$H-NMR: (400 MHz, DMSO): 9.8 (d, 1H), 8.5 (s, 1H), 7.4 (m, 1H), 7.2 (m, 2H), 7.0 (m, 2H), 6.8 (m, 2H), 4.2 (s, 2H), 4.0 (t, 2H), 3.8 (t, 2H), 3.6 (m, 6H), 3.5 (m, 2H), 3.0 (t, 3H), 2.78 (d, 1H), 2.6 (s, 3H), 2.5 (m, 3H), 2.0-1.8 (m, 2H), 1.6 (m, 2H), 0.9 (t, 3H).

General Procedure C15: Preparation of O-Substituted Bicyclic 4,5-Azepine N—H and N-Alkyl Compounds Scheme 15

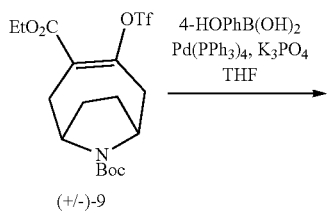

-continued

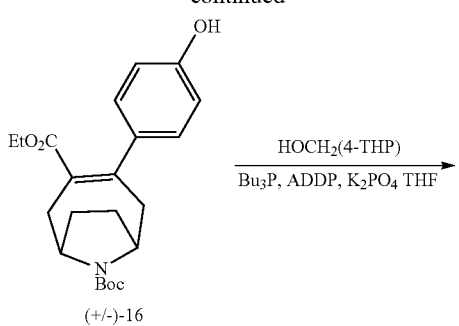
(+/−)-16

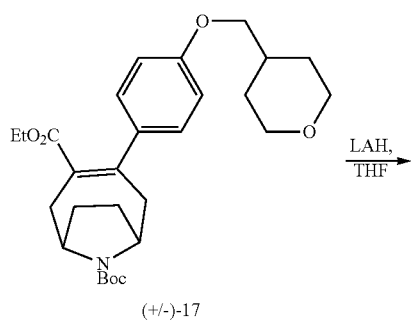
(+/−)-17

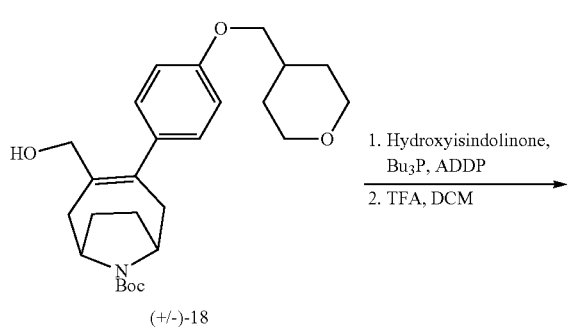
(+/−)-18

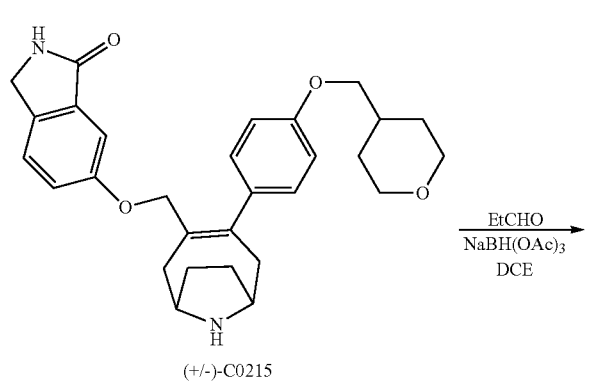
(+/−)-C0215

-continued

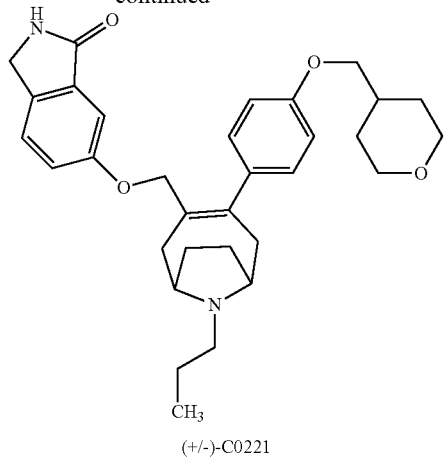
(+/−)-C0221

9-tert-butyl 3-ethyl 4-(4-hydroxyphenyl)-9-azabicyclo[4.2.1]non-3-ene-3,9-dicarboxylate (+/−)-16

Prepared according to General Procedure C1 from (+/−)-9 and commercial available 4-hydroxyphenylboronic acid to yield 1.78 g (86%) of (+/−)-16 as a white solid. LCMS of product peak ([M+Na]=410).

9-tert-butyl 3-ethyl 4-[4-(oxan-4-ylmethoxy)phenyl]-9-azabicyclo[4.2.1]non-3-ene-3,9-dicarboxylate (+/−)-17

A solution of (+/−)-16 (210 mg, 0.54 mmol) in anhydrous THF (18 mL) under nitrogen was chilled in an ice bath. Tri-n-butylphosphine (0.20 mL, 0.81 mmol) and 1,1'-(azodicabonyl)dipiperidine (205 mg, 0.81 mmol) were added and the mixture was stirred cold until the reaction color fades to a pale yellow (60 min.) Hydroxymethyl-4-tetrahydropyran (76 mg, 0.65 mmol) was added, the ice bath was removed, and the reaction was stirred overnight. The mixture was filtered and the resulting solution was concentrated. The residue was taken up in a small volume of EtOAc containing several drops of MeOH, filtered, and purified by flash column chromatography (5%-40% EtOAc/hexanes) to yield 181 mg of (+/−)-17 (~75% purity), which was used without further purification. LCMS of product peak ([M+Na]=508).

Tert-butyl 3-(hydroxymethyl)-4-[4-(oxan-4-ylmethoxy)phenyl]-9 azabicyclo[4.2.1]non-3-ene-9-carboxylate (+/−)-18

Prepared according to General Procedure C3 from (+/−)-17 to yield crude (+/−)-18 which was used without purification in the next step. LCMS of product peak ([M+Na]=466).

6-({4-[4-(oxan-4-ylmethoxy)phenyl]-9-azabicyclo[4.2.1]non-3-en-3-yl}methoxy)-2,3-dihydro-1H-isoindol-1-one (+/−)-C0215

Prepared according to General Procedure C3 from (+/−)-18 to yield 86 mg (61%) of (+/−)-C0215. LCMS of product peak ([M+Na]=475). $^1$H NMR (400 MHz, DMSO) δ 9.05 (s, 1H), 8.86-8.65 (m, 1H), 8.52 (s, 1H), 7.44 (d, J=8.3, 1H), 7.13 (d, J=8.6, 2H), 7.05 (dd, J=8.3, 2.4, 1H), 6.97 (d, J=2.3, 1H), 6.93 (d, J=8.7, 2H), 4.40 (dd, J=26.5, 10.7, 2H), 4.27

(s, 2H), 4.12 (d, J=20.6, 2H), 3.87 (dd, J=10.6, 3.7, 2H), 3.82 (d, J=6.4, 2H), 3.32 (t, J=10.8, 2H), 3.01 (d, J=17.0, 1H), 2.96-2.58 (m, 3H), 2.13-1.87 (m, 3H), 1.70 (dd, J=30.5, 10.7, 4H), 1.32 (qd, J=12.6, 4.4, 2H).

6-({4-[4-(oxan-4-ylmethoxy)phenyl]-9-propyl-9-azabicyclo[4.2.1]non-3-en-3-yl}methoxy)-2,3-dihydro-1H-isoindol-1-one (+/−)-C0221

Prepared according to General Procedure C8 from (+/−)-C0215 yielding 17 mg (49%) of (+/−)-C0221. LCMS of product peak ([M+Na]=517). $^1$H NMR (400 MHz, DMSO) δ 7.36 (d, J=8.3, 1H), 7.06 (d, J=8.5, 2H), 6.98 (dd, J=8.3, 2.3, 1H), 6.88 (dd, J=15.2, 5.4, 3H), 4.35 (dd, J=26.6, 10.8, 2H), 4.22 (s, 2H), 4.04 (d, J=25.0, 2H), 3.86-3.68 (m, 4H), 3.19-2.89 (m, 4H), 2.85-2.51 (m, 3H), 2.04 (d, J=113.1, 4H), 1.79-1.50 (m, 7H), 1.24 (dt, J=11.9, 8.1, 2H), 0.95-0.80 (m, 3H).

General Procedure C16: Preparation of Sulfonamide-Substituted 4,5-Azepine N—H Compounds

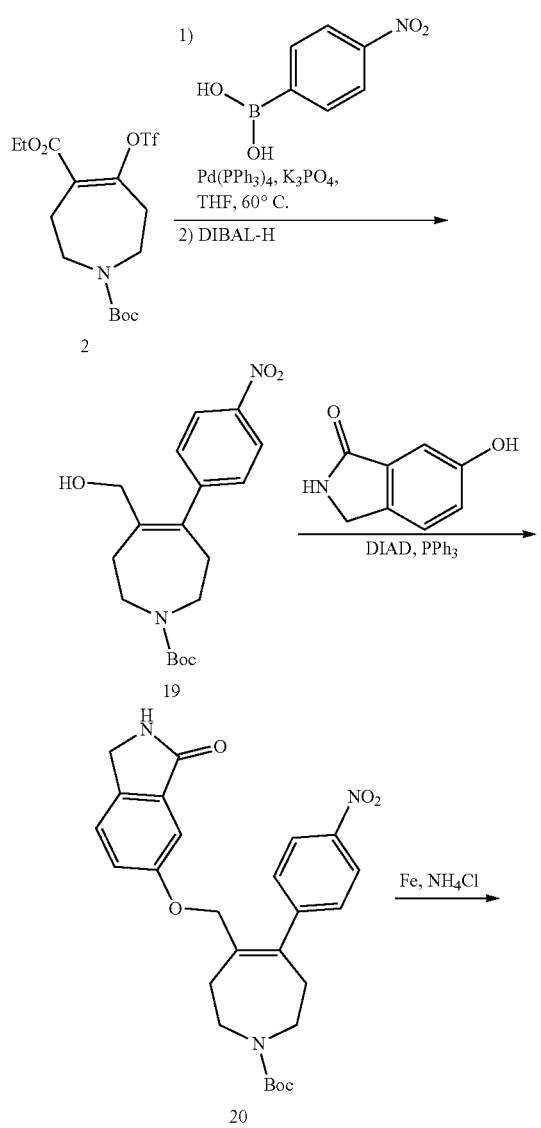

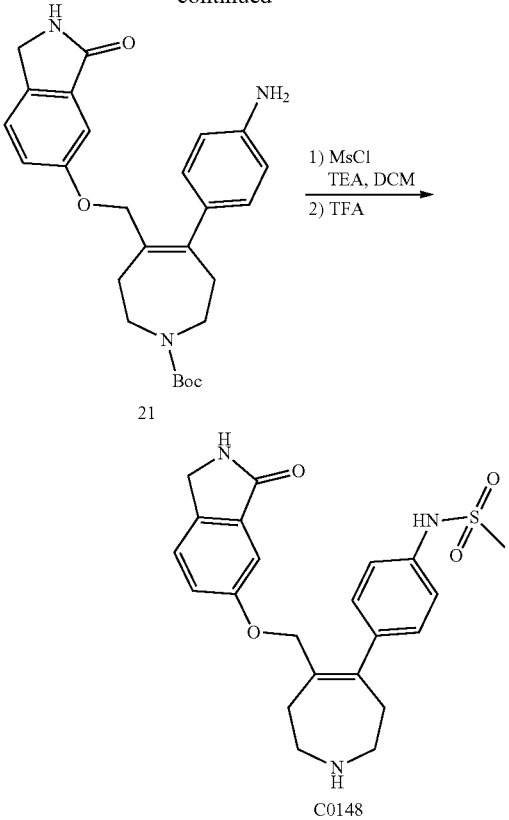

Tert-butyl 4-(hydroxymethyl)-5-(4-nitrophenyl)-2,3,6,7-tetrahydro-1H-azepine-1-carboxylate (19)

Prepared according to General Procedure C1 from 2 and the commercial available (4-nitrophenyl) boronic acid followed with General Procedure C3 to yield 6 g (56%) of 19 as yellow oil. LC-MS: (ES, m/z): 349 [M+H]

Tert-butyl 4-(4-nitrophenyl)-5-[((3-oxo-2,3-dihydro-1H-isoindol-5-yl)oxy]methyl]-2,3,6,7-tetrahydro-1H-azepine-1-carboxylate (20)

Prepared according to General Procedure C3 from 19 to yield 2 g (21%) of 20 as a yellow solid. LC-MS: (ES, m/z) 480 [M+H]

Tert-butyl 4-(4-aminophenyl)-5-[((3-oxo-2,3-dihydro-1H-isoindol-5-yl)oxy]methyl]-2,3,6,7-tetrahydro-1H-azepine-1-carboxylate (21)

Into a 50-mL round-bottom flask, was placed a solution of tert-butyl 4-(4-nitrophenyl)-5-[((3-oxo-2,3-dihydro-1H-isoindol-5-yl)oxy]methyl]-2,3,6,7-tetrahydro-1H-azepine-1-carboxylate 20 (1 g, 2.09 mmol, 1.00 equiv) in tetrahydrofuran (5 mL), a solution of NH$_4$Cl (170 mg, 3.18 mmol, 1.52 equiv) in water (5 mL), Fe (580 mg, 10.36 mmol, 4.97 equiv). The resulting solution was stirred for 2 h at 75° C. The solids were filtered out. The resulting mixture was concentrated under vacuum. The crude product (800 mg) was purified by Flash-Prep-HPLC with the following conditions (IntelFlash-1): Column, silica gel; mobile phase, PE:EA=100:0 increasing to PE:EA=0:100 within 40 min;

Detector, UV 254 nm. 500 mg product was obtained. This resulted in 500 mg (53%) of 21 as a yellow solid. LC-MS: (ES, m/z) 449 [M+H]

Tert-butyl 4-(4-methanesulfonamidophenyl)-5-[((3-oxo-2,3-dihydro-1H-isoindol-5-yl)oxy]methyl]-2,3,6,7-tetrahydro-1H-azepine-1-carboxylate (C0148)

Into a 10-mL round-bottom flask, was placed a solution of tert-butyl 4-(4-aminophenyl)-5-[((3-oxo-2,3-dihydro-1H-isoindol-5-yl)oxy]methyl]-2,3,6,7-tetrahydro-1H-azepine-1-carboxylate C0148 (50 mg, 0.11 mmol, 1.00 equiv) in dichloromethane (2 mL), methanesulfonyl chloride (15.2 mg, 0.13 mmol, 1.20 equiv), TEA (13.5 mg, 0.13 mmol, 1.19 equiv). The resulting solution was stirred for 2 h at room temperature. The resulting mixture was concentrated under vacuum. This resulted in 50 mg (85%) of tert-butyl 4-(4-methanesulfonamidophenyl)-5-[((3-oxo-2,3-dihydro-1H-isoindol-5-yl)oxy]methyl]-2,3,6,7-tetrahydro-1H-azepine-1-carboxylate as a yellow solid.

Into a 10-mL round-bottom flask, was placed a solution of tert-butyl 4-(4-methanesulfonamidophenyl)-5-[((3-oxo-2,3-dihydro-1H-isoindol-5-yl)oxy]methyl]-2,3,6,7-tetrahydro-1H-azepine-1-carboxylate (50 mg, 0.09 mmol, 1.00 equiv) in dichloromethane (2 mL), trifluoroacetic acid (1 mL). The resulting solution was stirred for 30 min at room temperature. The crude product (20 mg) was purified by Prep-HPLC with the following conditions (Prep-HPLC-010): Column, SunFire Prep C18 OBD Column, 5 um, 19*100 mm, 5 um, 19*100 mm; mobile phase, WATER WITH 0.05% TFA and MeCN (10.0% MeCN up to 30.0% in 10 min, up to 95.0% in 2 min, down to 10.0% in 1 min); Detector, Waters2545 UvDector 254&220 nm. 10 mg product was obtained. This resulted in 10 mg (19%) of C0148 as a yellow solid. LC-MS: (ES, m/z): 428 [M+H]. $^1$H-NMR: (CD$_3$OD, 400 MHz): 7.45 (d, 1H), 7.26-7.36 (m, 4H), 7.16 (d, 2H), 4.53 (s, 2H), 4.38 (s, 2H), 3.39-3.50 (m, 4H), 2.98-3.15 (m, 3H), 2.81-2.98 (m, 5H).

General Procedure C17: Preparation of Sulfonamide-Substituted 4,5-Azepine N-Alkyl Compounds

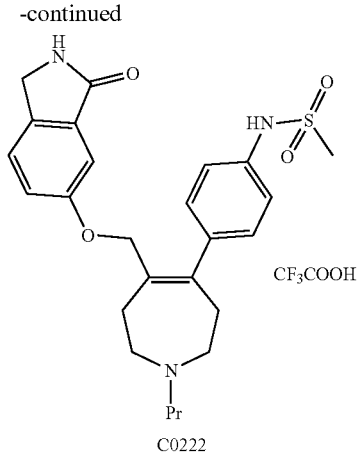

C0222

Example Preparation of N-[4-(5-{((3-oxo-2,3-dihydro-1H-isoindol-5-yl)oxy]methyl}-1-propyl-2,3,6,7-tetrahydro-1H-azepin-4-yl)phenyl]methanesulfonamide(C0222)

Prepared according to General Procedure C8 from C0148 to yield 20 mg (15%) of C0222 as a off-white solid. LC-MS: (ES, m/z): 470 [M+H]. $^1$H-NMR: (CD$_3$OD, 300 MHz): 7.39 (d, 1H), 7.19-7.24 (m, 4H), 7.05-7.08 (d, 2H), 4.47 (m, 2H), 4.33 (s, 2H), 3.64-3.70 (m, 2H), 3.11-3.16 (m, 1H), 2.78-2.83 (m, 5H), 1.76-1.83 (m, 2H), 0.95-1.03 (m, 3H).

General Procedure C18: Preparation of Acetamide-Substituted 4,5-Azepine N—H Compounds Scheme 17

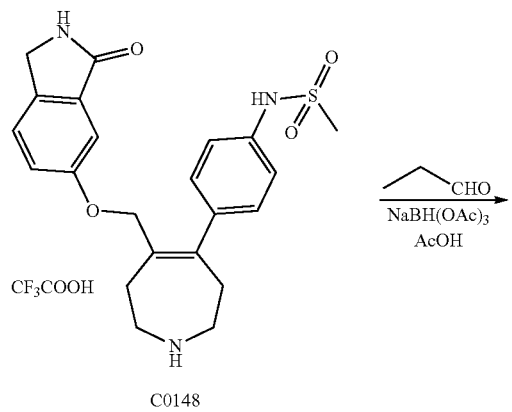

C0148

Scheme 18

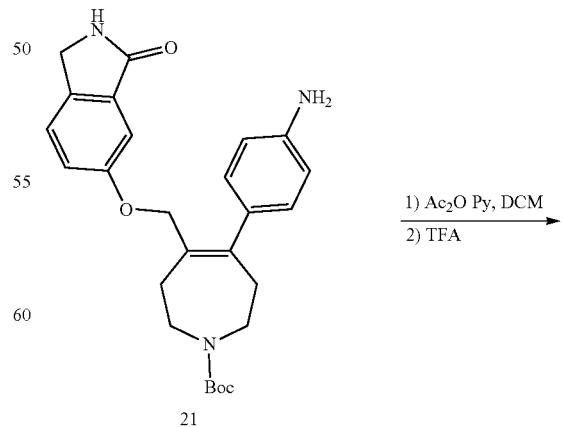

21

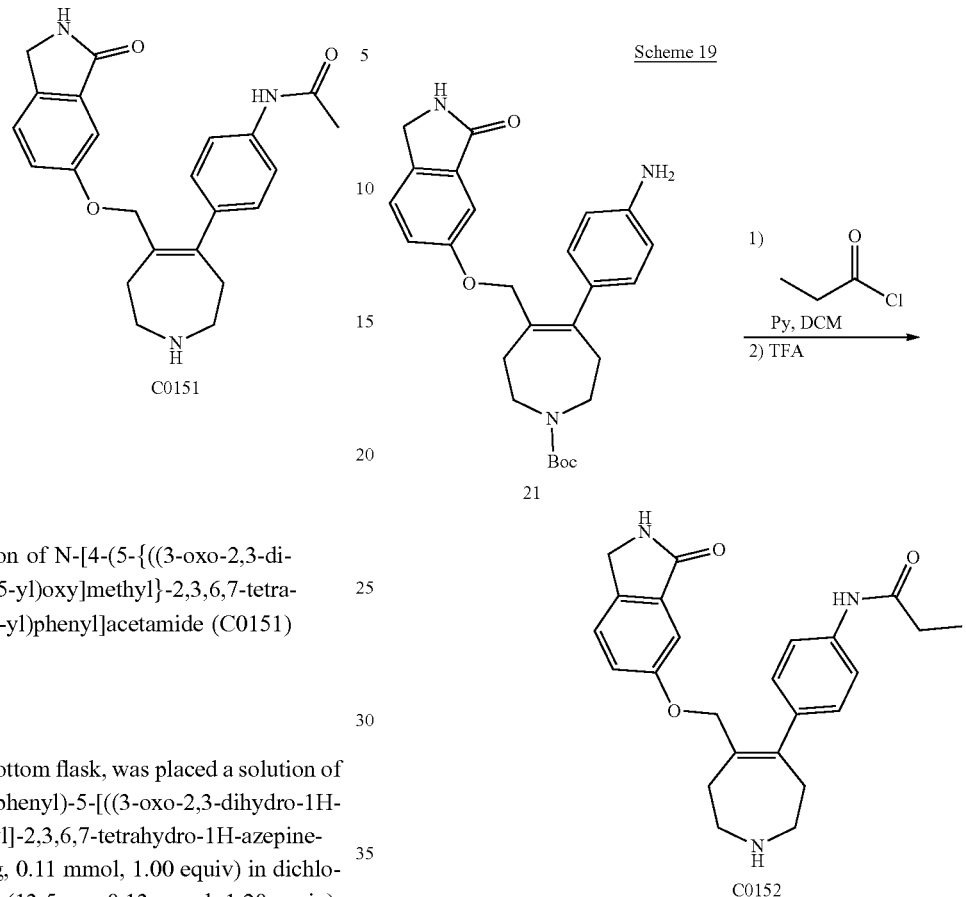

C0151

Example Preparation of N-[4-(5-{((3-oxo-2,3-di-hydro-1H-isoindol-5-yl)oxy]methyl}-2,3,6,7-tetra-hydro-1H-azepin-4-yl)phenyl]acetamide (C0151)

Into a 10-mL round-bottom flask, was placed a solution of tert-butyl 4-(4-aminophenyl)-5-[((3-oxo-2,3-dihydro-1H-isoindol-5-yl)oxy]methyl]-2,3,6,7-tetrahydro-1H-azepine-1-carboxylate 21 (50 mg, 0.11 mmol, 1.00 equiv) in dichloromethane (2 mL), TEA (13.5 mg, 0.13 mmol, 1.20 equiv), acetyl acetate (13.6 mg, 0.13 mmol, 1.20 equiv). The resulting solution was stirred for 2 h at room temperature. The resulting mixture was concentrated under vacuum. This resulted in 50 mg (91%) of tert-butyl 4-(4-acetamidophenyl)-5-[((3-oxo-2,3-dihydro-1H-isoindol-5-yl)oxy]methyl]-2,3,6,7-tetrahydro-1H-azepine-1-carboxylate as yellow oil. LC-MS: (ES, m/z) 492 [M+H]. Into a 10-mL round-bottom flask, was placed a solution of tert-butyl 4-(4-acetamidophenyl)-5-[((3-oxo-2,3-dihydro-1H-isoindol-5-yl)oxy]methyl]-2,3,6,7-tetrahydro-1H-azepine-1-carboxylate (50 mg, 0.10 mmol, 1.00 equiv) in dichloromethane (2 mL), trifluoroacetic acid (1 mL). The resulting solution was stirred for 30 min at room temperature. The crude product was purified by Prep-HPLC with the following conditions (Prep-HPLC-010): Column, SunFire Prep C18 OBD Column, 5 um, 19*150 mm; mobile phase, WATER WITH 0.05% TFA and MeCN (20.0% MeCN up to 40.0% in 10 min, up to 95.0% in 2 min, down to 20.0% in 1 min); Detector, Waters2545 UvDector 220 nm. 10 mg product was obtained. This resulted in 10 mg (19%) of C0151 as a white solid. LC-MS: (ES, m/z): 392 [M+H]. $^1$H-NMR: (CD$_3$OD, 300 MHz): 7.65 (d, 1H), 7.43 (d, 1H), 7.19 (d, 2H), 7.11 (d, 2H), 4.80 (s, 2H), 3.32-3.37 (m, 4H), 4.38 (s, 2H), 2.85-2.94 (m, 4H), 2.82-2.85 (m, 3H), 2.12 (s, 3H).

General Procedure C19: Preparation of Acetamide-Substituted 4,5-Azepine N-Alkyl Compounds Scheme 19

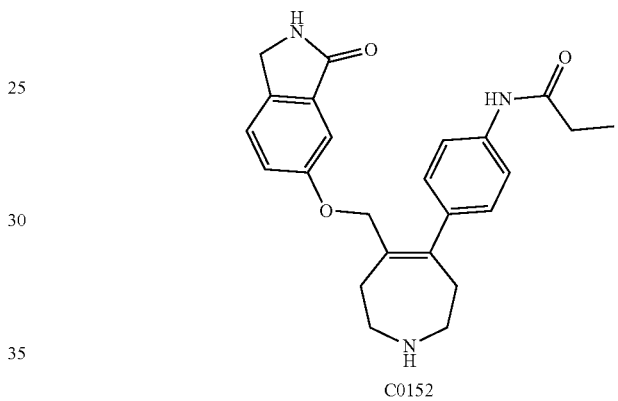

C0152

Example Preparation of N-[4-(5-{((3-oxo-2,3-di-hydro-1H-isoindol-5-yl)oxy]methyl}-2,3,6,7-tetra-hydro-1H-azepin-4-yl)phenyl]propanamide (C0152)

Prepared according to General Procedure C8 from 21 by replacing the acetic anhydride with propanoyl chloride to yield 8 mg (16%) of C0152 as a off-white solid. LC-MS: (ES, m/z): 406 [M+H]. $^1$H-NMR: (CD$_3$OD, 300 MHz): 7.57 (d, 2H), 7.43 (d, 1H), 7.19-7.29 (d, 2H), 7.10-7.19 (m, 2H), 4.51 (s, 2H), 4.36 (s, 2H), 3.34-3.38 (m, 4H), 2.91-2.95 (m, 2H), 2.82-2.91 (m, 2H), 2.35-3.37 (m, 2H), 1.17-1.19 (m, 2H).

General Procedure C20: Preparation of Methylated Acetamide-Substituted 4,5-Azepine N—H Compounds Scheme 20

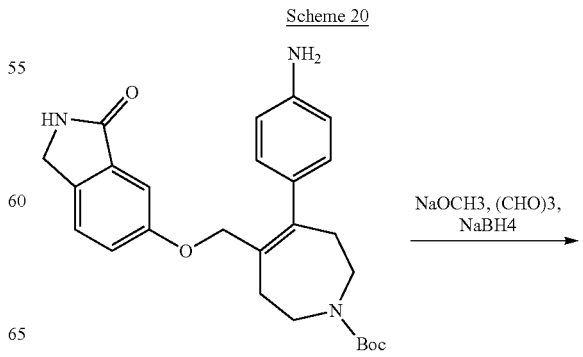

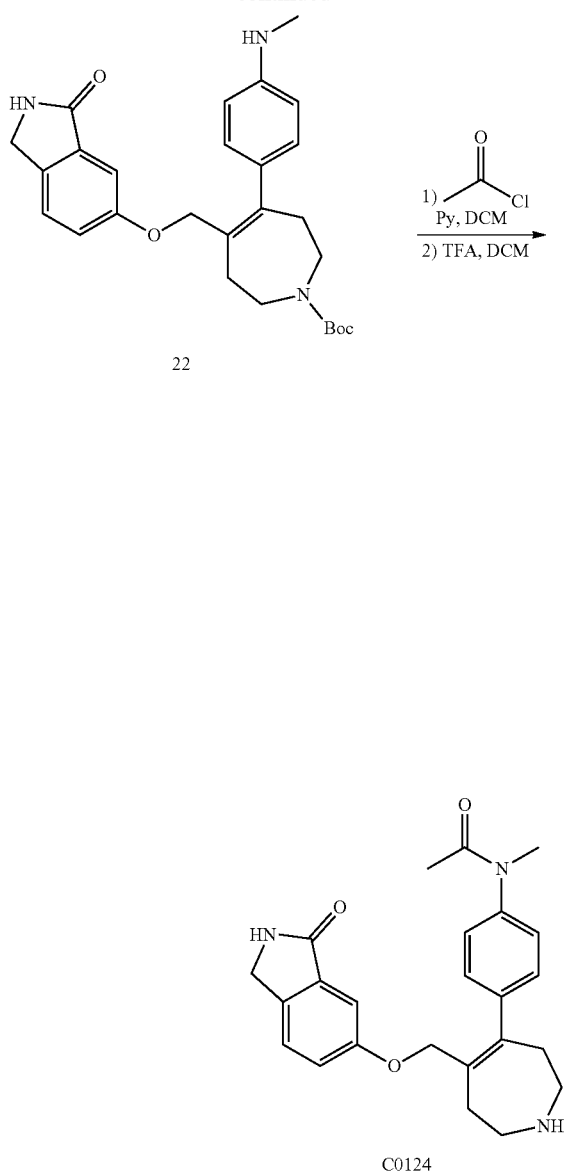

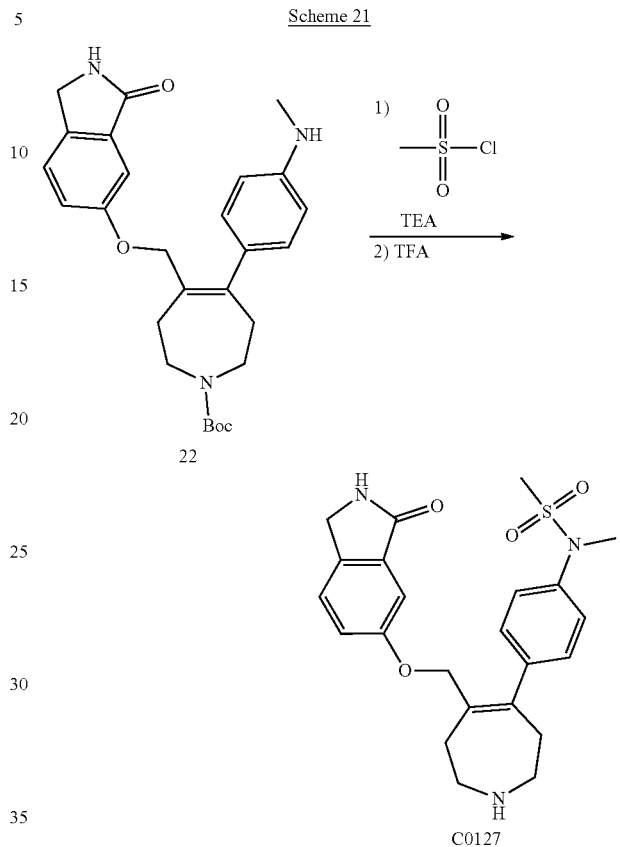

Tert-butyl 4-[4-(methylamino)phenyl]-5-{[(3-oxo-2,3-dihydro-1H-isoindol-5-yl)oxy]methyl}-2,3,6,7-tetrahydro-1H-azepine-1-carboxylate (22)

Prepared according to General Procedure C8 from 21 to yield 30 mg (29%) of 22 as a yellow solid. LC-MS: (ES, m/z) 464 [M+H]

N-methyl-N-[4-(5-[((3-oxo-2,3-dihydro-1H-isoindol-5-yl)oxy]methyl]-2,3,6,7-tetrahydro-1H-azepin-4-yl)phenyl]acetamide (C0124)

Prepared according to General Procedure C18 from 22 to yield 13.7 mg (22%) of C0124 as a colorless oil. LC-MS: (ES, m/z): 406 [M+H]. $^1$H-NMR: (300 MHz, CD3OD): 7.40 (d, 1H), 7.30 (m, 4H), 7.10 (t, 2H), 4.50 (s, 2H), 4.30 (s, 2H), 3.37 (m, 4H), 3.10 (s, 2H), 2.90 (m, 4H), 1.80 (s, 3H).

General Procedure C21: Preparation of Methylated Sulfonamide-Substituted 4,5-Azepine N-Alkyl Compounds Scheme 21

Example Preparation of N-methyl-N-[4-(5-{((3-oxo-2,3-dihydro-1H-isoindol-5-yl)oxy]methyl}-2,3,6,7-tetrahydro-1H-azepin-4-yl)phenyl]methanesulfonamide (C0127)

Into a 10-mL round-bottom flask, was placed a solution of 22 (50 mg, 0.11 mmol, 1.00 equiv) in dichloromethane (2 mL), methanesulfonyl chloride (14.78 mg, 0.13 mmol, 1.20 equiv), TEA (13.1 mg, 0.13 mmol, 1.20 equiv). The resulting solution was stirred for 2 h at room temperature. The resulting mixture was concentrated under vacuum. This resulted in 50 mg (86%) of tert-butyl 4-[4-(N-methylmethanesulfonamido)phenyl]-5-[((3-oxo-2,3-dihydro-1H-isoindol-5-yl)oxy]methyl]-2,3,6,7-tetrahydro-1H-azepine-1-carboxylate as a yellow solid. LC-MS: (ES, m/z) 542 [M+H]

Into a 10-mL round-bottom flask, was placed a solution of tert-butyl 4-[4-(N-methylmethanesulfonamido)phenyl]-5-[((3-oxo-2,3-dihydro-1H-isoindol-5-yl)oxy]methyl]-2,3,6,7-tetrahydro-1H-azepine-1-carboxylate (50 mg, 0.09 mmol, 1.00 equiv) in dichloromethane (4 mL), trifluoroacetic acid (2 mL). The resulting solution was stirred for 30 min at room temperature. The crude product was purified by Prep-HPLC with the following conditions (Prep-HPLC-010): Column, SunFire Prep C18 OBD Column, 5 um, 19*150 mm; mobile phase, WATER WITH 0.05% TFA and MeCN (35.0% MeCN up to 49.0% in 10 min, up to 95.0% in 2 min, down to 35.0% in 2 min); Detector, Waters2545 UvDector 254&220 nm. 14 mg product was obtained. This resulted in 14 mg (27%) of C0127 as a white solid.

LC-MS: (ES, m/z): 442 [M+H]. ¹H-NMR: (CD₃OD, 400 MHz): 7.45 (d, 1H), 7.46-7.48 (m, 3H), 7.33 (d, 2H), 7.13 (d, 2H), 4.52 (s, 2H), 4.38 (s, 2H), 3.40-3.50 (m, 2H), 2.37-3.39 (m, 3H), 2.99-3.15 (m, 2H), 2.87-2.95 (s, 3H), 2.73-2.87 (m, 2H).

General Procedure C22: Preparation of Methylated Acetamide-Substituted 4,5-Azepane N—H Compounds

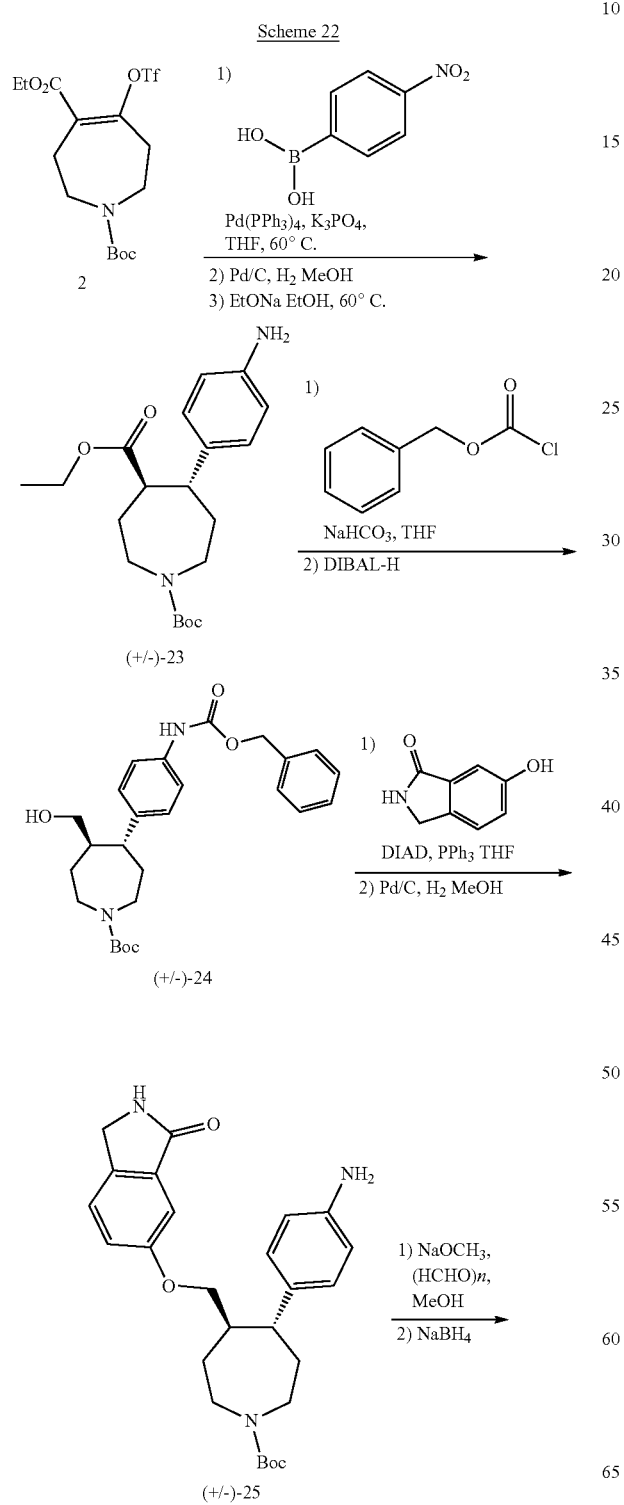

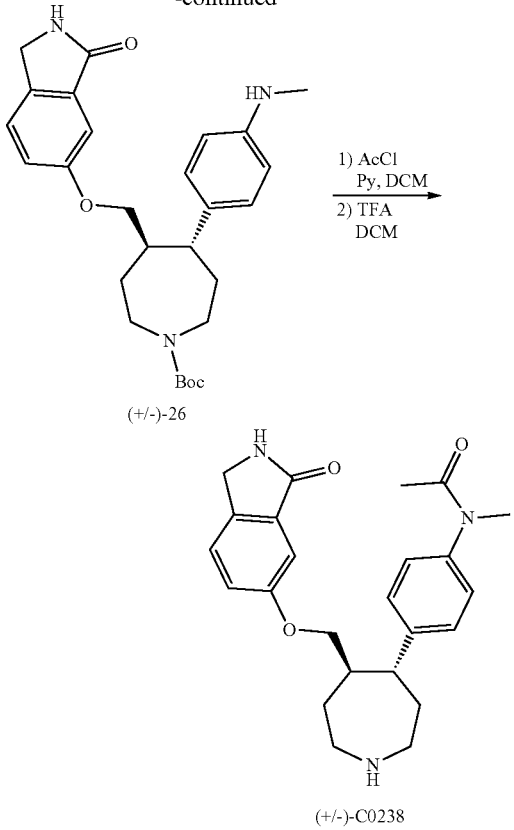

1-tert-butyl 4-ethyl(trans)-5-(4-aminophenyl)azepane-1,4-dicarboxylate(+/−)-23

Prepared according to General Procedure C2 from C2 followed by General Procedure C16 to yield 10 g (crude) of (+/−)-23 as yellow oil. LC-MS: (ES, m/z): 363 [M+H].

Tert-butyl (trans)-4-(4-[((benzyloxy)carbonyl]amino]phenyl)-5-(hydroxymethyl)azepane-1-carboxylate (+/−)-24

Into a 100-mL round-bottom flask, was placed a solution of (+/−)-23 (10 g, 27.59 mmol, 1.00 equiv) in tetrahydrofuran (100 mL), sodium methaneperoxoate (2.3 g, 27.38 mmol, 0.99 equiv), benzyl chloroformate (4.7 g, 27.55 mmol, 1.00 equiv). The resulting solution was stirred overnight at room temperature. The resulting mixture was concentrated under vacuum. The crude product (16 g) was purified by Flash-Prep-HPLC with the following conditions (IntelFlash-1): Column, silica gel; mobile phase, EA/PE=0% increasing to EA/PE=60% within 30 min; Detector, UV 254 nm. 13 g product was obtained. This resulted in 13 g (95%) of 1-tert-butyl 4-ethyl (trans)-5-(4-[((benzyloxy)carbonyl]amino]phenyl)azepane-1,4-dicarboxylate as a yellow solid. LC-MS: (ES, m/z): 497 [M+H].

Into a 250-mL 3-necked round-bottom flask, was placed a solution of 1-tert-butyl 4-ethyl (trans)-5-(4-[((benzyloxy)carbonyl]amino]phenyl)azepane-1,4-dicarboxylate (10 g, 20.14 mmol, 1.00 equiv) in dichloromethane (100 mL). This was followed by the addition of DIBAL-H (1M) (40 mL) dropwise with stirring at −30° C. The resulting solution was stirred for 3 h at −30° C. The reaction was then quenched by the addition of 60 mL of ethanol. The solids were collected by filtration. The crude product (5 g) was purified by Flash-Prep-HPLC with the following conditions (IntelFlash-1): Column, silica gel; mobile phase, EA/PE=0% increasing to EA/PE=60% within 30 min; Detector, UV 254 nm. 3.8 g product was obtained. This resulted in 3.8 g (42%) of (+/−)-24 as a white solid. LC-MS: (ES, m/z): 455 [M+H]

Tert-butyl (trans)-4-(4-aminophenyl)-5-[((3-oxo-2,3-dihydro-1H-isoindol-5-yl)oxy]methyl]azepane-1-carboxylate (+/−)-25

Into a 10-mL round-bottom flask, was placed a solution of tert-butyl (trans)-4-(4-[((benzyloxy)carbonyl]amino]phenyl)-5-(hydroxymethyl)azepane-1-carboxylate (+/−)-24 (100 mg, 0.22 mmol, 1.00 equiv) in tetrahydrofuran (2 mL), 6-hydroxy-2,3-dihydro-1H-isoindol-1-one (32.8 mg, 0.22 mmol, 1.00 equiv), PPh$_3$ (86.6 mg, 0.33 mmol, 1.00 equiv). This was followed by the addition of DIAD (66.7 mg, 0.33 mmol, 1.50 equiv) dropwise with stirring at 0° C. The resulting solution was stirred overnight at room temperature. The resulting mixture was concentrated under vacuum. The crude product (100 mg) was purified by Flash-Prep-HPLC with the following conditions (IntelFlash-1): Column, silica gel; mobile phase, EA/PE=0% increasing to EA/PE=100% within 30 min; Detector, UV 254 nm. 80 mg product was obtained. This resulted in 80 mg (62%) of tert-butyl (trans)-4-(4-[((benzyloxy)carbonyl]amino]phenyl)-5-[((3-oxo-2,3-dihydro-1H-isoindol-5-yl)oxy]methyl]azepane-1-carboxylate as a yellow solid. LC-MS: (ES, m/z): 586 [M+H] Into a 10-mL round-bottom flask, was placed a solution of tert-butyl (trans)-4-(4-[((benzyloxy)carbonyl]amino]phenyl)-5-[((3-oxo-2,3-dihydro-1H-isoindol-5-yl)oxy]methyl]azepane-1-carboxylate (100 mg, 0.17 mmol, 1.00 equiv) in methanol (3 mL), Palladium carbon (100 mg). To the above hydrogen was introduced in. The resulting solution was stirred for 2 h at room temperature. The solids were filtered out. The resulting mixture was concentrated under vacuum. This resulted in 50 mg (65%) of tert-butyl (trans)-4-(4-aminophenyl)-5-[((3-oxo-2,3-dihydro-1H-isoindol-5-yl)oxy]methyl]azepane-1-carboxylate (+/−)25 as a white solid. LC-MS: (ES, m/z): 452 [M+H]

Tert-butyl (trans)-4-[4-(methylamino)phenyl]-5-[((3-oxo-2,3-dihydro-1H-isoindol-5-yl)oxy]methyl] azepane-1-carboxylate (+/−)26

Prepared according to General Procedure C20 from (+/−)-25 to yield 60 mg (58%) of (+/−)-26 as a yellow solid. LC-MS: (ES, m/z): 466 [M+H]

N-methyl-N-[4-((trans)-5-[((3-oxo-2,3-dihydro-1H-isoindol-5-yl)oxy]methyl]azepan-4-yl]phenyl]acetamide (+/−)C0238

Prepared according to General Procedure C20 from (+/−)-26 to yield 95 mg (62%) of (+/−) C0238 as a white solid. LC-MS: (ES, m/z): 408 [M+H]. $^1$H-NMR: (400 MHz, CD$_3$OD): 7.45~7.41 (m, 3H), 7.27~7.25 (m, 4H), 7.12~7.09 (m, 2H), 4.37 (s, 2H), 3.83~3.41 (m, 6H), 3.32~3.01 (m, 4H), 2.40~2.14 (m, 5H), 1.80 (s, 3H)

General Procedure C23: Preparation of Methylated Acetamide-Substituted 4,5-Azepane N-Alkyl Compounds Scheme 23

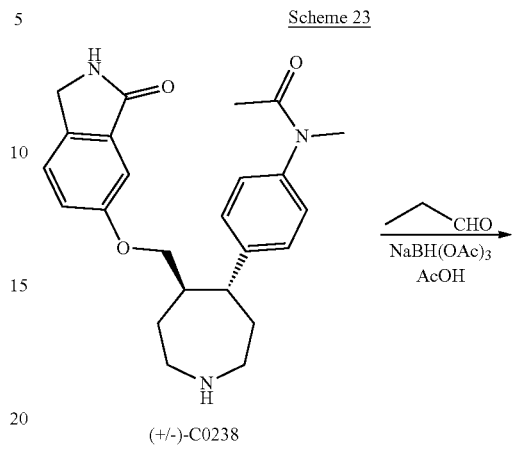

(+/−)-C0238

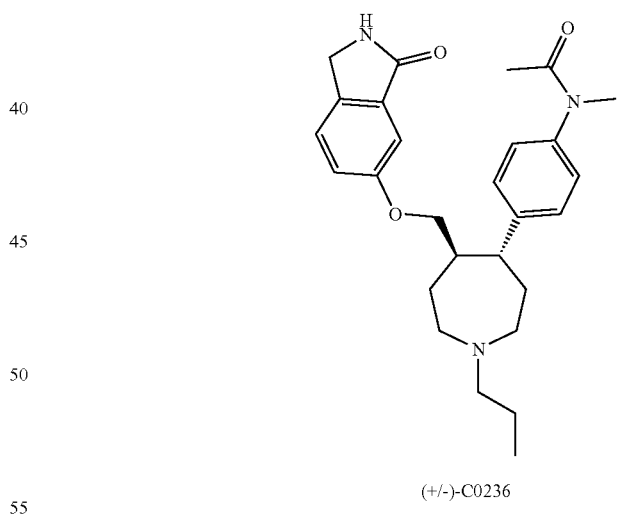

(+/−)-C0236

Example Preparation of N-methyl-N-{4-((trans)-5-{((3-oxo-2,3-dihydro-1H-isoindol-5-yl)oxy]methyl}-1-propylazepan-4-yl]phenyl}acetamide) (+/−)C0236

Prepared according to General Procedure C8 from (+/−)-C0238 to yield 26.7 mg (19%) of (+/−)-C0236 as a off-white solid. LC-MS: (ES, m/z): 450 [M+H] $^1$H-NMR: (300 MHz, CD$_3$OD): 7.45~7.41 (m, 3H), 7.27~7.25 (m, 4H), 7.12~7.09 (m, 2H), 4.37 (s, 2H), 3.80~3.22 (m, 6H), 3.28~3.26 (m, 1H), 3.17~2.97 (m, 5H), 2.36~2.05 (m, 6H), 1.79~1.63 (m, 5H), 1.04~0.99 (m, 3H)

General Procedure C24: Preparation of Methylated Sulfonamide-Substituted 4,5-Azepane N—H Compounds General Procedure C25: Preparation of Methylated Sulfonamide-Substituted 4,5-Azepane N-Alkyl Compounds Scheme 24

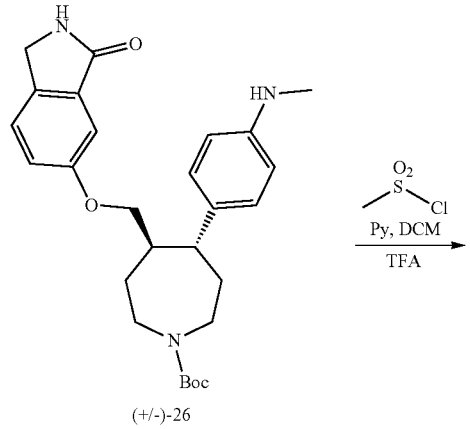

Scheme 25

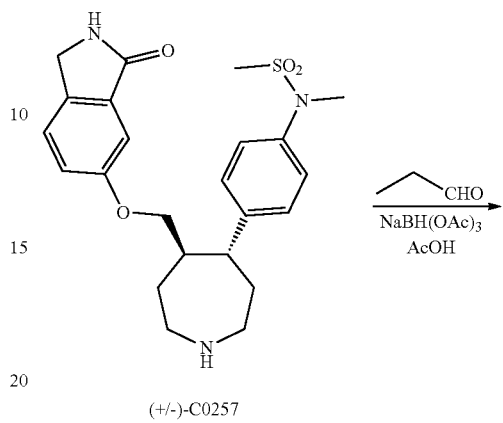

Example Preparation of N-methyl-N-{4-((trans)-5-{((3-oxo-2,3-dihydro-1H-isoindol-5-yl)oxy]methyl}azepan-4-yl]phenyl}methanesulfonamide (+/−)C0257

Prepared according to General Procedure C21 from (+/−)-26 to yield 50 mg (30%) of (+/−)-C0257 as a white solid. LC-MS: (ES, m/z): 444 [M+H] $^1$H-NMR: (400 MHz, CD$_3$OD): 7.45~7.33 (m, 5H), 7.13~7.08 (m, 2H), 7.13~7.08 (m, 2H), 4.37 (s, 2H), 3.80~3.40 (m, 6H), 3.33 (s, 3H), 3.02~2.99 (m, 1H), 2.98 (s, 3H), 2.39~2.08 (m, 5H)

Example Preparation of N-methyl-N-{4-((trans)-5-{((3-oxo-2,3-dihydro-1H-isoindol-5-yl)oxy]methyl}-1-propylazepan-4-yl]phenyl}methanesulfonamide (+/−)-C0261

Prepared according to General Procedure C8 from (+/−)-C0257 to yield 46.9 mg (69%) of (+/−)-C0261 as a light yellow solid. LC-MS: (ES, m/z): 486 [M+H]. $^1$H-NMR: (400 MHz, CD$_3$OD): 7.45~7.33 (m, 5H), 7.13~7.08 (m, 2H), 7.13~7.08 (m, 2H), 4.37 (s, 2H), 3.83~3.58 (m, 5H), 3.33 (s, 3H), 3.29~3.18 (m, 1H), 3.01~2.99 (m, 1H), 2.88 (s, 3H), 2.40~1.81 (m, 5H), 1.09~1.05 (m, 5H)

General Procedure C26: Preparation of Cyclic Sulfonamide-Substituted 4,5-Azepane N—H Compounds Scheme 26

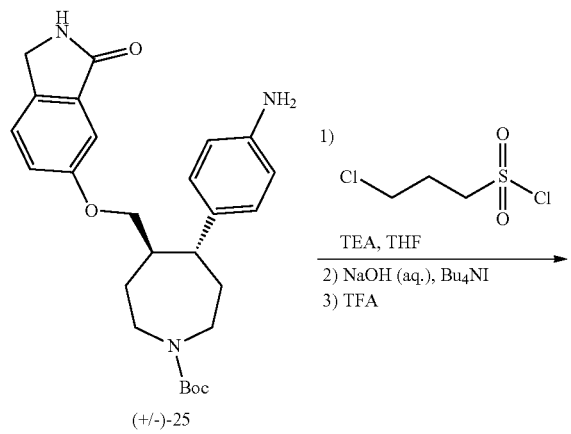

(+/−)-25

Example Preparation of 2-{4-((trans)-5-{[(3-oxo-2,3-dihydro-1H-isoindol-5-yl)oxy]Methyl}Azepan-4-yl]Phenyl}-1λ$^6$,2-Thiazolidine-1,1-Dione (+/−)-C0229

Into a 100-mL round-bottom flask, was placed tert-butyl (trans)-4-(4-aminophenyl)-5-[((3-oxo-2,3-dihydro-1H-isoindol-5-yl)oxy]methyl]azepane-1-carboxylate (+/−)-25 (170 mg, 0.38 mmol, 1.00 equiv), TEA (33.6 mg, 0.33 mmol, 0.88 equiv). This was followed by the addition of 3-chloropropane-1-sulfonyl chloride (66.7 g, 376.73 mmol, 1000.68 equiv). The mixture was stirred for 2 h at room temperature. To this was added sodium hydroxide (50% aq) (0.7 mL), Bu$_4$NI (6.2 mg, 0.02 mmol, 0.04 equiv). The resulting solution was stirred for 16 h at room temperature. The resulting mixture was concentrated under vacuum. The crude product (200 mg) was purified by Flash-Prep-HPLC with the following conditions (IntelFlash-1): Column, silica gel; mobile phase, EA/PE=0% increasing to EA/PE=100% within 30 min; Detector, UV 254 nm. 156 mg product was obtained. This resulted in 156 mg (74%) of tert-butyl (trans)-4-[((3-oxo-2,3-dihydro-1H-isoindol-5-yl)oxy]methyl]-5-[4-(2-oxo-3,4,5,6-tetrahydro-1,2,6-oxathiazin-6-yl)phenyl]azepane-1-carboxylate as a yellow solid. LC-MS: (ES, m/z): 556 [M+H]. Into a 100-mL round-bottom flask, was placed a solution of tert-butyl (trans)-4-[((3-oxo-2,3-dihydro-1H-isoindol-5-yl)oxy]methyl]-5-[4-(2-oxo-3,4,5,6-tetrahydro-1,2,6-oxathiazin-6-yl)phenyl]azepane-1-carboxylate (100 mg, 0.18 mmol, 1.00 equiv) in dichloromethane (5 mL), trifluoroacetic acid (1 mL). The resulting solution was stirred for 30 min at room temperature. The resulting mixture was concentrated under vacuum. The crude product (100 mg) was purified by Prep-HPLC with the following conditions (Prep-HPLC-010): Column, SunFire Prep C18 OBD Column, 5 um, 19*150 mm; mobile phase, WATER WITH 0.05% TFA and MeCN (10% MeCN up to 30% in 8 min, up to 95% in 2 min, down to 10% in 2 min); Detector, Waters2545 UvDector 254&220 nm. 21.4 mg product was obtained. This resulted in 21.4 mg (21%) of 2-[4-((trans)-5-[((3-oxo-2,3-dihydro-1H-isoindol-5-yl)oxy]methyl]azepan-4-yl]phenyl]-1,2-thiazolidine-1,1-dione; trifluoroacetic acid (+/−)-C0229 as a white solid. LC-MS: (ES, m/z): 456 [M+H]. $^1$H-NMR: (400 MHz, CD$_3$OD): 7.45~7.43 (m, 1H), 7.30~7.23 (m, 5H), 7.14~7.13 (m, 1H), 4.37 (s, 2H), 3.81~3.68 (m, 5H), 3.67~3.41 (m, 6H), 297~2.92 (m, 1H), 2.54~2,47 (m, 2H), 2.37~2.09 (m, 5H)

General Procedure C27: Preparation of Cyclic Sulfonamide-Substituted 4,5-Azepane N-Alkyl Compounds Scheme 27

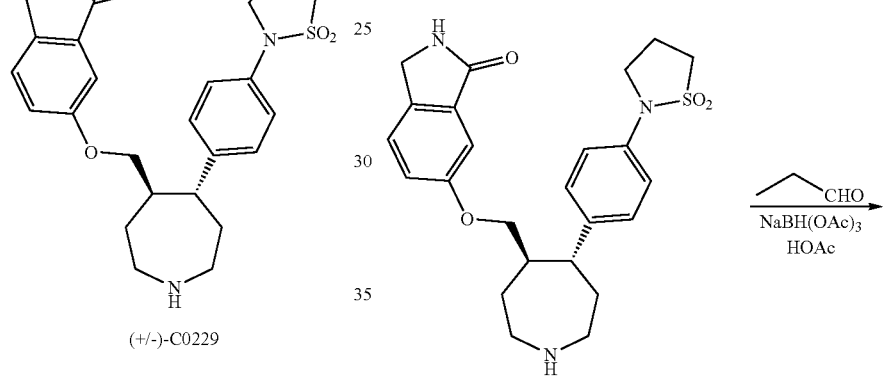

(+/−)-C0229

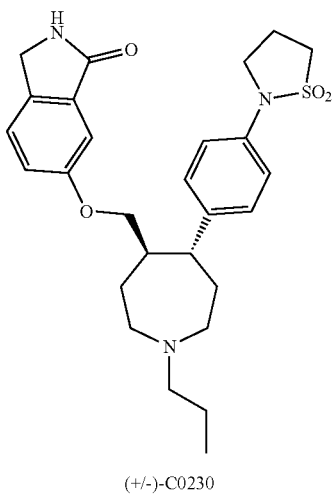

(+/−)-C0230

Example Preparation of 2-[4-((trans)-5-[((3-oxo-2,3-dihydro-1H-isoindol-5-yl)oxy]Methyl]-1-propylazepan-4-yl]Phenyl]-1-[6],2-thiazolidine-1,1-dione (+/−)-C0230

Prepared according to General Procedure C8 from (+/−)-C0229 to yield 32.4 mg (24%) of (+/−)-C0230 as a white solid. LC-MS: (ES, m/z): 498 [M+H]. ¹H-NMR: (300 MHz, CD₃OD): 7.41~7.32 (m, 1H), 7.29~7.21 (m, 4H), 7.14~7.08 (m, 2H), 4.36 (s, 2H), 3.78~3.35 (m, 2H), 3.45~3.40 (m, 3H), 3.40~3.15 (m, 3H), 2.99~2.80 (m, 1H), 2.54~2.28 (m, 5H), 2.07~2.05 (m, 1H), 1.85~1.78 (m, 2H), 1.08~1.03 (m, 3H).

General Procedure C28: Preparation of Nitrogen-Substituted Bicyclic 4,5-Azepine N—H and N-Alkyl Compounds Scheme 28

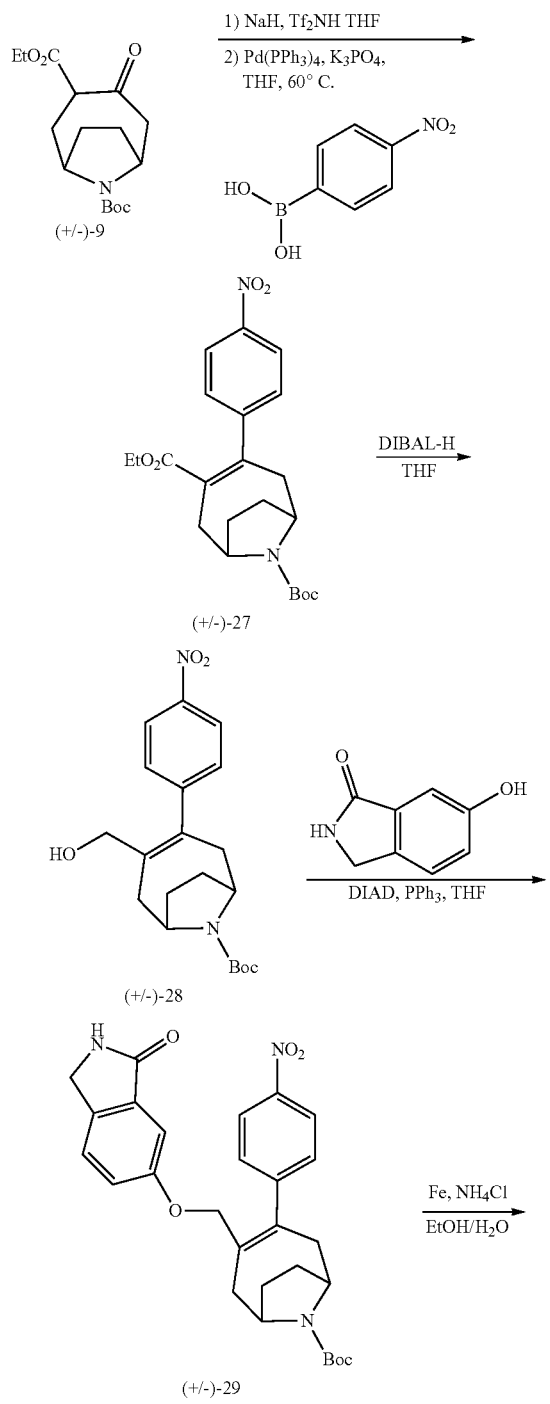

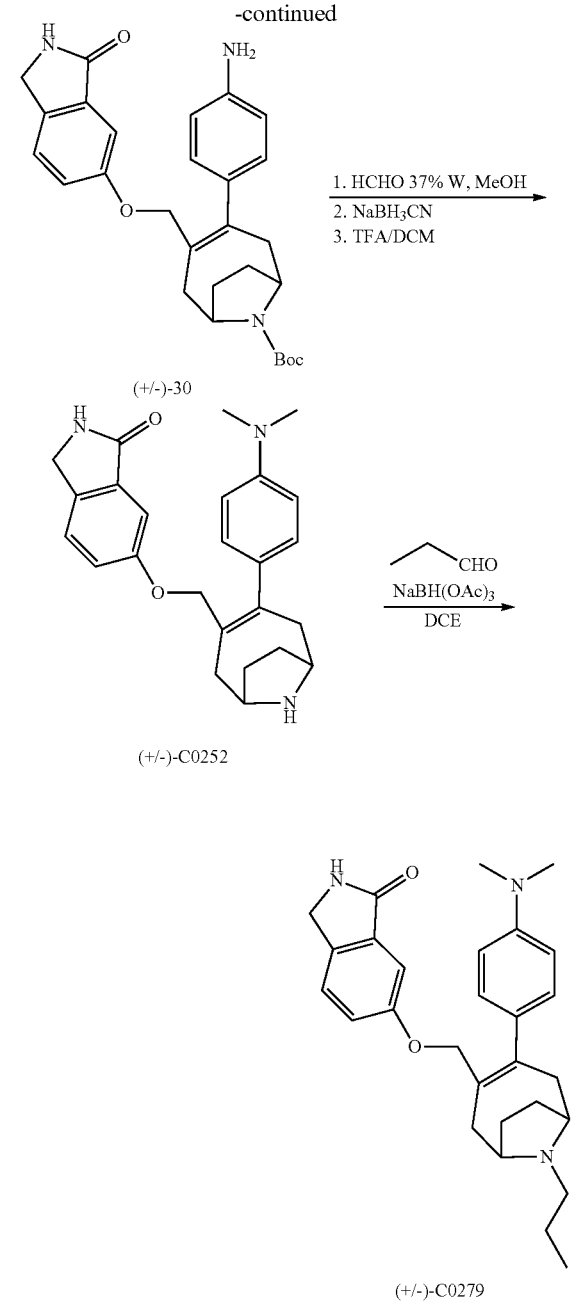

9-tert-butyl-3-ethyl 4-(4-nitrophenyl)-9-azabicyclo [4.2.1]non-3-ene-3,9-dicarboxylate (+/−)-27

Prepared according to General Procedure C16 from (+/−)-9 to yield 5.04 g of (+/−)-27 as yellow solids. LCMS of product peak ([M+Na]=440.1).

Tert-butyl-3-(hydroxymethyl)-4-(4-nitrophenyl)-9-azabicyclo[4.2.1]non-3-ene-9-carboxylate (+/−)-28

Prepared according to General Procedure C16 from (+/−)-27 to yield 1.58 g of (+/−)-28 was obtained as light yellow oil in 88%. LCMS of product peak ([M+Na]=397.2).

6-{[4-(4-nitrophenyl)-9-azabicyclo[4.2.1]non-3-en-3-yl]methoxy}-2,3-dihydro-1H-isoindol-1-one (+/−)-29

Prepared according to General Procedure C16 from (+/−)-28 to yield 2.31 g of (+/−)-29 in 71% yield. LCMS of product peak ([M+Na]=528.2).

Tert-butyl-3-(4-aminophenyl)-4-{((3-oxo-2,3-dihydro-1H-isoindol-5-yl)oxy]methyl}-9-azabicyclo[4.2.1]non-3-ene-9-carboxylate (+/−)-30

Prepared according to General Procedure C5 from (+/−)-9 to yield (+/−)-30 as light yellow solids (2200 mg, 101% yield). LCMS of product peak ([M+Na]=498.2).

6-({4-[4-(dimethylamino)phenyl]-9-azabicyclo[4.2.1]non-3-en-3-yl}methoxy)-2,3-dihydro-1H-isoindol-1-one (+/−)-C0252

To a solution of (+/−)-30 (150 mg, 0.32 mmol) were added and 37% formaldehyde in water (128 mg, 1.58 mmol) were added AcOH (54.17 mL, 0.95 mmol) and NaBH$_3$CN (39.64 mg, 0.64 mmol) at 0° C. After 2 h, the mixture was warmed to rt and quenched with 5 mL of water after 30 min. The aqueous was extracted with EtOAc (3×20 mL). The organics were combined and concentrated. The crude residue was then dissolved in the mixture of 2 mL of DCM and 0.5 mL of TFA. After 2 h, the solution was concentrated and the residue was subjected to HPLC purification. HPLC purification method: Luna acid medium column, 10-50% acetonitrile in H$_2$O over 15 min, followed by flashing with 100% acetonitrile, 0.1% TFA modifier was employed. The combined fractions were concentrated was participated in the mixture of 10 mL of DCM and 1 mL of N NaOH. Then the aqueous was extracted with DCM six times until the aqueous turned to be clear. The combined organics were passed through a phase separator and the filtrate was concentrated to give 103 mg of (+/−)-C0252 as white solids in 81% yields. $^1$H NMR (400 MHz, CDCl$_3$) δ 7.76 (s, 1H), 7.27 (d, J=8.4, 1H), 7.15 (d, J=2.3, 1H), 7.06-6.94 (m, 3H), 6.64 (d, J=8.8, 2H), 4.41 (d, J=10.1, 1H), 4.33 (s, 2H), 4.24 (d, J=9.3, 1H), 3.69 (d, J=21.4, 2H), 2.90 (s, 6H), 2.83 (d, J=17.6, 1H), 2.65-2.54 (m, 2H), 1.88 (dd, J=13.6, 6.5, 2H), 1.68 (d, J=7.4, 2H). LCMS of product peak (M+H=404.3).

6-({4-[4-(dimethylamino)phenyl]-9-propyl-9-azabicyclo[4.2.1]non-3-en-3-yl}methoxy)-2,3-dihydro-1H-isoindol-1-one (+/−)-C0279

Prepared according to General Procedure C8 from (+/−)-C0252 to yield 34.11 mg of (+/−)-C0279 as white solids in 51% yields. $^1$H NMR (400 MHz, CD3OD) δ 7.44 (d, J=8.3, 1H), 7.24 (dd, J=24.4, 8.6, 4H), 7.16-6.94 (m, 2H), 4.56-4.29 (m, 4H), 4.16 (d, J=22.3, 2H), 3.19-3.04 (m, 8H), 2.91 (d, J=5.4, 2H), 2.77 (dd, J=18.0, 5.7, 1H), 2.46-2.15 (m, 2H), 2.04-1.77 (m, 4H), 1.05 (t, J=7.4, 3H). LCMS of product peak (M+H=446.3).

General Procedure C29: Preparation of Carboxamide-Substituted 4,5-Azepane N—H and N-Alkyl Compounds Scheme 29

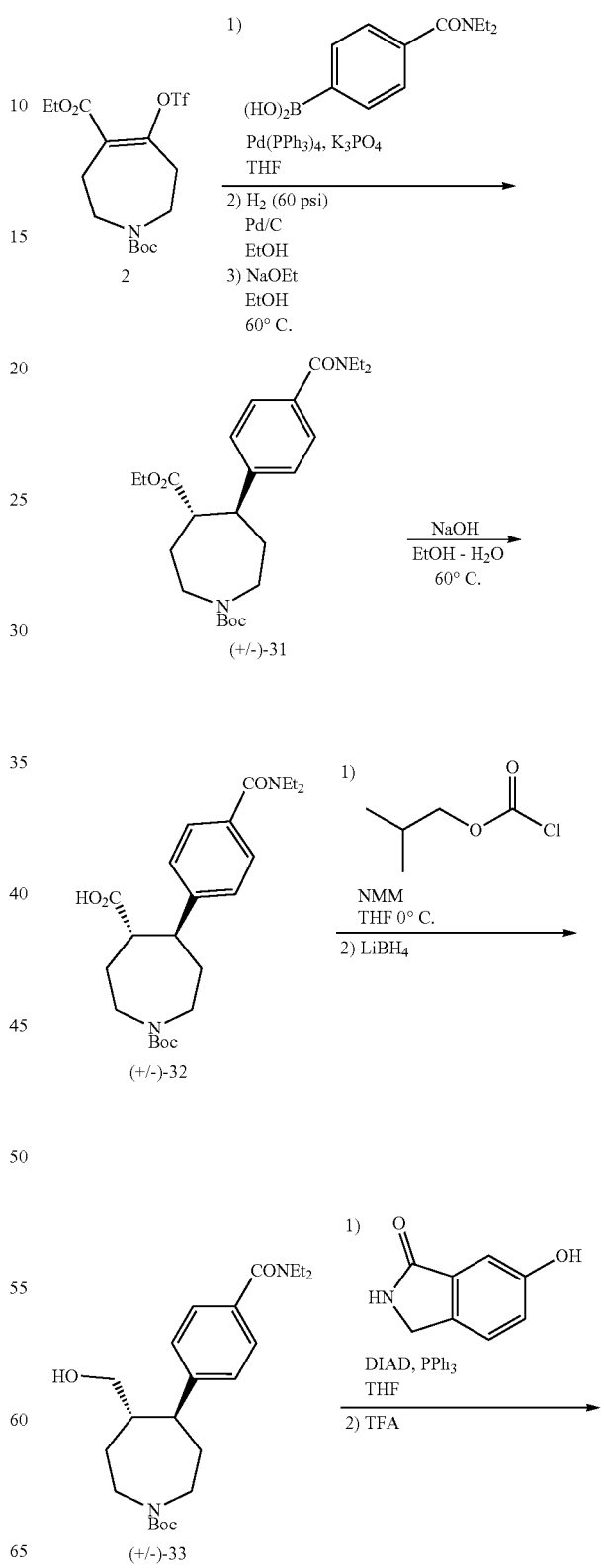

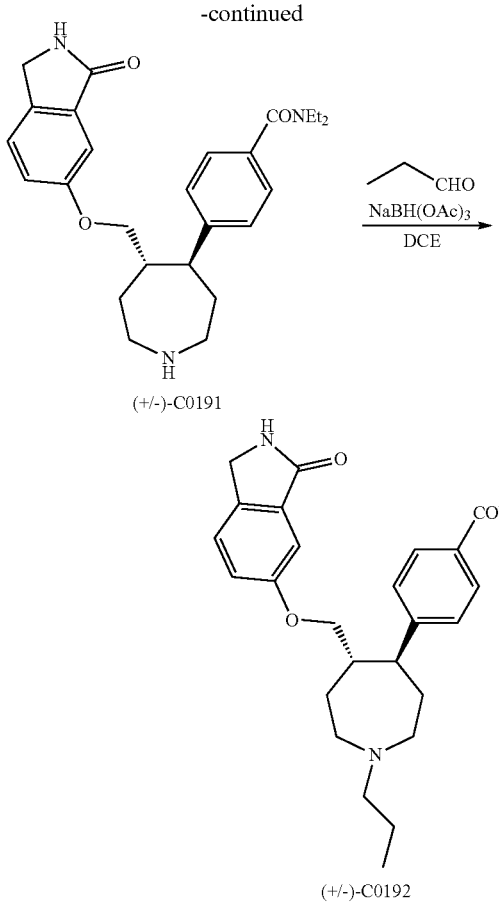

(+/−)-C0191

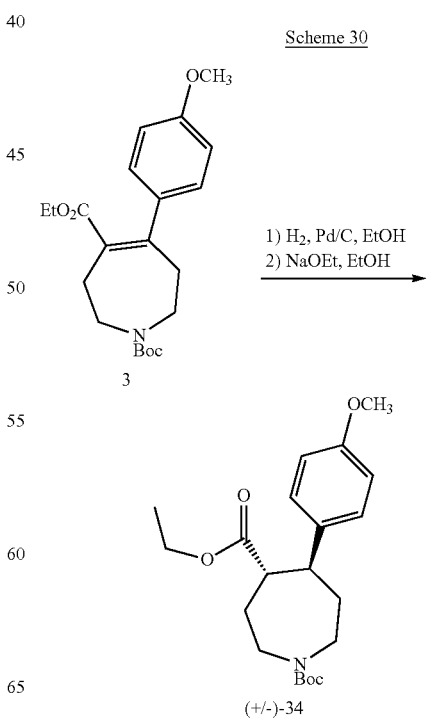

1-tert-butyl 4-ethyl(4S,5S)-5-[4-(diethylcarbamoyl)
phenyl]azepane-1,4-dicarboxylate (+/−)-31

Prepared according to General Procedures C1 and C2 from 2 and the commercial available boronic acid by 4-(N, N-diethylcarboxamide)phenylboronic acid to yield (+/−)-31.

(trans)-1-((tert-butoxy)carbonyl]-5-[4-(diethylcarbamoyl)phenyl]azepane-4-carboxylic Acid (+/−)-32

The crude (+/−)-31 (about 4.2 mmol) was then treated with 4.2 ml NaOH (1N, 4.2 mmol) and water (21 ml) at 60° C. overnight. The reaction was concentrated and the residual was taken into water (20 ml) and washed by EtOAc (2×10 ml), the aqueous was then acidified with HCl (2N) with cooling to pH 5 by pH paper, the product was extracted with EtOAc (4×50 ml), the combined extracts were washed by brine, dried and concentrated left 1.64 g of (+/−)-32 as an amber foam, which was used as is in the next reaction. LCMS: [M+H] —C$_4$H$_8$ at 363.2 and [M+Na] at 441.2.

Tert-butyl-(trans)-4-[4-(diethylcarbamoyl)phenyl]-5-(hydroxymethyl)azepane-1-carboxylate (+/−)-33

N-Methylmorpholine (488 µl, 4.44 mmol) was added to a solution of (trans)-1-((tert-butoxy)carbonyl]-5-[4-(diethylcarbamoyl)phenyl]azepane-4-carboxylic acid (1.55 g, 3.78 mmol) in THF (30 ml) at 0° C. under N$_2$ followed by Isobutyl chloroformate (576 µl, 4.44 mmol), the resulting mix was stirred at 0° C. for 2 h, TLC (80% EtOAc in hexane) showed the reaction had completed. Lithium borohydride (11.1 ml, 2 M in THF) was added and mix was allowed to stir and warm to room temperature overnight.

The reaction was cooled at an ice bath and MeOH was added slowly, the mix was stirred for 10 min and then water was added. The product was extracted with EtOAc (3×80 ml), a the combined extracts were washed by sat'd NaHCO$_3$, brine, dried and concentrated left 1.6 g which was purified by flash chromatography (80 g silica gel column, eluted by EtOAc in hexane: 20%, 1 CV; 20-50%, 4 CV; 50-100%, 12 CV, 100%, 8CV, the fractions were combined gave 1.11 g of (+/−)-33 (65% over 2 steps) as a white foam. LCMS: [M+H] —C$_4$H$_8$ at 349.2 and M+Na at 427.2 was observed.

(trans)-N,N-diethyl-4-[5-{((3-oxo-2,3-dihydro-1H-isoindol-5-yl)oxy]methyl}azepan-4-yl]benzamide (+/−)-C0191

Prepared according to General Procedure C3 from ((+/−)-33) to yield 141 mg (41%) of ((+/−)-C0191). $^1$H NMR (400 MHz, CD3OD) δ 7.35-7.30 (m, 1H), 7.27 (d, J=8.3, 2H), 7.24-7.19 (m, 2H), 7.02-6.95 (m, 2H), 4.25 (s, 2H), 3.67 (s, 1H), 3.60-3.49 (m, 1H), 3.49-3.22 (m, 6H), 3.18-3.06 (m, 2H), 2.91 (tt, J=12.1, 6.1, 1H), 2.33-2.22 (m, 2H), 2.21-1.91 (m, 3H), 1.12 (s, 3H), 0.96 (s, 3H). LCMS: [M+H] at 436.2.

(trans)-N,N-diethyl-4-[5-{((3-oxo-2,3-dihydro-1H-isoindol-5-yl)oxy]methyl}-1-propylazepan-4-yl]benzamide (+/−)-C0192

Prepared according to the General Procedure C8 from (+/−)-C0191 to yield 16 mg (27%) of (+/−)-C0192. $^1$H NMR (400 MHz, CD3OD) δ 7.45-7.18 (m, 5H), 7.00 (d, J=2.3, 2H), 4.25 (s, 2H), 3.76-3.36 (m, 7H), 3.35-3.22 (m, 2H), 3.09 (s, 5H), 2.41-1.86 (m, 5H), 1.71 (dd, J=14.6, 7.2, 2H), 1.13 (s, 3H), 0.95 (t, J=7.4, 6H). LCMS: [M+H] at 478.3.

General Procedure C30: Preparation of Amide Linked 4,5-Azepane N—H Compounds

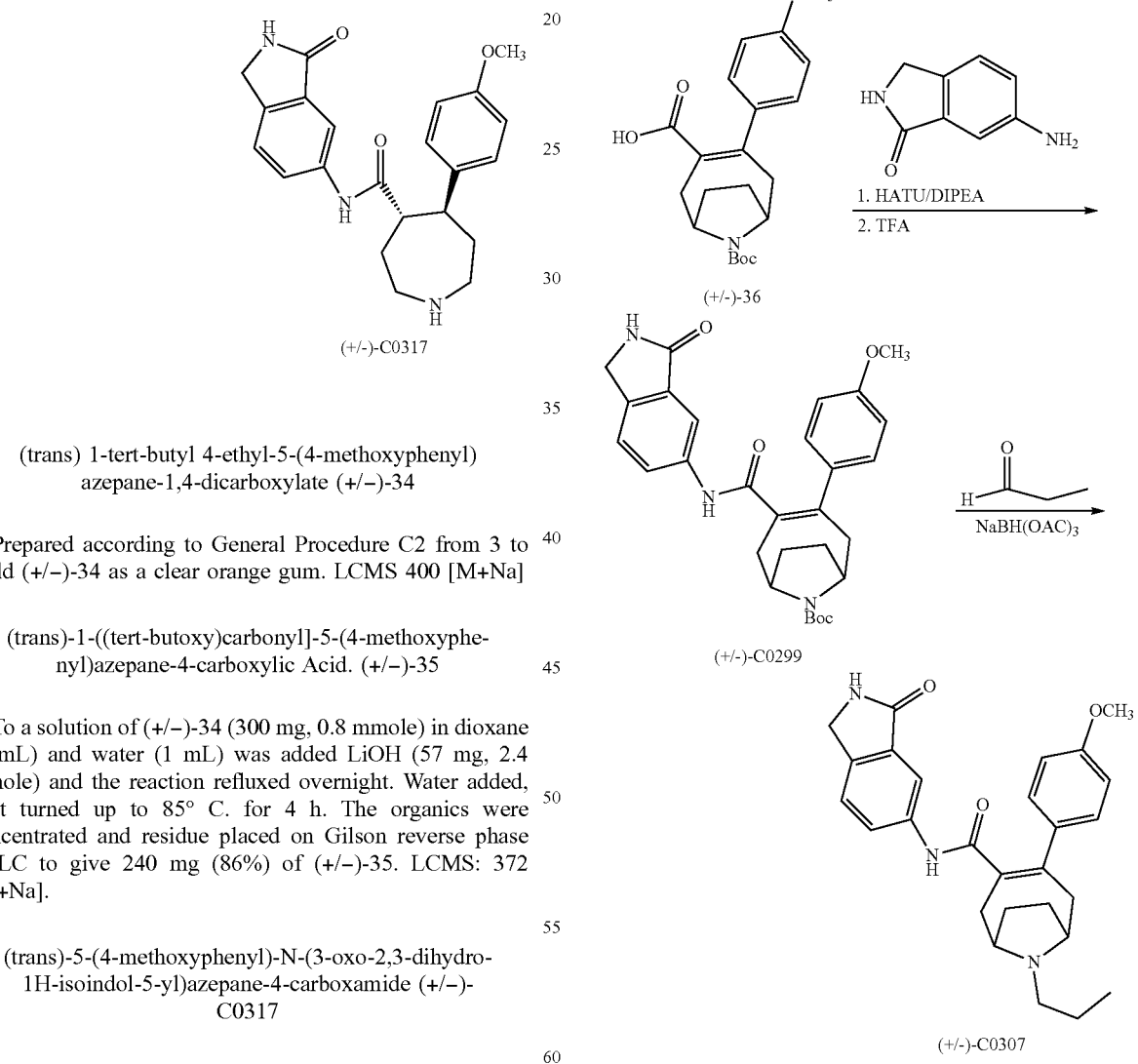

General Procedure C31: Preparation of Amide Linked Bicyclic 4,5-Azepine N—H and N-Alkyl Compounds Scheme 31

(trans) 1-tert-butyl 4-ethyl-5-(4-methoxyphenyl) azepane-1,4-dicarboxylate (+/−)-34

Prepared according to General Procedure C2 from 3 to yield (+/−)-34 as a clear orange gum. LCMS 400 [M+Na]

(trans)-1-((tert-butoxy)carbonyl]-5-(4-methoxyphenyl)azepane-4-carboxylic Acid. (+/−)-35

To a solution of (+/−)-34 (300 mg, 0.8 mmole) in dioxane (5 mL) and water (1 mL) was added LiOH (57 mg, 2.4 mmole) and the reaction refluxed overnight. Water added, heat turned up to 85° C. for 4 h. The organics were concentrated and residue placed on Gilson reverse phase HPLC to give 240 mg (86%) of (+/−)-35. LCMS: 372 [M+Na].

(trans)-5-(4-methoxyphenyl)-N-(3-oxo-2,3-dihydro-1H-isoindol-5-yl)azepane-4-carboxamide (+/−)-C0317

Prepared according to the General Procedure C29 from (+/−)-35 to yield 24 mg (38%) of (+/−)-C0317. $^1$H NMR (400 MHz, CD3OD) d 7.12 (d, J=8.7, 1H), 6.83 (d, J=8.7, 1H), 6.65 (t, J=4.1, OH), 6.53-6.47 (m, OH), 4.17 (s, 1H), 3.69 (s, 1H), 3.42-3.28 (m, 1H), 2.89-2.75 (m, OH), 2.68 (dt, J=8.3, 7.8, OH), 2.55-2.42 (m, 1H), 2.17 (ddd, J=15.7, 9.9, 3.7, OH), 2.10-1.98 (m, 1H). LCMS [M+H]=380.2

(trans)-1-((tert-butoxy)carbonyl]-5-[4-(diethylcarbamoyl)phenyl]azepane-4-carboxylic Acid (+/−)-36

Prepared according to General Procedure C2 from (+/−)-10 to yield 0.20 g of (+/−)-36. LCMS [M+Na]=396.

Tert-butyl 3-(4-methoxyphenyl)-4-((3-oxo-2,3-dihydro-1H-isoindol-5-yl)carbamoyl]-9-azabicyclo[4.2.1]non-3-ene-9-carboxylate (+/−)-C0299

Prepared according to General Procedure C30 from (+/−)-36 to yield 0.31 g of (+/−)-C0299 (55% pure by HPLC). LCMS [M+H]=404.2.

4-(4-methoxyphenyl)-N-(3-oxo-2,3-dihydro-1H-isoindol-5-yl)-9-propyl-9-azabicyclo[4.2.1]non-3-ene-3-carboxamide (+/−)-C0307

Prepared according to General Procedure C8 from (+/−)-C0299 to yield 11 mg (56%) of (+/−)-C0307. LCMS [M+H]=446. $^1$H NMR (400 MHz, DMSO) δ 9.48 (s, 1H), 7.60 (s, 1H), 7.31 (s, 2H), 7.15 (d, J=8.6, 2H), 6.76 (d, J=8.6, 2H), 4.18 (s, 2H), 4.07 (d, J=16.9, 2H), 3.59 (d, J=3.1, 3H), 3.22-3.06 (m, 1H), 3.06-2.96 (m, 3H), 2.92 (d, J=17.6, 1H), 2.76-2.56 (m, 2H), 2.30-2.10 (m, 3H), 1.94 (dd, J=25.7, 17.4, 2H), 1.67 (dt, J=23.3, 7.9, 2H), 0.96-0.80 (m, 3H).

General Procedure C32: Alternative Coupling Reaction for Bicyclic 4,5-Azepine Intermediates Scheme 32

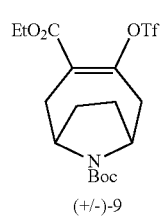
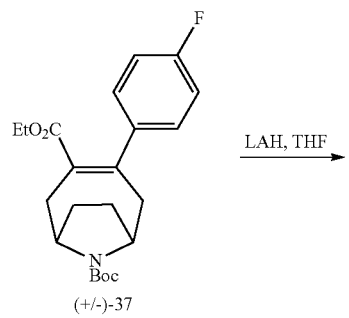
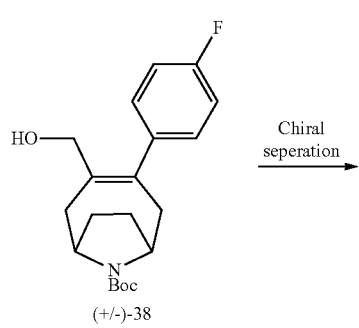

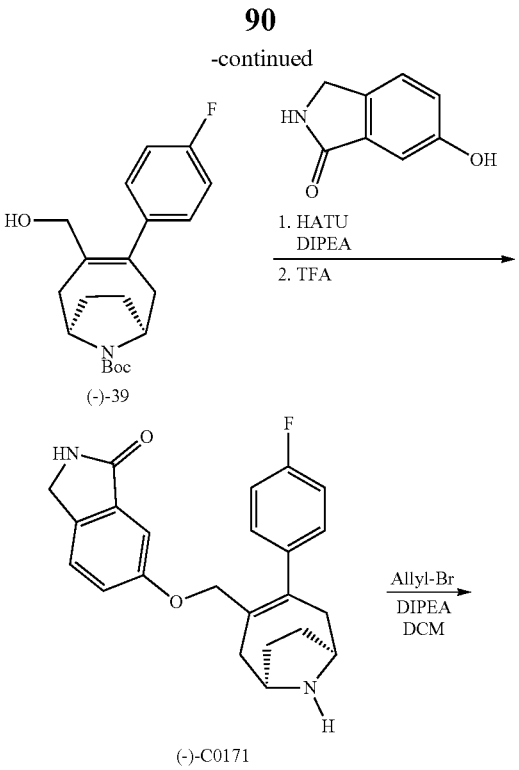

Example Preparation of 9-tert-butyl 3-ethyl 4-(4-fluorophenyl)-9-azabicyclo[4.2.1]non-3-ene-3,9-dicarboxylate (+/−)-37

A solution of (+/−)-9 (0.5 g, 1.13 mmol), 4-fluorophenyl zinc bromide (3.83 mL of a 0.5 M solution in THF, 1.92 mmol), and anhydrous THF (12 mL) was sparged with nitrogen for 15 min, after which tetrakis triphenylphospine Pd(0) (0.039 g, 0.034 mmol) was added and the reaction was stirred under nitrogen at room temperature. After 2 hr, the reaction was chilled on an ice bath and quenched by the addition of saturated aqueous NaHCO$_3$ (5 mL). The mixture was extracted three times with EtOAc, the combined organics washed twice with brine, filtered through cotton, concentrated, and purified by flash column chromatography (3%-24% EtOAc/hexanes) to yield (+/−)-37 as a semi-purified product in approximately 75% yield that was used without further purification in subsequent reactions. LCMS of product peak ([M+Na]=412).

Tert-butyl 3-(4-fluorophenyl)-4-(hydroxymethyl)-9-azabicyclo[4.2.1]non-3-ene-9-carboxylate (+/−)-38

Prepared according to General Procedure C3 from (+/−)-37 to yield (+/−)-38. LCMS [M+Na]=370.1.

(−)-tert-butyl-3-(4-fluorophenyl)-4-(hydroxymethyl)-9-azabicyclo[4.2.1]non-3-ene-9-carboxylate (−)-39

Prepared according to General Procedure C2 from (+/−) C9 to yield (+/−)-38. LCMS [M+Na]=370.1. The later eluting isomer provided (−)(+/−)-39: $[\alpha]_D^{25}$=−0.5°.

(−)-6-{[4-(4-fluorophenyl)-9-azabicyclo[4.2.1]non-3-en-3-yl]methoxy}-2,3-dihydro-1H-isoindol-1-one (−)-C0171

Prepared according to General Procedure C3 from (−)-39 to yield (+/−)-38. LCMS [M+H]=379.2.

(−)-6-{[4-(4-fluorophenyl)-9-(prop-2-en-1-yl)-9-azabicyclo[4.2.1]non-3-en-3-yl]methoxy}-2,3-dihydro-1H-isoindol-1-one (−)-C0203

To a hazy mixture of (−)-C0171 (20 mmg, 0.041 mmol) and diisopropyl amine (13 mg, 0.103 mmol) in 2 mL of dichloromethane was added ally bromide (7.3 mg, 0.061 mmol), and the reaction was stirred at rt. Then the mixture was concentrated and redissolved in methanol. The resulting solution was filtered through 0.45 um filter. The filtrated was subjected to HPLC purification. HPLC purification method: Luna acid medium column, 30-50% acetonitrile in H$_2$O over 6 min, followed by flashing with 100% acetonitrile, 0.1% TFA modifier was employed. The combined fraction were concentrated to give 15 mg (68% yield) of (−)-C0203. LCMS [M+H]=419.2. $^1$H NMR (400 MHz, DMSO) δ 9.69 (s, 1H), 8.53 (s, 1H), 7.44 (d, J=8.3, 2H), 7.35-7.14 (m, 8H), 7.05 (dd, J=8.3, 2.3, 2H), 6.97 (d, J=2.2, 2H), 6.05-5.90 (m, 2H), 5.72-5.43 (m, 4H), 4.38 (dd, J=23.3, 10.8, 4H), 4.27 (s, 4H), 4.09 (s, 2H), 4.02 (t, J=5.5, 3H), 3.79 (t, J=5.7, 3H), 3.09 (d, J=17.9, 2H), 2.78 (s, 3H), 2.66 (dd, J=17.9, 5.7, 1H), 2.35-2.10 (m, 6H), 1.90-1.70 (m, 5H).

General Procedure C33: Preparation of Methylated Analogs for Bicyclic 4,5-Azepine Intermediates Scheme 33

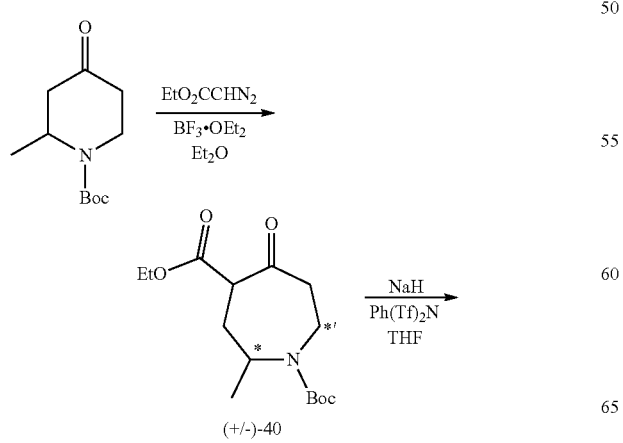

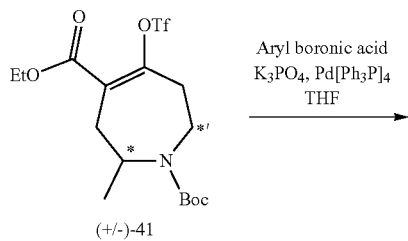

(+/−)-41

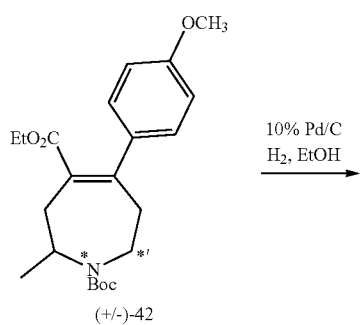

(+/−)-42

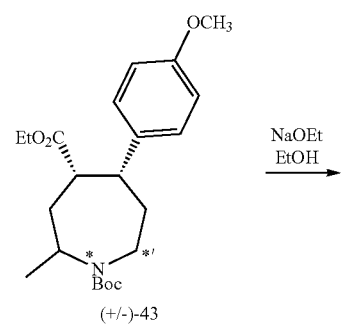

(+/−)-43

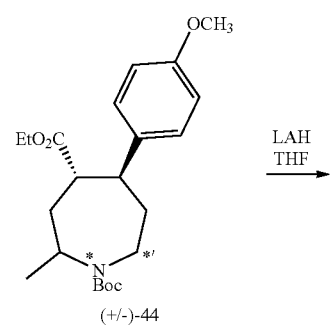

(+/−)-44

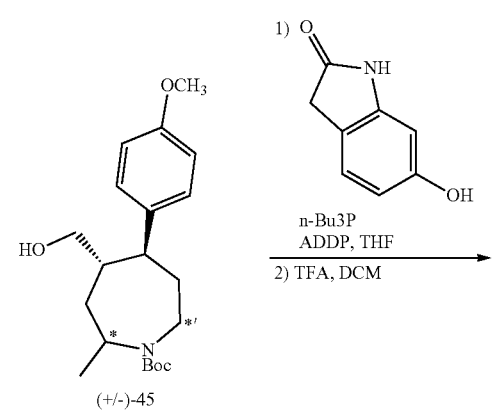

(+/−)-45

-continued

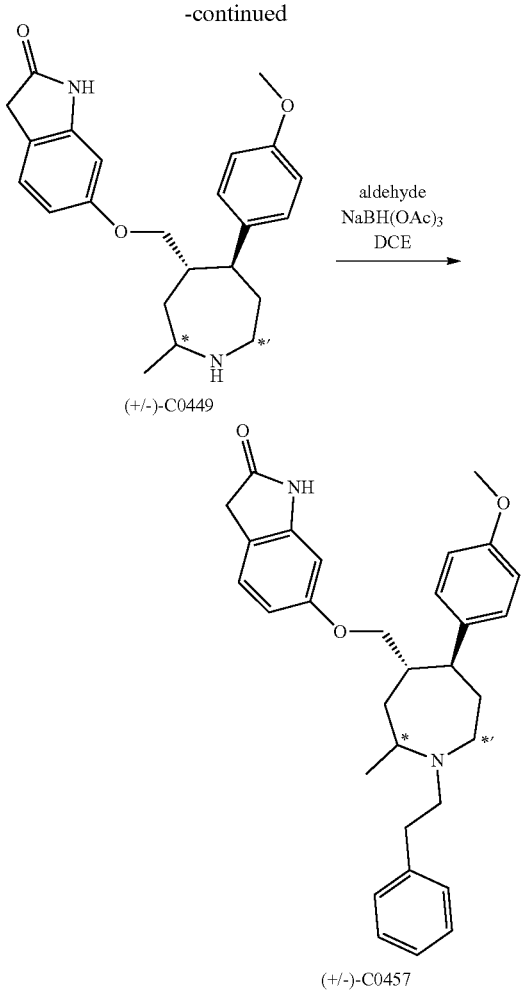

(+/-)-C0449

(+/-)-C0457

The methyl position shown at the carbon labeled with an * may alternatively be present at the carbon labeled with the *'.

Example Preparation of 1-tert-butyl 4-ethyl 2-methyl-5-oxoazepane-1,4-dicarboxylate ((+/−)-40)

Prepared according to General Procedure C1 from the commercial available (+/−)-1-Boc-2-methyl-4-piperidinone. LCMS of product peak ([M+Na]=334). LC-MS: (ES, m/z): 200 [M-Boc]

Example Preparation of 1-tert-butyl 4-ethyl 2-methyl-5-(trifluoromethane)sulfonyloxy]-2,3,6,7-tetrahydro-1H-azepine-1,4-dicarboxylate ((+/−)-41)

Prepared according to General Procedure C1 from (+/−)-40. LC-MS: (ES, m/z): 454 [M+Na]

Example Preparation of 1-tert-butyl 4-ethyl 5-(4-methoxyphenyl)-2-methyl-2,3,6,7-tetrahydro-1H-azepine-1,4-dicarboxylate ((+/−)-42)

Prepared according to General Procedure C1 from (+/−)-41. LC-MS: (ES, m/z): 412 [M+Na]

Example Preparation of 1-tert-butyl 4-ethyl (4S, 5R)-5-(4-methoxyphenyl)-2-methylazepane-1,4-dicarboxylate (((+/−)-43)

Prepared according to General Procedure C2 from (+/−)-42. LC-MS: (ES, m/z): 415 [M+Na]

Example Preparation of 1-tert-butyl 4-ethyl (4S, 5S)-5-(4-methoxyphenyl)-2-methylazepane-1,4-dicarboxylate (((+/−)-44)

Prepared according to General Procedure C2 from (+/−)-43. LC-MS: (ES, m/z): 415 [M+Na]

Example Preparation of Tert-butyl (4S,5S)-4-(hydroxymethyl)-5-(4-methoxyphenyl)-2-methyl-azepane-1-carboxylate (((+/−)-45)

Prepared according to General Procedure C2 from (+/−)-44. LC-MS: (ES, m/z): 372 [M+Na]

Example Preparation of 6-{[(trans)-5-(4-methoxyphenyl)-2-methylazepan-4-yl]methoxy}-2,3-dihydro-1H-isoindol-1-one ((+/−)-C0449)

Prepared according to General Procedure C2 from (+/−)-45. LC-MS: (ES, m/z): 381 [M+1]

Example Preparation of 6-{[(trans)-5-(4-methoxyphenyl)-2-methyl-1-(2-phenylethyl)azepan-4-yl]methoxy}-2,3-dihydro-1H-isoindol-1-one ((+/−)-C0457)

Prepared according to General Procedure C8 from (+/−)-C0449. LC-MS: (ES, m/z): 485 [M+1]. $^1$H NMR (400 MHz, MeOD) δ 7.47-6.92 (m, 10H), 6.77 (ddd, J=8.7, 5.8, 3.1, 2H), 4.26 (s, 2H), 3.98-3.29 (m, 9H), 3.13-2.53 (m, 4H), 2.48-1.88 (m, 4H), 1.81 (m, 1H), 1.54 (d, J=7.0, 1H), 1.49-1.25 (m, 2H).

General Procedure C34: Preparation of 4,5-Azepine Analog with Nitrogen Linker

Scheme 34

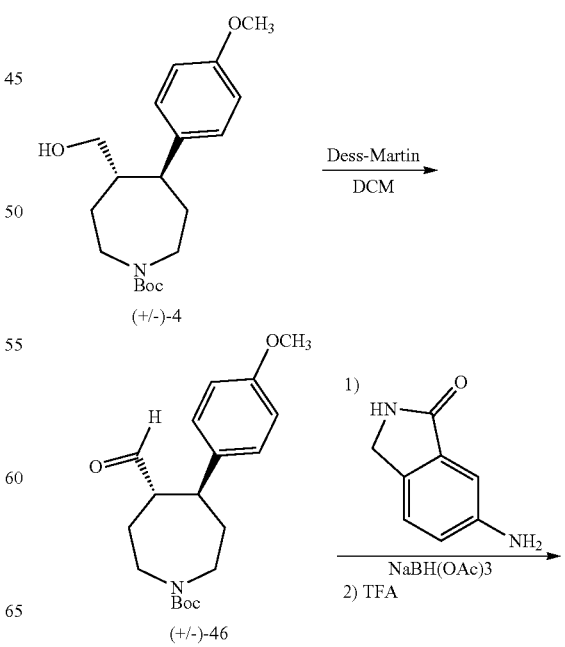

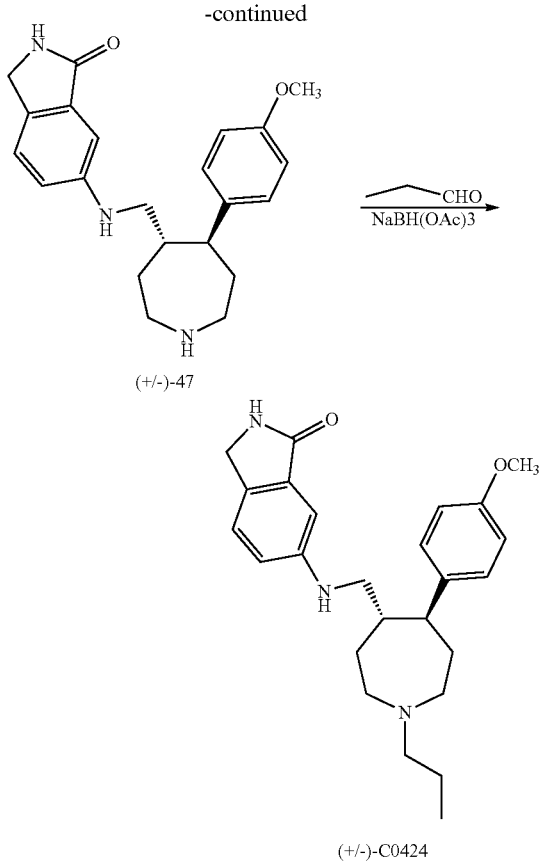

(+/−)-47

(+/−)-C0424

Tert-butyl (trans)-4-formyl-5-(4-methoxyphenyl) azepane-1-carboxylate (+/−)-C46

To a solution of (+/−)-C4 (430 mg, 1.3 mmole) in 10 mL DCM at 0° C. Dess-Martin reagent (707 mg, 1.7 mmole), stir 4 h, washed with $Na_2SO_4$, Saturated $NaHCO_3$ solution was added and extracted with EtOAc. The organics were combined to give a residue that was subjected purified by flash column chromatography (5%-80% EtOAc/hexanes) to yield 320 mg (74% yield) (+/−)-46. LCMS [M+Na]=356.2

6-({[(trans)-5-(4-methoxyphenyl)azepan-4-yl] methyl}amino)-2,3-dihydro-1H-isoindol-1-one (+/−)-C47

Prepared according to General Procedure C8 followed by Boc removal in General Procedure C2 from (+/−)-C46 to yield (+/−)-C47. LCMS [M+H]=366.2.

6-{[(trans)-5-(4-methoxyphenyl)-1-propylazepan-4-yl]methoxy}-2,3-dihydro-1H-isoindol-1-one (+/−)-C0424

Prepared according to General Procedure C8 from (−)-47 to yield (+/−)-C0424. LCMS [M+H]=408.3. $^1$H NMR (400 MHz, MeOD) δ 7.33 (d, J=8.3, OH), 7.17-6.92 (m, 1H), 6.77 (d, J=8.7, OH), 4.26 (s, OH), 3.95-3.81 (m, OH), 3.71 (d, J=9.1, OH), 3.60 (dd, J=16.3, 6.8, 1H), 3.43-3.35 (m, OH), 3.34 (d, J=2.4, OH), 3.03 (dt, J=3.3, 1.6, OH), 2.79 (s, OH), 2.21 (d, J=29.1, 1H), 1.98 (d, J=16.3, OH), 1.09-0.78 (m, 1H).

Other compounds, including compounds depicted in FIG. 1 were prepared according to the methods and schemes described herein with any modifications to the schemes being readily apparent to one of skill in the art based upon the present disclosure.

Example 2: The Compounds can Modulate δ-Opioid Receptor

The compounds described herein were tested as modulators of δ-opioid receptor. The compounds were found to be modulators of the receptors activity. Some of the compounds inhibited the β-arrestin pathway and the G-protein mediated pathway, whereas others would agonize or enhance either the β-arrestin mediated pathway or the G-protein mediated pathway. The activity was measured according to the methods described herein. The compounds described herein were also tested as modulators of μ and κ-opioid receptor.

In Vitro Assay

Plasmids encoding delta-opioid receptor (Accession NP_000902), mu-opioid receptor (Accession NP_000905) and kappa-opioid receptor (Accession Assession NP_000903) were generated in the pCMV-Prolink backbone and transfected into an EA-arrestin parental human embryonic kidney (HEK-293) cell line from DiscoveRx Corporation. Clonal stable lines were subsequently selected under G418.

Cell Culture and Plating

Cell lines were grown adherently in Minimum Essential Media (Cellgro cat #10-010-CM) containing 10% fetal bovine serum (Hyclone cat #SH30071.03), 4 mM glutamine (Cellgro cat #25-005-CI), 150 ug/ml hygromycin B (Cellgro cat #30-240-CR), 150 ug/ml G418 (Cellgro cat #30-234-CR), and 50 u/50 ug penicillin/streptomycin (Lonza cat #17-603E). Prior to the assay cells were removed from the flasks with CellStripper (Cellgro cat #25-056-CI), repeatedly pipetted to disperse cells, and spun at low speed for 5 min at room temperature. Cells were then resuspended at 250,000 cells/ml in growth media and plated at 5,000 cells/well in 384 well plates (Greiner part #784080). Plates were incubated overnight at 37° C., 5% C02 in a humidified incubator.

cAMP Assay

Receptor G-protein mediated responses were determined by measuring changes in intracellular cAMP using CisBio HTRF cAMP HiRange kit (cat #62AM6PEJ) based on time-resolved fluorescence resonance energy transfer (TR-FRET). Growth media was removed and replaced with Ham's F12 containing IBMX (500 uM), NKH-477 (1 uM, a water soluble forskolin derivative) and test or control compounds at the desired concentrations. Following a 30 minute incubation at 37° C. the components of the cAMP HiRange kit were added as directed and the plates were read after 1 hour on a BMG PheraStar plate reader. Responses were measured as the ratio of fluorescence at 665 nm/620 nm per manufacturer's instructions.

β-arrestin Assay

Receptor mediated beta-arrestin recruitment was determined using the DiscoveRx 0-arrestin PathHunter Detection kit (cat #93-0001). In this system, β-Arrestin is fused to an N-terminal deletion mutant of β-galactosidase (termed the enzyme acceptor of EA) and the GPCR of interest is fused to a smaller (42 amino acids), weakly complementing fragment termed ProLink™. In cells that stably express these fusion proteins, ligand stimulation results in the interaction of β-arrestin and the Prolink-tagged GPCR, forcing the complementation of the two β-galactosidase fragments and resulting in the formation of a functional enzyme that converts substrate to detectable signal. Growth media was removed and replaced with Ham's F12 containing HEPES (10 mM), IBMX (500 uM), NKH-477 (1 uM) and test or control compounds at the desired concentrations. Following a 60 minute incubation at 37° C. the components of the DiscoveRx 3-arrestin PathHunter Detection kit were added as directed and the plates were read after 1 hour on a BMG PheraStar plate reader.

The compounds as indicated herein were able to modulate the activities (cAMP and β-arrestin recruitment) of the δ-opioid receptor as indicated herein. The table includes the $pEC_{50}$ of the compounds as well as the efficacy of the compound as compared to a positive control as indicated. The values are normalized against DPDPE ([D-Pen2,5] Enkephalin, [D-Pen2,D-Pen5]Enkephalin), which is a known agonist of the receptor. Compound selectivity was also evaluated by testing compounds on the mu- and kappa-opioid receptors, the values from which were normalized against DAMGO ([D-Ala2, N-Me-Phe4, Gly5-ol]-Enkephalin acetate salt) and U69,593, respectively. The data is shown in FIG. 2.

In vitro experiments for paroxetine a non-selective agonist was also collected. Representative data is shown here:

|  | hDOR G pEC50 | hDOR G Span | hDOR G N | hDOR B pEC50 | hDOR B Span | hDOR B N |
|---|---|---|---|---|---|---|
| Paroxetine | <6 | <100 | 8 | <6 | <100 | 9 |

Many of the compounds were found to be selective against the delta-opioid receptor as indicated by the data, which is in contrast to the non-selectivity of paroxetine. Accordingly, the presently described compounds provide the unexpected and surprising result of being able to be selective against the delta-opioid receptor.

Example 3 Compounds Effective in Treating Depression and Anxiety

Assessment of Activity in the Tail Suspension Test (TST):

The compounds indicated below were determined to be efficacious and were evaluated for side effects in an in vivo model.

The experiments were performed using adult male C57 mice (6-10 weeks of age, 20-30 g, Hilltop Lab, PA). The mice were housed in standard rodent cages with stainless steel mesh wire bar lids in groups of 4 with controlled temperature and light cycle (6:00 a.m.-6:00 p.m.). Animals were given free access to food (Harlan Teklad Global 18% protein (Madison, Wis.)) and water during a minimum 2-day habituation period to the laboratory. Animals that were used in the study were handled, housed, and sacrificed (using compressed $CO_2$) in accord with the current NIH guidelines regarding the use and care of laboratory animals, and all applicable local, state, and federal regulations and guidelines. Animals are identified by cage number, and by markings applied to the proximal tip of the tail using a permanent marker. Group sizes (n=8, and therefore 30-50 animals per study) provide reliable estimates of treatment effects, and this species and strain of mouse has been recognized as appropriate for pharmacology studies.

To measure efficacy of the compounds the compounds were tested using a tail suspension test. The tail suspension test is a behavioral test used to evaluate the efficacy of antidepressant drugs in rodents. In the TST, mice (n=8/group) were suspended by the tail with tape approximately 30-50 cm above the lab bench. Mice are positioned such that the base of their tail is perpendicular to the lab bench. Each mouse is given 1 trial that last 6 minutes. The total duration of immobility is calculated as the percentage of time that the mouse is immobile. The duration of immobility is the main parameter measured. This is calculated from the cumulated time during which the animals is absent of initiated movements including passive swaying. When antidepressant drugs are administered, immobility is decreased by a variety of classes of antidepressant drugs. One or more of the compounds show antidepressant activity.

The compounds were also tested for side effects. The side effect tested is Acute Seizure Liability. Animals will acclimate to the vivarium for at least 48 hr prior to behavioral testing. Mice were placed into a glass jar (8 cm wide×17 cm tall for mice, 17 cm wide×31 cm tall for rats). Animals are administered various doses of test compounds at specified times prior to testing. Test drugs are administered by any of the following routes: s.c., p.o., i.v., or i.p. using a 1-2 ml/100 g injection volume (mice) or 1-5 ml/kg injection volume (rat). IV volumes will not exceed 2 ml and the tail vein is utilized for injection. Immediately after the injection, the animal is placed in the observational glass jar. Animals are observed for a minimum of 30 minutes for the presence of seizure-like behaviors. The behavior will be rated absent, mild, or severe. One or more of the compounds show no significant side effects at relevant doses.

The compounds below were found to be effective in the TST model at the doses indicated, although other doses may also be active. Other compounds described herein were not necessarily tested, but are expected to be able have some level of efficacy.

| Compound | TST Route | Active* TST Dose (mg/kg) |
|---|---|---|
| C0004 | sc | ≤30 |
| C0056 | sc | ≤10 |
| C0065 | sc | ≤10 |
| C0066 | sc | ≤10 |
| C0084 | sc | ≤30 |
| C0114 | sc | ≤10 |
| C0125 | sc | ≤10 |
| C0137 | sc | ≤30 |
| C0143 | sc | ≤30 |
| C0156 | sc | ≤10 |
| C0163 | sc | ≤10 |
| C0168 | sc | ≤30 |
| C0169 | sc | ≤10 |
| C0174 | sc | ≤10 |
| C0175 | sc | ≤60 |
| C0177 | sc | ≤30 |
| C0188 | sc | ≤30 |
| C0193 | sc | ≤30 |
| C0194 | sc | ≤30 |
| C0212 | sc | ≤30 |
| C0227 | sc | ≤10 |
| C0231 | sc | ≤30 |
| C0262 | po | ≤30 |
| C0269 | sc, po | ≤30 |
| C0270 | po | ≤30 |
| C0271 | sc, po | ≤30 |
| C0276 | po | ≤60 |
| C0286 | po | ≤30 |
| C0287 | po | ≤10 |
| C0289 | sc | ≤10 |
| C0333 | sc, po | ≤30 |
| C0334 | sc, po | ≤30 |
| C0342 | po | ≤30 |
| C0355 | sc | ≤10 |

-continued

| Compound | TST Route | Active* TST Dose (mg/kg) |
|---|---|---|
| C0396 | sc, po | ≤30 |
| C0455 | po | ≤60 |
| C0457 | po | ≤60 |
| C0460 | sc | ≤30 |

Compounds Effective in Treating Inflammation and Pain

Assessment of Tactile Allodynia Produced by Intraplantar Freund's Complete Adjuvant in Mice and Rats:

Animals were acclimated to the vivarium for at least 48 hr prior to behavioral testing. Inflammation was induced for both rodent species with the administration of an intraplantar (subcutaneous injection into the plantar surface of the hind paw, i.pl.) injection of 0.10 ml Freund's Complete Adjuvant (FCA).

For mouse studies, the experiments were conducted 48 hours after FCA administration. Tactile allodynia was measured using a series of von Frey monofilaments. These filaments are bendable, plastic and intended to poke, not penetrate, the skin. Animals were placed in a Plexiglas chamber (approximately 10 cm×20 cm×25 cm) and allowed to habituate for 5-10 minutes. The chamber was positioned on top of a mesh screen so that von Frey monofilaments can be presented to the plantar surface of the hind paw that is inflamed. The measurement of tactile sensitivity for the injected hind paw is obtained using the up/down method (LaBuda and Little, 2005, J Neurosci. Methods, 144, 175) with seven von Frey monofilaments (0.07, 0.16, 0.4, 0.6, 1, and 2 grams). Each trial will start with a von Frey force of 0.6 grams delivered to the hind paw for approximately 1-2 seconds. If there was no withdrawal response, the next higher force was be delivered. If there was a response, the next lower force was delivered. This procedure was performed until no response was made at the highest force (2 grams) or until four stimuli are administered following the initial response. The 50% paw withdrawal threshold for the hind paw was calculated using the following formula: [Xth]log=[vFr]log+ky where [vFr] is the force of the last von Frey used, k is the average interval (in log units) between the von Frey monofilaments, and y is a value that depends upon the pattern of withdrawal responses (Dixon, Annual Review Pharmacol Toxicol, 1980, 20, 441).

For rat studies, the experiments were conducted 24 hours after CFA administration. Rats are tested for mechanical allodynia in a Randall-Selitto apparatus. The inflamed paw is put on a pedestal and a pointed force of increasing intensity (0 to 250 grams) is applied to the paw. When the animal struggles to withdraw from the force the test is stopped and the force to induce that struggle is recorded. Data may be presented as mean grams of force to withdrawal or a percentage of the maximum possible effect.

The compounds below were found to be effective in the CFA model at the doses indicated, although other doses may also be active. Other compounds described herein were not necessarily tested, but are expected to be able have some level of efficacy.

| Compound | Species | CFA Route | Active* CFA Dose (mg/kg) |
|---|---|---|---|
| C0287 | mouse | po | ≤10 |

*p < 0.05 compared to vehicle-treated mice

Compounds Effective in Treating Migraines (Prophetic)

Assessment of Tactile Allodynia Produced by Nitroglycerin:

Compounds are tested for efficacy in rodent models of nitroglycerine induced migraine. In this model both rats and mice can be induced to have a behavioral response consistent with the progression of a migraine attack by the intraperitoneal injection of nitroglycerin. In this test mice or rats (n=8/group) are given an intraperitoneal injection of nitroglycerin at 10 mg/kg. After 90 minutes the animals are subcutaneously dosed with test compound. A measurement of mechanical allodynia will be obtained using the up/down method with seven von Frey monofilaments. There is a specific series used for rat and mouse. Each monofilament is delivered to the hind paw for approximately 1-2 seconds. If there is a response, the next lower force will be delivered. This procedure will be performed until no response was made at the highest force or until four stimuli are administered following the initial response. The 50% paw withdrawal threshold for the hind paw will be calculated using the following formula: [Xth]log=[vFr]log+ky where [vFr] is the force of the last von Frey used, k is the average interval (in log units) between the von Frey monofilaments, and y is a value that depends upon the pattern of withdrawal responses. Testing for tactile sensitivity will be performed and a withdrawal value will be assigned as the tactile sensitivity (expressed in grams of force required to elicit a response) for the injected paw for each animal. Data is presented as the mean grams required to produce a hind paw withdrawal from the von Frey stimulus. The compounds are found to be effective in treating migraines.

Compounds Effective in Parkinson's Disease (Prophetic)

Compounds are tested for efficacy in reversing akinesia and bradykinesia in two well accepted rodent Parkinson's disease (PD) models; the haloperidol-induced rat catalepsy [1] and 6-OHDA rat hemiparkinson lesion models [3].

In the haloperidol induced catalepsy model, compounds are dosed subcutaneously and motor impairments (akinesia/bradykinesia) were measured in the "bar test" [1] which measures the ability of the rat to respond to an externally imposed static posture as well as the "drag test" a modification of the "wheelbarrow" test [2] which measures the ability of the rat to balance its body posture using forelimbs in response to an externally imposed dynamic (dragging) stimulus. Compounds are administered subcutaneously and efficacy is evaluated between 60 min post dose.

The compounds are found to be effective in the haloperidol induced catalepsy model.

In the hemilesioned rat 6-OHDA model, the effect of compound on the akinetic response to lesioning of the contralateral forepaw in the bar test and stepping activity as measured by the drag test is determined. L-DOPA has been shown to be efficacious at relevant doses in this model. This assay examines efficacy for reversing PD motor symptoms (i.e. akinesia/bradykinesia and gait abilities). The behavioral readouts will include immobility time in the bar test (akinesia), number of steps in the drag test (akinesia/bradykinesia) and time spent on rod in the rotarod test (overall gait ability, gross motor behavior). Compounds are administered subcutaneously and efficacy is evaluated between 30 and 90 min post dose.

The compounds below are found to be effective in the hemilesioned rat 6-OHDA model.

The referenced referred to in the paragraphs above are: [1] Marti M, Mela F, Guerrini R, Calo G, Bianchi C, Moran M (2004). Blockade of nociceptin/orphanin FQ transmission in rat substantia nigra reverses haloperidol-induced akinesia and normalizes nigral glutamate release. J Neurochem 91(6): 1501-1504. [2] Mabrouk, O. S., et al., Stimulation of delta opioid receptors located in substantia nigra reticulata but not globus pallidus or striatum restores motor activity in 6-hydroxydopamine lesioned rats: new insights into the role of delta receptors in parkinsonism. Journal of Neurochemistry, 2008. 107(6): p. 1647-1659. [3]Sanberg, P. R., et al., The catalepsy test: its ups and downs. Behav Neurosci, 1988. 102(5): p. 748-59.

In summary, the compounds described herein were found to be selective against the delta-opioid receptor and are able to treat conditions associated with the same. The compounds described herein have been found to be active and effective against various conditions. The experiments described herein are exemplary in manner and are not intended, nor should they be used, to limit the scope of the embodiments. Each and every reference, publication, accession number, patent, document, etc, is hereby incorporated by reference in its entirety for its intended purpose.

What is claimed is:

1. A compound having Formula I, Ia, Ia-1, or Ia-2,

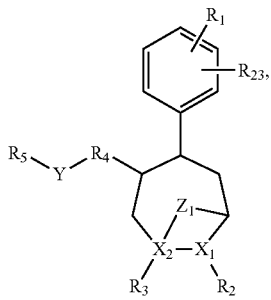
I

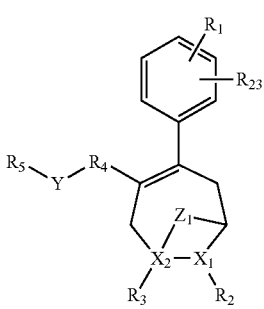
Ia

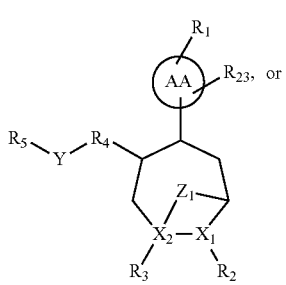
Ia-1

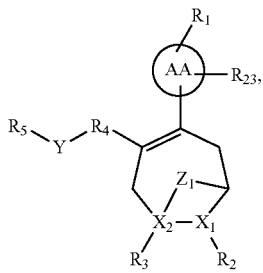
Ia-2 or a pharmaceutically acceptable salt thereof, wherein:

AA is independently, optionally substituted cycloalkyl, optionally substituted heterocycle, optionally substituted imidazole,

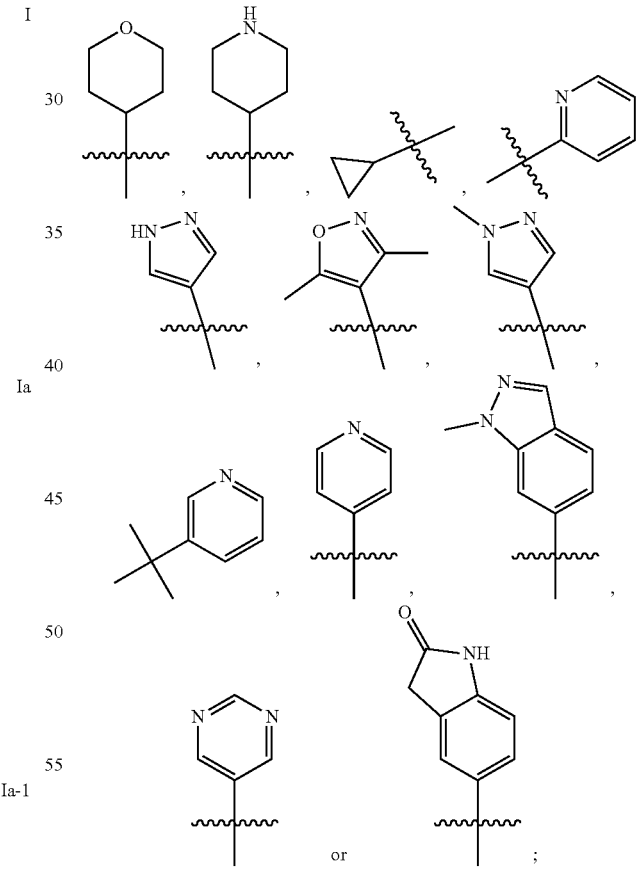

$X_1$ is CH or N;
$X_2$ is C or N provided that when $X_2$ is N, $X_1$ is CH and when $X_2$ is C, $X_1$ is N;
Y is O or NH,
$R_1$ is H, —SO$_2$C$_1$-C$_6$alkyl, —OCF$_3$, halo, —NR$_{30}$R$_{31}$, —NH—(CH$_2$) R$_{17}$ S—(CH$_2$)$_y$—R$_{17}$, —(CH$_2$)$_y$—R$_{17}$, —O—(CH$_2$)$_y$—R$_{17}$, —OR$_8$, or

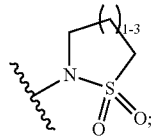

R$_{17}$ is H, C$_1$-C$_6$haloalkyl, —OR$_{18}$,

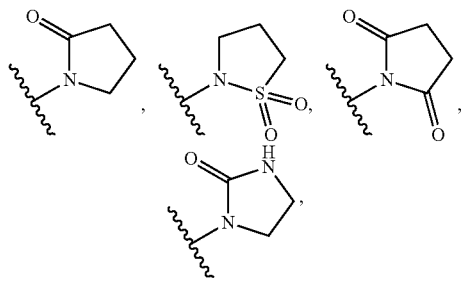

—C(=O)N(R$_{18}$)$_2$, optionally substituted cycloalkyl, —(CH$_2$)$_p$R$_{19}$, or optionally substituted heterocycle;

R$_{23}$ is H, halo, —SO$_2$C$_1$-C$_6$alkyl, —OCF$_3$, haloalkyl, or optionally substituted C$_1$-C$_6$ alkyl;

y is an integer from 0-6;

or R$_1$ and R$_{23}$ form a heterocycle that is fused to the phenyl ring;

R$_2$ and R$_3$ are each, independently, H, a protecting group, C(=O)OR$_{81b}$, optionally substituted aryl, optionally substituted C$_1$-C$_6$ haloalkyl, —R$_{20}$R$_{21}$, —NR$_{20}$R$_{21}$, optionally substituted C$_1$-C$_8$ branched or unbranched alkyl, optionally substituted C$_2$-C$_6$ alkenyl, optionally substituted C$_2$-C$_6$ haloalkenyl, —(CH$_2$)$_n$R$_{19}$, optionally substituted cycloalkyl, optionally substituted C$_1$-C$_6$ alkoxy, optionally substituted pyrrolinyl, optionally substituted morpholinyl, optionally substituted pyridyl, optionally substituted piperidyl, and C$_3$-C$_6$ cyclic ether; such that when X$_1$ is CH, R$_2$ is H or when X$_2$ is C, R$_3$ is H; provided that R$_2$ is not —NR$_{20}$R$_{21}$ when X$_1$ is N and R$_3$ is not —NR$_{20}$R$_{21}$ when X$_2$ is N, wherein R$_{81b}$ is H or optionally substituted branched or unbranched C$_1$-C$_6$;

—Z$_1$— is absent or Z$_1$ is C$_1$-C$_3$ alkyl, provided that when Z$_1$ is C$_1$-C$_3$ alkyl, X$_2$ is C;

R$_4$ is a bond, optionally substituted C$_1$-C$_6$ branched or unbranched alkyl or —C=O;

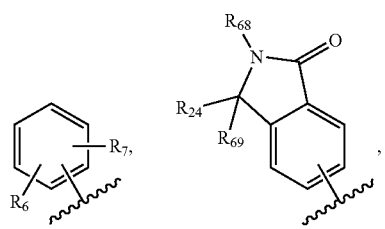

-continued

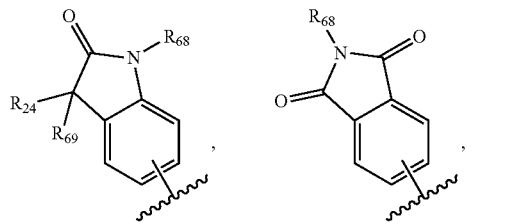

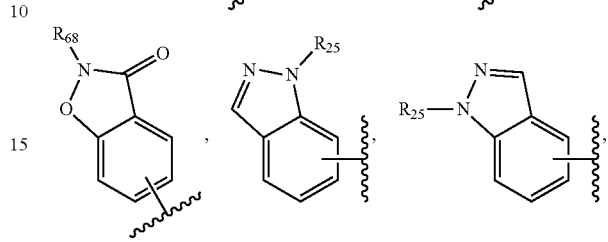

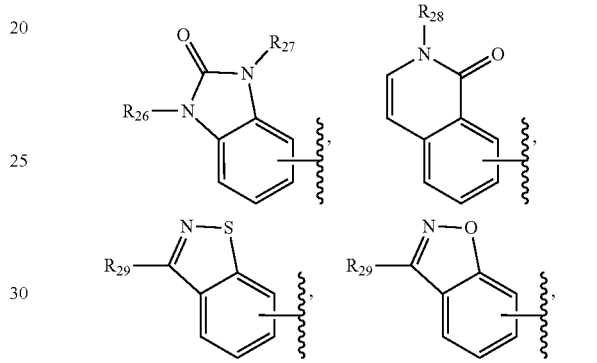

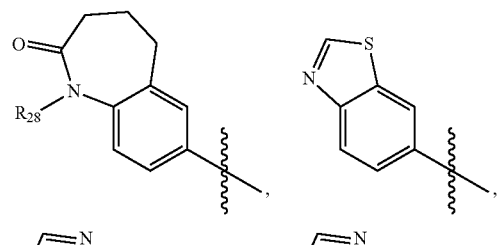

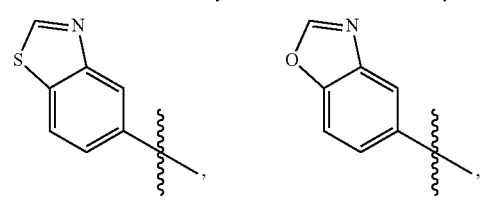

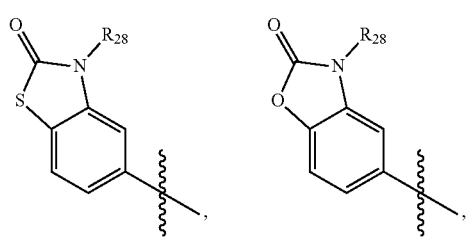

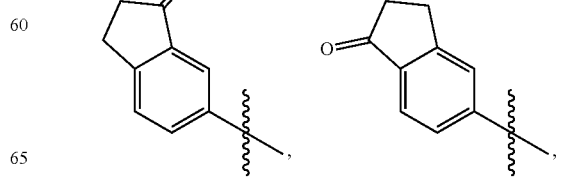

-continued

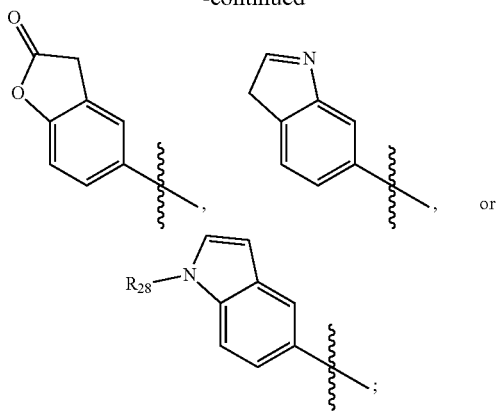

wherein:

$R_6$ and $R_7$ are each, independently, H, halo, cyano, —C(=O)N($R_{10}$)$_2$, —NHC(=O)$R_{11}$, or

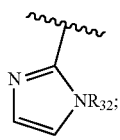

$R_8$ is optionally substituted $C_1$-$C_6$ branched or unbranched alkyl or —(CH$_2$)$_n$OR$_9$;

$R_9$ is optionally substituted $C_1$-$C_6$ branched or unbranched alkyl;

each $R_{10}$ is, independently, H or optionally substituted $C_1$-$C_6$ branched or unbranched alkyl;

each $R_{11}$ is, independently, optionally substituted $C_1$-$C_6$ branched or unbranched alkyl;

each $R_{18}$ is independently H, optionally substituted aryl, optionally substituted $C_1$-$C_6$ haloalkyl, —NR$_{20}$R$_{21}$, optionally substituted $C_1$-$C_6$ branched or unbranched alkyl, optionally substituted $C_2$-$C_6$ alkenyl, —(CH$_2$)$_v$R$_{19}$, optionally substituted cycloalkyl, —OH, optionally substituted alkoxy, optionally substituted pyrrolinyl, optionally substituted morpholinyl, or optionally substituted piperidyl;

each $R_{19}$ is, independently, H, cyano, optionally substituted $C_1$-$C_6$ haloalkyl, —NR$_{20}$R$_{21}$, optionally substituted $C_1$-$C_6$ branched or unbranched alkyl, optionally substituted aryl, optionally substituted heteroaryl, optionally substituted $C_2$-$C_6$ alkenyl, optionally substituted cycloalkyl, optionally substituted heterocycle, —OH, optionally substituted alkoxy, optionally substituted pyrrolinyl, optionally substituted morpholinyl, optionally substituted pyrazole, optionally substituted ketone, optionally substituted oxazole, optionally substituted thiazole, or optionally substituted piperidyl;

$R_{20}$ and $R_{21}$ are, each, independently, H, optionally substituted aryl, optionally substituted $C_1$-$C_6$ haloalkyl, optionally substituted $C_1$-$C_6$ branched or unbranched alkyl, optionally substituted $C_2$-$C_6$ alkenyl, —(CH$_2$)$_w$R$_{19}$, optionally substituted cycloalkyl, —OH, optionally substituted alkoxy, optionally substituted pyrrolinyl, optionally substituted morpholinyl, optionally substituted piperidyl; or $R_{20}$ and $R_{21}$ together form a 5-10 membered optionally substituted heterocycle or a 5-10 membered optionally substituted heteroaryl with the atom to which $R_{20}$ and $R_{21}$ are bonded to;

$R_{24}$ is H, optionally substituted alkyl, or optionally substituted $C_3$-$C_6$ cycloalkyl;

$R_{68}$ is H or optionally substituted $C_1$-$C_6$ alkyl;

$R_{69}$ is H or optionally substituted $C_1$-$C_6$ alkyl or $R_{24}$ or $R_{69}$ form a $C_3$-$C_6$ cycloalkyl including the carbon to which $R_{24}$ or $R_{69}$ are bound;

$R_{25}$ is H or optionally substituted $C_1$-$C_6$ alkyl;

$R_{26}$ is H or optionally substituted $C_1$-$C_6$ alkyl;

$R_{27}$ is H or optionally substituted $C_1$-$C_6$ alkyl;

$R_{28}$ is H or optionally substituted $C_1$-$C_6$ alkyl;

$R_{29}$ is H, —NR$_{20}$R$_{21}$ or optionally substituted $C_1$-$C_6$ alkyl;

$R_{30}$ and R31 are each, independently, H, $C_1$-$C_6$ alkyl, —C(=O)C$_1$-$C_6$ alkyl, —S(=O)$_2$C$_1$-$C_6$ alkyl; —S(=O)$_2$(CH$_2$)$_{1-4}$CF$_3$; —C(=O)O(CH$_2$)$_{1-4}$Ph; or —C(=O)N(C$_1$-$C_6$ alkyl)$_2$;

and each n, p, v, and w is, independently, an integer from 0-6.

2. The compound of claim 1, or a pharmaceutically acceptable salt thereof, wherein the compound has a Formula of Formula Ib, Ic, Id, or Ig,

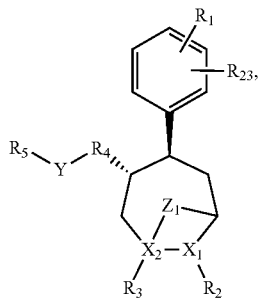

Ib

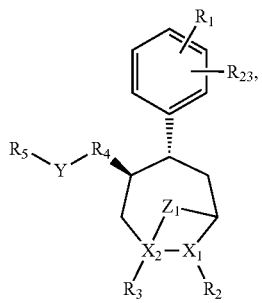

Ic

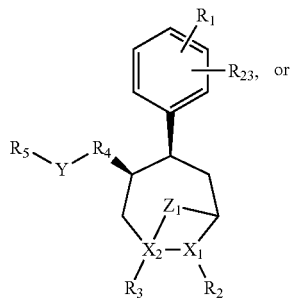

Id

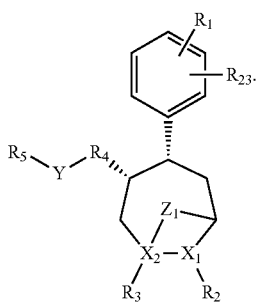

3. The compound of claim 1, wherein Y is O.

4. The compound of claim 3, wherein $R_4$ is a bond.

5. The compound of claim 1, or a pharmaceutically acceptable salt thereof, wherein $Z_1$ is ethyl.

6. The compound of claim 1, or a pharmaceutically acceptable salt thereof, wherein $R_2$ is H, optionally substituted $C_1$-$C_6$ branched or unbranched alkyl, —$CH_2R_{70}$, or —$CH_2CH_2R_{70}$, wherein $R_{70}$ is optionally substituted aryl, optionally substituted haloalkyl, optionally substituted ketone, optionally substituted cycloalkyl, optionally substituted $C_2$-$C_6$ alkenyl, optionally substituted $C_2$-$C_6$ haloalkenyl, or optionally substituted heteroaryl.

7. The compound of claim 6, or a pharmaceutically acceptable salt thereof, wherein $R_{70}$ is cyclopropyl, difluorocyclopropyl, —CH=$CF_2$, or 2,2-difluorocyclopropyl.

8. The compound of claim 1, or a pharmaceutically acceptable salt thereof, wherein $R_3$ is H, optionally substituted $C_1$-$C_6$ branched or unbranched alkyl, —$CH_2R_{70}$, or —$CH_2CH_2R_{80}$, and wherein $R_{80}$ is optionally substituted aryl, optionally substituted haloalkyl, optionally substituted ketone, optionally substituted cycloalkyl, optionally substituted $C_2$-$C_6$ alkenyl, optionally substituted $C_2$-$C_6$ haloalkenyl, or optionally substituted heteroaryl.

9. The compound of claim 8, or a pharmaceutically acceptable salt thereof, wherein $R_{80}$ is cyclopropyl, difluorocyclopropyl, 2,2-difluorocyclopropyl, or —CH=$CF_2$.

10. The compound of claim 1, or a pharmaceutically acceptable salt thereof, wherein $R_5$ is

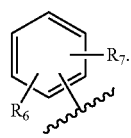

11. The compound of claim 1, or a pharmaceutically acceptable salt thereof, wherein when $R_6$ is halo, $R_7$ is cyano; when $R_6$ is halo, $R_7$ is H; when $R_6$ is cyano, $R_7$ is H; when $R_6$ is —C(=O)N($R_{10}$)$_2$, $R_7$ is H or halo; and when $R_6$ is —NHC(=O)$R_{11}$, $R_7$ is H.

12. The compound of claim 1, or a pharmaceutically acceptable salt thereof, wherein R5 is

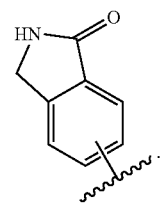

13. The compound of claim 1, or a pharmaceutically acceptable salt thereof, wherein $R_1$ is H, halo, or —$OR_8$.

14. A pharmaceutical composition comprising a compound, or a pharmaceutically acceptable salt thereof, of claim 1.

15. A method of treating pain, neuropathic pain, migraine, headache, depression, PTSD, Parkinson's disease, anxiety, or overactive bladder in a subject comprising administering to the subject one or more compounds, or a pharmaceutically acceptable salt thereof, of claim 1.

16. The method of claim 15, wherein the subject is a subject in need thereof.

17. The compound of claim 1, or a pharmaceutically acceptable salt thereof, wherein the compound is selected from the group consisting of

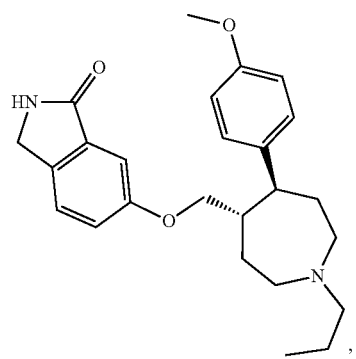

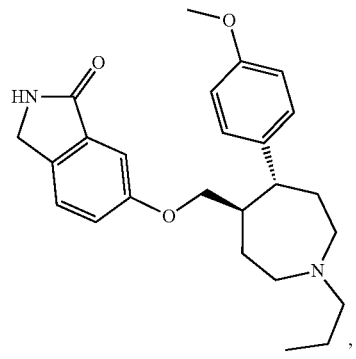

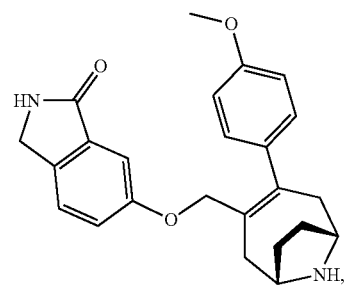

-continued
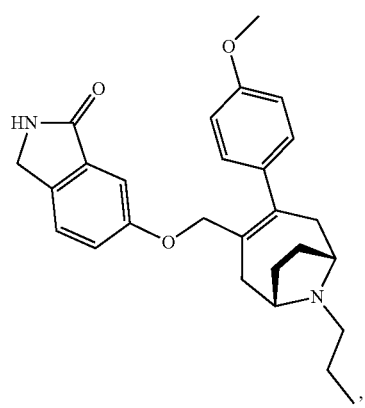
C0066
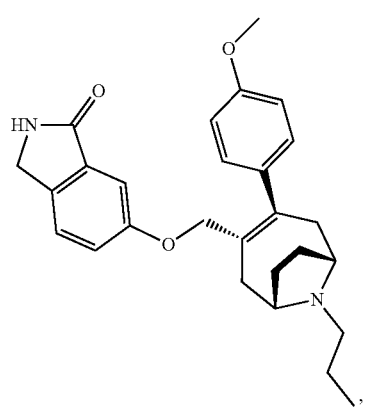
C0084
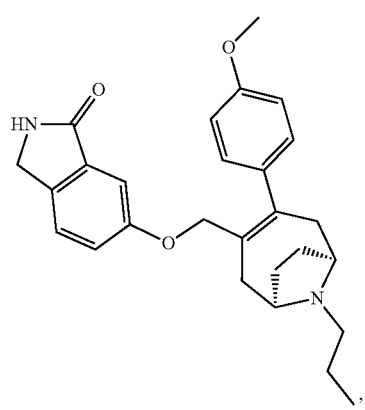
C0114
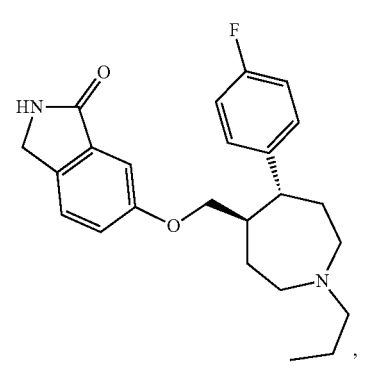
C0125
-continued
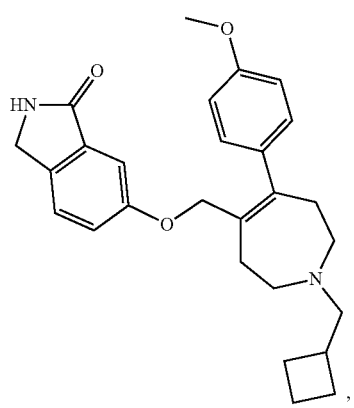
C0137
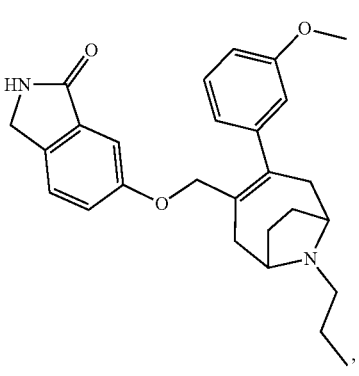
C0143
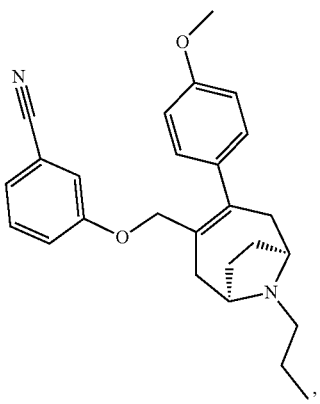
C0156

C0163
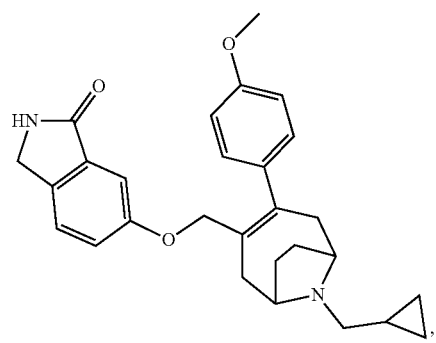
C0168
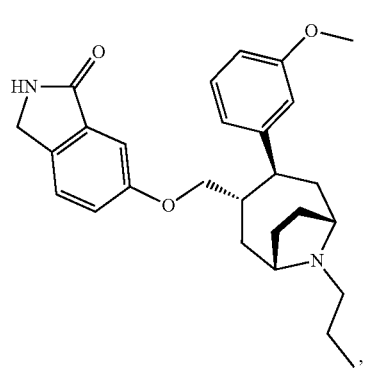
C0169
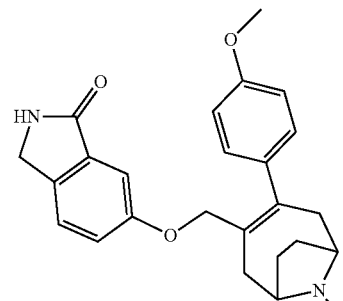
, and
C0287
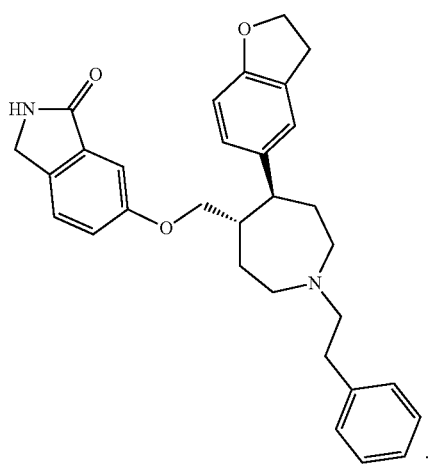
.
* * * * *